US012667592B2

(12) United States Patent
Schipper et al.

(10) Patent No.: US 12,667,592 B2
(45) Date of Patent: Jun. 30, 2026

(54) COMPOSITIONS FOR RESTORING GENE EXPRESSION IN NEUROPSYCHIATRIC OR NEURODEGENERATIVE DISORDERS

(71) Applicant: Immunotec Inc., Vaudreuil-Dorion (CA)

(72) Inventors: Hyman Morris Schipper, Vaudreuil-Dorion (CA); Marisa Emily Cressatti, Vaudreuil-Dorion (CA); Wei Song, Vaudreuil-Dorion (CA); Carmela Galindez, Vaudreuil-Dorion (CA); Ayda Tavitian, Vaudreuil-Dorion (CA); Adrienne Liberman, Vaudreuil-Dorion (CA); Daniel A. Linseman, Littleton, CO (US)

(73) Assignee: IMMUNOTEC INC., The Woodlands, TX (US)

( * ) Notice: Subject to any disclaimer, the term of this patent is extended or adjusted under 35 U.S.C. 154(b) by 271 days.

(21) Appl. No.: 17/836,475

(22) Filed: Jun. 9, 2022

(65) Prior Publication Data

US 2023/0029577 A1 Feb. 2, 2023

Related U.S. Application Data

(63) Continuation of application No. 16/335,914, filed as application No. PCT/US2017/052269 on Sep. 19, 2017, now abandoned.

(60) Provisional application No. 62/398,892, filed on Sep. 23, 2016.

(51) Int. Cl.
*A61K 35/20* (2006.01)
*A61P 25/18* (2006.01)
*A61P 25/28* (2006.01)

(52) U.S. Cl.
CPC .............. *A61K 35/20* (2013.01); *A61P 25/18* (2018.01); *A61P 25/28* (2018.01); *G01N 2800/28* (2013.01); *G01N 2800/30* (2013.01); *Y02A 50/30* (2018.01)

(58) Field of Classification Search
CPC .......... A61K 35/20; A61P 25/18; A61P 25/28; A61P 25/00; G01N 2800/28; G01N 2800/30; Y02A 50/30
See application file for complete search history.

(56) References Cited

U.S. PATENT DOCUMENTS

| | | | |
|---|---|---|---|
| 8,017,147 B2 | 9/2011 | Mazed et al. | |
| 10,052,359 B2 * | 8/2018 | Ano ........................ | A23J 3/343 |
| 10,398,729 B2 | 9/2019 | Russell | |
| 2013/0209580 A1 | 8/2013 | Russell | |

OTHER PUBLICATIONS

Kaplan et al., Am J Clin Nutr, 2001, 74:687-93.*
Camfield et al., British J Nutrition, 2011, 106: 159-74.*
Morris et al., Whey processing, Functionality and Health Benefits, 2008, Wiley&Sons, 285-343.*
Crichton et al., Int Dairy J, 2012, 22:15-23.*
Office Action issued Nov. 2, 2023 in corresponding Canadian Patent Application No. 3,038,048.
Ross et al., "Immunocal® and Preservation of Glutathione as a Novel Neuroprotective Strategy for Degenerative Disorders of the Nervous System", Recent Patents on CNS Drug Discovery, 2012, vol. 7, No. 3, pp. 230-235.
Bošković et al., "Oxidative Stress in Schizophrenia", Current Neuropharmacology, 2011, vol. 9, pp. 301-312.
Herring et al., "Reelin Depletion is an Early Phenomenon of Alzheimer's Pathology", Journal of Alzheimer's Disease, 2012, vol. 30, No. 4, pp. 963-979.
International Search Report and Written Opinion of the International Searching Authority, issued Dec. 1, 2017 in corresponding International Patent Application No. PCT/US2017/052269.
Ross et al., "Immunocal® and Preservation of Glutathione as a Novel Neuroprotective Strategy for Degenerative Disorders of the Nervous System", Recent Patents on CNS Drug Discovery, 7(3): 230-235 (2012).
Ross et al., "A Cystine-Rich Whey Supplement (Immunocal®) Delays Disease Onset and Prevents Spinal Cord Glutathione Depletion in the hSOD1$^{G93A}$ Mouse Model of Amyotrophic Lateral Sclerosis", Antioxidants, 3(4): 843-865 (2014).
Rice et al., "Role of the Reelin Signaling Pathway in Central Nervous System Development", Annu. Rev. Neurosci., 24: 1005-1039 (2001).
The Australian J. Dietary Technology, 2009, 64(1):117-21.
British J. Nutrition, 2011, 106:159-74.

* cited by examiner

*Primary Examiner* — Olga N Chernyshev
(74) *Attorney, Agent, or Firm* — Wenderoth, Lind & Ponack, L.L.P.

(57) ABSTRACT

Methods for increasing reelin (RELN) levels in the brain of a subject in need thereof, as well as compositions for use in such methods, are provided. In addition, methods and compositions are described herein which may be used in the treatment of neuropsychiatric or neurodegenerative disorders, such as schizophrenia and Alzheimer's disease (AD). Compositions described herein may comprise whey protein isolate and/or whey protein concentrate, a source of the glutathione precursor cysteine. The provided methods and compositions are not limited to increasing RELN levels, and may be used to correct a number of other neurological disregulations or abnormalities occurring in a subject in need thereof.

2 Claims, 39 Drawing Sheets
(12 of 39 Drawing Sheet(s) Filed in Color)
Specification includes a Sequence Listing.

FIGURE 11

SEQ ID NO: 1  Reelin (RELN) mRNA; human; complete coding sequence; GenBank U79716

>gi|1743884|gb|U79716.1|HSU79716 Human reelin (RELN) mRNA, complete cds

```
CACGCGTGGGCTCGGCGGGGGCCCGCTCCCAGGCCCGGTCCCGAGCCCGGTTCCGCTCCCGTCCGCCTTCT
TCTCGCCTTCTCTCCGCGTGGCTCCTCCGTCCCGGCGTCTCCAAAACTGAATGAGCGAGCGGCGCGTAGG
GCGGCGGCGGCGGCGGCGGCGGCGGCGGCGGCGGCATGGAGCGCAGTGGCTGGGCCCGGCAGACTTTCCT
CCTAGCGCTGTTGCTGGGGGGCGACGCTGAGGGCGCGCGCGGCGGCTGGCTATTACCCCCGCTTTTCGCCC
TTCTTTTTCCTGTGCACCCACCACGGGGAGCTGGAAGGGGATGGGGAGCAGGGCGAGGTGCTCATTTCCC
TGCATATTGCGGGCAACCCCACCTACTACGTTCCGGGACAAGAATACCATGTGACAATTTCAACAAGCAC
CTTTTTTGACGGCTTGCTGGTGACAGGACTATACACATCTACAAGTGTTCAGGCATCACAGAGCATTGGA
GGTTCCAGTGCTTTCGGATTTGGGATCATGTCTGACCACCAGTTTGGTAACCAGTTTATGTGCAGTGTGG
TAGCCTCTCACGTGAGTCACCTGCCCACAACCAACCTCAGTTTCATCTGGATTGCTCCACCTGCGGGCAC
AGGCTGTGTGAATTTCATGGCTACAGCAACACACCGGGGCCAGGTTATTTTCAAAGATGCTTTAGCCCAG
CAGTTGTGTGAACAAGGAGCTCCAACAGATGTCACTGTGCACCCACATCTAGCTGAAATACATAGTGACA
GCATTATCCTGAGAGATGACTTTGACTCCTACCACCAACTGCAATTAAATCCAAATATATGGGTTGAATG
TAACAACTGTGAGACTGGAGAACAGTGTGGCGCGATTATGCATGGCAATGCCGTCACCTTCTGTGAACCA
TATGGCCCACGAGAACTGATTACCACAGGCCTTAATACAACAACAGCTTCTGTCCTCCAATTTTCCATTG
GGTCAGGTTCATGTGCTTTAGTTATTCAGACCCCAGCATCATCGTGTTATATGCCAAGAATAACTCTGC
GGACTGGATTCAGCTAGAGAAAATTAGAGCCCCTTCCAATGTCAGCACAATCATCCATATCCTCTACCTT
CCTGAGGACGCCAAAGGGGAGAATGTCCAATTTCAGTGGAAGCAGGAAAATCTTCGTGTAGGTGAAGTGT
ATGAAGCCTGCTGGGCCTTAGATAACATCTTGATCATCAATTCAGCTCACAGACAAGTCGTTTTAGAAGA
TAGTCTCGACCCAGTGGACACAGGCAACTGGCTTTTCTTCCCAGGAGCTACAGTTAAGCATAGCTGTCAG
TCAGATGGGAACTCCATTTATTTCCATGGAAATGAAGGCAGCGAGTTCAATTTTGCCACCACCAGGGATG
TAGATCTTTCCACAGAAGATATTCAAGAGCAATGGTCAGAAGAATTTGAGAGCCAGCCTACAGGATGGGA
TGTCTTGGGAGCTGTCATTGGTACAGAATGTGGAACGATAGAATCAGGCTTATCAATGGTCTTCCTCAAA
GATGGAGAGAGGAAATTATGCACTCCATCCATGGACACTACCGGTTATGGGAACCTGAGGTTTTACTTTG
TGATGGGAGGAATTTGTGACCCTGGAAATTCTCATGAAAATGACATAATCCTGTATGCAAAAATTGAAGG
AAGAAAAGAGCATATAACACTGGATACCCTTTCCTATTCCTCATATAAGGTTCCGTCTTTGGTTTCTGTG
GTCATCAATCCTGAACTTCAGACTCCTGCTACCAAATTTTGTCTCAGGCAAAAGAACCATCAAGGACATA
ATAGGAATGTCTGGGCTGTAGACTTTTTCCATGTCTTGCCTGTTCTCCCTTCTACAATGTCTCACATGAT
ACAGTTTTCCATCAATCTGGGATGTGGAACGCATCAGCCTGGTAACAGTGTCAGCTTGGAATTTTCTACC
AACCATGGGCGCTCCTGGTCCCTCCTTCACACTGAATGCTTACCTGAGATCTGTGCTGGACCCCACCTCC
CCCACAGCACTGTCTACTCCTCTGAAAACTACAGTGGGTGGAACCGAATAACAATTCCCCTTCCTAACGC
AGCACTAACCCGGAACACCAGGATTCGCTGGAGACAAACAGGACCAATCCTTGGAAACATGTGGGCAATT
GATAATGTTTATATTGGCCCGTCATGTCTCAAATTCTGTTCTGGCAGAGGACAGTGCACTAGACATGGTT
GCAAGTGTGACCCTGGATTTTCTGGCCCAGCTTGTGAGATGGCATCCCAGACATTCCCAATGTTTATTTC
TGAAAGCTTTGGCAGTTCCAGGCTCTCCTCTTACCATAACTTTTACTCTATCCGTGGTGCTGAAGTCAGC
TTTGGTTGTGGTGTCTTGGCCAGTGGTAAGGCCCTGGTTTTCAACAAAGAAGGGCGGCGTCAGCTAATTA
CATCTTTCCTTGACAGCTCACAATCCAGGTTTCTCCAGTTCACACTGAGACTGGGGAGCAAATCTGTTCT
GAGCACGTGCAGAGCCCCTGATCAGCCTGGTGAAGGAGTTTGCTGCATTATTCTTATGATAATGGGATA
ACTTGGAAACTCCTGGAGCATTATTCATATCTCAGCTATCATGAGCCCAGAATAATCTCCGTAGAACTAC
CAGGTGATGCAAAGCAGTTTGGAATTCAGTTCAGATGGTGGCAACCGTATCATTCTTCCCAGAGAGAAGA
TGTATGGGCTATTGATGAGATTATCATGACATCTGTGCTTTTCAACAGCATTAGTCTTGACTTTACCAAT
CTTGTGGAGGTCACTCAGTCTCTGGGATTCTACCTTGGAAATGTTCAGCCATACTGTGGCCACGACTGGA
CCCTTTGTTTTACAGGAGATTCTAAACTTGCCTCAAGTATGCGCTATGTGGAAACACAATCAATGCAGAT
AGGAGCATCCTATATGATTCAGTTCAGTTTGGTGATGGGATGTGGCCAGAAATACACCCCACACATGGAC
AACCAGGTGAAGCTGGAGTACTCAACCAACCACGGCCTTACCTGGCACCTCGTCCAAGAAGAATGCCTTC
CAAGTATGCCAAGTTGTCAGGAATTACATCAGCAAGTATTTACCATGCCAGTGAGTTTACACAGTGGAG
GAGAGTCATAGTGCTTCTTCCCCAGAAAACTTGGTCCAGTGCTACCCGTTTCCGCTGGAGCCAGAGCTAT
TACACAGCTCAAGACGAGTGGGCTTTGGACAGCATTTACATTGGGCAGCAGTGCCCCAACATGTGCAGTG
GGCATGGCTCATGCGATCATGGCATATGCAGGTGTGACCAGGGGTACCAAGGCACTGAATGCCACCCAGA
```

FIGURE 11 con't.

```
AGCTGCCCTTCCGTCCACAATTATGTCAGATTTTGAGAACCAGAATGGCTGGGAGTCTGACTGGCAAGAA
GTTATTGGGGGAGAAATTGTAAAACCAGAACAAGGGTGTGGTGTCATCTCTTCTGGATCATCTCTGTACT
TCAGCAAGGCTGGGAAAAGACAGCTGGTGAGTTGGGACCTGGATACTTCTTGGGTGGACTTTGTCCAGTT
CTACATCCAGATAGGCGGAGAGAGTGCTTCATGCAACAAGCCTGACAGCAGAGAGGAGGGCGTCCTCCTT
CAGTACAGCAACAATGGGGGCATCCAGTGGCACCTGCTAGCAGAGATGTACTTTTCAGACTTCAGCAAAC
CCAGATTTGTCTATCTGGAGCTTCCAGCTGCTGCCAAGACCCCTTGCACCAGGTTCCGCTGGTGGCAGCC
CGTGTTCTCAGGGGAGGACTATGACCAGTGGGCAGTCGATGACATCATCATTCTGTCCGAGAAGCAGAAG
CAGATCATCCCAGTTATCAATCCAACTTTACCTCAGAACTTTTATGAGAAGCCAGCTTTTGATTACCCTA
TGAATCAGATGAGTGTGTGGTTGATGTTGGCTAATGAAGGAATGGTTAAAAATGAAACCTTCTGTGCTGC
CACACCATCAGCAATGATATTTGGAAAATCAGATGGAGATCGATTTGCAGTAACTCGAGATTTGACCCTG
AAACCTGGATATGTGCTACAGTTCAAGCTAAACATAGGTTGTGCCAATCAATTCAGCAGTACTGCTCCAG
TTCTTCTTCAGTACTCTCATGATGCTGGTATGTCCTGGTTTCTGGTGAAAGAAGGCTGTTACCCGGCTTC
TGCAGGCAAAGGATGCGAAGGAAACTCCAGAGAACTAAGTGAGCCCACCATGTATCACACAGGGGACTTT
GAAGAATGGACAAGAATCACCATTGTTATTCCAAGGTCTCTTGCATCCAGCAAGACCAGATTCCGATGGA
TCCAGGAGAGCAGCTCACAGAAAAACGTGCCTCCATTTGGTTTAGATGGAGTGTACATATCCGAGCCTTG
TCCCAGTTACTGCAGTGGCCATGGGGACTGCATTTCAGGAGTGTGTTTCTGTGACCTGGGATATACTGCT
GCACAAGGAACCTGTGTGTCAAATGTCCCCAATCACAATGAGATGTTCGATAGGTTTGAGGGGAAGCTCA
GCCCTCTGTGGTACAAGATAACAGGTGCCCAGGTTGGAACTGGCTGTGTGGAACACTTAACGATGGCAAATC
TCTCTACTTCAATGGCCCTGGGAAAAGGGAAGCCCGGACGGTCCCTCTGGACACCAGGAATATCAGACTT
GTTCAATTTTATATACAAATTGGAAGCAAAACTTCAGGCATTACCTGCATCAAACCAAGAACTAGAAATG
AAGGGCTTATTGTTCAGTATTCAAATGACAATGGGATACTCTGGCATTTGCTTCGAGAGTTGGACTTCAT
GTCCTTCCTGGAACCACAGATCATTTCCATTGACCTGCCACAGGACGCGAAGACACCTGCAACGGCATTT
CGATGGTGGCAACCGCAACATGGGAAGCATTCAGCCCAGTGGGCTTTGGATGATGTTCTTATAGGAATGA
ATGACAGCTCTCAAACTGGATTTCAAGACAAATTTGATGGCTCTATAGATTTGCAAGCCAACTGGTATCG
AATCCAAGGAGGTCAAGTTGATATTGACTGTCTCTCTATGGATACTGCTCTGATATTCACTGAAAACATA
GGAAAACCTCGTTATGCTGAGACCTGGGATTTTCATGTGTCAGCATCTACCTTTTTGCAGTTTGAAATGA
GCATGGGCTGTAGCAAGCCCTTCAGCAACTCCCACAGTGTACAGCTCCAGTATTCTCTGAACAATGGCAA
GGACTGGCATCTTGTCACCGAAGAGTGTGTTCCTCCAACCATTGGCTGTCTGCATTACACGGAAAGTTCA
ATTTACACCTCGGAAAGATTCCAGAATTGGAAGCGGATCACTGTCTACCTTCCACTCTCCACCATTTCTC
CCAGGACCCGGTTCAGATGGATTCAGGCCAACTACACTGTGGGGGCTGATTCCTGGGCGATTGATAATGT
TGTACTGGCCTCAGGGTGCCCTTGGATGTGGCTCAGGACGAGGGATTTGTGATGCTGGACGCTGTGTGTGT
GACCGGGGCTTTGGTGGACCCTATTGTGTTCCTGTTGTTCCTCTGCCCTCGATTCTTAAAGACGATTTCA
ATGGGAATTTACATCCTGACCTTTGGCCTGAAGTGTATGGTGCAGAGAGGGGGAATCTGAATGGTGAAAC
CATCAAATCTGGAACATCTCTAATTTTTAAAGGGGAAGGACTAAGGATGCTTATTTCAAGAGATCTAGAT
TGTACAAATACAATGTATGTCCAGTTTTTCACTTAGATTTATAGCAAAAAGTACCCCAGAGAGATCTCACT
CTATTCTGTTACAATTCTCCATCAGTGGAGGAATCACTTGGCACCTGATGGATGAATTTTACTTTCCTCA
AACAACGAATATACTTTTCATCAATGTTCCCTTGCCATACACTGCCCAAACCAATGCTACAAGATTCAGA
CTCTGGCAACCTTATAATAACGGTAAGAAAGAAGAAATCTGGATTGTTGATGACTTCATTATCGATGGAA
ATAATGTAAACAACCCTGTGATGCTCTTGGATACATTTGATTTTGGGCCCAGAGAAGACAATTGGTTTTT
CTATCCTGGTGGTAACATCGGTCTTTATTGTCCATATTCTTCAAAGGGGGCACCTGAAGAAGATTCAGCT
ATGGTGTTTGTTTCAAATGAAGTTGGTGAGCATTCCATTACCACCGGTGACCTAAATGTGAATGAGAACA
CCATCATACAATTTGAGATCAACGTTGGCTGTTCGACTGATAGCTCATCCGCGGATCCAGTGAGACTGGA
ATTTTCAAGGGACTTCGGGGCGACCTGGCACCTTCTGCTGCCCCTCTGCTACCACAGCAGCAGCCACGTC
AGCTCTTATGCTCCACCGAGCACCACCCCAGCAGCACCTACTACGCAGGAACCATGCAGGGCTGGAGGA
GGGAGGTCGTGCACTTTGGGAAGCTGCACCTTTGTGGATCTGTCCGTTCAGATGGTACCAGGGATTTTA
CCCTGCCGGCTCTCAGCCAGTGACATGGGCCATTGATAATGTCTACATCGGTCCCCAGTGTGAGGAGATG
TGTAATGGACAGGGGAGCTGTATCAATGGAACCAAATGTATATGTGACCCTGGCTACTCAGGTCCAACCT
GTAAAATAAGCACCAAAAATCCTGATTTTCTCAAAGATGATTTCGAAGGTCAGCTAGAATCTGATAGATT
CTTATTAATGAGTGGTGGGAAACCATCTCGAAAGTGTGGAATCCTTTCTAGTGGAAACAACCTCTTTTTC
AATGAAGATGGCTTGCGCATGTTGATGACACGAGACCTGGATTTATCACATGCTAGATTTGTGCAGTTCT
TCATGAGACTGGGATGTGGTAAAGGCGTTCCTGACCCCAGGAGTCAACCCGTGCTCCTACAGTATTCTCT
CAACGGTGGCCTCTCGTGGAGTCTTCTTCAGGAGTTCCTTTTCAGCAATTCCAGCAATGTGGGCAGGTAC
ATTGCCCTGGAGATACCCTTGAAAGCCCGTTCTGGTTCTACTCGCCTTCGCTGGTGGCAACCGTCTGAGA
ATGGGCACTTCTACAGCCCCTGGGTTATCGATCAGATTCTTATTGGAGGAAATATTTCTGGTAATACGGT
CTTGGAAGATGATTTCACAACCCCTTGATAGTAGGAAATGGCTGCTTCACCCAGGAGGCACCAAGATGCCC
```

FIGURE 11 con't.

```
GTGTGTGGCTCTACTGGTGATGCCCTGGTCTTCATTGAAAAGGCCAGCACCCGTTACGTGGTCAGCACAG
ACGTTGCCGTGAATGAGGATTCCTTCCTACAGATAGACTTCGCTGCCTCCTGCTCAGTCACAGACTCTTG
TTATGCGATTGAATTGGAATACTCAGTAGATCTTGGATTGTCATGGCACCCATTGGTAAGGGACTGTCTG
CCTACCAATGTGGAATGCAGTCGCTATCATCTGCAACGGATCCTGGTGTCAGACACTTTCAACAAGTGGA
CTAGAATCACTCTGCCTCTCCCTCCTTATACCAGGTCCCAAGCCACTCGTTTCCGTTGGCATCAACCAGC
TCCTTTTGACAAGCAGCAGACATGGGCAATAGATAATGTCTATATCGGGGATGGCTGCATAGACATGTGC
AGTGGCCATGGGAGATGCATCCAGGGAAACTGCGTCTGTGATGAACAGTGGGGTGGCCTGTACTGTGATG
ACCCCGAGACCTCTCTTCCAACCCAACTCAAAGACAACTTCAATCGAGCTCCATCCAGTCAGAACTGGCT
GACTGTGAACGGAGGGAAATTGAGTACAGTGTGTGGAGCCGTGGCGTCGGGAATGGCTCTCCATTTCAGT
GGGGGTTGTAGTCGATTATTAGTCACTGTGGATCTAAACCTCACTAATGCTGAGTTCATCCAATTTTACT
TCATGTATGGGTGCCTGATTACACCAAACAACCGTAACCAAGGTGTTCTCTTGGAATATTCTGTCAATGG
AGGCATTACCTGGAACCTGCTCATGGAGATTTTCTATGACCAGTACAGTAAGCCCGGATTTGTGAATATC
CTTCTCCCTCCTGATGCTAAAGAGATTGCCACTCGCTTCCGCTGGTGGCAGCCAAGACATGACGGCCTGG
ATCAGAACGACTGGGCCATTGACAATGTCCTCATCTCAGGCTCTGCTGACCAAAGGACCGTTATGCTGGA
CACCTTCAGCAGCGCCCCAGTACCCCAGCACGAGCGCTCCCCTGCAGATGCCGGCCCTGTCGGGAGGATC
GCCTTTGACATGTTTATGGAAGACAAAACTTCAGTGAATGAGCACTGGCTATTCCATGATGATTGTACAG
TAGAAAGATTCTGTGACTCCCCTGATGGTGTGATGCTCTGTGGCAGTCATGATGGACGGGAGGTGTATGC
AGTGACCCATGACCTGACTCCCACTGAAGGCTGGATTATGCAATTCAAGATCTCAGTTGGATGTAAGGTG
TCTGAAAAAATTGCCCAGAATCAAATTCATGTGCAGTATTCTACTGACTTCGGTGTGAGTTGGAATTATC
TGGTCCCTCAGTGCTTGCCTGCTGACCCAAAAATGCTCTGGAAGTGTTTCTCAGCCATCTGTATTCTTTCC
AACTAAAGGGTGGAAAAGGATCACCTACCCACTTCCTGAAAGCTTAGTGGGAAATCCGGTAAGGTTTAGG
TTCTATCAGAAGTACTCAGACATGCAGTGGGCAATCGATAATTTCTACCTGGGCCCTGGATGCTTGGACA
ACTGCAGGGGCCATGGAGATTGCTTAAGGGAACAGTGCATCTGTGATCCGGGATACTCAGGGCCAAACTG
CTACTTGACCCACACTCTGAAGACTTTCCTGAAGGAACGCTTTGACAGTGAAGAAATCAAACCTGACTTA
TGGATGTCCTTAGAAGGTGGAAGTACTTGCACTGAGTGTGGAATTCTTGCCGAGGACACTGCACTCTATT
TTGGGGGATCCACTGTGAGACAAGCGGTTACACAAGATTTGGATCTTCGAGGTGCAAAGTTCCTGCAATA
CTGGGGGCGCATCGGTAGTGAGAACAACATGACCTCTTGCCATCGTCCCATCTGCCGGAAGGAAGGCGTG
CTGTTGGACTACTCTACCGATGGAGGAATTACCTGGACTTTGCTCCATGAGATGGATTACCAGAAATACA
TTTCTGTTAGACACGACTACATACTTCTTCCTGAAGATGCCCTCACCAACACAACTCGACTTCGCTGGTG
GCAGCCTTTTGTGATCAGCAATGGAATTGTGGTCTCTGGGGTGGAGCGTGCTCAGTGGGCACTGGACAAC
ATTTTGATTGGTGGAGCAGAAATCAATCCCAGCCAATTGGTGGACACTTTTGATGATGAAGGCACTTCCC
ATGAAGAAAACTGGAGTTTTTACCCTAATGCTGTAAGGACAGCAGGATTTTTGTGGCAATCCATCCTTTCA
CCTCTATTGGCCAAATAAAAAGAAGGACAAGACTCACAATGCTCTCTCCTCCCGAGAACTCATTATACAG
CCAGGATACATGATGCAGTTTAAAAATTGTGGTGGGTTGTGAAGCCACTTCTTGTGGTGACCTTCATTCCG
TAATGCTGGAATACACTAAGGATGCAAGATCGGGATTCCTGGCAGCTCGTACAGACCCAGTGCCTTCCTTC
CTCTTCTAACAGCATTGGCTGCTCCCCTTTCCAGTTCCATGAAGCCACCATCTACAACTCTGTCAACAGC
TCAAGCTGGAAAAGAATCACCATCCAGCTGCCTGACCATGTCTCCTCTAGTGCAACACAGTTCCGCTGGA
TCCAGAAGGGAGAAGAAACTGAGAAGCAAAGCTGGGCAATTGACCACGTGTACATTGGAGAGGCTTGCCC
CAAGCTCTGCAGCGGGCACGGATACTGCACGACCGGTGCCATCTGCATCTGCGACGAGAGCTTCCAAGGT
GATGACTGCTCTGTTTTCAGTCACGACCTTCCCAGTTATATTAAAGATAATTTTGAGTCCGCAAGAGTCA
CCGAGGCAAACTGGGAGACCATTCAAGGTGGAGTCATAGGAAGTGGCTGTGGGCAGCTGGCCCCCTACGC
CCATGGAGACTCACTGTACTTTAATGGCTGTCAGATCAGGCAAGCAGCTACCAAGCCTCTGGATCTCACT
CGAGCAAGCAAAATCATGTTTGTTTTGCAAATTGGGAGCATGTCGCAGACGGACAGCTGCAACAGTGACC
TGAGTGGCCCCCACGCTGTGGACAAGGCGGTGCTGCTGCAATACAGCGTCAACAACGGGATCACCTGGCA
TGTCATCGCCCAGCACCAGCCAAAGGACTTCACACAAGCTCAGAGAGTGTCTTACAATGTCCCCCTGGAG
GCACGGATGAAAGGAGTCTTACTGCGCTGGTGGCAACCACGCCACAATGGAACAGGTCATGATCAATGGG
CTTTGGACCATGTGGAGGTCGTCCTAGTAAGCACTCGCAAACAAAATTACATGATGAATTTTTCACGACA
ACATGGGCTCAGACATTTCTACAACAGAAGACGAAGGTCACTTAGGCGATACCCATGAAGAATCAAAAAG
TTTATTTTTTTTCTTCCAACATGTGATGTGTTGCTCTCCATTCTTTTAAATCTGCACTACATCTGATAT
CAGGAAATATCTGTGAAGGACTTGGTGATTACCTGAAAGCCCTTCTCAAGACCGAGTGTACACCACTTTC
CCACACTGTGAACTAATGACAAGTGACTTATTTGCTCATAAGTAAATGTCTTCATGTTGATGTGTCCGTG
AAAGTTGTGATCTGTTGTAATATCAGTTACAGTGGCAGTATTGACAATAAGAAACAGTTTAACAGAAAAA
TGAAATTTAAGCACAAAAAATTTAAGAGATTTTATGTTTAAAATGGCATTTAGCACAGTATTTAACATTC
TTGGTCACAAAGCTATTTAAGTGGACTGTATTTCAGCTATGTCTCATGTTTTATATGATTAAATTATCAT
TGTTTGTCCTTTATGTATTCTCTTCTACAATACAACACATTGAAACTGTATTTACTTGTTATGTTGTAAT
```

FIGURE 11 con't.

```
ATTTTGCTGCTGAATTTGGGGCTACTTATATTCTGCAGAAAATTAATTGAAATACCTATTCAAGAAGATA
GTTGTAAAGATATTGTATCTCCTTTAATATACTCCTTAAAAATGTATGTTGGTTTAGCGTTGTTTTGTGG
ATAAGAAAAATGCTTGACCCTGAAATATTTTCTACTTTAAATTGTGGATGAAGACCCTATCTCCCACAAA
TAAGTTCCCATTTCCTTGTCTAAAGATCTTTTTTTAAGTGTTCTGTGGCTGATTTACTAACAGTAACTGC
CATTTTTGTCTGTGATAACAGAGTGATTTGTAAAACAGTGGTTGTTTTTTCATTGTGTTTTCTTCGTGG
ATTGTTTTTCTGCGGGTCATATTCATACCTTCTGATGAAGTTGTACAACACCAGCAACATTATAATGGC
CCTGTAGCTCTGAATGCTATTTGTGTAACTGAAAGGTTGCACTCTAGGGTGAACCAAGCTATAAAAGCCC
ATGCTTAAATAAAAATTATGTCCAAAAGCC
```

SEQ ID NO: 2 - Reelin (RELN) protein; human; GenBank AAC51105.1

```
>gi|1743885|gb|AAC51105.1| reelin [Homo sapiens]
MERSGWARQTFLLALLLGATLPARAAAGYYPRFSPFFFLCTHHGELEGDGEQGEVLISLHIAGNPTYYVP
GQEYHVTISTSTFFDGLLVTGLYTSTSVQASQSIGGSSAFGFGIMSDHQFGNQFMCSVVASHVSBLPTTN
LSFIWIAPPAGTGCVNFMATATHRGQVIFKDALAQQLCEQGAPTDVTVRPHLAEIRSDSIILRDDFDSYH
QLQLNPNIWVECNNCETGEQCGAIMHGNAVTFCEPYGPRELITTGLNTTTASVLQFSIGSGSCRFSYSDP
SIIVLYAKNNSADWIQLEKIRAPSNVSTIIHILYLPEDAKGENVQFQWKQENLRVGEVYEACWALDNILI
INSAHRQVVLEDSLDPVDTGNWLFFFGATVKHSCQSDGNSIYFBGNEGSEFNFATTRIVDLSTEDIQEQW
SEEFESQPTGWDVLGAVIGTECGTIESGLSMVFLKDGERKLCTPSMDTTGYGNLRFYFVMGGICDFGNSH
ENDIILYAKIEGRKEHITLDTLSYSSYKVPSLVSVVINPELQTPATKFCLRQKNHQGHNRNVWAVDFFHV
LPVLPSTMSHMIQFSINLGCGTHQPGNSVSLEFSTNHGRSWSLLHTECLPEICAGPHLPHSTVYSSENYS
GWNRITIPLPNAALTRNTRIRWPQTGPILGNMWAIDNVYIGPSCLKFCSGRGQCTRHGCKCDPGFSGPAC
EMASQTFPMFISESFGSSRLSSYHNFYSIRGAEVSFGCGVLASGKALVFNKEGRRQLITSFLDSSQSRFL
QFTLRLGSKSVLSTCRAPDQPGEGVLLHYSYDNGITWKLLEHYSYLSYHEPRIISVELPGDAKQFGIQFR
WWQPYHSSQREDVWAIDEIIMPSVLFNSISLDFTNLVEVTQSLGFYLGNVQPYCGHDWTLCFTGDSKLAS
SMRYVETQSMQIGASYMIQFSLVMGCGQKYTPHMDNQVKLEYSTNHGLTWHLVQEECLPSMPSCQEFTSA
SIYHASEFTQWRRVIVLLFQKTWSSATRFRWSQSYYTAQDEWALDSIYIGQQCPNMCSGHGSCDHGICRC
DQGYQGTECHFEAALPSTIMSDFENQNGWESDWQEVIGGEIVKPEQGCGVISSGSSLYFSKAGKRQLVSW
DLDTSWVDFVQFYIQIGGESASCNKFDSREEGVLLQYSNNGGIQWHLLAEMYFSDFSKPRFVYLELFAAA
KTPCTRFRWWQPVFSGEDYDQWAVDDIIILSEKQKQIIPVINPTLPQNFYEKPAFDYPMNQMSVWLMLAN
EGMVKNETFCAATPSAMIFGKSDGDRFAVTRDLTLKFGYVLQFKLNIGCANQFSSTAPVLLQYSHDAGMS
WFLVKEGCYPASAGKGCEGNSPELSEPTMYHTGDFEEWTRITIVIPRSLASSKTRFRWIQESSSQKNVPP
FGLDGVYISEPCPSYCSGHGDCISGVCFCDLGYTAAQGTCVSNVPNHNEMFDRFEGKLSPLWYKITGAQV
GTGCGTLNDGKSLYFNGPGKPEARTVPLDTRNIRLVQFYIQIGSKTSGITCIKFRTRNEGLIVQYSNDNG
ILWHLLRELDFMSFLEPQIISIDLPQDAKTPATAFRWWQPQRGKHSAQWALDDVLIGMNDSSQTGFQDKF
DGSIDLQANWYRIQGGQVDIDCLSMDTALIFTENIGKPRYAETWDFHVSASTFLQFEMSMGCSKPFSNSH
SVQLQYSLNNGKDWHLVTEECVPPTIGCLHYTESSIYTSERFQNWKRITVYLPLSTISPRTRFRWIQANY
TVGADSWAIDNVVLASGCPWMCSGRGICDAGRCVCDRGFGGPYCVPVVPLFSILKDDFNGNLHPDLWPEV
YGAERGNLNGETIKSGTSLIFKGEGLRMLISRDLDCTNTMYQFSLRFIAKSTPERSHSILLQFSISGGI
TWHLMDEFYFPQTTNILFINVPLPYTAQTNATRFRLWQPYNNGKKEEIWIVDDFIIDGNNVNNPVMLLDT
FDFGFREDNWFFYPGGNIGLYCPYSSKGAPEEDSAMVFVSNEVGEHSITTRDLNVNENTIIQFEINVGCS
TDSSSADPVRLEFSRDFGATWHLLLPLCYHSSSHVSSLCSTEHHPSSTYYAGTMQGWRREVVHFGKLHLC
GSVRFRWYQGFYPAGSQPVTWAIDNVYIGPQCEEMCNGQGSCINGTKCICDPGYSGPTCKISTKNPDFLK
DDFEGQLESDRFLLMSGGKPSPKCGILSSGNNLFFNEIGLRMLMTRDLDLSHARFVQFFMRLGCGKGVPD
PRSQPVLLQYSLNGGLSWSLLQEFLFSNSSNVGRYIALEIPLKARSGSTRLRWWQPSENGHFYSFWVIDQ
ILIGGNISGNTVLEDDFTTLDSRKWLLHPGGTKMPVCGSTGDALVFIEKASTRYVVSTDVAVNEDSFLQI
DFAASCSVTDSCYAIELEYSVDLGLSWHPLVRDCLPTNVECSRYHLQRILVSDTFNKWTRITLPLPPYTR
SQATRFRWHQPAPFDKQQTWAIDNVYIGDGCIDMCSGHGRCIQGNCVCDEQWGGLYCDDPETSLFTQLKD
NFNRAPSSQNWLTVNGGKLSTVCGAVASGMALHFSGGCSRLLVTVDLNLTNAEFIQFYFMYGCLITPNNR
NQGVLLEYSVNGGITWNLLMEIFYDQYSKPGFVNILLPPDAKEIATRFRWWQPRHDGLDQNDWAIDNVLI
SGSADQRTVMLDTFSSAPVPQHERSPADAGPVGRIAFDMFMEDKTSVNEHWLFHDDCTVERFCDSPDGVM
LCGSHDGREVYAVTHDLTPTEGWIMQFKISVGCKVSEKIAQNQIHVQYSTDFGVSWNYLVPQCLPADPKC
SGSVSQPSVFFPTKGWKRITYPLPESLVGNPVRFRFYQKYSDMQWAIDNFYLGPGCLDNCRGHGDCLREQ
CICDPGYSGPNCYLTHTLKTFLKERFDSEEIKFDLWMSLEGGSTCTECGILAEDTPALYFGGSTVRQAVTQ
DLDLRGAKFLQYWGRIGSENNMTSCHRPICRKEGVLLDYSTDGGITWTLLHEMDYQKYISVRHDYILLPE
```

FIGURE 11 con't.

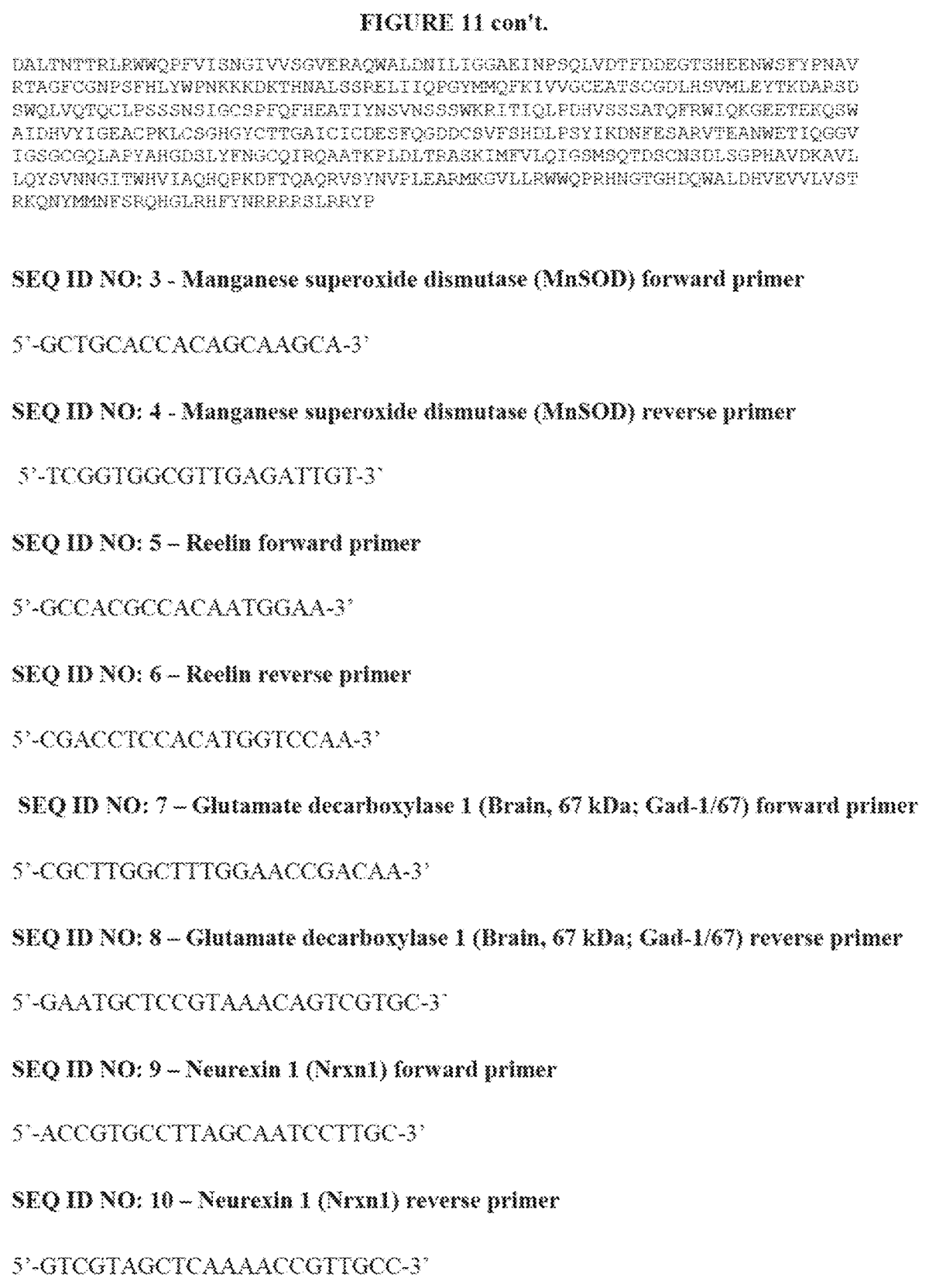

```
DALTNTTRLRWWQPFVISNGIVVSGVERAQWALDNILIGGAKINPSQLVDTFDDEGTSHEENWSFYPNAV
RTAGFCGNPSFHLYWPNKKKDKTHNALSSRELIIQPGYMMQFKIVVGCEATSCGDLHSVMLEYTKDAPSD
SWQLVQTQCLPSSSNSIGCSPFQFHEATIYNSVNSSSWKRITIQLPUHVSSSATQFRWIQKGEETEKQSW
AIDHVYIGEACPKLCSGHGYCTTGAICICDESFQGDDCSVFSHDLPSYIKDNFESARVTEANWETIQGGV
IGSGCGQLAPYAHGDSLYFNGCQIRQAATKPLDLTEASKIMFVLQIGSMSQTDSCNSDLSGPHAVDKAVL
LQYSVNNGITWHVIAQHQPKDFTQAQRVSYNVPLEARMKGVLLRWWQPRHNGTGHDQWALDHVEVVLVST
RKQNYMMNFSRQHGLRHFYNRRPPSLRRYP
```

SEQ ID NO: 3 - Manganese superoxide dismutase (MnSOD) forward primer

5'-GCTGCACCACAGCAAGCA-3'

SEQ ID NO: 4 - Manganese superoxide dismutase (MnSOD) reverse primer

5'-TCGGTGGCGTTGAGATTGT-3'

SEQ ID NO: 5 – Reelin forward primer

5'-GCCACGCCACAATGGAA-3'

SEQ ID NO: 6 – Reelin reverse primer

5'-CGACCTCCACATGGTCCAA-3'

SEQ ID NO: 7 – Glutamate decarboxylase 1 (Brain, 67 kDa; Gad-1/67) forward primer

5'-CGCTTGGCTTTGGAACCGACAA-3'

SEQ ID NO: 8 – Glutamate decarboxylase 1 (Brain, 67 kDa; Gad-1/67) reverse primer

5'-GAATGCTCCGTAAACAGTCGTGC-3'

SEQ ID NO: 9 – Neurexin 1 (Nrxn1) forward primer

5'-ACCGTGCCTTAGCAATCCTTGC-3'

SEQ ID NO: 10 – Neurexin 1 (Nrxn1) reverse primer

5'-GTCGTAGCTCAAAACCGTTGCC-3'

FIGURE 11 con't.

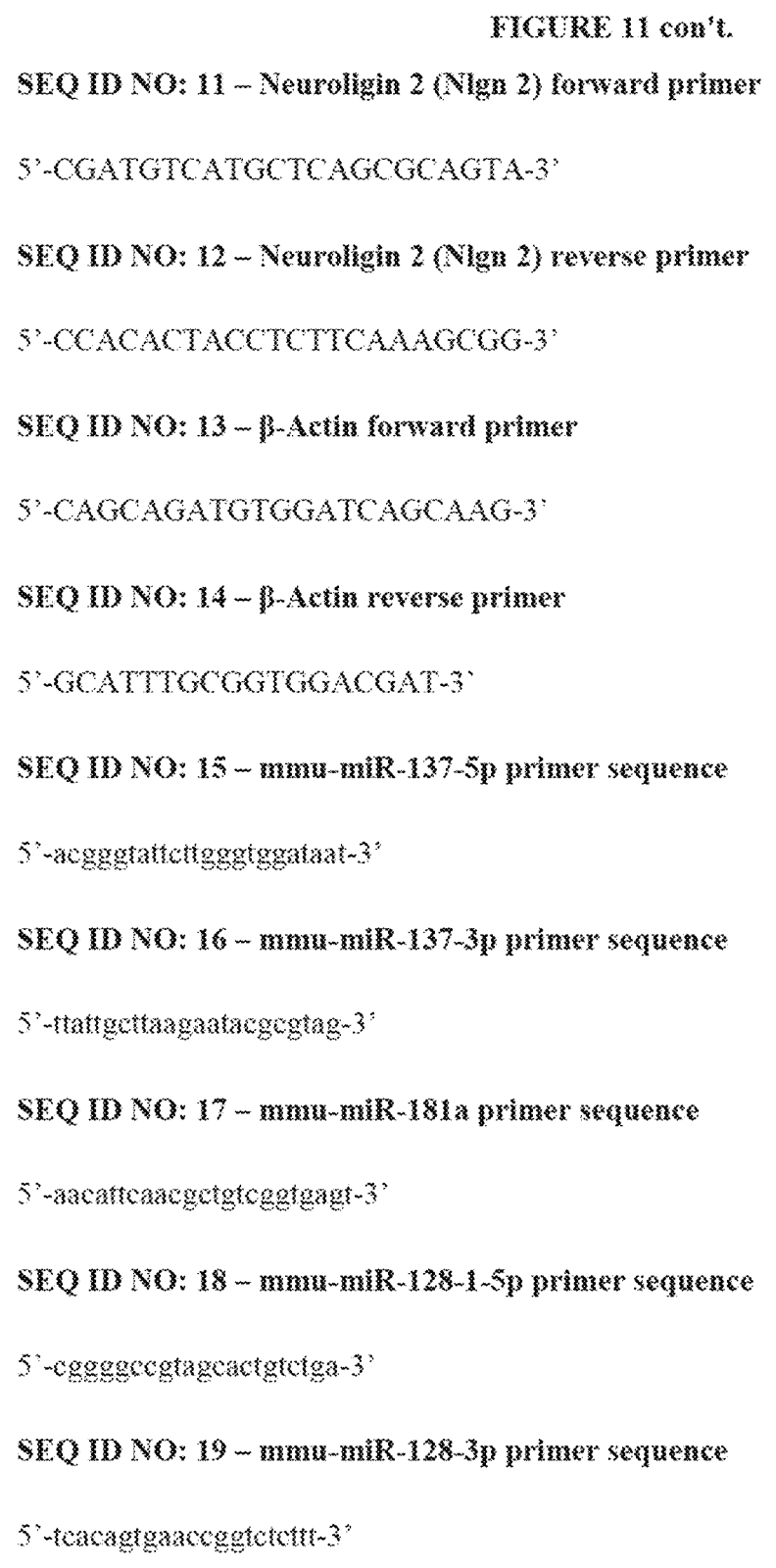

SEQ ID NO: 11 – Neuroligin 2 (Nlgn 2) forward primer

5'-CGATGTCATGCTCAGCGCAGTA-3'

SEQ ID NO: 12 – Neuroligin 2 (Nlgn 2) reverse primer

5'-CCACACTACCTCTTCAAAGCGG-3'

SEQ ID NO: 13 – β-Actin forward primer

5'-CAGCAGATGTGGATCAGCAAG-3'

SEQ ID NO: 14 – β-Actin reverse primer

5'-GCATTTGCGGTGGACGAT-3'

SEQ ID NO: 15 – mmu-miR-137-5p primer sequence

5'-acgggtattcttgggtggataat-3'

SEQ ID NO: 16 – mmu-miR-137-3p primer sequence

5'-ttattgcttaagaatacgcgtag-3'

SEQ ID NO: 17 – mmu-miR-181a primer sequence

5'-aacattcaacgctgtcggtgagt-3'

SEQ ID NO: 18 – mmu-miR-128-1-5p primer sequence

5'-cggggccgtagcactgtctga-3'

SEQ ID NO: 19 – mmu-miR-128-3p primer sequence

5'-tcacagtgaaccggtctcttt-3'

FIGURE 11 con't.

SEQ ID NO: 20 – mmu-miR-138 primer sequence

5'-agctggtgttgtgaatcaggccg-3' (

SEQ ID NO: 21 – mmu-miR-200c primer sequence

5'-taatactgccgggtaatgatgga-3'

SEQ ID NO: 22 – small nucleolar RNA 202 (snoRNA-202) internal forward primer

5'-agtacttttgaacccttttcca-3'

SEQ ID NO: 23 –Reelin (RELN) mRNA; Mouse; complete coding sequence; GenBank U24703

```
>gi|2702252|gb|U24703.1|MMU24703 Mus musculus reelin mRNA, complete cds
GGGGCGTCGCGTGCACACCGGCGGCGGCGGCGCTCGGAGGCGGACGACGCGCTCTCGGCGCCCGCGGCCC
CGGTTCCCCCCGCGCTCTCGCTCCGCGGCCCAAAGTAACTTCGGGAGCCTCGGTCTCCGGCTAACTTCC
CCCCGCGGGCTCGGTTGCCCGGACCCGCTCGGCTCGAGCCCGCCGCCGGCTCGCCTTCCGCGCACGCGGC
TCCTCCGTGCCGGTGCCTCCGAAAGTGGATGAGAGAGCGCGCGGGGCGCGCGGCGGCACGGAGCGCGGCG
GCATGGAGCGCGGCTGCTGGGCGCCGCGGGCTCTCGTCCTGGCCGTGCTGCTGCTGCTGGCGACGCTGAG
GGCGCGCGCGGCCACCGGCTACTACCCGCGCTTCTCGCCTTTCTTTTTCCTGTGCACCCACCACGGGGAG
CTGGAAGGGGATGGGGAGCAGGGCGAGGTGCTCATTTCCCTGCACATTGCGGGCAACCCCACCTACTACG
TACCGGGACAGGAATACCATGTTACAATTTCAACAAGCACCTTCTTTGATGGCTTGCTGGTGACGGGACT
CTATACCTCGACAAGCATCCAGTCTTCTCAGAGCATTGGAGGCTCCAGCGCCTTTGGATTCGGGATCATG
TCCGACCACCAGTTTGGTAACCAGTTTATGTGCAGTGTGGTGGCCTCTCATGTGAGTCACCTGCCTACAA
CCAACCTCAGCTTTGTCTGGATTGCCCCACCAGCTGGCACAGGCTGTGTGAATTTCATGGCTACTGCAAC
ACATAGGGGCCAGGTGATTTTCAAAGACGCACTGGCCCAGCAGCTGTGTGAACAAGGAGCTCCCACAGAG
GCCACTGCTTACTCGCACCTTGCTGAAATACACAGTGACAGTGTGATCCTACGAGATGACTTTGACTCCT
ACCAGCAACTGGAATTGAACCCCAACATATGGGTTGAATGCAGCAACTGTGAGATGGGAGAGCAGTGTGG
CACCATCATGCATGGCAATGCTGTCACCTTCTGTGAGCCGTACGGCCCTCGAGAGCTGACCACCACATGC
CTGAACACAACAACAGCATCTGTCCTCCAGTTTTCCATTGGGTCAGGATCATGTCGATTTAGTTACTCTG
ACCCCAGCATCACTGTGTCATACGCCAAGAACAATACCGCTGATTGGATTCAGCTGGAGAAAATTAGAGC
CCCTTCCAATGTGAGCACAGTCATCCACATCCTGTACCTCCCCGAGGAAGCCAAAGGGGAGAGCGTGCAG
TTCCAGTGGAAACAGGACAGCCTGCGAGTGGGTGAGGTGTATGAGGCCTGCTGGCCCTGGATAACATCC
TGGTCATCAATTCAGCCCACAGAGAAGTCGTTCTGGAGGACAACCTCGACCCGGTCGACACGGGCAACTG
GCTCTTCTTCCCTGGAGCAACGGTCAAGCATAGCTGTCAGTCAGATGGGAACTCCATTTATTTCCATGGA
AATGAAGGCAGCGAGTTCAATTTTGCCACCACCCGGGATGTAGATCTTTCTACAGAGGATATTCAAGAGC
AGTGGTCAGAAGAATTTGAGAGCCAGCCCACAGGATGGGATATCTTGGGAGCAGTAGTTGGTGCAGACTG
TGGAACCGTAGAATCAGGACTATCACTGGTGTTCCTCAAAGATGGAGAGAGGAAGCTTTGCACCCCCTAC
ATGGATACAACTGGTTATGGCAACCTGAGGTTCTACTTCGTTATGGGAGGAATCTGTGACCCTGGAGTCT
CTCATGAAAACGATATCATCTTATATGCAAAGATTGAAGGAAGAAAAGAACACATTGCACTGGACACTCT
TACCTATTCTTCCTATAAGGTTCCGTCTTTGGTTCTGTGGTCATCAACCCTGAACTTCAGACACCTGCC
ACCAAATTTTGTCTCAGGCAAAAGAGCCACCAAGGGTATAATCGGAATGTCTGGGCTGTGGACTTCTTCC
ATGTGCTGCCCGTTCTCCCTTCAACAATGTCTCACATGATCCAGTTTTCTATTAATTTGGGATGCGGCAC
ACACCAGCCTGGGAACAGCGTCAGCTTGGAGTTTTCTACTAACCATGGACGGTCCTGGTCCCTACTCCAC
ACTGAGTGCTTGCCGGAGATCTGTGCAGGCCCCCACCTCCCCACAGCACTGTCTACTCCTCAGAAAACT
ACAGCGGGTGGAACCGAATCACGATTCCTCTCCCTAATGCAGCACTCACCCGAGACACCAGGATTCGCTG
GAGACAAACAGGCCCAATCCTGGGAAATATGTGGGCAATTGATAATGTTTATATAGGTCCTTCGTGTCTC
AAATTCTGTTCTGGCAGAGGACAATGCACTCGGCATGGCTGCAAGTGTGACCCAGGATTTTCTGGCCCAG
```

FIGURE 11 con't.

```
CTTGTGAGATGGCATCTCAGACATTCCCAATGTTTATTTCGGAAAGCTTTGGCAGTGCCAGACTTTCCTC
TTACCATAACTTTTACTCTATCCGTGGTGCTGAAGTCAGCTTTGGTTGTGGTGTCTTAGCCAGTGGTAAG
GCTCTGGTTTTCAACAAAGATGGGAGGCGGCAGCTAATCACGTCCTTTCTGGACAGCTCGCAGTCCAGGT
TTCTTCAGTTTACACTGAGGCTGGGGAGCAAGTCTGTGCTGAGCACGTGCAGAGCCCCTGACCAGCCGGG
GGAGGGAGTCCTGCTGCACTATTCATATGACAACGGGATAACATGGAAACTCCTGGAGCACTATTCCTAC
GTCAACTACCACGAGCCCAGAATAATCTCTGTAGAGCTACCGGATGATGCAAGACAGTTTGGAATCCAGT
TCAGATGGTGGCAGCCTTACCATTCTTCCCAAGGAGAAGACGTGTGGGCCATTGATGAGATTGTCATGAC
CTCAGTCCTGTTCAACAGCATCAGTCTCGACTTTACCAATCTTGTGGAAGTCACTCAATCCCTGGGATTC
TACCTTGGCAATGTTCAACCATACTGTGGCCATGACTGGACGCTTTGTTTTACGGGAGATTCTAAACTTG
CCTCAAGCATGCGCTATGTGGAAACACAGTCCATGCAGATCGGAGCATCCTATATGATTCAGTTCAGCCT
AGTGATGGGATGTGGCCAGAAATACACTCCTCACATGGACAACCAGGTGAAGCTGGAGTACTCAGCCAAC
CACGGCCTTACATGGCACCTTGTACAAGAAGAATGCCTTCCCAGTATGCCAAGCTGCCAGGAATTTACAT
CTGCCAGCATTTACCATGCCAGCGAGTTCACACAGTGGAGAAGAGTCACTGTTGTTCTTCCCCAGAAAAC
ATGGTCGGGTGCCACCCGCTTCCGTTGGAGTCAGAGCTATTACACAGCCCAGGATGAGTGGGCTTTAGAC
AACATTTACATTGGGCAGCAGTGCCCCAACATGTGCAGTGGGCATGGCTCATGTGACCATGGCGTGTGCA
GGTGTGACCAGGGATACCAGGGCACTGAATGCCACCCAGAAGCTGCACTTCCTTCCACGATTATGTCAGA
TTTTGAGAACCCGAGCAGTTGGGAATCAGACTGGCAGGAAGTTATTGGGGGAGAAGTTGTAAAGCCTGAG
CAAGGCTGTGGAGTCGTGTCTTCTGGATCTTCTCTGTACTTCAGCAAGGCTGGGAAGAGGCAGCTGGTGA
GCTGGGACCTGGACACATCCTGGGTGGACTTTGTCCAGTTCTACATCCAGATAGGAGGAGAGAGTGCTGC
ATGCAACAAGCCTGACAGCAGAGAGGAGGGCATTCTGCTCCAGTATAGCAACAACGGGGGCATCCAGTGG
CACCTGCTGGCAGAGATGTACTTCTCAGACTTCAGCAAACCCAGATTTGTCTACCTGGAGCTCCCAGCTG
CTGGGAAGACCCCTTGTACCAGGTTCCGCTGGTGGAAGCCTGTGTTCTCGGGGGAGGACTATGACCAGTG
GGCCGTTGATGATATCATCATTCTGTCAGAGAAGCAGAAGCAGGTTATCCCAGTTGTCAACCCAACTTTG
CCCCAGAACTTCTATGAGAAGCCAGCTTTCGATTACCCTATGAACCAAATGAGTGTGTGGCTAATGTTGG
CCAATGAAGGCATGGCTAAAAACGACAGCTTCTGTGCGACCACGCGGTCAGCCATGGTGTTTGAAAGTC
AGATGGAGACCGGTTTGCAGTAACTCGAGATCTGACCCTGAAACCTGGATATGTGCTGCAGTTCAAGCTA
AACATAGGCTGCACCAGCCAGTTCAGCAGCACTGCCCCGGTTCTCCTGCAGTATTCACATGATGCCGGCA
TGTCGTGGTTTCTGTTGAAGGAAGGATGCTTCCCAGCGTCAGCAGCCAAAGGATGTGAAGGGAACTCCAG
GGAATTGAGTGAGCCTACTGTCTATTATACTGGGGACTTCGAAGAATGGACTAGAATCACCATTGCCATT
CCAAGGTCCCTTGCATCCAGCAAGACCAGATTCCGATGGATCCAAGAGAGCAGCTCTCAGAAGAATGTGC
CCCCGTTTGGCTTAGATGGGGTGTACATATCTGAGCCCTTGTCCCAGTTACTGCAGTGGCCATGGAGACTG
CATCTCGGGGGTGTGTTTTTGTGACCTGGGGTACACAGCTGCACAAGGAACCTGTGTGTCAAACACCCCT
AACCACAGTGAGATGTTCGACAGGTTTGAGGGGAAGCTAAGCCCACTGTGGTACAAAATCACCGGGGGTC
AGGTTGGCACGGGCTGTGGCACCCTCAATGACGGCAGGTCCCTCTACTTTAATGGCCTTGGGAAAAGGGA
AGCCAGGACAGTCCCACTGGACACCAGGAATATCAGTCTTGTTCAGTTTTATATACAAATTGGAAGTAAA
ACATCAGGGATTACGTACATCACCCCACGGGCTAGATATGAGGGGCTTGTTGTTCAGTATTCCAATGATA
ATGGGATACTTTGGCATTTGCTGAGAGAGTTGGATTCATGTCATTCCTGGAGCCACAGATCATTTCCAT
TGACCTGCCCCGGGAAGCAAAGACACCTGCCACAGCTTTCCGGTGGTGGCAGCCGCAGCATGGGAAGCAT
TCGGCCCAGTGGGCTTTGGGTGATGTCCTTATAGGAGTGAATGACAGCTCTCAAACTGGATTTCAAGATA
AATTGGATGGCTCCATAGACTTGCAAGCCAACTGGTATCGAATCCAGGGAGGCCAAGTTGATATCGACTG
CCTCTCTATGGACACTGCCCTTATATTCACTGAAAACATAGGAAACCCTCGCTATGCTGAGACCTGGGAC
TTCCATGTGTCAGAGTCAAGCTTCTTACAGTGGGAAATGAACATGGGCTGCAGCAAGCCTTTCAGTGGTG
CCCACGGCATACAGCTCCAGTACTCTCTGAACAACGGCAAGGACTGGCAGCTTGTCACCGAAGAGTGTGT
CCCTCCAACCATTGGGTGCGTGCACTACACAGAGAGTTCAACTTACACATCAGAAAGATTCCAGAACTGG
AGGCGGGTCACGGTCTACCTGCCACTCGCCACCAATTCTCCCAGGACTCGGTTCAGATGGATTCAGACCA
ACTATACTGTTGGAGCAGATTCCTGGGCTATTGATAATGTCATCCTGGCCTCGGGCTGTCCTTGGATGTG
CTCAGGACGAGGGATCTGTGATTCGGGGCGCTGTGTGTGTGACCGGGGGCTTCGGTGGACCCTTCTGTGTT
CCTGTTGTTCCTCTTCCCTCCATTCTAAAAGATGATTTCAATGGGAACTTACATCCTGACCTTTGGGCTG
AAGTGTACGGGGCAGAGAGGGGCAATCTGAATGGGCGAAACCATCAAATCCGGAACATGTCTGATCTTTAA
AGGGGAGGGACTAAGAATGCTTATTTCCAGAGATCTAGATTGTACCAATACTATGTATGTCCAGTTCTCT
CTCCGATTTATAGCGAAAGGTACCCCAGAGAGGGTCTCACTCCATCCTTCTACAGTTCTCTGTCAGTGGAG
GAGTCACCTGGCACCTGATGGATGAATTCTACTTCCCTCAAACGACCAGCATACTTTTCATCAATGTTCC
CTTACCATACGGTGCCCAAACCAACGCTACAAGATTCAGACTCTGGCAACCGTACAATAATGGTAAGAAA
GAAGAAATCTGGATCATTGATGACTTTATTATTGATGGAAACAATTTGAACAACCCCGTGCTGCTGCTGG
ACACGTTCGACTTTGGGCCCAGGGAAGACAATTGGTTTTTCTATCCGGGTGGTAATATCGGACTTTACTG
```

FIGURE 11 con't.

```
CCCGTATTCTTCAAAGGGAGCTCCTGAGGAGGATTCGGCCATGGTGTTTGTTTCAAACGAAGTTGGAGAA
CACTCCATTACCACACGAGACCTAAGTGTGAACGAGAACACCATCATTCAATTTGAGATCAATGTTGGCT
GCTCCACTGATAGTTCTTCTGCTGATCCGGTCAGACTGGAATTCTCAAGGGACTTTGGAGCCACCTGGCA
CCTGCTGCTGCCTCTCTGCTACCACAGCAGCAGCCTCGTCAGCTCCTTATGCTCCACTGAGCATCACCCG
AGCAGCACCTACTACGCGGGGACCACCCAGGGCTGGCGGCGGGAGGTCGTGCACTTCGGAAAGCTGCACC
TTTGTGGATCTGTGCGTTTCCGTTGGTACCAGGGATTTTATCCTGCTGGCTCTCAGCCGGTCACATGGGC
CATTGACAATGTCTACATTGGTCCCCAGTGTGAAGAGATGTGCTATGGGCACGGGAGCTGCATCAATGGA
ACCAAGTGTATATGTGACCCGGGCTACTCTGGGCCAACCTGTAAAATAAGCACCAAAAATCCTGATTTTC
TCAAAGACGACTTTGAAGGTCAACTGGAATCCGATCGATTCTTACTGATGAGCGGTGGGAAGCCGTCTCG
TAAGTGTGGCATCCTTTCCAGTGGGAACAACCTCTTCTTCAATGAGGACGGCTTGCGCATGCTAGTAACA
CGGGACCTGGATTPATCACATGCAAGGTTTGTGCAGTTCTTCATGAGACTGGGATGTGGTAAAGGTGTTC
CAGACCCCAGGAGCCAGCCCGTGCTTCTGCAGTACTCCCTCAATGGCGGCCTCTCCTGGAGTCTTCTTCA
AGAGTTCCTCTTCAGCAACTCCAGCAATGTGGGCAGGTACATTGCCCTGGAAATGCCCCTGAAAGCCCGT
TCTGGTTCGACACGCCTCCGCTGGTGGCAGCCATCTGAAAATGGGCACTTCTATAGCCCCTGGGTGATCG
ACCAGATTCTTATTGGAGGAAATATCTCTGGTAATACAGTCTTAGAAGATGATTTCTCAACTCTGGACAG
CAGAAAGTGGCTGCTTCACCCAGGAGGCACCAAGATGCCTGTGTGTGGCTCCACAGGCGATGCCCTGGTC
TTTATTGAAAAGGCCAGCACCCGTTACGTGGTCACGACAGACATCGCTGTGAATGAGGACTCATTCCTAC
AGATAGACTTTGCTGCCTCCTGCTCAGTCACAGACTCCTGCTATGCTATTGAACTGGAGTACTCGGTGGA
TCTCGGTCTGTCGTGGCACCCGCTGGTGAGGGACTGCCTGCCTACCAATGTTGAGTGTAGTCGTTACCAC
CTGCAGCGGATCCTGGTGTCAGATACTTTCAACAAGTGGACCAGAATCACTCTGCCCCTGCCTTCCTACA
CCAGGTCTCAAGCCACTCGTTTCCGCTGGCATCAGCCAGCGCCTTTTGACAAGCAGCAGACCTGGGCAAT
AGATAATGTCTATATTGGGGATGGTTGCCTAGACATGTGCAGTGGCCACGGGAGATGCGTCCAGGGAAGC
TGTGTCTGTGATGAACAGTGGGGAGGCCTGTACTGTGATGAGCCTGAGACCTCCCTTCCCACCCAGCTCA
AAGACAACTTCAACCGAGCCCCCTCCAACCAGAACTGGCTGACTGTGAGCGGTGGGAAGCTGAGTACAGT
GTGTGGGGCTGTGGCTTCCGGCCTGGCTCTCCATTTCAGTGGGGGCTGCAGCCGATTGTTAGTCACTGTG
GATCTGAACCTCACCAATGCTGAGTTTATCCAGTTTTACTTTATGTATGGATGCCTCATTACGCCGAGCA
ACCGTAACCAGGGAGTCCTGCTGGAGTACTCTGTCAATGGAGGGCATCACCTGGAACTTGCTGATGGAGAT
TTTCTATGACCAGTACAGCAAACCTGGATTTGTGAATATCCTTCTCCCTCCTGATGCTAAAGAGATTGCC
ACTCGCTTCCGATGGTGGCAGCCACGACATGATGGCCTTGACCAGAATGACTGGGCCATTGACAATGTCC
TCATCTCGGGCTCTGCGGACCAGAGGACAGTCATGCTGGACACCTTTAGCAGCGCCCCCAGTACCACAGCA
TGAGCGCTCCCCCGCAGACGCTGGCCCTGTTGGAAGAATTGCTTTTGAAATGTTCTTAGAAGACAAAACT
TCAGTGAATGAGAATTGGCTCTTCCATGATGACTGTACAGTGGAAAGATTCTGTGACTCGCCAGATGGTG
TCATGCTCTGTGGCAGCCATGATGGACGAGAGGTGTATGCAGTGACTCATGACCTGACGCCCACTGAGAA
CTGGATCATGCAGTTCAAGATCTCTGTTGGATGCAAAGTGCCTGAAAAAATTGCCCAGAATCAAATTCAC
GTGCAGTTTCTACTGACTTTGGCGTGAGCTGGAGTTATTTAGTCCCTCAGTGCTTACCCGCCGACCCAA
AGTGTTCTGGAAGCGTTTCTCAACCGTCTGTGTTCTTCCCAACTGAAGGGTGGAAAAGGATCACCTACCC
GCTTCCTGAAAGCTTAACGGGGAATCCTGTAAGATTTAGGTTCTACCAAAAGTACTCAGATGTGCAGTGG
GCAATTGACAATTTCTACCTTGGCCCTGGATGTTTGGACAACTGTGGAGGCCACGGAGACTGCCTAAAGG
AACAGTGTATCTGTGACCCAGGCTACTCAGGGCCAAACTGCTACTTAACTCACAGCCTGAAGACTTTCCT
GAAGGAGCGCTTTGACAGTGAGGAGATCAAGCCTGACTTATGGATGTCCTTGGAAGGCGGAAGCACTTGT
ACAGAGTGCGGGGTCCTCGCCGAGAACACTGCACTCTATTTTGGGGGATCCACTGTGAGACAAGCTATTA
CTCAAGACTTAGATCTCAGAGGTGCAAAATTCCTGCAGTACTGGGGACGTATCGGCAGTGAGAACAACAT
GACATCTTGCCATCGGCCTGTCTGCCGGAAGGAAGGCGTGCTGCTGGACTTCTCTACGGATGGAGGAATC
ACTTGGACCTTGCTTCACGAGATGGATTTCCAGAAATACATTTCTGTGAGGCACGACTACATCCTCCTGC
CTGAGGGGGCCCTCACCAACACAACTCGACTTCGCTGGTGGCAGCCTTTTGTCATCAGCAATGGGCTCGT
GGTTTCCGGGGTGGAGCGTGCGCAGTGGGCACTGGACAACATTCTGATTGGTGGAGCAGAAATCAATCCA
AGCCAACTGGTGGACACTTTCGATGACGAAGGCTCCTCCCATGAAGAAACTGGAGTTTTTACCCTAATG
CAGTAAGGACAGCAGGATTCTGTGGCAACCCATCCTTCCACCTCTACTGGCCAAATAAAAAGAAGGACAA
GACCCACAATGCACTCTCCTCCCGAGAGCTCATTATACAGCCAGGATACATGATGCAATTTAAAATTGTG
GTGGGTTGTGAAGCCACTTCATGTGGTGACCTTCATTCCGTGATGCTGGAGTACACCAAGGATGCAAGGT
CCGATTCCTGGCAGCTCGTGCAGACCCAGTGCCTACCTTCCTCTTCCAATAGCATTGGCTGCTCCCCGTT
CCAGTTCCATGAAGCCACCATTTATAATGCTGTCAACAGCTCAAGCTGGAAGAGGATCACCATCCAGCTC
CCAGACCACGTCTCGTCAAGTGCCACACAGTTCCGCTGGATCCAGAAGGGAGAAGAAACCGAGAAGCAAA
GCTGGGCCATCGACCACGTGTACATCGGAGAGGCTTGTCCCAAGCTCTGCAGCGGGCATGGCTACTGCAC
CACAGGGGCCGTCTGCATCTGCGATGAAAGCTTCCAAGGTGACGACTGCTCTGTCTTCAGTCACGAGCTT
```

FIGURE 11 con't.

```
CCTAGTTACATTAAAGATAATTTTGAATCAGCAAGAGTCACTGAAGCCAACTGGGAAACCATCCAGGGTG
GAGTGATCGGAAGTGGCTGTGGGCAGCTGGCGCCCTATGCCCATGGAGATTCGCTCTACTTTAATGGTTG
TCAGATAAGGCAAGCTGCCACCAAGCCACTGGACCTCACTCGAGCAAGCAAAATTATGTTTGTCTTGCAA
ATTGGGAGCCCAGCCCAGACAGACAGTTGCAACAGCGACCTCAGCGGCCCCCACACCGTGGACAAAGCAG
TACTGCTGCAGTACAGTGTCAACAATGGCATCACCTGGCACGTCATCGGCTCAGCACCAGCCGAAGGACTT
CACACAAGCTCAGCGGGTGTCTTACAACGTCCCCCTGGAAGCTCGGATGAAAGGAGTTCTACTGCGCTGG
TGGCAGCCACGCCACAATGGAACAGGTCATGATCAATGGGCTTTGGACCATGTGGAGGTCGTCCTAGTAA
GCACTCGCAAACAAAATTACATGATGAATTTTTCACGGCAACATGGGCTCAGGCACTTCTACAACAGAAG
ACGAAGGTCGCTTAGGCGATACCCATGAAGAATCCAAGTTTATTTCCCTTTCCAGCGTACAATGTGTCCC
TTCCTGGTTTTTTTGAAACACCTCTCACTGCATCTGATATCAGGAAACAAAGATGAAGGACTTGGCGAACA
GAAAGCCCTTCGAGATCTTGTGTACCCCACCTTCCCACACTGTGAGCTAATGATGTGTGGTTTCTCTGCA
CATAAGTAAATGTCTTCACGTCAGTGCGTCCGTGGAAATTGTGATCTGTTGTAATATCAGTTACAGTGGC
AGTATTGAGAATAAGAAATAGTTTAACAGGAAAAAACGTTTAAGCACAAACATTTTTAAGATCTTATGTT
TTAAGTGGCATTTTAGCACAGTATTTAACATTGTTGGTCACCGAGCTATTTAAGTAGACTGTATTTCAGC
TCTGTCTCTTGTTTAATATGAATAAGTTCTCGTCGTTTGTCCTTTATGTATTCTTCTCTACCGTATAACA
CACTGAAACTGTATCTACTTGCTGTGTTGCAATATTTTGCTGCTGGACTTTGACCTACTTGTATTATGCA
GAAAGTTAATGCAGATACCTATTCAAGATGATAACTGTAAAGACACTGCTGTCTCCTTAATATGCTCCTT
AACACGTATGTTGATGTAGCATCATTTTGTGGATAGGAAAAAAATGTTTGACCTTCAGATATTTTCTAC
TTAAAAAATTGTGGATGAACGCCCTATCTCCCTCCCACAGTGAGTCCCCATTACCTTGTCTAAAACAATT
TTTTAATGTGTTCTGTGGCCGTTTTACTGACAGTAACTGCCATTTCGTGTCTGTGGTAACAAAGTGACTT
GTAAAATGGTGGATGTTTCCCTCACTGTGTTCTCTTCGTGGGTTGTTTCCTTGTGGGTCATAGTCATACC
TTCTGATGAGGTGGAGCCAACACCAGCAAAGTATGATGGCCCTGTAGCCTCTGACTAGTCCTGAAACAGA
AGGCTGCACTCTAGGCTGAACCATGCTAAAAGCCCATGCTTAAATAAAAATG
```

SEQ ID NO: 24 - Reelin (RELN) protein; Mouse; GenBank AAB91599.1

```
>gi|2702253|gb|AAB91599.1| reelin [Mus musculus]
MERGCWAPRALVLAVLLLLATLRAPAATGYYPRFSPFFFLCTHHGELEGLGEQGEVLISLSIAGNPTYYV
PGQEYHVTISTSTFFDGLLVTGLYTSTSIQSSQSIGGSSAFGFGIMSDHQFGNQFMCSVVASHVSHLPTT
NLSFVWIAPPAGTGCVNFMATATHRGQVIFKDALAQQLCEQGAPTEATAYSHLAEIHSDSVILRDDFDSY
QQLELNPNIWVECSNCEMGEQCGTIMHGNAVTFCEPYGFRELTTTCLNTTTASVLQFSIGSGSCRFSYSD
PSITVSYAKNNTADWIQLEKIRAPSNVSTVIHILYLPEEAKGESVQFQWKQDSLRVGEVYEACWALDNIL
VINSAHREVVLEDNLDFVDTGNWLFFPGAPVKHSCQSDGNSIYFHGNEGSEFNFATTRDVDLSTEDIQEQ
WSEEFESQPTSWDILGAVVGADCGTVESGLSLVFLKDGERKLCTPYMDTTGYGNLRFYFVMGGICDPGVS
HENDIILYAKIEGRKEHIALDTLTYSSYKVPSLVSVVINPELQTPATKFCLRQKSHQGYNRNVWAVDFFH
VLPVLPSTMSHMIQFSINLGCGTHQFGNSVSLEFSTNHGRSWSLLHTECLPEICAGPHLPHSTVYSSENY
SGWNRITIPLPNAALTRDTRIRWRQTGPILGNMWAIDNVYIGPSCLKFCSGRGQCTRHGCKCDPGFSGPA
CEMASQTFPMFISESFGSARLSSYHNFYSIRGAEVSFSCGVLASGKALVFNKDGRRQLITSFLDSSQSRF
LQFTLRLGSKSVLSTCRAPDQPGEGVLLHYSYDNGITWKLLEHYSYVNYHEFRIISVELFDDARQFGIQF
RWWQPYHSSQGEDVWAIDEIVMTSVLFNSISLDFTNLVEVTQSLGFYLGNVQPYCGHDWTLCFTGDSKLA
SSMRYVETQSMQIGASYMIQFSLVMGCGQKYTPHMDNQVKLEYSANHGLTWHLVQEECLPSMFSCQEFTS
ASIYHASEFTQWRRVTVVLPQKTWSGATRFRWSQSYYFAQDEWALDNIYIGQQCPNMCSGHGSCDHSVCR
CDQGYQGTECHPEAALFSTIMSDFENPSSWESDWQEVIGGEVVKPEQGCGSVVSSGSSLYFSKAGKRQLVS
WDLDTSWVDFVQFYIQISGGESAACNKPDSREEGILLQYSNNGGIQWHLLAEMYFSDFSKPRFVYLELPAA
GKTPCTRFRWWEPVFSGEDYDQWAVDDIIILSEKQRQVIPVVNFTLPQNFYEKPAFDYPMNQMSVWLMLA
NEGMAKNDSFCATTPSAMVFGKSDGDRFAVTRDLTLKPGYVLQFKLNIGCTSQFSSTAFVLLQYSHDAGM
SWFLLKEGCFPASAAKGCEGNSRELSEPTVYYTGDFEEWTRITIAIPRSLASSKTRFRWIQESSSQKNVP
PFGLDGVYISEPCPSYCSGHGDCISGVCFCDLGYTAAQGTCVSNTPNHSEMFDRFEGKLSFLWYKITGGQ
VGTGCGTLNDGRSLYFNGLGKREARTVPLDTRNISLVQFYIQISGKTSGITYITPRARYEGLVVQYSNDN
GILWHLLRELDFMSFLEPQIISIDLPREAKTPATAFRWWQPQHGKHSAWALGDVLIGVNDSSQTGFQDK
LDGSIDLQANWYRIQGGQVDIDCLSMDTALIFTENIGNFRYAETWDFHVSESSFLQWEMNMGCSKPFSGA
RGIQLQYSLNNGKDWQLVTEECVPPTIGCVHYTESSTYTSERFQNWRRVTVYLPLATNSPRTRFRWIQTN
YTVGADSWAIDNVILASGCPWMCSGRGICDSGRCVCDRGFGGPFCVPVVPLPSILKDDFNGNLHFDLWPE
VYGAERGNLNGETIKSGTCLIFKGEGLPMLISRDLDCTNTMYVQFSLRFIAKGTPERSHSILLQFSVSGG
VTWHLMDEFYFPQTTSILFINVPLPYGAQTNATRFRLWQPYNNGKKEEIWIIDDFIIDGNNLNNPVLLLD
```

FIGURE 11 con't.

```
TFDFGPREDNWFFYPGGNIGLYCPYSSKGAPEEDSAMVFVSNEVGEHSITTRDLSVNENTIIQFEINVGC
STDSSSADFVRLEFSRDFGATWHLLLPLCYHSSSLVSSLCSTEHHFSSTYYAGTTQGWRREVVHFGKLHL
CGSVRFRWYQGFYPAGSQPVTWAIDNVYIGPQCEEMCYGHGSCINGTKCICDPGYSGPTCKISTKNPDFL
KDDFEGQLESDRFLLMSGGKPSRKCGILSSGNNLFFNEDGLRMLVTRDLDLSHARFVQFFMRLGCGKGVF
DPRSQPVLLQYSLNGGLSWSLLQEFLFSNSSNVGRYIALEMPLKARSGSTRLRWWQPSENGHFYSPWVID
QILIGGNISGNTVLEDDFSTLDSRKWLLHPGGTKMPVCGSTGDALVFIEKASTRYVVTTDIAVNEDSFLQ
IDFAASCSVTDSCYAIELEYSVDLGLSWHPLVRDCLPTNVECSRYHLQRILVSDTFNKWTRITLPLPSYT
RSQATRFRWHQPAPFDKQQTWAIDNVYIGDGCLDMCSGHGRCVQGSCVCDEQWGGLYCDEPETSLFTQLK
DNFNRAPSNQNWLTVSGGKLSTVCGAVASGLALHFSGGCSRLLVTVDLNLTNAKFIQFYFMYGCLITPSN
RNQGVLLEYSVNGGITWNLLMEIFYIQYSKPGFVNILLPPDAKEIATRFRWWQPRHDGLIQNDWAIDNVL
ISGSADQRTVMLDTFSSAPVPQHERSFADAGPVGRIAFEMFLEDKTSVNENWLFHDDCTVERFCDSPDGV
MLCGSHDGREVYAVTHDLTPTENWIMQFKISVGCKVPEKIAQNQIHVQFSTDFGVSWSYLVPQCLPADPK
CSGSVSQPSVFFPTEGWKRITYPLPESLTGNPVRFRFYQKYSDVQWAIDNFYLGPGCLDNCGGHGDCLKE
QCICDPGYSGPNCYLTHSLKTFLKERFDSEEIKPDLWMSLEGGSTCTECGVLAENTALYFGGSTVRQAIT
QDLDLRGAKFLQYWGRIGSENNMTSCHRPVCRKEGVLLDFSTDGGITWTLLHEMDFQKYISVRHDYILLP
EGALTNPTRLRWWQPFVISNGLVVSGVERAQWALDNILIGGAEINPSQLVDTFDDEGSSHEENWSFYPNA
VRTAGFCGNPSFHLYWPNKKKDKTHNALSSRELIIQPGYMMQFKIVVGCEATSCGDLHSVMLEYTKDARS
DSWQLVQTQCLPSSSNSIGCSPFQFHEATIYNAVNSSSWKRITIQLPDHVSSSATQFRWIQKGEETEKQS
WAIDHVYIGEACPKLCSGHGYCTTGAVCICDESFQGDDCSVFSHELPSYIKDNFESARVTEANWETIQGG
VIGSGCSQLAFYARGDSLYFNGCQIRQAATKPLDLTRASKIMFVLQIGSPAQTDSCNSDLSGPHTVIKAV
LLQYSVNNGITWHVIAQHQPKDFTQAQRVSYNVPLEARMKGVLLRWWQPRHNGTSHDQWALDHVEVVLVS
TRKQNYMMNFSRQHGLRHFYNRRRRSLRRYP
```

FIGURE 14
B
Brain Slices - IB: Reelin
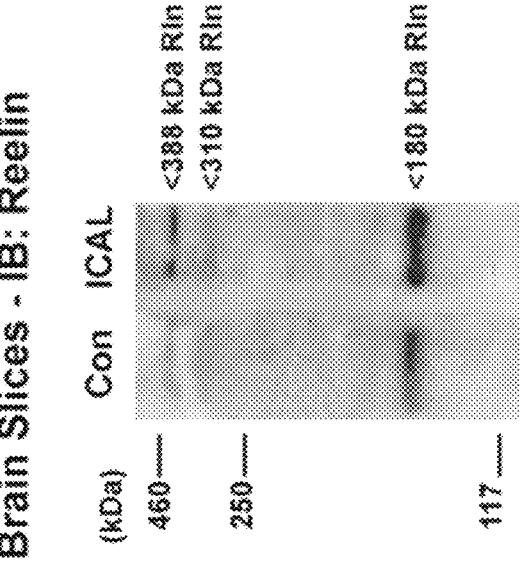
A
Brain Slices - IP: DAB1
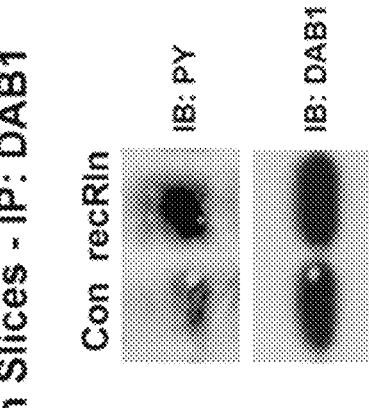

FIGURE 16
A    Entorhinal Cortex
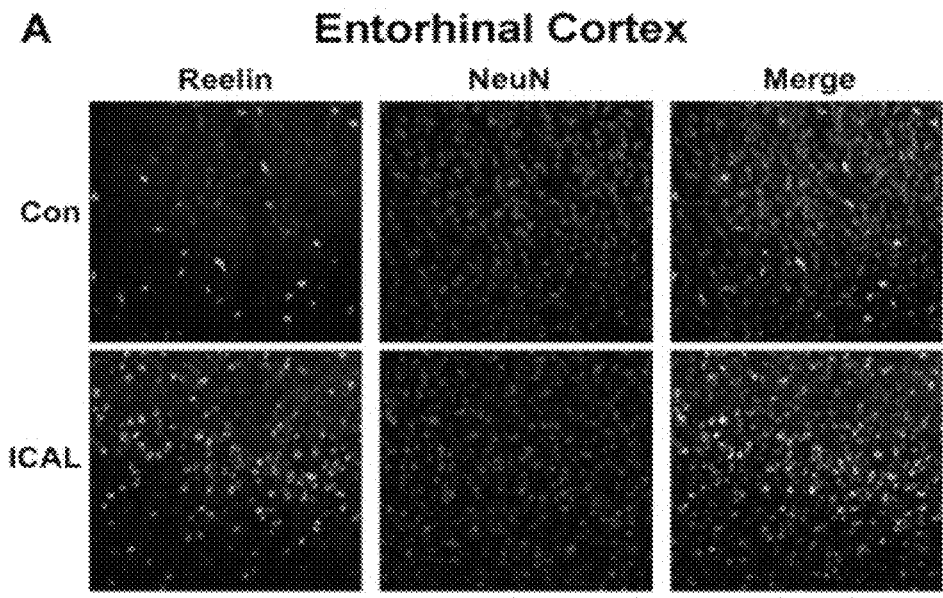
B    Dentate Gyrus
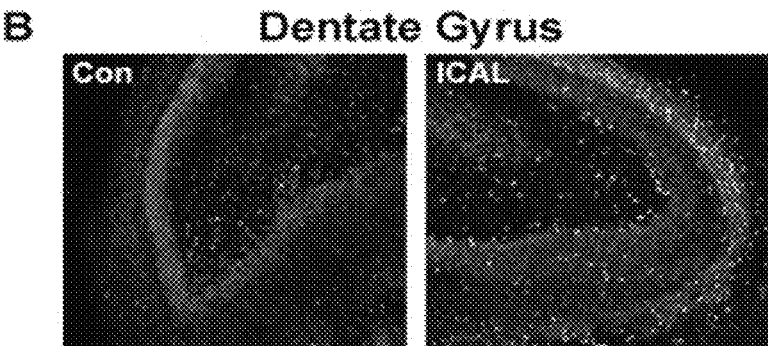
Reelin(FITC); NeuN (Cy3)
C    CA1 Hippocampus
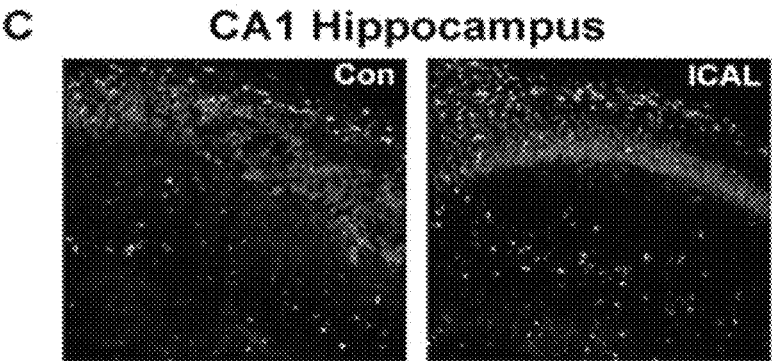
Reelin(FITC); NeuN (Cy3)

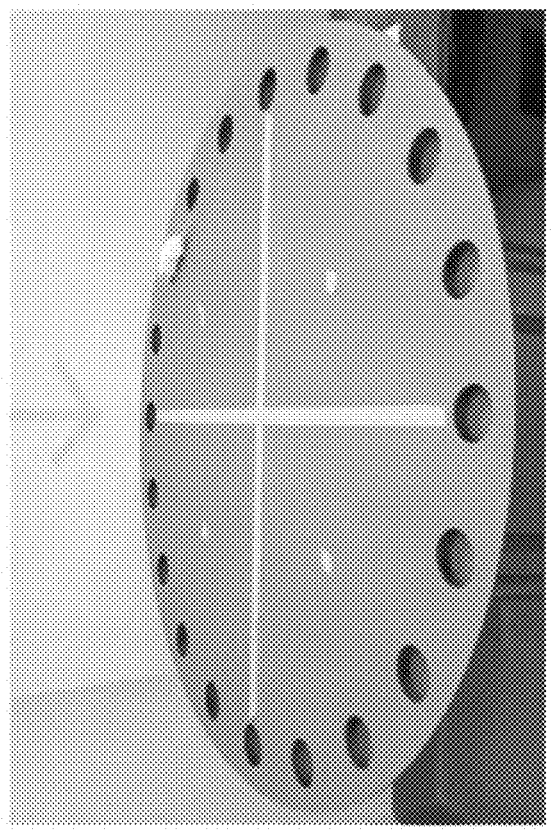
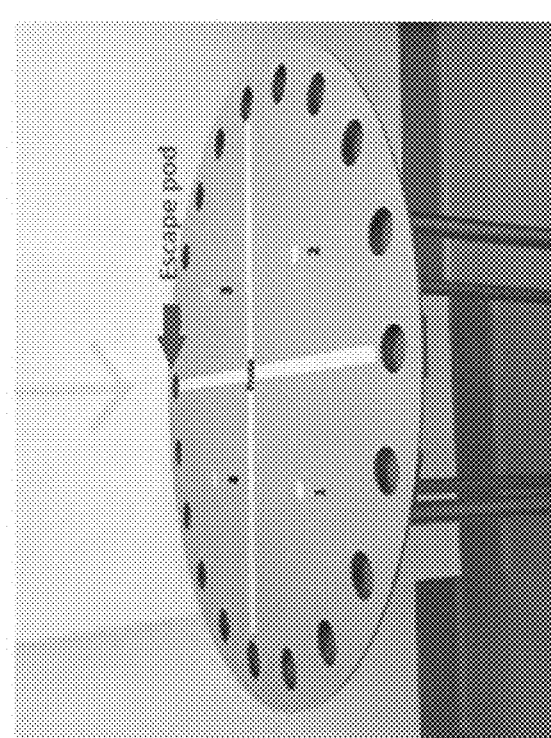
FIGURE 17

Non-carrier   Hemi (Unt)   Hemi (ICAL)

FIGURE 29
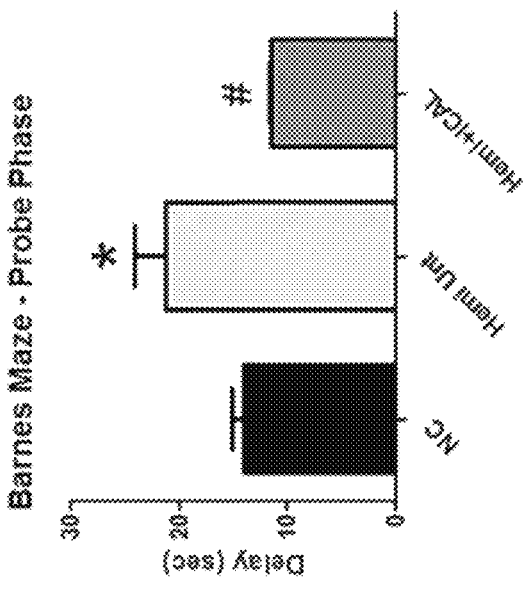
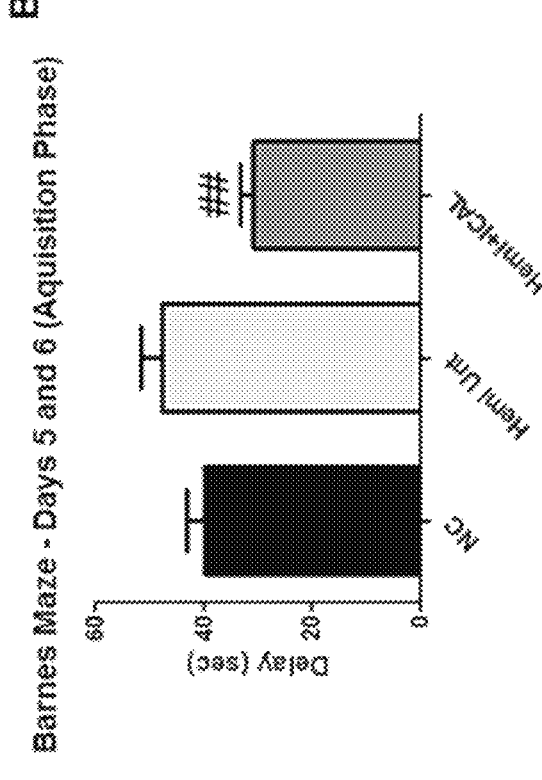

COMPOSITIONS FOR RESTORING GENE EXPRESSION IN NEUROPSYCHIATRIC OR NEURODEGENERATIVE DISORDERS

CROSS REFERENCE TO RELATED APPLICATIONS

This application is a continuation of U.S. application Ser. No. 16/335,914, filed Mar. 22, 2019, which is a National Phase under 35 U.S.C. § 371 of International Application No. PCT/US2017/052269, filed Sep. 19, 2017, which claims priority to U.S. Provisional Application No. 62/398,892, filed Sep. 23, 2016, the entire contents of which are incorporated herein by reference.

FIELD OF INVENTION

The present invention relates generally to methods and compositions for treating neurological or neurodegenerative diseases or conditions. More specifically, the present invention relates to compositions comprising whey protein isolate and/or concentrate, and their use in increasing reelin (RELN) levels and/or in restoring other imbalances or abnormalities of gene expression linked with a neuropsychiatric or neurodegenerative disorder in a subject in need thereof.

BACKGROUND

Neuropsychiatric and neurodegenerative disorders represent a significant and ongoing concern for public health and wellbeing. Millions of individuals have suffered, or will suffer from, some form of mental disorder during their lifetime. These diseases and conditions are highly complex, and as a result successful treatment can be quite challenging. Schizophrenia (SCZ), for example, is a complex neuropsychiatric condition including disordered thought and behavior that afflicts approximately 1% of the population[1]. Alzheimer's disease (AD), as another example, affects millions of people worldwide and has only limited treatment options available.

While the majority of neuropsychiatric and neurodegenerative disorders are believed to stem from diseases of the nervous system, their root causes and mechanisms of disease progression have proven complex and difficult to treat. Even still, a number neuropsychiatric and neurodegenerative disorders have been linked or attributed at least in part to imbalances or genetic abnormalities arising in connection with environmental factors, gene mutations, and/or dysregulation of expression of particular genes.

Indeed, a host of prenatal and early postnatal stressors have been implicated as risk factors or triggers for human neurodevelopmental disorders[2,3] such as SCZ[4,5], autism[6,7] and attention deficit-hyperactivity disorder (ADHD)[8]. Candidate perinatal stressors include exposure to noxious chemicals during pregnancy, maternal infection (bacterial, viral, or parasitic) and attendant immune activation, and maternal psychotrauma and associated activation of the hypothalamic-pituitary-adrenal axis. While the etiopathogenesis of SCZ, as with many other neuropsychiatric and neurodegenerative disorders, remains incompletely understood, there is evidence suggesting that many genetic and perinatal risk factors converge on limited neurodevelopmental pathways to elicit the disease.

Alzheimer's disease is another particularly relevant example of a complex neurodegenerative disease which affects millions worldwide, and for which treatment has proven difficult. Hallmarks of AD include amyloid plaques (insoluble deposits of amyloid beta peptide) and neurofibrillary tangles containing hyper-phosphorylated tau protein. Treatment options are limited, and are generally not curative.

Substantial research efforts have been directed toward the identification of genes which are linked with neuropsychiatric and neurodegenerative disorders, and toward the identification of therapeutic agents capable of restoring such genes to healthy expression and/or activity levels. Although certain genes believed to be involved in the onset and/or progression of particular neuropsychiatric and neurodegenerative disorders have been identified, treatment options successfully taking advantage of these gene targets are still lacking.

Reelin (RELN; human NCBI Gene ID: 5649; human mRNA and amino acid sequences shown in FIG. 11 as SEQ ID NO:1 and SEQ ID NO: 2, respectively; mouse NCBI Gene ID: 19699; mouse genome ID: gi:372099105; mouse mRNA and amino acid sequences shown in FIG. 11 as SEQ ID NO: 23 and SEQ ID NO: 24, respectively) is an example of a gene which has been linked to a variety of different neuropsychiatric and neurodegenerative disorders. According to the NCBI. RELN may be involved in schizophrenia, autism, bipolar disorder, and major depression. RELN expression levels are significantly reduced in both schizophrenia and Alzheimer's disease, for example. Reelin overexpression may protect against, or rescue, certain aspects of Alzheimer's disease (see Pujadas, L., et al., 2013, Reelin delays amyloid-beta fibril formation and rescues cognitive deficits in a model of Alzheimer's disease, *Nature Communications*, DOI: 10.1038/ncomms4443), for example.

Reelin is secreted by specific cells within the central nervous system, and plays a key role in patterning and layering of the cerebral cortex and other regions of the brain during development. In adults, Reelin is thought to be a central regulator of synapse formation and critical neuronal processes required for learning and memory. Alzheimer's disease is the most prevalent cognitive disorder in adults and is characterized by substantial deficits in learning and memory. The entorhinal cortex layer II neurons are one of the first populations to die in AD, resulting in a severe loss of synaptic contacts to the dentate gyrus. Many of the entorhinal cortex layer II neurons express Reelin, and these Reelin-expressing cells are significantly reduced in the brains of human amyloid precursor protein (hAPP) transgenic mice expressing the Swedish and Indiana mutant form of the hAPP gene (J20 strain). Similar loss of Reelin-expressing entorhinal cortex layer II neurons is also observed in the brains of patients with AD (Chin. J., et al., 2007, *J Neurosci*, 27(11): 2727-2733; Herring, A., et al., 2012, *J Alz Dis*, 30(4): 963-979). In a transgenic rat model of AD (McGill-R-Thy1-APP strain). Reelin-expressing neurons of the entorhinal cortex layer II were found to selectively express increased levels of soluble intracellular Aβ early in disease, prior to the deposition of amyloid plaques (Kobro-Flatmoen, A., et al., 2016, *Neurobiol Dis* 93: 172-183). Collectively, these studies suggest that Reelin-expressing neurons of entorhinal cortex layer II play a central role in the early pathogenic changes in AD, and that loss of these Reelin-expressing cells and their synaptic projections to the hippocampus are early markers of disease (Krstic, D., et al., 2013, *Neuroscience* 246: 108-116).

Alternative, additional, and/or improved methods and compositions for restoring healthy levels of gene products linked to neuropsychiatric and neurodegenerative disorders, such as RELN, are highly desirable.

SUMMARY OF INVENTION

Methods and compositions for treating neurological, neuropsychiatric, or neurodegenerative diseases or conditions in a subject in need thereof are provided. It has been found that, as described in detail herein, compositions comprising whey protein isolate and/or whey protein concentrate allow for restoration of reelin (RELN) levels in the brain of a subject in need thereof. The provided methods and compositions are not limited to increasing or restoring RELN levels, and may also, or alternatively, be used to correct a number of other neurological conditions, imbalances, dysregulations, or abnormalities occurring in a subject. Subjects suffering from neuropsychiatric or neurodegenerative diseases may particularly benefit from treatment with such compositions, however other subjects may also benefit from such treatment with whey protein isolate and/or concentrate compositions as described herein.

In an embodiment, there is provided herein a method for increasing reelin (RELN) levels in the brain a subject in need thereof, said method comprising:

administering a composition comprising whey protein isolate and/or whey protein concentrate to the subject.

In another embodiment of the above method, the method may further comprise a step of:

measuring an initial RELN level of the subject and comparing the measured initial RELN level to a healthy RELN level, wherein the subject is identified as having a reduced RELN level in need of increase when the measured initial RELN level is less than the healthy RELN level.

In still another embodiment of the above method or methods, administration of the composition comprising whey protein isolate and/or whey protein concentrate may increase expression levels of GAD67, a gene acting downstream of RELN.

In still another embodiment of the above method or methods, the subject in need thereof may be a subject suffering from a neuropsychiatric or neurodegenerative disorder.

In yet another embodiment of the above method or methods, the subject in need thereof may be a subject suffering from schizophrenia.

In another embodiment of the above method or methods, the subject in need thereof may be a subject suffering from Alzheimer's disease (AD).

In still another embodiment of the above method or methods, the subject in need thereof may be a subject suffering from a neurological disorder characterized by enhanced expression of heme oxygenase-1 and/or increased oxidative stress in brain such as Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, or autism.

In yet another embodiment of the above method or methods, the reelin (RELN) levels may be neuronal reelin (RELN) levels.

In another embodiment, there is provided herein a method for treating, preventing, or ameliorating symptoms of a neuropsychiatric disease or a neurodegenerative disorder in a subject in need thereof, said method comprising:

administering a composition comprising whey protein isolate and/or whey protein concentrate to the subject.

In another embodiment of the above method, the composition comprising whey protein isolate and/or whey protein concentrate may be administered to increase reelin (RELN) levels in the brain of the subject.

In still another embodiment of the above method, the method may further comprise a step of:

measuring an initial RELN level of the subject and comparing the measured initial RELN level to a healthy RELN level, wherein the subject is identified as being particularly susceptible to treatment when the measured initial RELN level is less than the healthy RELN level.

In yet another embodiment of the above method or methods, the neuropsychiatric disease or neurodegenerative disorder may be schizophrenia or Alzheimer's disease (AD).

In still another embodiment of the above method or methods, the neuropsychiatric disease or neurodegenerative disorder may be a neurological disorder characterized by enhanced expression of heme oxygenase-1 and/or increased oxidative stress in brain such as Alzheimer's disease, Parkinson's disease, dementia with Lewy bodies, frontotemporal dementia, amyotrophic lateral sclerosis, other motor neuron disorders, Down's syndrome. Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, or autism.

In yet another embodiment of the above method or methods, the reelin (RELN) levels may be neuronal reelin (RELN) levels.

In another embodiment, there is provided herein a use of a composition comprising whey protein isolate and/or whey protein concentrate for increasing reelin (RELN) levels, such as but not limited to neuronal reelin levels, in a subject in need thereof.

In yet another embodiment, there is provided herein a use of a composition comprising whey protein isolate and/or whey protein concentrate in the manufacture of a medicament for increasing reelin (RELN) levels, such as but not limited to neuronal reelin levels, in a subject in need thereof.

In another embodiment, there is provided herein a use of a composition comprising whey protein isolate and/or whey protein concentrate for treating, preventing, or ameliorating symptoms of a neuropsychiatric disease or a neurodegenerative disorder in a subject in need thereof.

In still another embodiment, there is provided herein a use of a composition comprising whey protein isolate and/or whey protein concentrate in the manufacture of a medicament for treating, preventing, or ameliorating symptoms of a neuropsychiatric disease or a neurodegenerative disorder in a subject in need thereof.

In another embodiment, there is provided herein a method for restoring serotonin levels: normalizing MnSOD mRNA levels; augmenting glutathione (GSH) levels in brain cells; augmenting whole brain GSH/glutathione disulfide (GSSG) ratios; restoring GAD67 levels; reversing reduction of Nrxn1; reversing reduction of Nlgn2; preventing HMOX1-related dysregulation of miR-128 expression; improving HMOX1-related changes in brain dopamine, dopamine metabolites, serotonin, norepinephrine, and epinephrine: restoring deficient DOPAC/DA ratios; augmenting norepinephrine and dopamine concentrations in the prefrontal cortex: and/or correcting prefrontal cortex hypodopaminergia in a subject in need thereof, said method comprising:

administering a composition comprising whey protein isolate and/or whey protein concentrate to the subject.

In yet another embodiment, there is provided herein a method for augmenting GSH reserves in the brain; normalizing brain MnSOD mRNA levels: restoration of redox homeostasis; normalization of brain dopamine, serotonin, norepinephrine, and/or epinephrine levels; normalization of brain DOPAC/DA ratios: restoring GAD67 levels; reversing reduction of Nrxn1; reversing reduction of Nlgn2; preventing HMOX1-related dysregulation of miR-128 expression; and/or ameliorating hyperlocomotion and/or stereotypic behaviour; or any combination thereof; in a subject in need thereof, said method comprising:

administering a composition comprising whey protein isolate and/or whey protein concentrate to the subject.

In another embodiment of the above method or methods, the subject may be a subject suffering from, or may be at risk of developing, a neuropsychiatric or neurodegenerative disorder.

In yet another embodiment of the above method, the neuropsychiatric or neurodegenerative disorder may be schizophrenia or Alzheimer's disease (AD).

In still another embodiment of the above method or methods, the neuropsychiatric or neurodegenerative disorder may be a neurological disorder characterized by enhanced expression of heme oxygenase-1 and/or increased oxidative stress in brain such as Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, or autism.

In yet another embodiment of the above method or methods, the composition comprising whey protein isolate and/or whey protein concentrate may be administered for restoring serotonin levels; normalizing MnSOD mRNA levels: augmenting glutathione (GSH) levels in brain cells; augmenting whole brain GSH/glutathione disulfide (GSSG) ratios: restoring GAD67 levels; reversing reduction of Nrxn1; reversing reduction of Nlgn2; preventing HMOX1-related dysregulation of miR-128 expression: improving HMOX1-related changes in brain dopamine, dopamine metabolites, serotonin, norepinephrine, and epinephrine; restoring deficient DOPAC/DA ratios; augmenting norepinephrine and dopamine concentrations in the prefrontal cortex; and/or correcting prefrontal cortex hypodopaminergia in the subject.

In still another embodiment of the above method or methods, the composition comprising whey protein isolate and/or whey protein concentrate may be administered for augmenting GSH reserves in the brain; normalizing brain MnSOD mRNA levels; restoration of redox homeostasis: normalization of brain dopamine, serotonin, norepinephrine, and/or epinephrine levels: normalization of brain DOPAC/DA ratios; restoring GAD67 levels; reversing reduction of Nrxn1; reversing reduction of Nlgn2; preventing HMOX1-related dysregulation of miR-128 expression: and/or ameliorating hyperlocomotion and/or stereotypic behaviour; or any combination thereof; in the subject.

In an embodiment, there is provided herein a use of a composition comprising whey protein isolate and/or whey protein concentrate for restoring serotonin levels; normalizing MuSOD mRNA levels; augmenting glutathione (GSH) levels in brain cells; augmenting whole brain GSH/glutathione disulfide (GSSG) ratios; restoring GAD67 levels; reversing reduction of Nrxn1: reversing reduction of Nlgn2; preventing HMOX1-related dysregulation of miR-128 expression; improving HMOX1-related changes in brain dopamine, dopamine metabolites, serotonin, norepinephrine, and epinephrine: restoring deficient DOPAC/DA ratios: augmenting norepinephrine and dopamine concentrations in the prefrontal cortex: and/or correcting prefrontal cortex hypodopaminergia in a subject in need thereof.

In still another embodiment, there is provided herein a use of a composition comprising whey protein isolate and/or whey protein concentrate for augmenting GSH reserves in the brain; normalizing brain MnSOD mRNA levels: restoration of redox homeostasis; normalization of brain dopamine, serotonin, norepinephrine, and/or epinephrine levels: normalization of brain DOPAC/DA ratios; restoring GAD67 levels; reversing reduction of Nrxn1; reversing reduction of Nlgn2; preventing HMOX1-related dysregulation of miR-128 expression: and/or ameliorating hyperlocomotion and/or stereotypic behaviour: or any combination thereof: in a subject in need thereof.

In yet another embodiment, there is provided herein a use of a composition comprising whey protein isolate and/or whey protein concentrate in the manufacture of a medicament for restoring serotonin levels; normalizing MnSOD mRNA levels; augmenting glutathione (GSH) levels in brain cells; augmenting whole brain GSH/glutathione disulfide (GSSG) ratios: restoring GAD67 levels; reversing reduction of Nrxn1; reversing reduction of Nlgn2; preventing HMOX1-related dysregulation of miR-128 expression; improving HMOX1-related changes in brain dopamine, dopamine metabolites, serotonin, norepinephrine, and epinephrine: restoring deficient DOPAC/DA ratios: augmenting norepinephrine and dopamine concentrations in the prefrontal cortex; and/or correcting prefrontal cortex hypodopaminergia in a subject in need thereof.

In another embodiment, there is provided herein a use of a composition comprising whey protein isolate and/or whey protein concentrate in the manufacture of a medicament for augmenting GSH reserves in the brain; normalizing brain MnSOD mRNA levels; restoration of redox homeostasis; normalization of brain dopamine, serotonin, norepinephrine, and/or epinephrine levels; normalization of brain DOPAC/DA ratios; restoring GAD67 levels; reversing reduction of Nrxn1; reversing reduction of Nlgn2; preventing HMOX1-related dysregulation of miR-128 expression; and/or ameliorating hyperlocomotion and/or stereotypic behaviour; or any combination thereof: in a subject in need thereof.

In another embodiment, there is provided herein a method for increasing GAD67 levels, such as but not limited to neuronal GAD67 levels, in a subject in need thereof, said method comprising:

administering a composition comprising whey protein isolate and/or whey protein concentrate to the subject.

In still another embodiment, there is provided herein a use of a composition comprising whey protein isolate and/or whey protein concentrate for increasing GAD67 levels, such as but not limited to neuronal GAD67 levels, in a subject in need thereof.

In yet another embodiment, there is provided herein a use of a composition comprising whey protein isolate and/or whey protein concentrate in the manufacture of a medicament for increasing GAD67 levels, such as but not limited to neuronal GAD67 levels, in a subject in need thereof.

In another embodiment of the above methods or uses, the RELN levels may be levels in the prefrontal cortex of the brain.

In still another embodiment of the above methods or uses, the subject may be a mammal, such as a human.

In another embodiment, there of provided herein a method for inducing or restoring RELN expression and/or signalling in the entorhinal cortex and/or hippocampus of a subject in need thereof, said method comprising:

administering a composition comprising whey protein isolate and/or whey protein concentrate to the subject.

In yet another embodiment of the above method, the subject may have or may be at risk of developing schizophrenia or Alzheimer's Disease.

In still another embodiment, there is provided herein a use of a composition comprising whey protein isolate and/or whey protein concentrate for inducing or restoring RELN expression and/or signalling in the entorhinal cortex and/or hippocampus of a subject in need thereof.

In yet another embodiment, there is provided herein a use of a composition comprising whey protein isolate and/or whey protein concentrate in the manufacture of a medicament for inducing or restoring RELN expression and/or signalling in the entorhinal cortex and/or hippocampus of a subject in need thereof In another embodiment of the above uses, the subject may have or may be at risk of developing schizophrenia or Alzheimer's Disease.

In another embodiment, there is provided herein a method for treating, preventing, or ameliorating symptoms of Alzheimer's Disease in a subject in need thereof, said method comprising:

administering a composition comprising whey protein isolate and/or whey protein concentrate to the subject.

In another embodiment, there is provided herein a use of a composition comprising whey protein isolate and/or whey protein concentrate for treating, preventing, or ameliorating symptoms of Alzheimer's Disease in a subject in need thereof.

In still another embodiment, there is provided herein a use of a composition comprising whey protein isolate and/or whey protein concentrate in the manufacture of a medicament for treating, preventing, or ameliorating symptoms of Alzheimer's Disease in a subject in need thereof.

In another embodiment of the above methods or uses, the composition maybe for preserving or restoring cognitive function in the subject.

In yet another embodiment of the above methods or uses, the composition may be administered in an amount sufficient to provide at least one of:

an increase in RELN levels in the entorhinal cortex;

an increase in RELN levels in the dentate gyrus;

an increase in RELN levels in the CA1 region;

an increase in RELN levels in the CA3 region;

a correction in a deficit in cortical GSH levels;

a restoration of GAD67 expression in the hippocampal-entorhinal cortex sub-region;

a restoration of p-CREB levels in the hippocampal-entorhinal cortex sub-region;

an increase in RELN levels in layer II of the entorhinal cortex;

a prevention of loss of RELN positive neurons in the entorhinal cortex: or a restoration of GAD67 expression in the dentate gyrus and/or CA3 region of the hippocampus;

or any combination thereof.

In still another embodiment of the above methods or uses, the subject may be a mammal, such as a human.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 11 provides the sequences of certain nucleic acids and amino acids referred to herein.

FIG. 14 shows results of studies in which Immunocal® treatment increased Reelin expression in vitro in hippocampal-entorhinal cortex slices. A) Brain slices were incubated for 24 h in either control medium alone (Con) or containing recombinant Reelin (recRln). Following incubation, slices were lysed and DAB1 was immunoprecipitated (IP). The immune complexes were resolved by SDS-PAGE and immunoblotted (IB) for phosphotyrosine (PY) followed by stripping and reprobing for DAB1. B) Brain slices were incubated for 24 h in either Con medium or containing Immunocal® (ICAL). Protein lysates were IB for Reelin.

FIG. 16 shows results of studies in which Immunocal® treatment increased Reelin expression in vitro in hippocampal-entorhinal cortex slices. Brain slices were incubated for 24 h in either control medium alone (Con) or containing Immunocal® (ICAL). Following treatment, free floating slices were stained for Reelin (shown in green) and NeuN (shown in red). Images shown represent specific brain regions including entorhinal cortex (A), dentate gyrus (B), and CA1 region of hippocampus (C), z-stacked images were captured on a laser scanning confocal microscope using identical laser intensities and exposure times for each tissue slice.

FIG. 17 depicts Barnes maze apparatus employed for cognitive testing. During the acquisition phase of testing, the mouse is placed in one of the four quadrants as indicated, and allowed 90 seconds to explore the maze and find the escape pod, as indicated by the line and filled arrows. During the probe phase, the mouse is placed in the center of the maze and the time it takes for the mouse to find the escape pod or the hole to either side of the escape pod is recorded.

Figure 24:
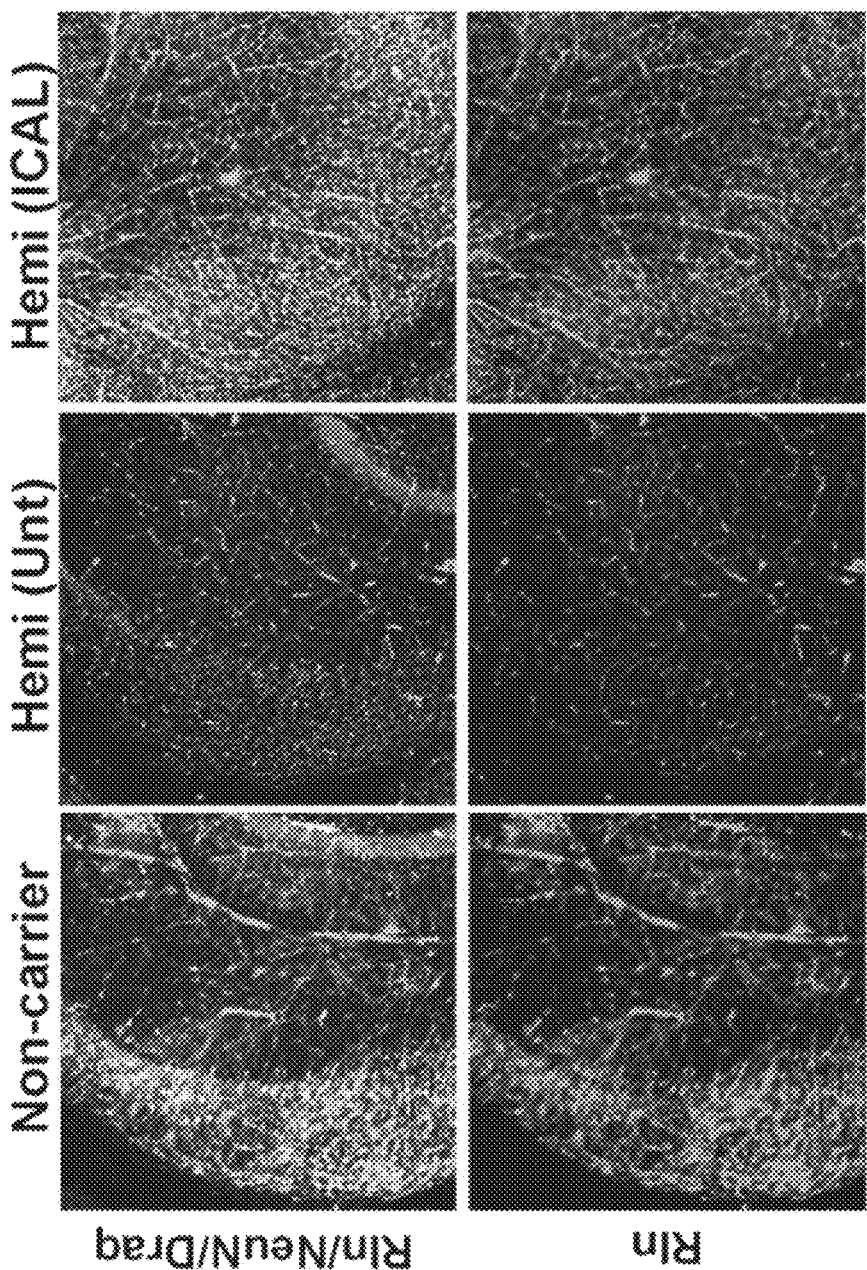

FIG. 24 shows results of studies in which Immunocal® treatment rescued Reelin expression in hippocampus CA1 of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to Reelin (Rln, shown in green) and NeuN (shown in red), along with Draq (nuclear stain, shown in blue).

Figure 25:
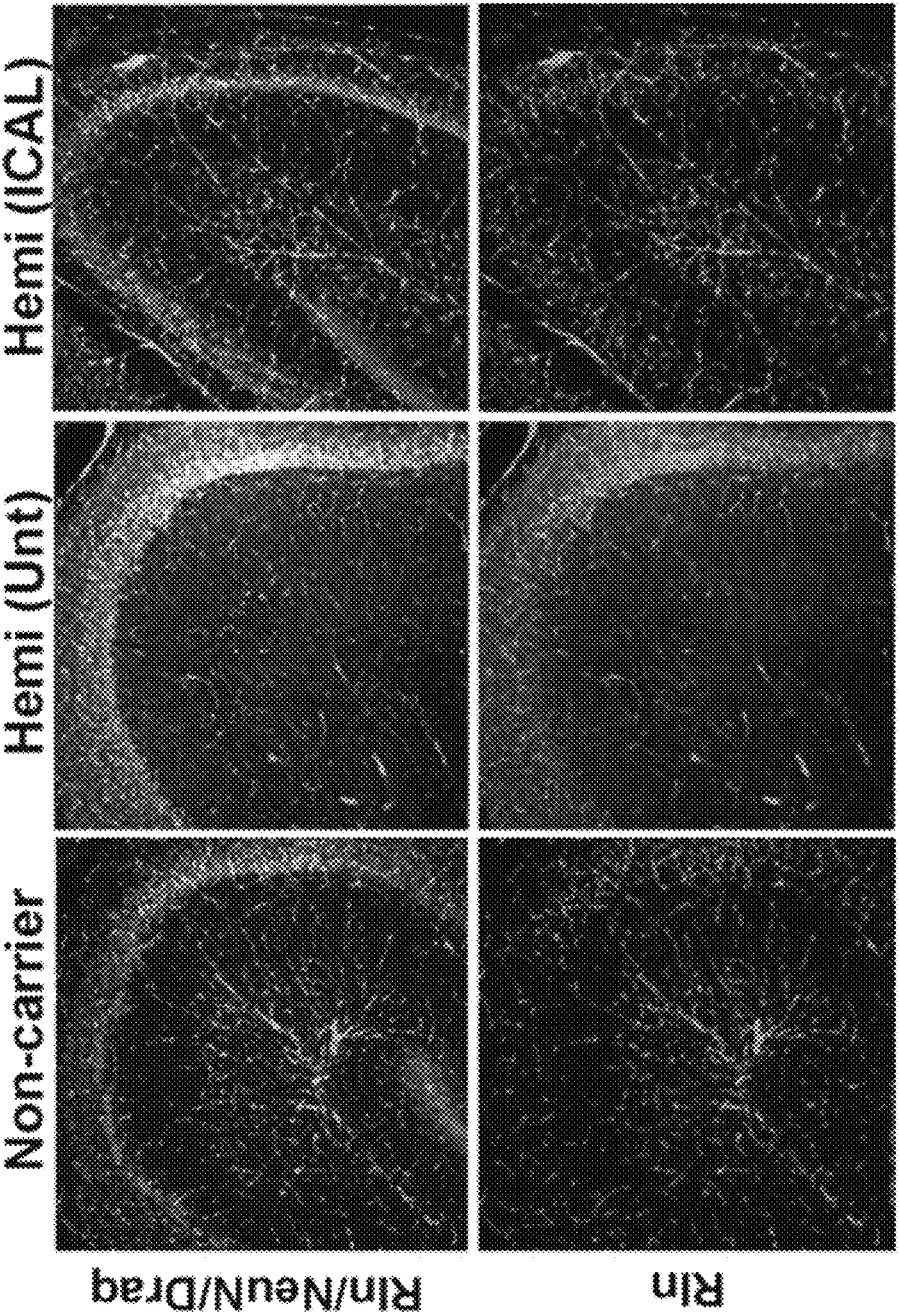

FIG. 25 shows results of studies in which Immunocal® treatment preserved Reelin expression in hippocampus CA3 of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to Reelin (Rln, shown in green) and NeuN (shown in red), along with Draq (nuclear stain, shown in blue).

Figure 26:
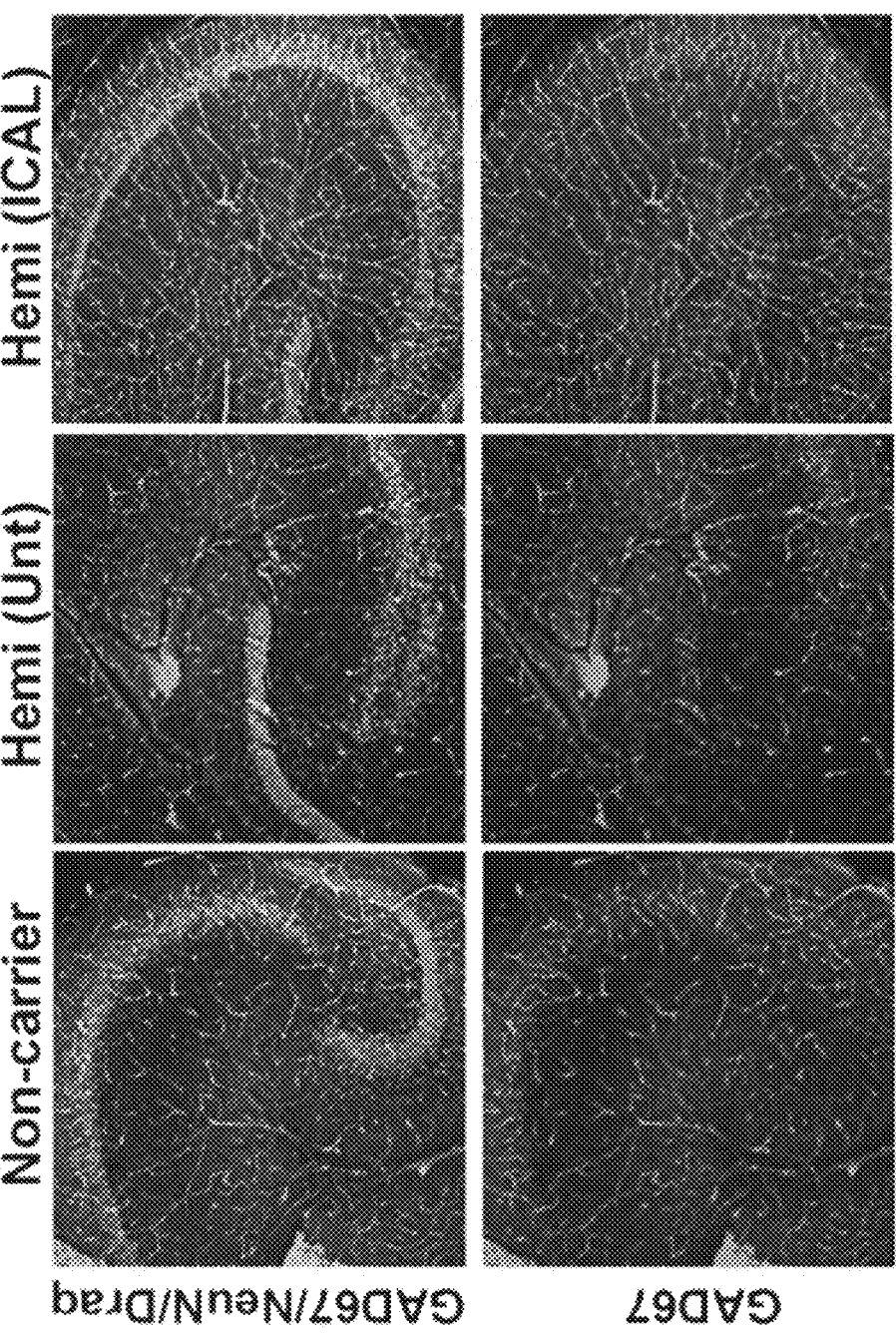

FIG. 26 shows results of studies in which Immunocal® treatment increased GAD67 expression in dentate gyrus of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to GAD67 (shown in green) and NeuN (shown in red), along with Draq (nuclear stain, shown in blue).

Figure 27:
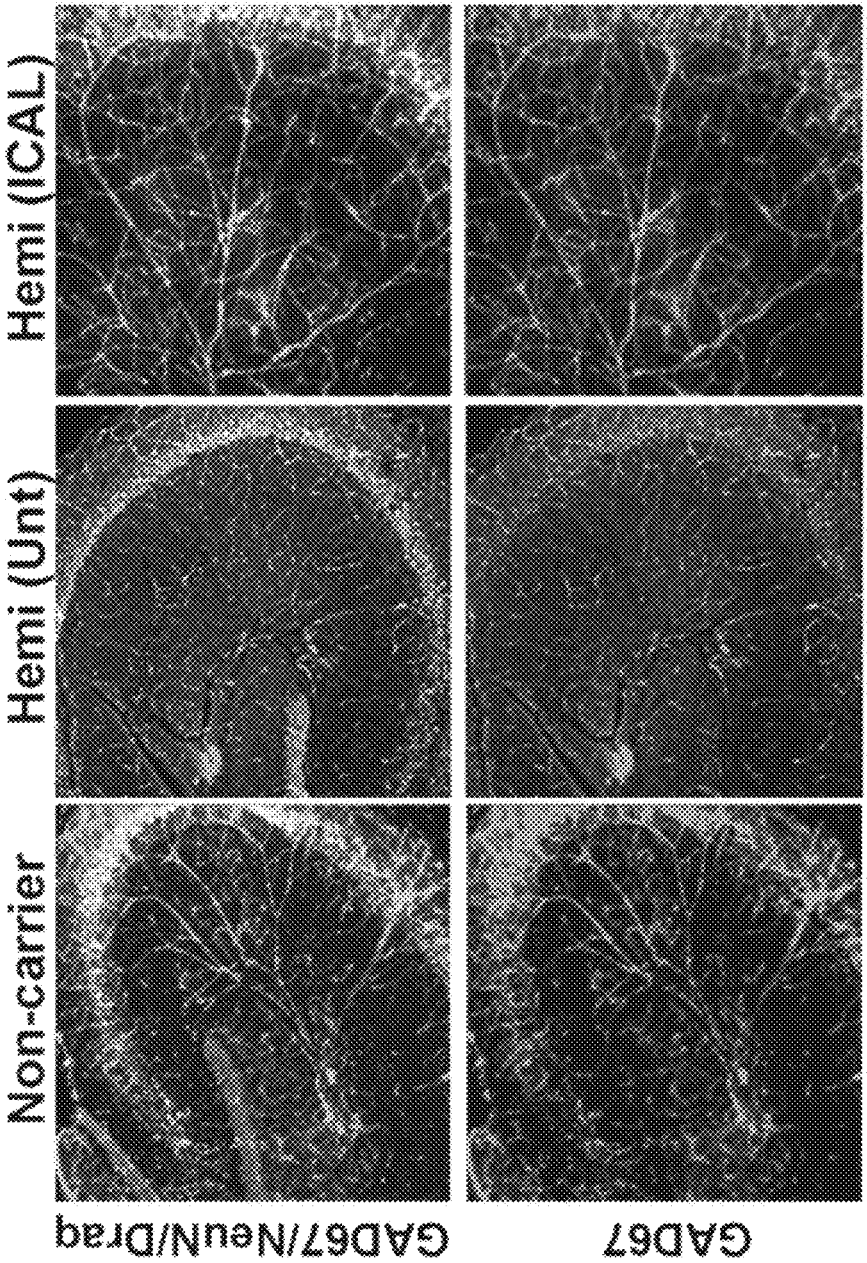

FIG. 27 shows results of studies in which Immunocal® treatment preserved GAD67 expression in hippocampus CA3 of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to GAD67 (shown in green) and NeuN (shown in red), along with Draq (nuclear stain, shown in blue).

Figure 28:
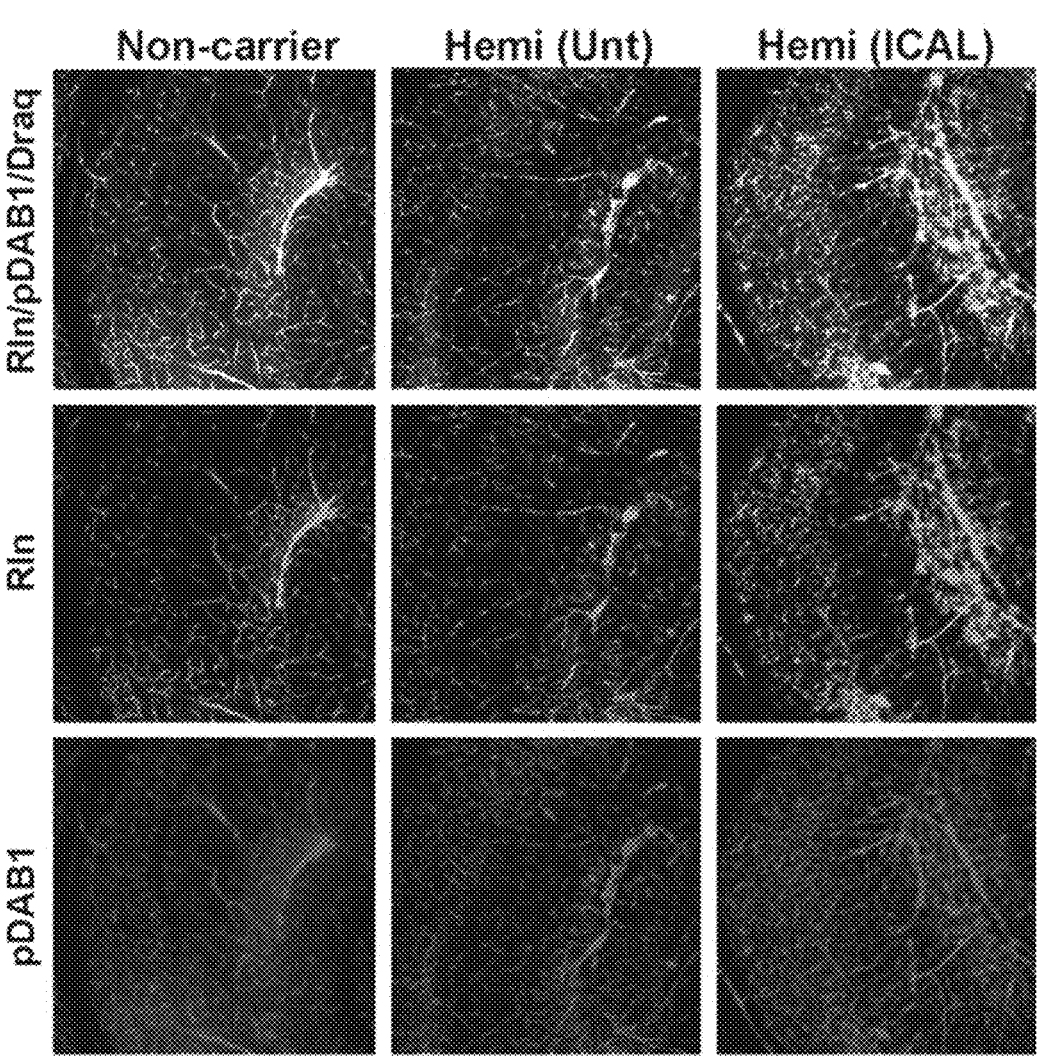

FIG. 28 shows results of studies in which Immunocal® treatment enhanced co-staining of Reelin and phospho-DAB1 in hippocampus CA1 of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to Reelin (shown in green) and phospho-DAB1 (pTyr232: shown in red), along with Draq (nuclear stain, shown in blue).

FIG. 29 shows results of studies in which Immunocal® treatment improved cognitive performance in the Barnes maze in J20 AD model mice. Following two months of Immunocal® treatment from 3 months-old to 5 months-old, hemizygous, female J20 AD mice were subjected to the Barnes maze to test spatial learning and memory. A) The delay in seconds for mice to find the escape pod during days 5 and 6 of the acquisition phase (combined) is shown. ##significantly different than hemizygous untreated (Hemi Unt) at $p < 0.01$. B) The delay in seconds for mice to find the escape pod during the probe phase (day 7) is shown. *significantly different than non-carrier control at $p < 0.05$. #significantly different than Hemi Unt at $p < 0.05$. ICAL=Immunocal® treated, NC=non-carrier. All statistical comparisons were made by one-way ANOVA with a post-hoc Tukey's test (n=4 mice per group).

DETAILED DESCRIPTION

Described herein are methods for increasing reelin (RELN) levels and/or in restoring other imbalances or abnormalities of gene expression in a subject in need thereof, as well as compositions for use in such methods. Methods and compositions provided herein may be used in the treatment of neuropsychiatric or neurodegenerative disorders, such as schizophrenia and Alzheimer's disease, for example. Compositions described herein may comprise whey protein isolate and/or whey protein concentrate, which is a source of the glutathione precursor cysteine. The provided methods and compositions are not limited to increasing or restoring RELN levels, and may alternatively or additionally be used to correct a number of other neurological dysregulations or abnormalities occurring in a subject in need thereof as described in detail herein.

It will be appreciated that embodiments and examples are provided herein for illustrative purposes intended for those skilled in the art, and are not meant to be limiting in any way. One or more illustrative embodiments have been described by way of example. It will be understood to persons skilled in the art that a number of variations and modifications can be made without departing from the scope of the invention as defined in the claims.

In an embodiment, there is provided herein a method for increasing or restoring reelin (RELN) levels in the brain of a subject in need thereof, said method comprising:

administering a composition comprising whey protein isolate and/or whey protein concentrate to the subject.

As will be understood, in certain embodiments, a subject in need thereof may include any subject for which increasing or restoring reelin (RELN) levels (and/or other gene expression imbalances or abnormalities as described in further detail hereinbelow) in the brain may be beneficial or desirable. By way of example, in certain embodiments, the subject may include a subject exhibiting at least one symptom or characteristic of a disease or disorder associated with low RELN levels. In certain embodiments, the subject may be a subject exhibiting at least one symptom or characteristic of a neuropsychiatric or neurodegenerative disorder such as schizophrenia or Alzheimer's disease, for example. By way of example, in certain embodiments, a subject in need of treatment may be determined as simply a subject exhibiting one or more symptoms of a disease or disorder for which the compositions described herein may prevent, ameliorate, reduce, or treat as further described hereinbelow.

As will be understood, an increase in RELN levels may refer to any increase in RELN gene expression in brain cells of the subject in need thereof. In certain embodiments, the RELN levels may be, for example, neuronal RELN levels, although RELN levels in other brain cells is also contemplated. In certain embodiments, the increase in RELN levels may be sufficient to restore RELN levels to, near, or above those of a healthy control subject or group. Gene expression may refer to the production of a polypeptide from the nucleic acid sequence of a gene. As well, gene expression may include both transcription and translation processes, and so an increase in RELN levels may refer to any increase in the production of a nucleic acid sequence such as a RELN mRNA (i.e. transcription), production of a RELN protein (i.e. translation), or both. In certain embodiments, RELN expression may include expression of full-length RELN protein (388 kDa), RELN cleavage product(s) (including, for example, 310 kDa and/or 180 kDa cleavage products), or any combination thereof. Increases in gene expression may be determined with reference to wild-type, healthy, baseline, or untreated levels, or levels measured at a previous time point, for example, as would be understood by a person of skill in the art.

Without wishing to be bound by theory, it will be understood that effective gene expression levels of a particular gene may also be considered increased if the rate of protein turnover/degradation of the expression product of the gene can be slowed or prevented.

Regardless of the underlying mechanism, references herein to increasing levels of a particular gene may include any suitable increase in mRNA levels and/or protein levels and/or activity levels of the gene as compared to wild-type, healthy, baseline, or untreated levels, or levels measured at a previous time point, or with reference to another suitable comparator level selected by the skilled person to suit a particular application.

As will also be understood, in additional embodiments, increases in RELN levels may refer to increases in signalling pathway activation, either as a result of increased RELN gene expression, or as a result of other factors resulting in increased pathway activation. In certain embodiments, a RELN level increase may be accompanied by, signalled by, or phenotypically represented by increased mRNA expression levels of GAD67, a gene acting downstream of RELN.

It will be understood that increases in neuronal RELN levels may occur generally throughout the brain of the subject, or may be limited to certain regions of the brain. In certain embodiments, RELN levels may be generally increased throughout the brain, or may be increased in particular brain regions such as the prefrontal cortex (PFC), the striatum (STM), the substantia nigra (SN), or the entorhinal cortex layer II, for example. In certain embodiments, a RELN level increase in a brain region may be accompanied by, signalled by, or phenotypically linked with increased mRNA expression levels of GAD67, a gene acting downstream of RELN. For example, GAD67 expression levels may be increased in the STM and/or the SN following treatment. In certain embodiments, neuronal RELN levels may be increased.

Compositions comprising whey protein isolate and/or whey protein concentrate may comprise any suitable composition comprising whey protein isolate and/or whey protein concentrate which may serve as a glutathione precursor by providing an enriched source of bioavailable cysteine after administration. As will be understood, whey proteins may generally be considered as a group a milk proteins which remain soluble in "milk serum" or whey after precipitation of caseins at pH 4.6 and 20° C. Major whey proteins in cow's milk, for example, may include beta-lactoglobulin ($\beta$L), alpha-lactalbumin ($\alpha$L), immunoglobulin, and serum albumin (SA). The product of industrial separation of this protein mixture from whey is typically referred to as whey protein isolate (WPI; also known as whey protein concentrate, WPC).

Compositions may, optionally, additionally comprise one or more pharmaceutically acceptable excipients, diluents, and/or carriers, one or more vitamins, essential amino acids, or minerals, one or more antioxidants, one or more additional glutathione precursors, and/or one or more nutritional diet supplement components, for example.

Compositions may also include, and/or be used in simultaneous or sequential combination with, one or more other drugs, pharmaceutical compositions, or therapies used in the treatment or management of neuropsychiatric diseases or neurodegenerative disorders known to the person of skill in the art, as will be selectable by the skilled person to suit the particular subject and/or application. By way of example, drugs used in the treatment of schizophrenia may include antipsychotics such as amisulpride, olanzapine, risperidone, and clozapine, and neuroleptics for controlling psychosis in schizophrenia. Drugs used in the treatment of Alzheimer's disease may include acetylcholinesterase inhibitors such as tacrine, rivastigmine, galantamine, and donepezil, and/or NMDA receptor antagonists such as memantine. Drugs used in the treatment of Parkinson's disease may include 1-dopa replacement therapy, for example.

A pharmaceutically acceptable carrier, diluent, or excipient may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disintegrants known in the art (see, for example, Remington: The Science and Practice of Pharmacy (2006); herein incorporated by reference in its entirety). Examples of pharmaceutically acceptable carriers, diluents, and excipients may be found in, for example, Remington's Pharmaceutical Sciences (2000—20th edition) and in the United States Pharmacopeia: The National Formulary (USP 24 NF19) published in 1999.

In certain embodiments, a whey protein isolate or a whey protein concentrate as described herein may include any suitable extract, isolate, concentrate, or other product which is obtainable from whey protein. As will be understood, whey protein comprises a mixture of milk proteins that remain soluble in milk serum or whey after precipitation of caseins, for example. Whey is often encountered as a by-product of cheese or casein manufacture. Major whey protein components may include, for example but without wishing to be limiting, beta-lactoglobulin, alpha-lactalbumin, immunoglobulin, and serum albumin. Although bovine milk is commonly used for obtaining whey protein, it will be understood that other sources of milk are also contemplated. Whey protein isolate (WPI) is generally considered in the field as having $\geq$90% protein, while whey protein concentrate (WPC) may have protein concentrations below 90%; however, for the present purposes, WPI and WPC may be considered as generally interchangeable unless otherwise explicitly specified.

In particular embodiments, a whey protein isolate or whey protein concentrate as described herein is preferably an undenatured whey protein isolate or whey protein concentrate. Undenatured isolates and concentrates are those in which one or more of the protein component(s) obtainable from whey protein remain substantially undenatured (i.e. tertiary protein structure is substantially maintained and/or disulfide bonds between cysteine residues remain substantially intact) in the whey protein isolate or whey protein concentrate.

Whey proteins contain sulfur-containing amino acids such as cysteine (Cys). These Cys amino acid residues may occur as free residues (i.e. —SH; reduced), or two Cys residues may form intramolecular disulfide bonds (S—S; oxidized) so as to produce cystine dimers. Such disulfide bonds play a role in protein folding. In certain embodiments, undenatured whey protein isolates or whey protein concentrates as described herein may include those having at least about 2 wt % cystine dimer. Examples of undenatured whey protein isolates and whey protein concentrates may include those having about 2 wt % cystine dimer, or more than about 2 wt % cystine dimer. For example, the wt % of cystine dimer may be about 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 wt %, or the wt % cystine dimer may fall within a range spanning between any two such values, or a range bounded at the lower end by any such value.

Whey protein isolates and whey protein concentrates may be obtained using any suitable technique(s) as will be known to the person of skill in the art having regard to the teachings herein. Such techniques may include ultrafiltration using membranes, ion exchange methods, and membrane methods, for example. Discussions of suitable techniques may be found in, for example, Advanced Dairy Chemistry, McSweeney and Mahony (Ed.), Volume 1B: Proteins: Applied Aspects, 4th Edition, Springer, ISBN: 978-1-4939-2799-9 (herein incorporated by reference in its entirety).

Examples of suitable compositions comprising whey protein isolate and/or whey protein concentrate are described in Canadian patent nos. 1,333,471, 1,338,682, 2,142,277, and 2,090,186, each of which is herein incorporated by reference in its entirety. CA 2,142,277, for example, provides detailed preparation processes and analytical characterization of particularly preferred compositions comprising whey protein isolate, including the composition known as Immunocal®. This exemplary whey protein isolate composition as described in CA 2,142,277 may be characterized by having a solubility index of about 99.5% at pH 4.6; about 58% βL (beta-lactoglobulin) protein composition, about 11% αL (alpha-lactalbumin) protein composition, about 10% serum albumin (i.e. BSA) protein composition, and about 22% immunoglobulin (i.e. Ig) protein composition. A process for preparing such a composition is also described in detail in CA 2,142,277. Immunocal® (Natural Product Number (NPN) 80004370 issued with Health Canada) is now a commercially available whey protein isolate composition available from Immunotec®.

Further description of whey protein isolates and concentrates may be found in Example 2 below.

In an embodiment, compositions as described herein may be administered orally. For example, compositions as described herein may be reconstituted in, or may comprise, a liquid carrier (for example, water or juice), allowing for straightforward oral administration. The person of skill in the art having regard to the teachings herein will be able to select a suitable administration to suit a particular subject and/or particular therapeutic application.

In certain non-limiting embodiments, it is contemplated that compositions as described herein may be administered orally in an amount suitable for achieving a desired effect. In certain non-limiting embodiments, compositions as described herein may be administered orally in a dosage of about 20-40 grams per day, for example, and may be administered once or more than once daily, for example.

Compositions as described herein may, in certain embodiments, be used in combination with a nucleic acid or expression vector which can cause overexpression of RELN or a functional RELN mimic, or may be used in combination with RELN protein or a functional RELN protein mimic, in order to increase effective RELN levels in the subject. The nucleic acid and amino acid sequences of human RELN are provided in FIG. 11 as SEQ ID NOs. 1 and 2, respectively. Murine RELN sequences are also shown in FIG. 11, and homologs in other species are available from the national center for biotechnology information (NCBI).

In a further embodiment of the methods described above, the methods may further comprise an additional step of:

measuring an initial RELN level of the subject and comparing the measured initial RELN level to a healthy RELN level, wherein the subject is identified as having a reduced RELN level in need of increase when the measured RELN level is less than the healthy RELN level.

As will be understood, a healthy RELN level may be a RELN level as determined in a wild type, control, or healthy subject or a group of healthy subjects, or as determined from the subject at a previous time point where the subject was healthy, for example. The healthy level may be a specific or approximate threshold level, or may be a range spanning between upper and lower thresholds.

It will be understood that such a step of measuring may be performed either before or after administration of the composition comprising the whey protein isolate and/or whey protein concentrate, or both. Where the step of measuring is performed before the administration, the measuring step may be considered as a screening step, allowing for the identification of subjects in need of the treatment, of subjects who may particularly benefit from the treatment, and/or of subjects belonging to a patient subpopulation which may be particularly susceptible to the treatment. Where the step of measuring is performed after the administration, the measuring step may be considered as a step of determining treatment efficacy, allowing for the identification of subjects in need of a subsequent, repeated, or adjusted treatment, of subjects who may particularly benefit from a repeated treatment, and/or of subjects belonging to a patient subpopulation which may be particularly susceptible to the treatment.

As will be recognized, the RELN level of the subject may be measured using any suitable method capable of identifying a reduced neuronal RELN level. RELN levels generally representative of whole-brain RELN levels may be determined, or RELN levels in particular brain regions may be determined. In certain embodiments, neuronal RELN levels may be determined. Methods for measuring RELN levels may include those quantitating RELN mRNA levels, RELN protein levels, or both, in the brain or in relevant brain region(s). Methods may involve PCR. ELISA, mass spectrometry, and/or neuroimaging methods, among others. While direct monitoring of Reelin levels in brain parenchyma of living humans may be challenging, indirect monitoring may be possible by analyzing cerebrospinal fluid (CSF), which may be used to correlate with brain tissue concentrations by, for example, immunoassay and/or mass spectrometry.

In certain embodiments, neuronal RELN levels of the subject may be determined through analysis of a sample obtained from the subject, such as a biopsy sample, or a fluid sample such as a blood sample or cerebrospinal fluid sample. In certain embodiments, it is contemplated herein that neuronal RELN levels of the subject may be measured by determining RELN levels in neuronal exosomes circulating in bodily fluids such as blood. As will be understood, neuronal exosomes carry particular cell surface markers allowing their isolation, at which point RELN levels may be quantitated using techniques such as ELISA or others.

In certain embodiments, it is contemplated that reelin expression levels may be ascertained or estimated by determining reelin expression levels in neural-derived exosomes isolated from human plasma, for example. Such plasma exosomes may be enriched in neural sources by, for example, anti-human L1CAM antibody immunoabsorption. By way of example, reelin and other extracted exosomal proteins may be quantified by ELISA and normalized with the exosomal marker, CD81 (Goetzl et al., *Neurology*, 85:40-47, 2015; herein incorporated by reference in its entirety).

In certain embodiments of the above methods, the subject in need of treatment may be any subject having a reduced RELN level which is below that of a healthy subject or healthy control group. The reduced RELN level may occur generally throughout the brain tissue of the subject, or may be localized to particular regions such as the prefrontal cortex, the striatum, the substantia nigra, and/or the entorhinal cortex layer II, for example. The RELN level may be, for example, a neuronal RELN level. In certain further embodiments, the subject in need of treatment may be a subject suffering from, or at risk of developing, a neuropsychiatric or neurodegenerative disorder. The neuropsychiatric or neurodegenerative disorder may be, for example, schizophrenia, Alzheimer's disease, bipolar disease with psychosis, Parkinson's disease (PD), or another such disease or condition.

In certain embodiments, a neuropsychiatric or neurodegenerative disorder may include neurological disorders characterized by enhanced expression of heme oxygenase-1 and/or increased oxidative stress in brain. Such diseases may include, but are not limited to, Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, and/or autism.

In still another embodiment, there is provided herein a method for treating, preventing, or ameliorating/reducing the symptoms of, a neuropsychiatric disease or a neurodegenerative disorder in a subject in need thereof, said method comprising:

administering a composition comprising whey protein isolate and/or whey protein concentrate to the subject.

As will be understood, the composition comprising whey protein isolate and/or whey protein concentrate, which has already been described in detail hereinabove, may be administered to increase reelin (RELN) levels, for example neuronal RELN levels, in the subject, or to restore RELN levels in the subject to or above a healthy level, or to within a healthy range as determined by measuring RELN levels in a healthy subject, or in a group of healthy subjects, for example.

In a further embodiment, the method may further comprise a step of:

measuring an initial RELN level of the subject and comparing the measured RELN level to a healthy RELN level, wherein the subject is identified as having a reduced RELN level in need of increase when the measured initial RELN level is less than the healthy RELN level.

It will be understood that such a step of measuring may be performed either before or after administration of the composition comprising the whey protein isolate and/or whey protein concentrate, or both. Where the step of measuring is performed before the administration, the measuring step may be considered as a screening step, allowing for the identification of subjects in need of the treatment, of subjects who may particularly benefit from the treatment, and/or of subjects belonging to a patient subpopulation which may be particularly susceptible to the treatment. Where the step of measuring is performed after the administration, the measuring step may be considered as a step of determining treatment efficacy, allowing for the identification of subjects in need of a subsequent, repeated, or adjusted treatment, of subjects who may particularly benefit from a repeated treatment, and/or of subjects belonging to a patient subpopulation which may be particularly susceptible to the treatment. Examples of methods for measuring neuronal RELN levels have already been described hereinabove.

As will be understood, neuropsychiatric and neurodegenerative disorders may be characterized by multiple imbalances or abnormalities in gene expression. Without wishing to be bound by theory or considered limiting in any manner, the results presented herein suggest that treatment with a composition comprising whey protein isolate may not only increase or restore RELN levels, but may also, or alternatively, be used to at least partially alleviate or otherwise restore several imbalances or abnormalities in gene expression which are believed to be involved in certain neuropsychiatric and neurodegenerative disorders. As such, in certain alternative, or additional embodiments, the compositions comprising whey protein isolate as described herein may be administered for restoring serotonin levels; normalizing MnSOD mRNA levels; restoring GAD67 levels; augmenting GSH reserves in the brain; reversing reduction of Nrxn1; reversing reduction of Nlgn2; preventing HMOX1-related disregulation of miR-128 expression: improving HMOX1-related changes in brain dopamine, dopamine metabolites, serotonin, norepinephrine, and epinephrine; restoring deficient DOPAC/DA ratios; augmenting norepinephrine and dopamine concentrations in the prefrontal cortex; and/or correcting prefrontal cortex hypodopaminergia in the subject. As well, in certain further alternative or additional embodiments, the compositions comprising whey protein isolate as described herein may be administered for augmenting GSH reserves in the brain; normalizing brain MnSOD mRNA levels, restoration of redox homeostasis; normalization of brain dopamine, serotonin, norepinephrine, and/or epinephrine levels; normalization of brain DOPAC/DA ratios; restoring GAD67 levels: reversing reduction of Nrxn1; reversing reduction of Nlgn2; preventing HMOX1-related dysregulation of miR-128 expression; and/or ameliorating hyperlocomotion and/or stereotypic behaviour; or any combination thereof; in the subject.

As will be understood, the neuropsychiatric disease or neurodegenerative disorder may be, for example, schizophrenia or Alzheimer's disease, wherein one or more of these imbalances or abnormalities in gene expression may be occurring. In certain embodiments, it is contemplated that a neuropsychiatric or neurodegenerative disorder may include neurological disorders characterized by enhanced expression of heme oxygenase-1 and/or increased oxidative stress in brain. Such diseases may include, but are not limited to, Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, and/or autism.

In certain embodiments, compositions comprising whey protein isolate and/or whey protein concentrate as described herein may be used for increasing reelin (RELN) levels (such as, for example, neuronal RELN levels) in a subject in need thereof, or may be used in the manufacture of a medicament for increasing reelin (RELN) levels in a subject in need thereof, for example. Alternatively, or in addition, such compositions may be used for treating, preventing, or ameliorating the symptoms of, a neuropsychiatric disease or a neurodegenerative disorder, or may be used in the manufacture of a medicament for treating, preventing, or ameliorating the symptoms of a neuropsychiatric disease or a neurodegenerative disorder, in a subject in need thereof, for example.

In still other embodiments, compositions comprising whey protein isolate and/or whey protein concentrate as described herein may be for use in restoring serotonin levels; augmenting GSH reserves in the brain: normalizing MnSOD mRNA levels; restoring GAD67 levels; reversing reduction of Nrxn1; reversing reduction of Nlgn2; preventing HMOX1-related dysregulation of miR-128 expression; improving HMOX1-related changes in brain dopamine, dopamine metabolites, serotonin, norepinephrine, and epinephrine: restoring deficient DOPAC/DA ratios; augmenting norepinephrine and dopamine concentrations in the prefrontal cortex; and/or correcting prefrontal cortex hypodopaminergia in a subject in need thereof, or in the manufacture of a medicament for achieving such a result.

In still other embodiments, compositions comprising whey protein isolate and/or whey protein concentrate as described herein may be for use in augmenting GSH reserves in the brain; normalizing brain MnSOD mRNA levels: restoration of redox homeostasis; normalization of brain dopamine, serotonin, norepinephrine, and/or epinephrine levels: normalization of brain DOPAC/DA ratios; restoring GAD67 levels; reversing reduction of Nrxn1; reversing reduction of Nlgn2; preventing HMOX1-related dysregulation of miR-128 expression; and/or ameliorating hyperlocomotion and/or stereotypic behaviour: or any combination thereof: in a subject in need thereof, or in the manufacture of a medicament for achieving such a result.

It will be understood that compositions as described herein may be administered as part of a treatment regimen including other drugs, pharmaceutical compositions, or therapies used in the treatment of neuropsychiatric diseases or neurodegenerative disorders. Compositions as described herein may be for administration simultaneously, sequentially, in combination with, or separately from such other drugs, pharmaceutical compositions, or therapies.

Compositions as described herein may be for use in treating a neuropsychiatric or neurodegenerative disease or disorder, or may be for use as part of a preventative strategy for preventing or delaying onset of a neuropsychiatric or neurodegenerative disease or disorder such as schizophrenia or Alzheimer's disease, or both.

In certain embodiments, compositions as described herein may be for use in treating neurological disorders characterized by enhanced expression of heme oxygenase-1 and/or increased oxidative stress in brain. Such diseases may include, but are not limited to, Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, cerebral malaria, schizophrenia, bipolar disease with psychosis, and/or autism.

In still another embodiment, there is provided herein a method for restoring serotonin levels; normalizing MnSOD mRNA levels: augmenting GSH reserves in the brain; restoring GAD67 levels; reversing reduction of Nrxn1; reversing reduction of Nlgn2; preventing HMOX1-related dysregulation of miR-128 expression; improving HMOX1-related changes in brain dopamine, dopamine metabolites, serotonin, norepinephrine, and epinephrine: restoring deficient DOPAC/DA ratios; augmenting norepinephrine and dopamine concentrations in the prefrontal cortex; and/or correcting prefrontal cortex hypodopaminergia in a subject in need thereof, said method comprising:

administering a composition comprising whey protein isolate and/or whey protein concentrate to the subject.

In certain embodiments of the above method, the subject may be a subject suffering from, or at risk of developing, a neuropsychiatric or neurodegenerative disorder such as, for example, schizophrenia or Alzheimer's disease.

In certain embodiments of the above method, the subject may be suffering from, or at risk of developing, a neurological disorder characterized by enhanced expression of heme oxygenase-1 and/or increased oxidative stress in brain. Such diseases may include, but are not limited to, Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, and/or autism.

In yet another embodiment, there is provided herein a method for augmenting GSH reserves in the brain; normalizing brain MnSOD mRNA levels: restoration of redox homeostasis; normalization of brain dopamine, serotonin, norepinephrine, and/or epinephrine levels; normalization of brain DOPAC/DA ratios: restoring GAD67 levels; reversing reduction of Nrxn1; reversing reduction of Nlgn2; preventing HMOX1-related dysregulation of miR-128 expression; and/or ameliorating hyperlocomotion and/or stereotypic behaviour; or any combination thereof; in a subject in need thereof, said method comprising:

administering a composition comprising whey protein isolate and/or whey protein concentrate to the subject.

In certain embodiments of the above method, the subject may be a subject suffering from, or at risk of developing, a neuropsychiatric or neurodegenerative disorder such as, for example, schizophrenia or Alzheimer's disease.

In certain embodiments of the above method, the subject may be suffering from, or at risk of developing, a neurological disorder characterized by enhanced expression of heme oxygenase-1 and/or increased oxidative stress in brain. Such diseases may include, but are not limited to, Alzheimer's disease, Parkinson's disease, dementia with Lewy bodies, frontotemporal dementia, amyotrophic lateral sclerosis, other motor neuron disorders, Down's syndrome, Creutzfeldt-Jakob disease, other prion diseases, multiple sclerosis, cerebral ischemia, cerebral hemorrhage, traumatic brain injury, spinal cord injury, cerebral malaria, schizophrenia, bipolar disease with psychosis, and/or autism.

As will be understood, compositions comprising whey protein isolate and/or whey protein concentrate as described herein may serve as a glutathione precursor by providing an enriched source of bioavailable cysteine following administration. Several neuropsychiatric and neurodegenerative disorders have been linked to oxidative stress and/or glutathione (GSH) deficits in brain tissue. As discussed in detail herein, treatment with a composition comprising whey protein isolate has been observed to restore GSH homeostasis in the CNS of a mouse disease model, and to augment GSH reserves in the brains of wild-type animals. These results demonstrate that compositions as described herein may be used to augment GSH stores and antioxidant defenses in the healthy and diseased brain.

As such, in certain embodiments, there is provided herein a method for augmenting glutathione (GSH) levels in brain cells, or augmenting whole brain GSH/glutathione disulfide (GSSG) ratios, of a subject in need thereof, said method comprising:

administering a composition comprising whey protein isolate and/or whey protein concentrate to the subject.

As will be understood, in certain embodiments, such augmentation of glutathione (GSH) levels, or GSH/GSSG ratios, in the subject may accompany an increase or restoration of RELN levels or other imbalances or abnormalities in gene expression achieved using any of the other methods as described hereinabove. In additional embodiments, compositions as described herein may be used simultaneously, or sequentially, with other glutathione precursor compounds or compositions.

In still another embodiment, there is provided herein a kit comprising a composition comprising whey protein isolate and/or whey protein concentrate as described hereinabove, and one or more of a pharmaceutically acceptable excipient, diluent, carrier, vitamin, essential amino acid, mineral, antioxidant, glutathione precursor, nutritional diet supplement component, or drug, pharmaceutical composition, or therapy used in the treatment of a neuropsychiatric disease or neurodegenerative disorder.

Such kits may additionally, or alternatively, comprise instructions for use of the kit in the treatment of a neuropsychiatric disease or neurodegenerative disorder, or for use of the kit in increasing or restoring RELN levels (for example, but not limited to, neuronal RELN levels); augmenting GSH reserves in the brain: restoring serotonin levels: normalizing MnSOD mRNA levels: restoring GAD67 levels; reversing reduction of Nrxn1; reversing reduction of Nlgn2; preventing HMOX1-related dysregulation of miR-128 expression; improving HMOX1-related changes in brain dopamine, dopamine metabolites, serotonin, norepinephrine, and epinephrine; restoring deficient DOPAC/DA ratios; augmenting nonepinephrine and dopamine concentrations in the prefrontal cortex; and/or correcting prefrontal cortex hypodopaminergia in a subject in need thereof.

In further embodiments, such kits may additionally, or alternatively, comprise instructions for use of the kit in the treatment of a neuropsychiatric disease or neurodegenerative disorder, or for use of the kit in augmenting GSH reserves in the brain: normalizing brain MnSOD mRNA levels: restoration of redox homeostasis; normalization of brain dopamine, serotonin, norepinephrine, and/or epinephrine levels: normalization of brain DOPAC/DA ratios; restoring GAD67 levels; reversing reduction of Nrxn1; reversing reduction of Nlgn2; preventing HMOX1-related dysregulation of miR-128 expression; and/or ameliorating hyperlocomotion and/or stereotypic behaviour; or any combination thereof; in a subject in need thereof In yet another embodiment, there is provided herein a method for measuring reelin (RELN) levels in a subject, said method comprising:

isolating or enriching a neuronal exosome sample from a bodily fluid sample obtained from the subject using one or more neuronal exosome-specific cell surface markers; and measuring a RELN level of the neuronal exosome sample.

In an embodiment of the method above, the bodily fluid sample may be a cerebrospinal fluid (CSF) sample, whole blood sample, plasma sample, or another processed or unprocessed blood sample obtained from the subject. In still another embodiment, the step of isolating or enriching may involve a pull-down type assay targeting the one more neuronal exosome-specific cell surface markers, or another suitable isolating method. In still another embodiment, the RELN level may be measured by quantitating RELN mRNA levels, protein levels, or both, and may be determined using a suitable PCR assay, immunoassay such as ELISA, mass spectrometry, or another suitable assay for quantitating RELN.

As will be understood, neuronal exosomes carry particular cell surface markers allowing their isolation. Neuronal exosomes may be isolated/enriched by, for example, antihuman L1CAM antibody immunoabsorption techniques. By way of example, reelin and other extracted exosomal proteins may be quantified by ELISA and normalized with the exosomal marker. CD81 (Goetzl et al., *Neurology*, 85:40-47, 2015; herein incorporated by reference in its entirety).

Example 1—Amelioration of Deficits in GFAP.HMOX1 Mouse Model of Schizophrenia

The following example describes experimental results obtained from treating wild type mice, and a mouse model of schizophrenia, with Immunocal®, a composition comprising whey protein isolate. Under the experimental conditions used, a number of beneficial effects were observed in the animals, indicating the potential such compositions may possess in the treatment of neuropsychiatric or neurodegenerative disorders and/or in restoring neuronal imbalances or gene expression abnormalities.

Schizophrenia is a neuropsychiatric disorder that features neural oxidative stress and glutathione (GSH) deficits. Oxidative stress is augmented in brain tissue of GFAP.HMOX1 transgenic mice which exhibit schizophrenia-relevant characteristics. The whey protein isolate, Immunocal®, serves as a GSH precursor upon oral administration. In this Example, GFAP.HMOX1 transgenic mice were treated daily with Immunocal between the ages of 5 and 6.5 months. Immunocal attenuated many of the behavioral, neurochemical and redox abnormalities observed in GFAP.HMOX1 mice. In addition to restoring GSH homeostasis in the CNS of the transgenic mice, the whey protein augmented GSH reserves in the brains of wild-type animals. These results demonstrate that whey protein consumption augments GSH stores and antioxidant defenses in the healthy and diseased mammalian brain. Furthermore, administration of Immunocal was found to increase reelin (RELN) levels in the animal models tested, a particularly interesting experimental finding. Results obtained indicate that whey protein supplementation may constitute a safe and effective modality for the management of schizophrenia and other neuropsychiatric and neurodegenerative disorders.

The HMOX1 gene coding for the 32 kDa stress protein, heme oxygenase-1 (HO-1) is exquisitely sensitive to induction by stressors implicated in the development of SCZ[9]. We previously demonstrated that the accumulation of heme-derived ferrous iron and carbon monoxide accruing from transfection of HMOX1 in cultured rat astrocytes promotes mitochondrial damage and predisposes co-cultured neuronal elements to oxidative injury. Our laboratory recently engineered a conditional GFAP.HMOX1 transgenic mouse that selectively over-expresses human HO-1 in the astrocytic compartment under temporal control by the Tet-Off system. After 48 weeks of continuous HMOX1 induction, these mice exhibit a set of robust behavioural (some sex-specific), neurochemical, neuropathological and developmental features reminiscent of human SCZ and animal models of the disease. Specific abnormalities documented in the GFAP.HMOX1 mice germane to SCZ include hyperlocomotion, behavioral stereotypy and impaired prepulse inhibition to acoustic startle; increased basal ganglia dopamine (DA) and serotonin concentrations; suppressed neuronal reelin immunoreactivity; dysgenesis of the hippocampal dentate gyrus[9]; and ventriculomegaly (unpublished results). As in the HMOX1-transfected glial cultures (vide supra), pathological deposition of redox-active iron, oxidative mitochondrial damage and mitophagy are clearly demonstrable in the brains of GFAP.HMOX1 mice[9, 10]. Depletion of the intracellular antioxidant tripeptide, glutathione (GSH) and oxidative stress have been documented in SCZ-affected human neural tissues[11-13]. Moreover, administration of glutathione precursors has been shown to improve symptomatology in animal models of SCZ and in patients with the disease[14].

The delivery of the amino acids, cysteine and cystine is believed to be the rate-limiting factor for the synthesis of intracellular glutathione in brain and other tissues. Immunocal® is an un-denatured bovine whey protein isolate which serves as a glutathione precursor by providing an enriched source of bioavailable cysteine after oral administration. Immunocal has been tested in human clinical trials for its role in the management of diverse conditions including HIV/AIDS, cancer and cystic fibrosis, and the optimization of sports performance in healthy subjects[15-18].

As part of the studies described herein, experiments were performed in order to ascertain, among other things, whether (i) GSH concentrations and GSH:GSSG ratios are deficient in salient brain regions of GFAP.HMOX1 mice by 6.5 months of age; (ii) whether Immunocal treatment augments brain GSH stores and alleviates SCZ-like abnormalities in these animals; and (iii) whether Immunocal treatment is able to restore neuronal levels of RELN and/or other imbalances or abnormalities of gene expression in these animal models of neuropsychiatric or neurodegenerative disorders.

Materials and Methods

The GFAP.HMOX1 mouse: Transgenic (TG) mice (FVB strain) were generated expressing GFAP.tTA.TRE.Flag.hHO-1 final constructs, as previously described. Incorporation of the Glial Fibrillary Acidic Protein (GFAP) promoter selectively targets human HMOX1 gene expression to the astrocytic compartment. To permit conditional expression of the transgene during select periods of neuroembryogenesis, perinatal and mature life, a tetracycline-suppressible ('tet-off') promoter element was included in the experimental design[10].

Whey protein (Immunocal) supplementation: Immunocal® is a dietary natural health product with an NPN 80004370 issued by Natural Health Product Directorate (NHPD) Health Canada. It is a natural source of the glutathione precursor, cysteine. Immunocal is fat-free, contains less than 1% lactose and has a high protein biological value (>110 BV) providing all essential amino acids. It has been tested in experimental animals[19-21] and human clinical trials[22-24] and is marketed worldwide for enhancement of the immune system.

Experimental protocols have been approved by the Animal Care Committee of McGill University in accordance with the guidelines of the Canadian Council on Animal Care. Mice were kept at a room temperature of 21±1° C. with a 12 h light/dark schedule. All the mice were bred and cared for in the Animal Care Facilities at the Lady Davis Institute for Medical Research. Male and female heterozygous GFAP.HMOX1 (continuously expressing the HMOX1 transgene) and wild-type (WT) mice at 5 months of age were treated daily with Immunocal at 33 mg/ml drinking water vs.

drinking water containing 33 mg/nil casein (control). Daily drinking volume per mouse was recorded. After 4-6 weeks of treatment, all animals were assessed for the behavioral, neurochemical and neuropathological endpoints described below. Fur texture, body weight and survival rates were monitored as indices of general health.

Behavioral tests: GFAP.HMOX1 mice and their WT littermates were transferred to the Neurophenotyping Centre of the Douglas Mental Health University Institute (Montreal) for behavioral analyses. The animals were tested for locomotor activity 25 and startle response [prepulse inhibition (PPI)][26].

Surgical procedures: (1) Mouse brains were fixed by transcardial perfusion as previously described[27] with minor modifications[9]. Briefly, the animals were deeply anesthetized with rodent mixture containing ketamine, xylazine, acepromazine and saline and perfused with 200 ml of ice-cold saline followed by 250 ml of cold 4% paraformaldehyde in 0.1M PBS, pH 7.4, for light-microscopic analysis, or cold 2.5% glutaraldehyde in 0.1 M sodium cacodylate buffer, pH 7.5, containing 0.1% $CaCl_2$) for transmission electron microscopy (TEM). The brains were removed and immersed in the same fixatives for 24 h at 4° C. For histomorphology, brains were embedded in paraffin. For RNA and protein expression assays, mouse brains were frozen in dry ice immediately after transcardial perfusion with 200 ml of ice-cold PBS and stored at −80° C. (2) For HPLC and glutathione assays, animals were decapitated and brains were removed and frozen in 2-methylbutane at −40° C. and stored at −80° C. until use[28].

Glutathione assay: An HPLC method was utilized to measure reduced (GSH) and oxidized (GSSG) glutathione concentrations in brain hemispheres[29]. GSH and GSSG levels were determined in four sub-regions: prefrontal cortex (PFC), hippocampus (HC), striatum (STM) and the remainder of the hemisphere (excluding cerebellum; REM).

Neurotransmitter measurement: Brains were cut in 400-500 micron serial sections using a cryostat and selected regions (PFC, HC, STM, and substantia nigra (SN)) were dissected using 0.5-2.0 mm micropunches[30, 31]. Tissues were homogenized in 0.25 M perchloric acid and centrifuged at 4° C. (10,000 rpm, 15 min), and supernatants were collected. The concentrations of monoamines [i.e., dopamine (DA), norepinephrine (NE), epinephrine (E), and 5-hydroxytryptamine (5-HT)] and monoamine metabolites [i.e., 3,4-dihydroxyphenylacetic acid (DOPAC), homovanillic acid (HVA), and 5-hydroxyindoleacetic acid (5-HIAA)] were determined using HPLC with electrochemical detection (HPLC-EC), in the laboratory of Dr. A. Gratton (Douglas Hospital. Montreal), as previously described[9, 32].

mRNA and miRNA Expression:

Total RNA extraction, polyadenylation, and cDNA synthesis—Total RNA from each dissected brain region was extracted in Trizol according to the manufacturer's instructions (Invitrogen). Two and half micrograms of total RNA were subjected to RT-qPCR using RevertAid First Strand cDNA Synthesis Kit (Thermo Fisher) and anchored-oligo-dT18 primer. miRNA polyadenylation was performed followed by cDNA synthesis using 2 μg of polyadenylated total RNA with miScript II RT Kit (Qiagen).

mRNA and miRNA RT-qPCR—The Applied Biosystems 7500 Fast Real-Time PCR System (Applied Biosystems by Life Technologies) was used to quantify mRNA and miRNA with EvaGreen RT-qPCR Mastermix-Low ROX reagent (Diamed) according to manufacturer's instructions. Twenty nanograms (ng) and 2.5 ng of cDNA were quantified for mRNA and miRNA, respectively, using the above reagent (Diamed) via RT-qPCR. The forward (F) and reverse (R) primer sequences used to detect mouse mRNA were a) provided by OriGene Technologies (Rockville, MD), which were designed to span an exon-intron boundary and the possible contaminating genomic DNA was not amplified because the primer cannot anneal to the template[33], b) designed with Primer Express Software Version 3.0 (Applied Biosystems by Life Technologies) and validated by published study, c) validated by published study. Additional checks of melting curve for each reaction was always carried out to assess contamination of genomic DNA or poor primer design (primer dimer formation) (Applied Biosystems by Life Technologies). Primer sequences were as follows:

```
(1) manganese superoxide dismutase (MnSOD) b:
                                      (SEQ ID NO: 3)
5'-GCTGCACCACAGCAAGCA-3' (F)

(SEQ ID NO: 4)
and
5'-TCGGTGGCGTTGAGATTGT-3' (R);

(2) Reelin (Reln) b:
                                      (SEQ ID NO: 5)
5'-GCCACGCCACAATGGAA-3' (F)
and (SEQ ID NO: 6)
5'-CGACCTCCACATGGTCCAA-3' (R);

(3) Glutamate Decarboxylase 1 (Brain, 67 kDa;
Gad-1/67) a:
                                      (SEQ ID NO: 7)
5'-CGCTTGGCTTTGGAACCGACAA-3' (F)
and (SEQ ID NO: 8)
5'-GAATGCTCCGTAAACAGTCGTGC-3' (R);

(4) Neurexin 1 (Nrxn1) a:
                                      (SEQ ID NO: 9)
5'-ACCGTGCCTTAGCAATCCTTGC-3' (F)
and (SEQ ID NO: 10)
5'-GTCGTAGCTCAAAACCGTTGCC-3' (R);

(5) Neuroligin 2 (Nlgn 2) a:
                                      (SEQ ID NO: 11)
5'-CGATGTCATGCTCAGCGCAGTA-3' (F)
and (SEQ ID NO: 12)
5'-CCACACTACCTCTTCAAAGCGG-3' (R);

(6) As an internal reference, β-Actin c mRNA was
usedand probed using a pair of primers
[5'-CAGCAGATGTGGATCAGCAAG-3' (F) (SEQ ID NO: 13)

and 5'-GCATTTGCGGTGGACGAT-3' (R)] 34 (SEQ ID NO: 14).
```

Mature DNA sense sequences (obtained from miRBase: http://microma.sanger.ac.uk/) were used as forward primers to detect miRNA. The miRNA primer sequences used were mmu-miR-137-5p (5'-acgggtattcttgggtggataat-3') (SEQ ID NO: 15), mmu-miR-137-3p (5'-ttattgcttaagaatacgcgtag-3') (SEQ ID NO: 16), nunu-miR-181a (5'-aacattcaacgctgtcggt-gagt-3') (SEQ ID NO: 17), mmu-miR-128-1-5p (5'-cggggccgtagcactgtctga-3') (SEQ ID NO: 18), mmu-miR-128-3p (5'-tcacagtgaaccggtctcttt-3') (SEQ ID NO: 19), mmu-miR-138 (5'-agctggtgttgtgaatcaggccg-3') (SEQ ID NO: 20), and mmu-miR-200c (5'-taatactgccgggtaatgatgga-3') (SEQ ID NO: 21).

As a reference sequence, mouse small nucleolar RNA 202 (snoRNA-202) was probed using an internal forward primer (5'-agtacttttgaacccttttcca-3')[35]. (SEQ ID NO: 22) mRNA and miRNA expression fold changes between groups were calculated using the ΔΔCt method relative to controls following normalization with levels of snoRNA-202[36].

Data mining for candidate targets of lead miRNAs— microRNA target predictions were adduced from the literature or the following databases: miRBase website (http://microma.sanger.ac.uk) 37; TargetScan (http://www.targetscan.org), RNA22 (http://cbcsrv.watson.ibm.com/rna22_targets.html) and PicTar (http://pictar.mdcberlin.de).

Neuromorphological analysis: Coronal brain sections (4 μm) were deparaffinized in toluene and rehydrated in a series of graded alcohol solutions followed by $H_2O$. Sections were stained with hematoxylin and eosin (H&E). The preparations were examined using a Leica DM LB2 microscope. Bregma coordinates were identified using the mouse brain atlas of Paxinos and Franklin[38]. The lateral ventricles of left and right hemispheres were examined at +0.50 mm from bregma. The width and height of the hippocampus and the length of the dentate gyrus granule cell layer were measured at −1.55 mm to −1.99 mm from bregma with the aid of an ocular grid by a single investigator unaware of the tissue source.

Statistical analyses: Data are expressed as means f SEM. For locomotor activity, analyses were performed in cases with more than two groups using a genotype (TG and WT) by treatment (Immunocal and casein) ANOVA followed by Newman-Keuls post hoc comparisons to assess significant main effects within groups. For PPI assessment of WT and TG mice (with Immunocal or casein), two-way ANOVA was used to analyze serial intensity tests considering two factors (genotype and intensity). For GSH assay and quantitative hippocampal pathology, the comparison was made between two genotypes for each item using Student's t test (one or two-tailed with 95% confidence intervals). Fold changes in TG mice versus WT mice for qPCR assays were analyzed with paired Student's t test (two-tailed). Unless stated otherwise in the figure legends, statistical significance was set at $P<0.05$.

Results

Toxicity:

Immunocal exposure resulted in no overt toxicity as evidenced by normal body weights, fur texture and survival rates relative to age-matched, casein-treated (current study) and untreated 9 FVB control mice (data not shown).

Figure 1:
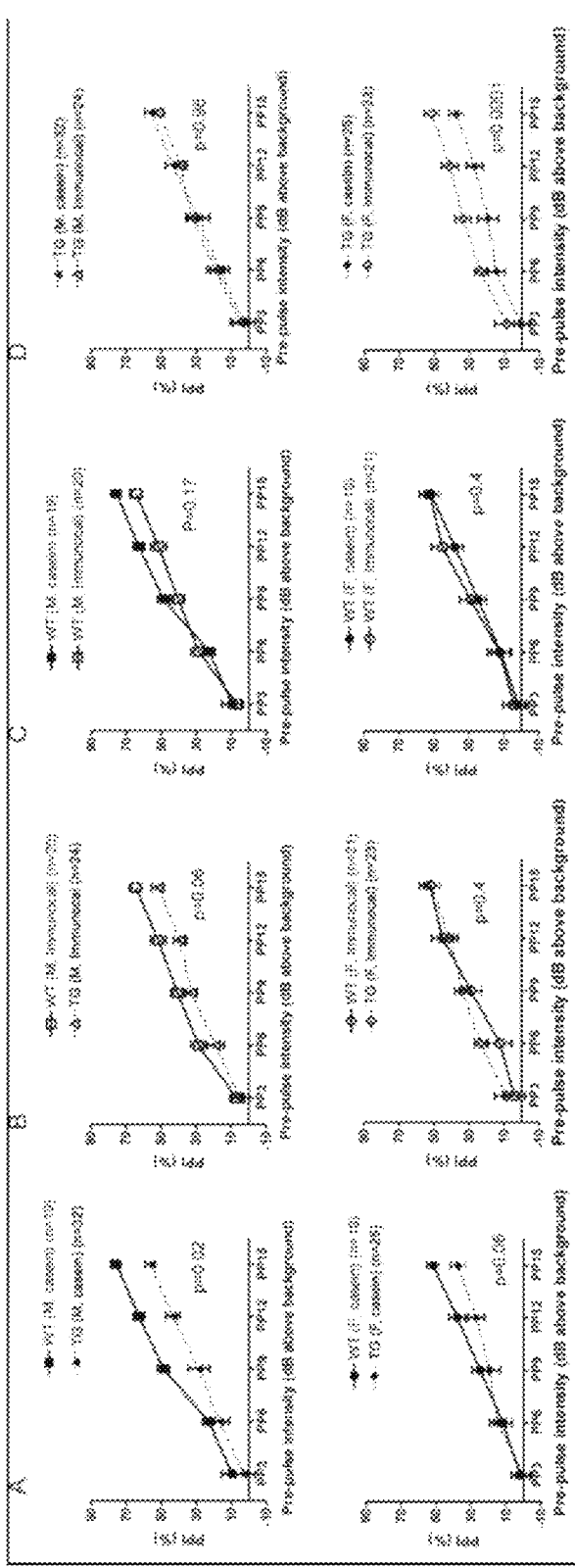
FIG. 1 shows results of prepulse inhibition studies. (A.) Casein-treated (control) GFAP.HMOX1 transgenic (TG) and wild-type (WT) male (top panel) and female (bottom panel) mice. (B.) Immunocal-treated TG and WT male (top panel) and female (bottom panel) mice. (C.) Comparison of Immunocal- and casein-treated WT mice (top panel, males; bottom panel, females). (D.) Comparison of Immunocal- and casein-treated TG mice (top panel, male; bottom panel, female).

Behavior:

Prepulse inhibition (FIG. 1)—PPI occurred in male and female WT mice treated with casein (controls), although the effect was less robust in the females (FIG. 1A) as previously reported in rodents[9] and humans[39]. Relative to casein-treated WT animals, PPI was significantly attenuated in male TG mice (FIG. 1A). We observed a trend towards impairment of PPI in casein-treated female TG mice (P=0.06, relative to WT subjects, FIG. 1A), particularly following exposure to high pre-pulse levels, as noted in an earlier report[40]. Impairment of PPI was significantly ameliorated in female TG mice receiving Immunocal treatment (P<0.0001 relative to casein-treated TG group, FIG. 1D). In male mice, no significant differences in PPI rescue could be evinced between the Immunocal and casein-treated TG mice because the baseline PPI level of WT mice exposed to Immunocal was lower (albeit not statistically significantly) than that of the WT-casein group (FIG. 1C), whereas the PPI levels of the TG-Immunocal and TG-casein groups were comparable (FIG. 1D).

Figure 2:
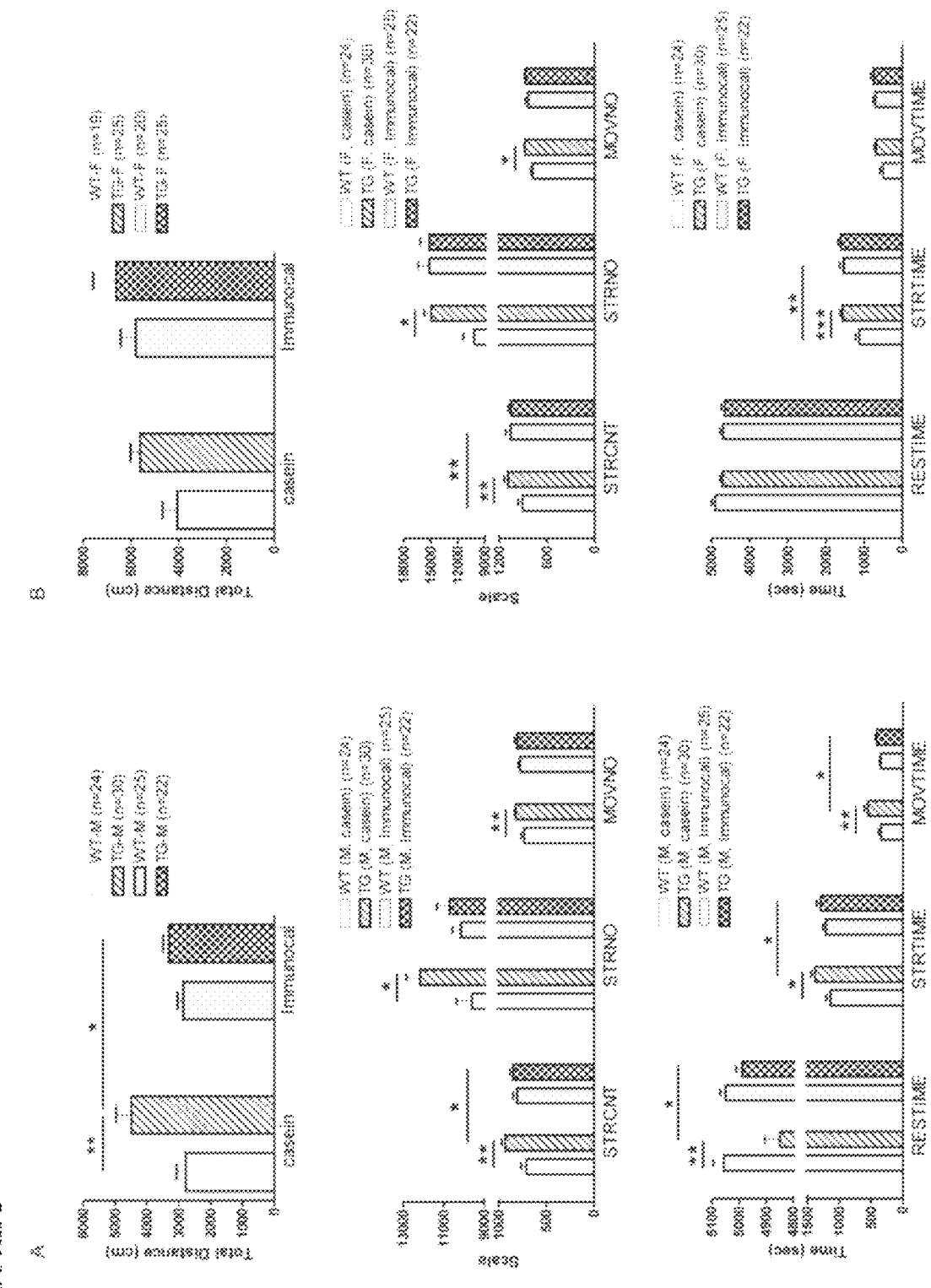
FIG. 2 shows results of locomotor activity studies. (A.) Male; (B.) Female. Total distance (top panels); STRCNT-stereotypy count. STRNO-stereotypy number, and MOVNO-movement number (middle panels); RESTIME-rest time, STRTIME-stereotypy time, and MOVTIME-movement time (bottom panels). *P<0.05, P<0.01, *P<0.001, relative to WT controls.

Locomotor activity—Casein-treated male TG mice displayed a robust hyperkinetic profile as reflected in all locomotor measurements, whereas female TG mice exhibited partial hyperlocomotor activity (FIG. 2). Immunocal treatment significantly attenuated the hyperlocomotor activity in male TG mice, as evidenced by changes in total distance, stereotypy count and time, movement time, and rest time (FIG. 2A). Certain measures of locomotor activity were enhanced in Immunocal-treated female WT mice relative to those exposed to casein, thereby masking potential differences in locomotor activity between the Immunocal-exposed TG and WT females (FIG. 2B).

Figure 3:
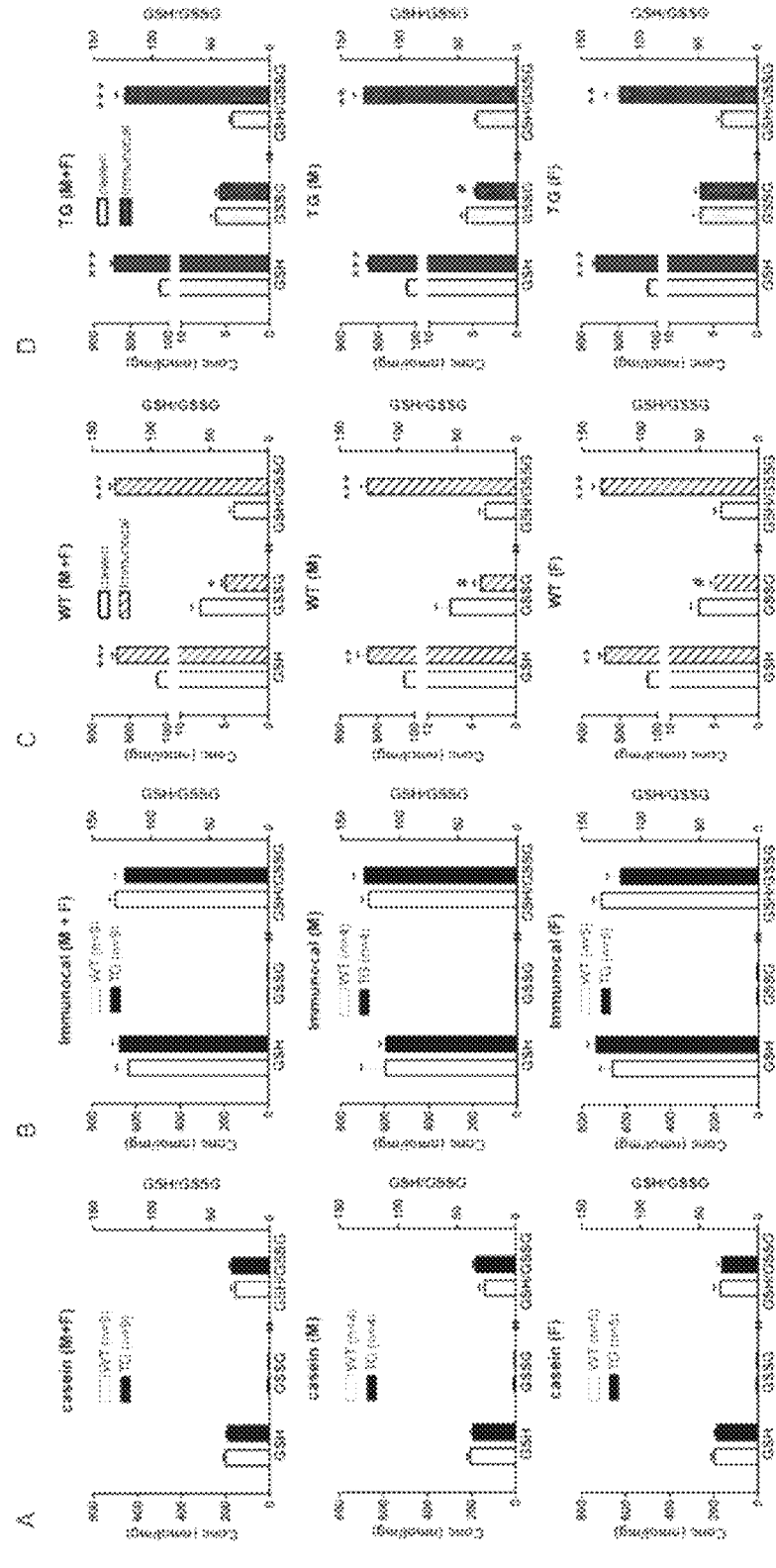
FIG. 3 shows results of whole brain glutathione concentration studies. (A.) Casein treatment (control): (B.) Immunocal treatment; (C.) Comparison of Immunocal- and casein-treated WT mice; (D.) Comparison of Immunocal- and casein-treated TG mice. Top panels, male and female mice: middle panels, males; bottom panels, females. *P<0.05. P<0.01. *P<0.001, relative to WT preparations.
Figure 4:
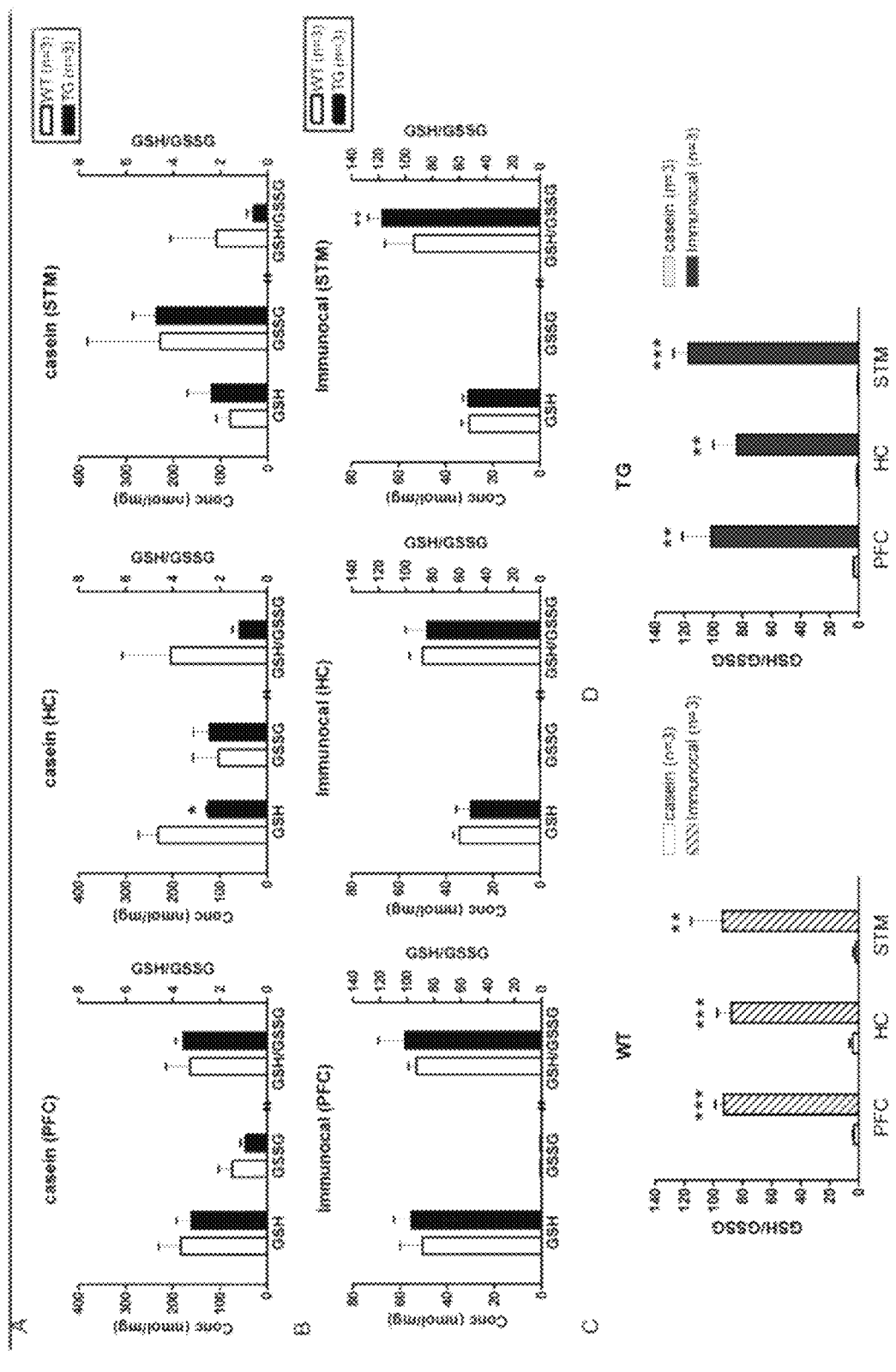
FIG. 4 shows results of sub-regional brain glutathione concentration studies. (A.) PFC, HC, and STM of casein-treated (control) group. (B.) PFC, HC, and STM of Immunocal-treated group. (C.) Comparison of Immunocal- and casein-treated WT mice. (D.) Comparison of Immunocal- and casein-treated TG mice. *P<0.05, P<0.01. *P<0.001, relative to WT preparations.

Brain GSH Concentrations:

Whole brain measurements revealed no significant differences in GSH concentrations, GSSG concentrations or GSH/GSSG ratios between casein-treated WT and TG mice, and glutathione levels were similar between the males and females (p>0.05 for all comparisons) (FIG. 3A). A subregional analysis of the brain samples showed a significant reduction of GSH content in the HC of casein-treated TG mice relative to WT values (p<0.05; FIG. 4A), and a trend towards lower GSH/GSSG ratios in the TG HC and STM compared with WT preparations (FIG. 4A). Glutathione values in the WT and TG PFC were similar (p>0.05, FIG. 4A, B).

Immunocal supplementation significantly augmented whole brain GSH/GSSG ratios in both WT and TG mice compared with casein-treated animals (p<0.01-0.001; FIG. 3C, D). The latter was achieved mainly through marked elevations of GSH concentrations (634.2-676 vs. 188.5-201.1 nmol/mg, P<0.001) accruing from exposure to the whey protein. A significant reduction of brain GSSG content following Immunocal supplementation was observed in WT but not TG brains (WT: 4.9±0.5 vs. 7.7±0.5 nmol/mg, p<0.05; TG: 5.7±0.4 vs. 6.1±0.5 nmol/mg, p>0.05.). There were similar alterations in GSH content and GSH:GSSG ratios between male and female mice (p>0.05), and the diminished GSSG concentrations resulting from Immunocal treatment were observed in both WT males and females, but only in TG males (p<0.05 for each comparison; FIG. 3C. D).

Immunocal treatment diminished the differences in hippocampal GSH content and GSH/GSSG ratio between the WT and TG groups (FIG. 4B). Immunocal treatment significantly elevated striatal GSH/GSSG ratios in TG mice relative to WT preparations (p<0.01. FIG. 4B). Immunocal treatment significantly increased GSH/GSSG ratios in all three brain regions surveyed of both WT and TG mice compared with casein-treated preparations (83.7-117.2 vs. 0.6-4.1, P<0.01-0.001; FIG. 4C, D).

Figure 5:
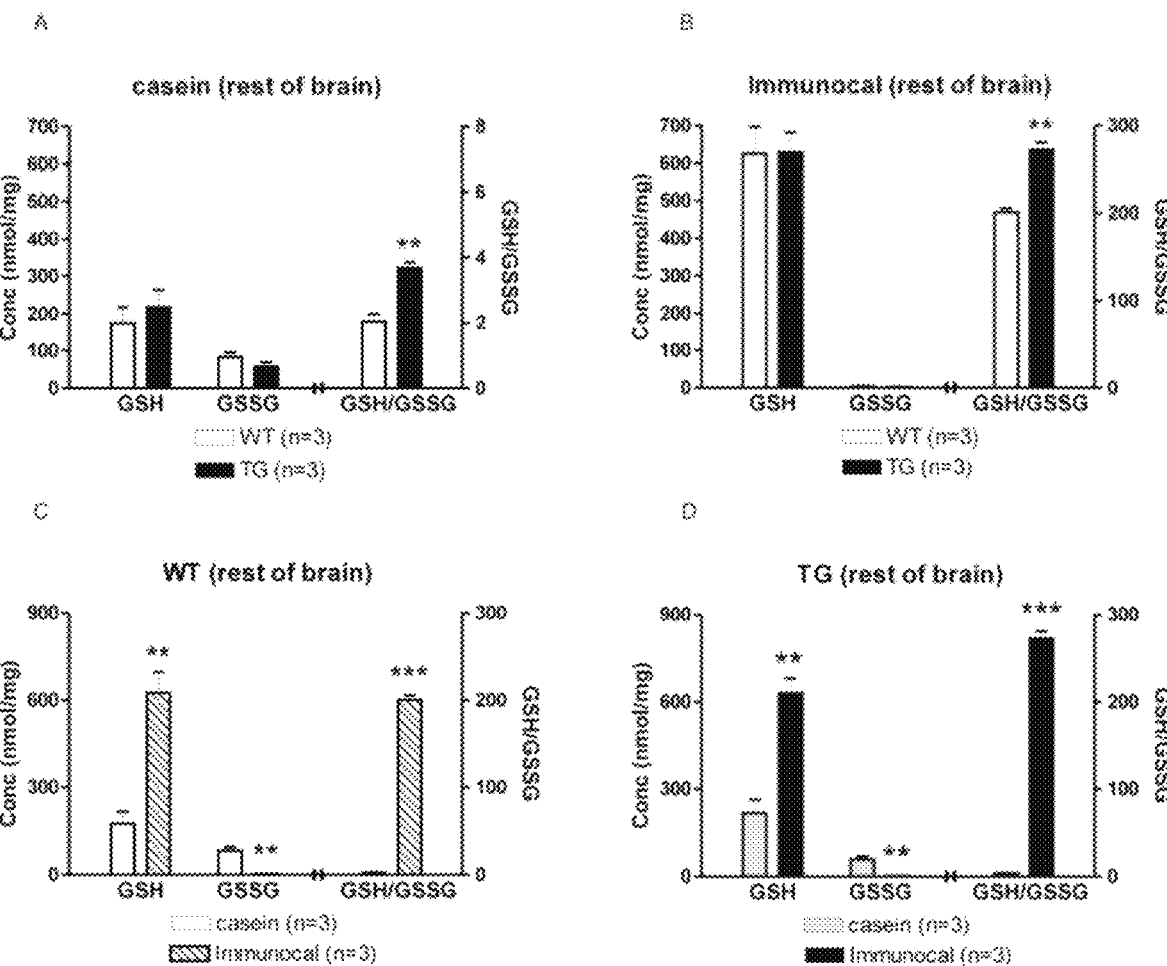
FIG. 5 shows results of studies of glutathione levels in remaining brain tissue after removal of the PFC, HC, and STM. (A.) Casein-treated (control) group; (B.) Immunocal-treated group; (C.) Comparison of Immunocal- and casein-treated WT mice. (D.) Comparison of Immunocal- and casein-treated GFAP.HMOX1 mice.*P<0.05, P<0.01, *P<0.001, relative to WT preparations.

The GSH % GSSG ratio in the remainder of the hemisphere (REM) was greater in the TG mice relative to the WT animals (P<0.01), was not significantly affected by Immunocal exposure (FIG. 5), and likely accounts for the absence of differences in whole brain glutathione concentrations between these groups (FIG. 3A).

Figure 8:
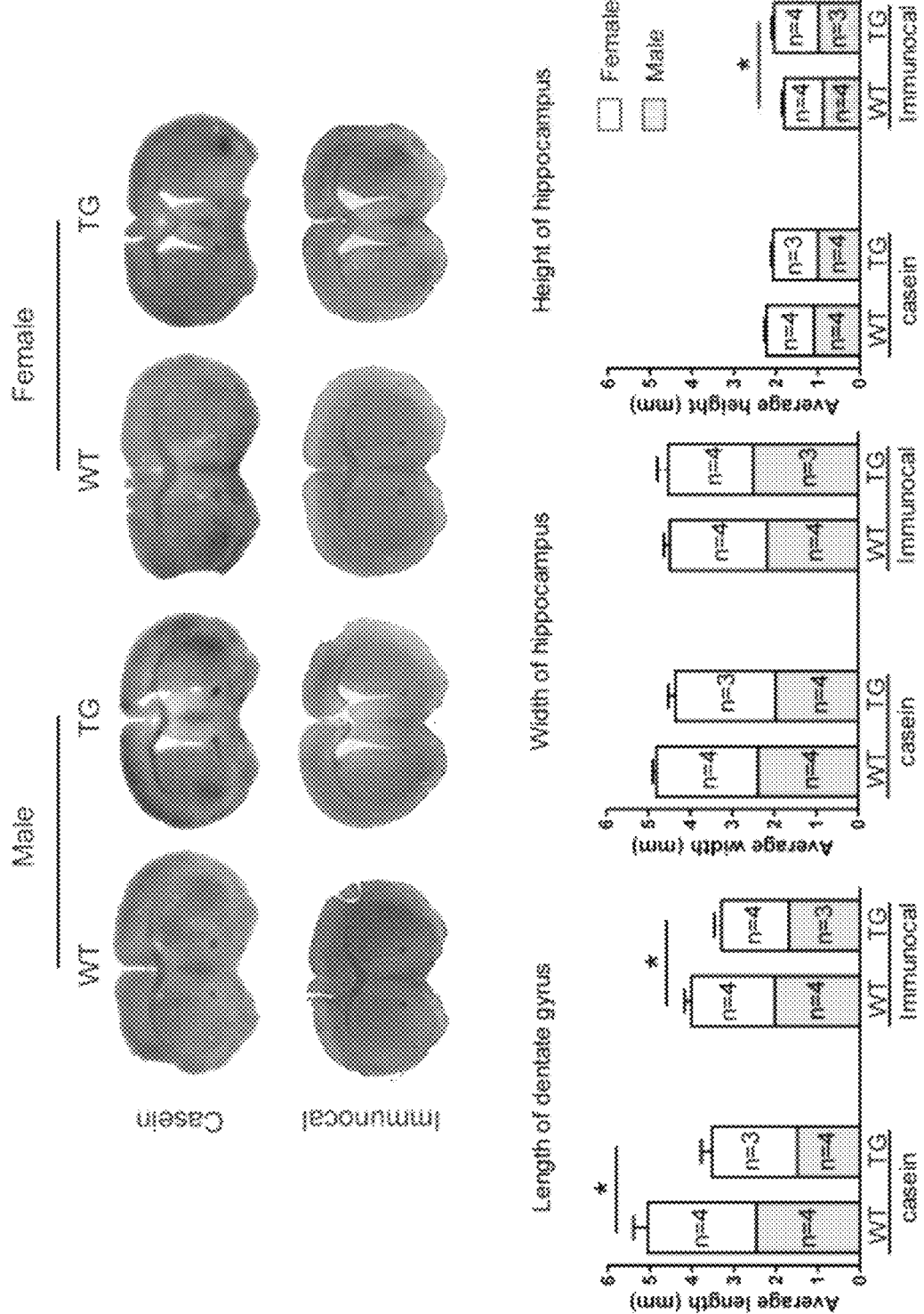
FIG. 8 shows results of studies of brain histomorphology. (A.) Six-micron thick coronal sections (bregma—4.52 mm) stained with H & E. Note dilatation of lateral ventricles in the GFAP.HMOX1 preparations. (B.) Morphometrics of hippocampus and dentate gyrus. *P<0.05, relative to WT preparations.

Hippocampal and Ventricular Pathology:

H&E staining of coronal brain sections revealed markedly enlarged lateral ventricles (ventriculomegaly) (FIG. 8A) and altered hippocampal cytoarchitectonics (dentate gyrus dysgenesis) (FIG. 8B) in both male and female TG mice, features characteristic of human SCZ neuropathology[41-43]. A morphometric analysis of the HC showed that the granule cell layer of the dentate gyrus in TG mice was significantly diminished in size compared to WT mice (p<0.05, FIG. 8B). The ventriculomegaly and dentate gyrus dysgenesis observed in both male and female TG mice were not improved by Immunocal supplementation (FIG. 8). In contradistinction to 12 month old GFAP.HMOX1 TG mice[9]. Gallyas-positive (degenerate) neurites were rarely encountered in the Immunocal- or casein-treated 6.5 month-old TG animals.

Figure 6:
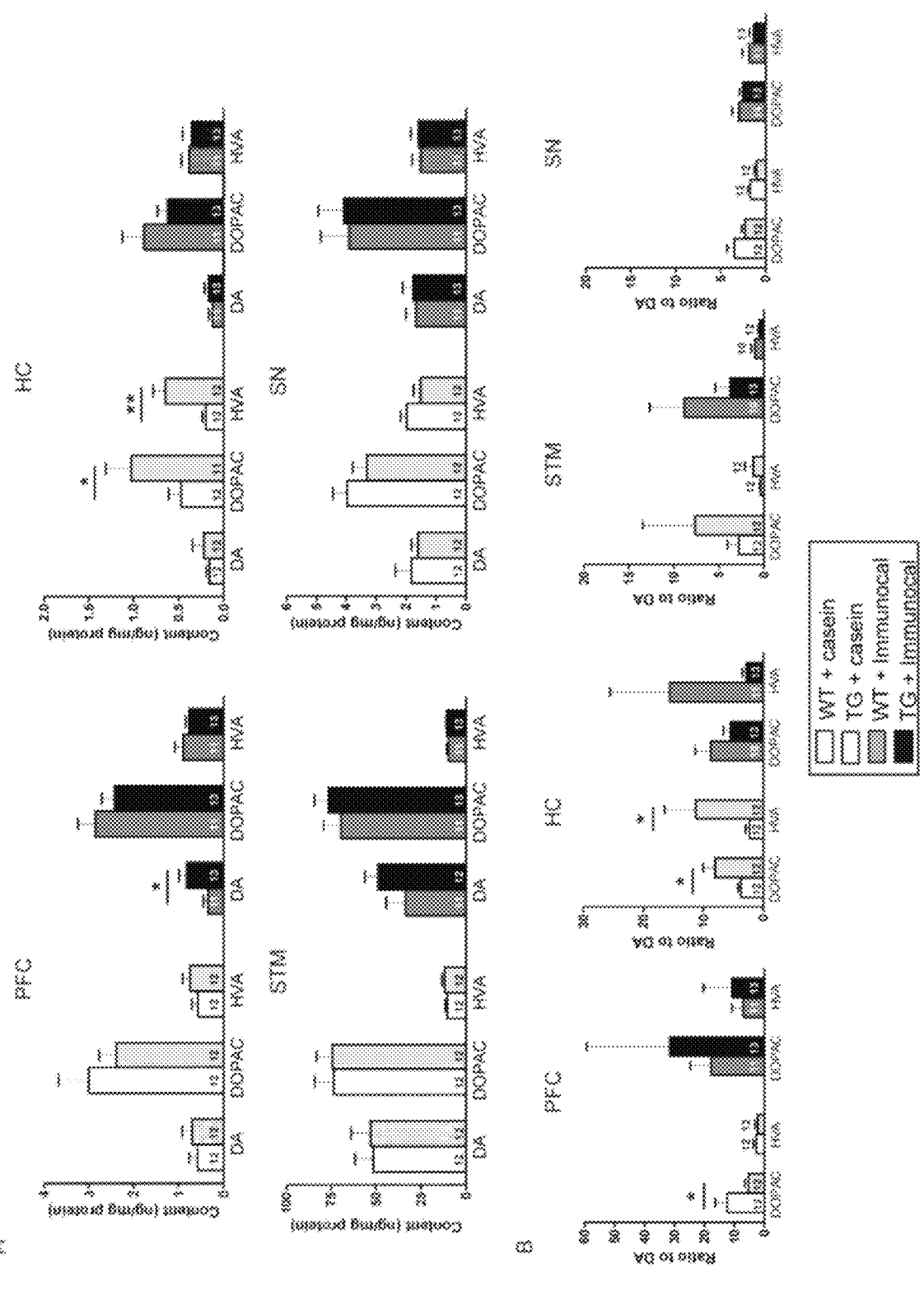
FIG. 6 shows results of studies of content of brain DA and metabolites. (A.) DA and metabolites. (B.) Ratio of DA to DOPAC or HVA. Number of animals per group are indicated in the bars. *P<0.05, **P<0.0.01, relative to WT preparations.

Neurotransmitters:

A) DA and metabolites—Among the casein-treated groups, DOPAC and HVA were significantly increased in the TG HC compared to WT preparations (p<0.05-0.01, FIG. 6A). The ratios of hippocampal DOPAC/DA and HVA/DA were also significantly augmented in the TG mice (p<0.05, FIG. 6B). No significant changes in the levels of DA or DA metabolites were found in PFC, STM and SN of TG brains relative to WT mice (FIG. 6A). The DOPAC/DA ratio was reduced in the TG PFC (p<0.05) without significant alterations in the concentrations of DA or DA metabolites per se (FIG. 6B). All HMOX1-related changes in brain DA and DA metabolites were attenuated by Immunocal supplementation (FIG. 6A, B). Of note, the DA content of the TG PFC was significantly increased after Immunocal treatment (p<0.05, FIG. 1A).

Figure 7:
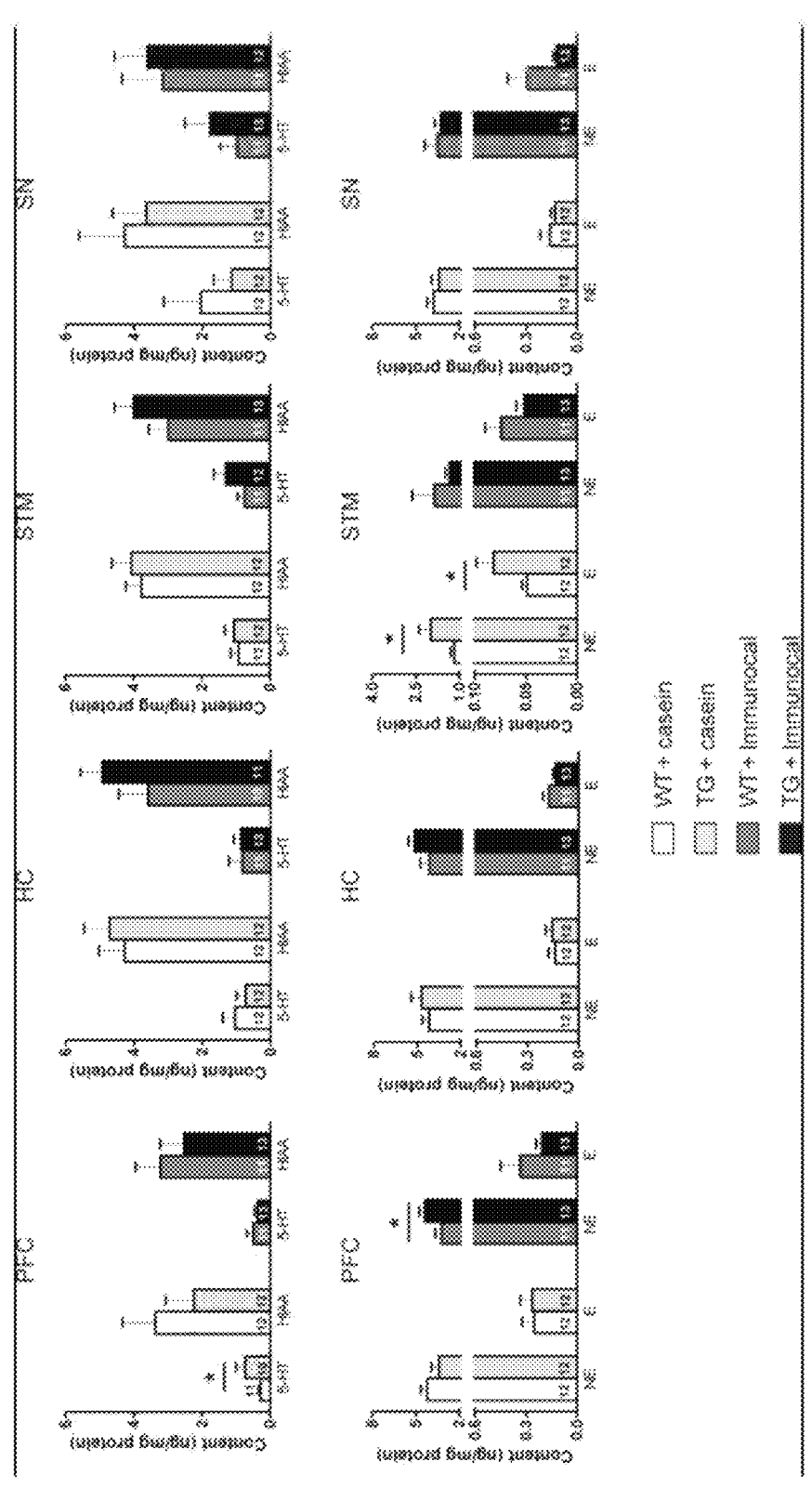
FIG. 7 shows results of studies of content of brain serotonin (5-HT), serotonin metabolite (5-HIAA), norepinephrine (NE) and epinephrine (E). (A.) Serotonin and metabolites; (B.) Norepinephrine and epinephrine. Number of animals per group are indicated in the bars. *P<0.05, relative to WT preparations.

B) Serotonin and metabolites—Among the casein-treated animals, serotonin levels were significantly greater in the TG PFC compared to its WT counterpart (p<0.05, FIG. 7A). Immunocal treatment restored serotonin concentrations in the TG PFC to WT values (FIG. 7A).

Figure 9:
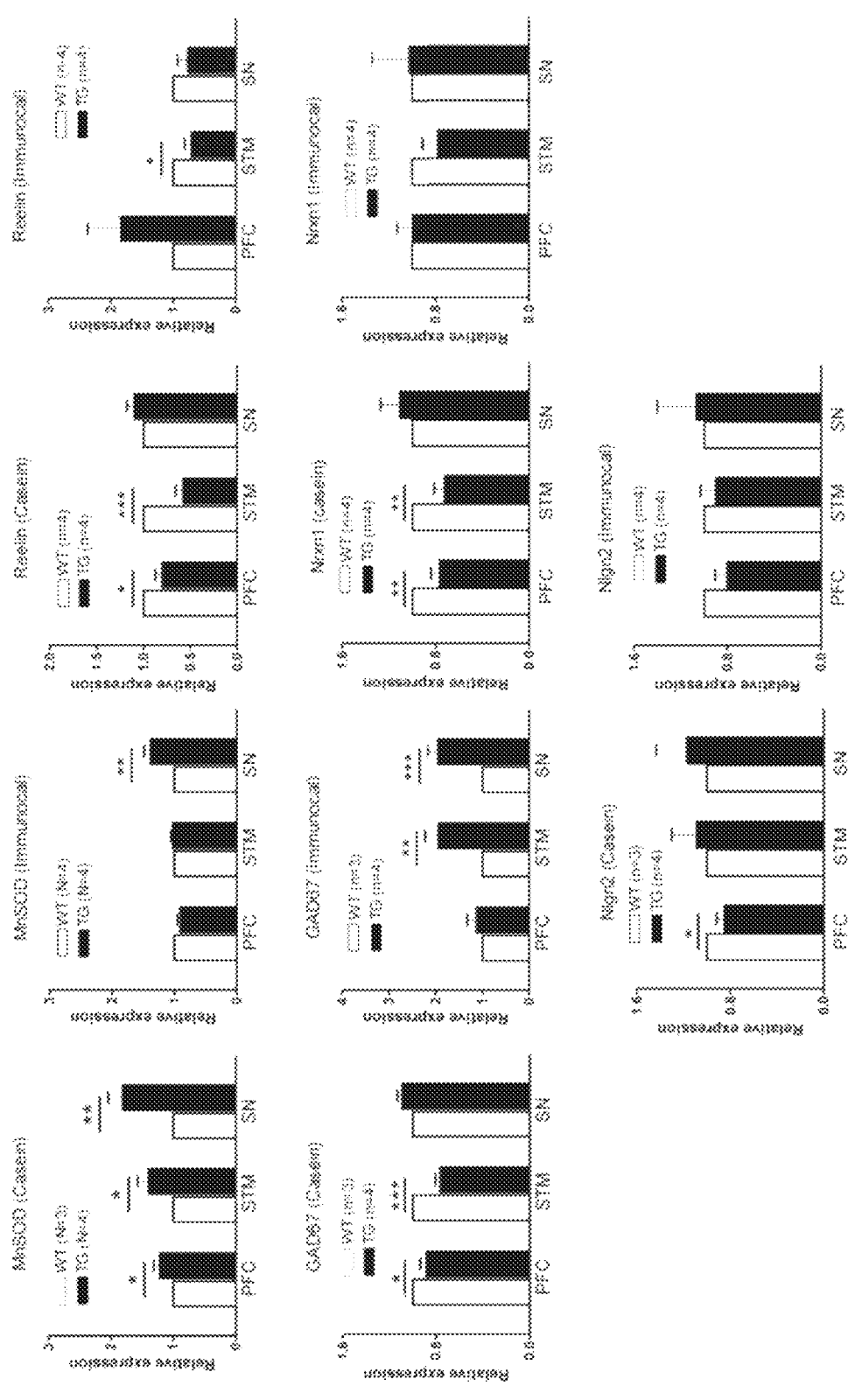
FIG. 9 shows results of studies of brain mRNA profiles. (A.) MnSOD. (B.) Neuronal reelin (RELN). (C.) GAD67. (D.) Nrxn 1. E. Nlgn 2. *P<0.05, P<0.01, *P<0.001, relative to WT preparations.

C) NE and E—Among the casein-treated mice, levels of NE and E were significantly higher in the TG STM compared to WT STM (p<0.05, FIG. 7B). Concentrations of NE and E in the TG STM were normalized following Immunocal exposure (FIG. 7B).

mRNA and miRNA Expression Levels:

A) Neuronal reelin (RELN), GAD67 and MnSOD—MnSOD mRNA, a marker of oxidative stress, was significantly up-regulated in casein-treated TG PFC, STM, and SN compared to WT preparations (p<0.05-0.01, FIG. 9A). The mRNA expression levels of reelin (RELN; a protein involved in the regulation of neuronal migration and positioning in the developing brain[44]) and GAD67 (a GABA-synthesizing enzyme that is co-regulated with reelin[45]) were significantly reduced in casein-treated TG PFC and STM compared to WT PFC and STM (p<0.05-0.001, FIG. 9B, C). In the GFAP/HMOX1 mice, Immunocal treatment normalized the MnSOD mRNA levels in the PFC and STM (but not SN); restored reelin and GAD67 expression in the PFC (p>0.05 relative to casein-treated WT mice; FIG. 9A-C); and augmented GAD67 mRNA levels in the STM and SN (p<0.01-0.001 relative to casein-treated WT mice; FIG. 9C). The Immunocal-treated TG mice also exhibited a trend towards recovery of reelin expression in the STM, although reelin mRNA concentrations in this brain region remained significantly (p<0.05) below WT values (FIG. 9B).

Figure 10:
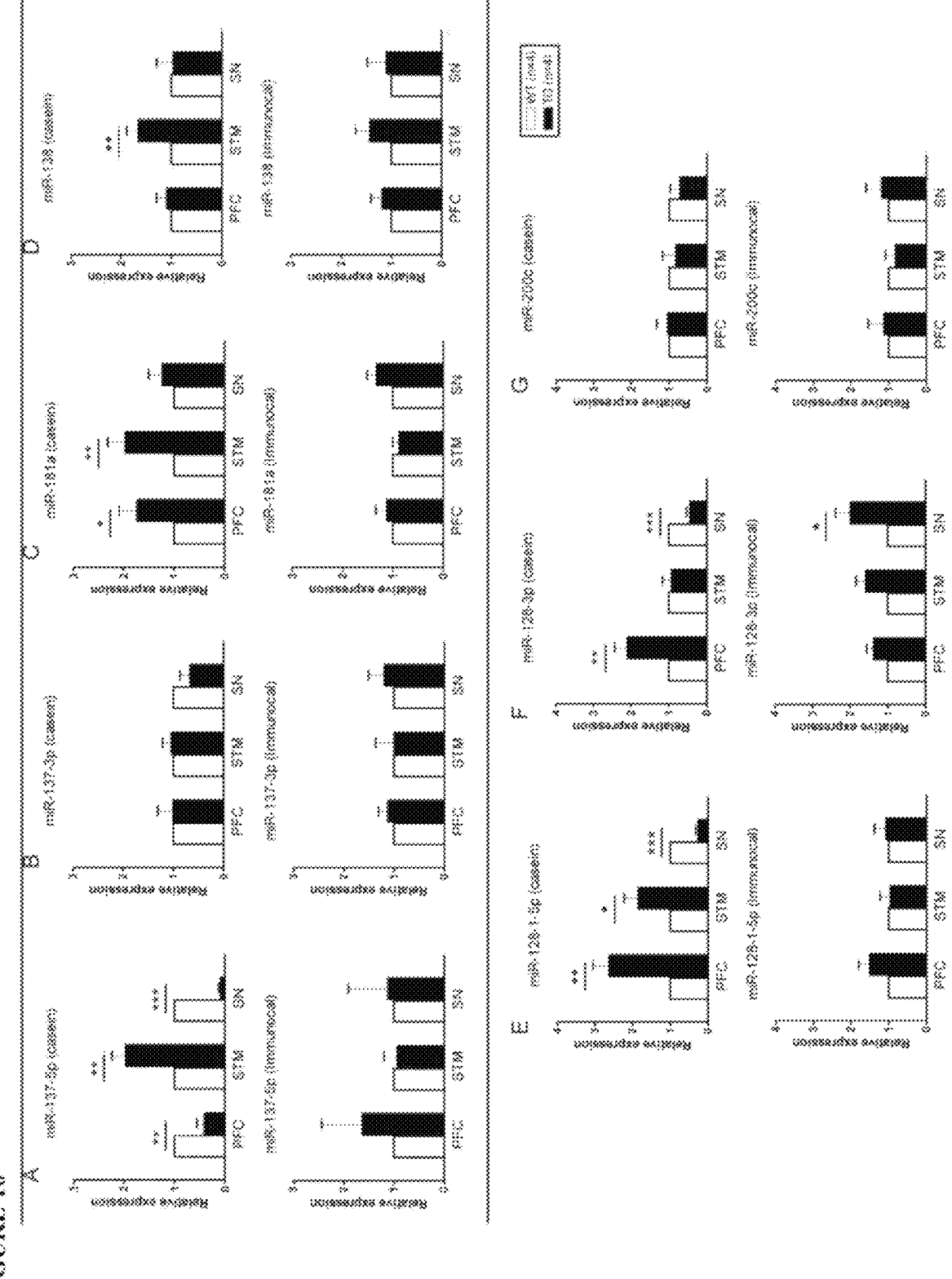
FIG. 10 shows results of studies of brain miRNA profiles. (A.) mmu-miR-137-5p. (B.) mmu-miR-137-3p. (C.) mmu-miR-181a. (D.) mmu-miR-138. (E.) mmu-miR-128-1-5p. (F.) mmu-miR-128-3p. (G.) mmu-miR-200c. *P<0.05, P<0.01. *P<0.001, relative to WT preparations.

B) miR-137, Nrxn1 and Nlgn2—Mutations in Nrxn1 and Nlgn2 genes have previously been linked to SCZ, autism and intellectual disability[46-52]. GFAP.HMOX1 mice exhibited significant down-regulation of Nrxn1 in PFC and STM, and Nlgn2 in PFC, relative to WT values (p<0.05-0.01, FIG. 9D, E). Administration of Immunocal reversed the reduction of Nrxn1 and Nlgn2 in the TG brains (FIG. 9D, E). The TG mice exhibited up-regulation of miR-137, a putative SCZ susceptibility gene[53] and predicted suppressor of Nrxn1 (www.targetscan.org), in STM and suppression of miR-137 in the PFC and SN (p<0.01-0.001. FIG. 10A). The differences in neural miR-137 expression between the GFAP.HMOX1 and WT animals were obviated by Immunocal treatment (FIG. 10A).

C) miR-181a & miR-138—miR-181a may play important roles in SCZ because it regulates synaptic plasticity, is induced by dopamine signaling in hippocampal neurons[54] and is predicted to suppress reelin and sirt1 gene expression. In the casein-treated groups, the expression of mmu-miR-181a was significantly up-regulated in the TG PFC and STM relative to their WT counterparts (p<0.05-0.01, FIG. 10C) and correlated inversely with reelin gene expression which it may target (www.targetscan.org). Similarly, mmu-miR-138, a miRNA implicated in several human neuropsychiatric disorders[55], and impacted by HMOX1 transfection in cultured astroglia[57], was up-modulated in the TG STM vs. WT values (p<0.01, FIG. 10D).

D) miR-128 & miR-200c—miR-128 is highly expressed during neuronal differentiation[58] and de-regulated in patients with SCZ[59]. miR-200c is up-regulated by oxidative stress[60] and suppresses reelin[61], a protein implicated in the pathogenesis of SCZ. miR-128 was up-regulated in the GFAP.HMOX1 PFC (miR-128-1-5p and miR-128-3p) and STM (miR-128-1-5p), and down-regulated in SN (miR-128-1-5p and miR-128-3p) compared to WT controls (p<0.05-0.001, FIG. 10E, F). Immunocal treatment prevented HMOX1-related dysregulation of miR-128 expression in the TG brains, as evidenced by unaltered levels of miR-128-1-5p between the WT and TG animals and enhancement of miR-128-3p expression in TG SN (FIG. 10E, F). Expression of miR-200c, an miRNA that targets reelin[61], remained unchanged in all three TG brain regions relative to WT controls (FIG. 10G) and was not affected by Immunocal exposure (FIG. 10G).

DISCUSSION

In these experiments, the 6.5 month-old GFAP.HMOX1 transgenic mice exhibited schizophrenia-relevant behavioral, neuropathological and neurochemical features akin to those previously reported by our laboratory in these mice at 12 months of age[9]. Documentation of the full neuroendophenotype at this earlier, 6.5-month time point is significant because it is equivalent to approximately 30 human years[62] when first psychotic presentation (diagnosis) of schizophrenia is often manifest[63]. Behavioral abnormalities in the 6.5 month-old GFAP.HMOX1 TG mice included hyperkinesia, stereotypy and impaired PPI of the acoustic startle response. As previously noted in the 12 month-old animals[9] and in human SCZ[39], the behavioral deficits were often more prominent in the males (see below). In contrast, there were no sex predilections for the striking neuromorphological anomalies which consisted of dysgenesis of the hippocampal dentate gyrus and enlargement of the lateral ventricles. Dysregulation of neurotransmitter systems in 6.5 month-old GFAP.HMOX1 TG mice included elevated serotonin content in the PFC, augmented norepinephrine and epinephrine concentrations in the STM and a trend towards increased dopamine levels in the HC. Dopamine turnover was accelerated in the HC, as evidenced by significant increases in the DA metabolites, DOPAC and HVA as well as in DOPAC/DA and HVA % DA ratios. These changes in DOPAC and HVA are indicative of enhanced dopaminergic activity in this brain region[64-67]. By contrast, the DOPAC/DA ratio in the PFC of TG mice was significantly lower than that of WT mice, similar to what has been observed in the isolation-reared rat model of schizophrenia[68]. This reduced DA turnover may point to PFC hypodopaminergia which is a characteristic feature ("hypofrontality") of the human schizophrenic brain[69]. Altered PFC physiology may contribute to the behavioral sensitization and hyperkinesia observed in psychotic states[70]. Furthermore, the cognitive deficits characteristic of SCZ may be due, at least partly, to aberrant catecholaminergic transmission within the lateral PFC and its interactions with related brain regions[71]. Conceivably, the elevated serotonin content in the GFAP.HMOX1 PFC, possibly recapitulating the 5-HT1A receptor increases in PFC of schizophrenic patients[72,73], may have exerted an inhibitory effect on dopamine turnover in this region[74], thereby contributing to the hypodopaminergia.

The 6.5 month-old GFAP.HMOX1 TG mice exhibited altered gene expression profiles of key neurodevelopmental proteins implicated in the etiopathogenesis of SCZ including reelin (RELN), GAD67, Nrxn1 and Nlgn2. As previously hypothesized[9], abnormal expression of these genes may contribute to the neuroanatomical anomalies and aberrant neurotransmission characteristic of the GFAP.HMOX1 mice. In addition, neural concentrations of miR-137, miR-181a, miR-138, and miR-128, miRNAs known or predicted to regulate the expression of these neurodevelopmental genes, and reportedly altered in the brains of persons with SCZ and related disorders[46,49,52,59,61,75-77], deviated substantially from WT values. Annotation of the targeted genes relevant to the etiopathogenesis of human neurodevelopmental disorders is provided in Table 1. Of note, 30 predicted targets have been implicated in SCZ whereas 1-15 gene targets may contribute to autism and other developmental CNS conditions. Among the former, 50% are purportedly regulated by miR-137, a SCZ susceptibility gene[53] heavily impacted in the GFAP.HMOX1 basal ganglia and PFC. A smaller proportion (13.3-33.3%) of the putative gene targets are regulated by the other miRNAs surveyed here (i.e. miR-138, -128, -181a, and -200c).

TABLE 1

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

| (A) | miR-137 | miR-181a | miR-138 | miR-128 | miR-200c |
|---|---|---|---|---|---|
| AD (10) | GRIN2A (Hu)[90] <br> PHF3 (Hu, Rt, Ms)[67]* <br> PXN (Hu)[56]* <br> STK40 (Hu, Rt, Ms) [67]* | Kcnn3 (Ms)[91]* | PTP4A1 (Hu, Rt, Ms)[67]* <br> SLC6A11 (Hu, Rt, Ms)[67]* | Kcnn3 (Ms)[91]* <br> PXN (Hu)[56]* <br> STK40 (Hu, Rt, Ms)[67]* | DRD2 (Hu)[48]* <br> KIAA0040 (Hu)[67]* <br> TPH2 (Hu)[57]* |
| ADHD (8) | NF1 (Hu)[83]* | KCNJ5 (Hu)[65]* <br> MAP1B (Hu)[62]* | SNAP25 (Hu)[85]* | KCNJ5 (Hu)[65]* <br> NCAM1 (Hu)[76]* <br> NF1 (Hu)[83]* <br> SNAP25 (Hu)[85]* <br> STX1A (Hu)[85]* | NCAM1 (Hu)[76]* <br> SNAP25 (Hu)[85]* <br> STX1A (Hu)[85]* <br> TPH1 (Hu)[58]* <br> YWHAQ (Hu)[58]* |

TABLE 1-continued

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

| | miR-137 | miR-181a | miR-138 | miR-128 | miR-200c |
|---|---|---|---|---|---|
| ASD (7) | CSMD1 (Hu)[4]*<br>EN2 (Hu, Ms)[50]<br>RORA (Hu)[52]<br>STXBP5 (Hu)[4]* | EN2 (Hu, Ms)[50]<br>RORA (Hu)[52] | EN2 (Hu, Ms)[50] | EN2 (Hu, Ms)[50]<br>RORA (Hu)[52] | EN2 (Hu, Ms)[50]<br>F0XG1 (Hu)[51]<br>NLGN4X (Hu)[39]*<br>NRG1 (Hu)[43]* |
| BD (12) | GSK3B (Hu)[87]*<br>IMPA2 (Hu)[87]*<br>NRXN1 (Hu)[36] | BRD1 (Hu)[14]*<br>CDH13 (Hu)[77]*<br>CNTNAP2 (Hu)[88]*<br>HLA-C (Hu)[80]*<br>NRXN1 (Hu)[36]<br>YWHAG (Hu)[58]* | RELN (Hu)[89]* | GSK3B (Hu)[87]*<br>HLA-DRA (Hu)[80]* | NDUFS1 (Hu)[38]<br>SYNJ1 (Hu)[40]*<br>YWHAG (Hu)[58]* |
| IDD (ID) (6) | CSMD1 (Hu)[4]*<br>DDX3X (Hu)[86]*<br>NRXN1 (Hu)[64]* | ARID2 (Hu)[75]*<br>DDX3X (Hu)[86]*<br>IQSEC2 (Hu)[63]*<br>NRXN1 (Hu)[64]* | KDM5C (Hu)[63]* | ARID2 (Hu)[75]* | DDX3X (Hu)[86]* |

| (B) | miR-137 | miR-181a | miR-138 | miR-128 | miR-200c |
|---|---|---|---|---|---|
| MDD (13) | CACNA1C (Hu)[2]*<br>GRIA2 (Hu)[82]<br>GRIN2A (Hu)[82]<br>GRM5 (Hu)[82]<br>GSK3B (Hu)[10]*<br>SLIT3 (Hu)[4]* | CNTNAP2 (Hu)[88]*<br>ESR1 (Hu)[81]*<br>GRM1 (Hu)[82]<br>GRM5 (Hu)[82]<br>GRM7 (Hu)[82] | PTK2 (Hu)[78] | GRM5 (Hu)[82]<br>GSK3B (Hu)[10]*<br>KCNK2 (Hu)[66]* | YWHAQ (Hu)[58]* |
| OCD (15) | CHGA (Hu)[93]*<br>DLGAP1 (Hu)[71, 72]*<br>PVRL1 (Hu)[93]* | MYCBP2 (Hu)[93]*<br>PBX1-LMX1A (Hu)[74]* ®<br>RYR3 (Hu)[71, 73]*<br>TNF (Hu)[70]* | CLN5 (Hu)[93]* | ATP9A (Hu)[93]*<br>LSAMP (Hu)[93]*<br>MEIS2 (Hu)[74]*<br>NFATC2 (Hu)[93]*<br>NGFR (Hu)[92]*<br>WDR7 (Hu)[93]* | GPC6 (Hu)[79]*<br>LSAMP (Hu)[93]* |
| PTHS (1) | TCF4 (Hu)[1] | ? | TCF4 (Hu)[49] | TCF4 (Hu)[49] | TCF4 (Hu)[49] |
| SCZ (30) | CACNA1C (Hu)[2]*<br>CSMD1 (Hu)[4]*<br>C10orf26 (Hu)[7]*<br>Erbb4 (Rt)[5]<br>GABRA1 (Hu)[6]<br>GRIN2B (Hu)[8]*<br>Grm5 (Ms, Rt)[9]<br>GSK3B (Hu)[10]*<br>HTR2C (Hu)[11]<br>NRG2 (Hu)[12]*<br>NRG3 (Hu)[34]*<br>NRXN1 (Hu)[36]<br>NRXN3 (Hu)[28]*<br>TCF4 (Hu)[1]<br>ZNF804A (Hu)[3] | BRD1 (Hu)[14]*<br>CNTNAP2 (Hu)[88]*<br>GABRA1 (Hu)[6]<br>Grm5 (Ms, Rt)[9]<br>HLA-C (Hu)[80]*<br>NRXN1 (Hu)[36]<br>TNF-α (Hu)[15]<br>WDR60 (Hu)[4]*<br>YWHAB (Hu)[58]*<br>YWHAZ (Hu)[58]* | Erbb4 (Rt)[5]<br>NEUROD1 (Hu)[16]<br>RELN (Hu)[16, 89]*<br>TCF4 (Hu)[1] | C10orf26 (Hu)[7]*<br>Grm5 (Ms, Rt)[9]<br>GSK3B (Hu)[10]*<br>HLA-DRA (Hu)[80]*<br>RELN (Hu)[16]<br>TCF4 (Hu)[1]<br>YWHAB (Hu)[58]* | CACNA1C (Hu)[2]*<br>C10orf26 (Hu)[7]*<br>Erbb4 (Rt)[5]<br>MAP2 (Hu)[42]<br>NRG1 (Hu)[44]*<br>RELN (Hu)[16]<br>SLC6A1 (Hu)[41]<br>TCF4 (Hu)[1]<br>TPH1 (Hu)[58]*<br>YWHAB (Hu)[58]* |
| TS (10) | CHGA (Hu)[93]*<br>PVRL (Hu)[93]* | DPP6 (Hu)[86]*<br>KCNJ5 (Hu)[65]*<br>MYCBP2 (Hu)[93]*<br>TNF (Hu)[70]* | CLN5 (Hu)[93]* | ATP9A (Hu)[93]*<br>KCNJ5 (Hu)[65]*<br>LSAMP (Hu)[93]* | DRD2 (Hu)[47]*<br>LSAMP (Hu)[93]*<br>PVRL (Hu)[93]* |

| (C) | miR-137 | miR-181a | miR-138 | miR-128 | miR-200c |
|---|---|---|---|---|---|
| OS (18) | GPD2 (Hu)[33]<br>GPX7 (Hu)[31]<br>Mtfr1 (Ms)[29]<br>Rgs6 (Ms)[32]<br>Serp1 (Yst)[30]@ | Gpx1 (Rt)[54]<br>GRM1 (Hu)[17]<br>IL1A (Hu)[18]<br>MMP14 (Hu)[19]<br>Sirt1 (Ms)[26]<br>Tnf-α (Rt)[20] | Gnai2 (Rt)[22]<br>Psen1 (Ms)[23]<br>RARA (Hu)[24]<br>Sin3a (Dm)[25]<br>Sirt1 (Ms)[26] | PARK7 (Hu)[13]<br>RARA (Hu)[24]<br>Sirt1 (Ms)[26] | HYOU1 (Hu)[45]<br>Maf (Ms)[46] ©<br>Sin3a (Dm)[25]<br>Sirt1 (Ms)[26] |
| Mitochondrial dysfunction (8) | NOTCH1 (Hu)[68] | Bcl-2 (Ms)[37]<br>Mcl-1 (Ms)[37]<br>Tnf-α (Rt)[20] | PPARD (Hu)[27] | Bnip3 (Ms)[59]<br>PARK7 (Hu)[13] | Bnip3 (Ms)[59] |
| Macroautophagy (9) | ATG14 (Hu)[35]<br>FUNDC1 (Hu)[53]<br>NIX (Hu)[53] | Atg5 (Ms)[21, 84] | Atg7 (Ms)[69] | Bnip3 (Ms)[59] | Arntl (Ms)[60]<br>Bnip3 (Ms)[59]<br>Ctse (Ms)[61]<br>UBQLIN1 (Hu)[54] |

TABLE 1-continued

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

| (D) | Table 1 Footnotes |
|---|---|

Genes referenced without underlining were down-regulated in literature reports. Genes referenced
with underlining were reportedly up-regulated. Genes referenced with character shading were either
up- or down-modulated contingent on clinical/experimental context. Genes referenced with stars are
considered susceptibility genes with associated risk variants including single nucleotide
polymorphism (SNP) and copy number variants (CNVs). Interrogation marks imply absence of
published reports or uncertain relationships to neuropathological processes. Number of predicted
targets for each disorder are listed in parentheses below disorder names. Prediction algorithms for
miR-181a and -200c are derived from their broadly conserved miRNA families: miR-181abcd/4262
and miR-200bc/429/548a. (Reference index and full names for the genes listed in the table are
provided in Table 1 E) and F) below). Species associated with studied targets (genes) are also listed.
AD, Alcohol dependence; ASD, Autism spectrum disorder; BP, bipolar disorder; Dm, Drosophila
melanogaster; Hu, human; ID, Intellectual disability; IDD, Intellectual development disorder; MDD,
Major depression disorder; Ms, mouse; OCD, Obsessive compulsive disorder; OS, oxidative stress;
PTHS, Pitt-Hopkins syndrome; Rt, rat; SCZ, schizophrenia; TS, Tourette syndrome. Yst, yeast.
Sirt1 (underlined) exhibits dual effects, i.e. moderate overexpression of Sirt1 reduced oxidative stress
and high levels of Sirt1 increased oxidative stress. @, Serp1 SERP1 represents an oxidative stress-
associated endoplasmic reticulum (ER) protein with chaperone-like functions thought to play a
cytoprotective role against ER stress. ©, Small Maf proteins variably impact gene expression:
complexes with Bach1 repress MARE-dependent gene expression, whereas heterodimers with NF-E2
p45 or related factors (Nrf1, Nrf2, and Nrf3) activate MARE-driven genes[85](Igarashi, K., Sun, J.,
*Antioxid. Redox Signal*, 2006, 8: 107-118). ®, SNP was between PBX1 and LMX1A[86](Nestadt, G., et
al., *Am. J. Med. Genet. B Neuropsychiatr. Genet.*, 2012, 159B: 53-60).

| (E) | Table 1 Reference Index |
|---|---|

1. Blake, D. J., et al. TCF4, Schizophrenia, and Pitt-Hopkins Syndrome. Schizophr Bull. (2010) 36 (3): 443-447.
2. He, K., et al. CACNA1C, schizophrenia and major depressive disorder in the Han Chinese population. Br J Psychiatry. (2014) 204(1): 36-9.
3. Kim, A. H., et al. Experimental validation of candidate schizophrenia gene ZNF804A as target for hsa-miR-137. Schizophr Res. (2012) 141(1): 60-64.
4. Cukier, H. N., et al. Exome sequencing of extended families with autism reveals genes shared across neurodevelopmental and neuropsychiatric disorders. Mol Autism. 2014; 5(1): 1-10.
5. Pither, G. M., et al. Schizophrenia susceptibility pathway neuregulin 1-ErbB4 suppresses Src upregulation of NMDA receptors. Nat Med. (2011) 17(4): 470-8.
6. Hoftman, G. D., et al. Altered cortical expression of GABA-related genes in schizophrenia: illness progression vs developmental disturbance. Schizophr Bull. (2015) 41(1): 180-91.
7. Ripke, S. et al. Genome-wide association analysis identifies 13 new risk loci for schizophrenia. Nat Genet., (2013) 45 (10): 1150-59.
8. Demontis, D., et al. Association of GRIN1 and GRIN2A-D with schizophrenia and genetic interaction with maternal herpes simplex virus-2 infection affecting disease risk. Am J Med Genet B Neuropsychiatr Genet. (2011) 156B(8): 913-22.
9. Newel, K. A. et al. Metabotropic glutamate receptor 5 in schizophrenia: emerging evidence for the development of antipsychotic drugs. Future Med Chem. (2013) 5(13): 1471-1474
10. Chen, J., et al. The GSK3B gene confers risk for both major depressive disorder and schizophrenia in the Han Chinese population. J Affect Disord. (2015) 185: 149-155.
11. Castensson, A., et al. Serotonin receptor 2C (HTR2C) and schizophrenia: examination of possible medication and genetic influences on expression levels. Am J Med Genet B Neuropsychiatr Genet. (2005) 134B(1): 84-9.
12. Benzel, I., et al. Interactions among genes in the ErbB-Neuregulin signalling network are associated with increased susceptibility to schizophrenia. Behav Brain Funct. (2007) 3: 31-41
13. Pantcheva, P., et al. The role of DJ-1 in the oxidative stress cell death cascade after stroke. Neural Regen Res. (2014) 9(15): 1430-3.
14. Severinsen, J. E., et al. Evidence implicating BRD1 with brain development and susceptibility to both schizophrenia and bipolar affective disorder. Mol Psychiatry. (2006) 11(12): 1126-38.
15. O'Brien, S. M., et al. Increased tumor necrosis factor-alpha concentrations with interleukin-4 concentrations in exacerbations of schizophrenia. Psychiatry Res. (2008) 160(3): 256-62.
16. Brennand, K., et al. Phenotypic differences in hiPSC NPCs derived from patients with schizophrenia. Mol Psychiatry. (2015) 20, 361-368.
17. Wall, B. A., et al. Disruption of GRM1-mediated signalling using riluzole results in DNA damage in melanoma cells. Pigment Cell Melanoma Res. (2014) 27(2): 263-74.
18. Bissonnette, C. J., et al. Interleukin 1alpha and interleukin 6 protect human neuronal SH-SY5Y cells from oxidative damage. Neurosci Lett. (2004) 361(1-3): 40-3.
19. Gencer, S., et al. Matrix metalloproteinase gene expressions might be oxidative stress targets in gastric cancer cell lines. Chin J Cancer Res. (2013) 25(3): 322-333.
20. Mariappan, N., et al. TNF-alpha-induced mitochondrial oxidative stress and cardiac dysfunction: restoration by superoxide dismutase mimetic Tempol. Am J Physiol Heart Circ Physiol. (2007) 293(5): H2726-37.

TABLE 1-continued

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

21.     Pyo, J. O., et al. Overexpression of Atg5 in mice activates autophagy and extends lifespan. Nat
        Commun. (2013) 4: 2300
22.     Li, Y., et al. Role of oxidative stress in high glucose-induced decreased expression of Gialpha
        proteins and adenylyl cyclase signaling in vascular smooth muscle cells. Am J Physiol Heart Circ
        Physiol. (2008) 294(6): H2845-54.
23.     Warner, T. A., et al. Low brain ascorbic acid increases susceptibility to seizures in mouse models
        of decreased brain ascorbic acid transport and Alzheimer's disease. Epilepsy Res. (2015) 110: 20-5.
24.     Hoshikawa, Y., et al. c-Jun N-terminal kinase activation by oxidative stress suppresses retinoid
        signaling through proteasomal degradation of retinoic acid receptor α protein in hepatic cells.
        Cancer Sci. (2011) 102(5): 934-41.
25.     Barnes, V. L., et al. SIN3 is critical for stress resistance and modulates adult lifespan. Aging
        (Albany NY). (2014) 6(8): 645-60.
26.     Alcendor, R. R., et al. Sirt1 regulates aging and resistance to oxidative stress in the heart. Circ Res.
        (2007) 100(10): 1512-21.
27.     Barlaka, E., et al. Activation of PPARβ/δ protects cardiac myocytes from oxidative stress-induced
        apoptosis by suppressing generation of reactive oxygen/nitrogen species and expression of matrix
        metalloproteinases. Pharmacol Res. (2015) 95-96: 102-10
28.     Hu, X., et al. Association study of NRXN3 polymorphisms with schizophrenia and risperidone-
        induced bodyweight gain in Chinese Han population. Prog Neuropsychopharmacol Biol
        Psychiatry. (2013) 43: 197-202.
29.     Monticone, M., et al. Impaired expression of genes coding for reactive oxygen species scavenging
        enzymes in testes of Mtfr1/Chppr-deficient mice. Reproduction. (2007) 134(3): 483-92.
30.     Schaafhausen, A., et al. Identification of VKORC1 interaction partners by split-ubiquitin system
        and coimmunoprecipitation. Thromb Haemost. (2011) 105(2): 285-94.
31.     Peng, D., et al. Glutathione peroxidase 7 protects against oxidative DNA damage in oesophageal
        cells. Gut. (2012) 61(9): 1250-60.
32.     Stewart, A., et al. Regulator of G protein signaling 6 is a critical mediator of both reward-related
        behavioral and pathological responses to alcohol. Proc Natl Acad Sci USA. (2015) 112(7): E786-95.
33.     Kamiński, M. M., et al. T cell activation is driven by an ADP-dependent glucokinase linking
        enhanced glycolysis with mitochondrial reactive oxygen species generation. Cell Rep. (2012) 2(5):
        1300-15.
34.     Morar, B., et al. Neuregulin 3 (NRG3) as a susceptibility gene in a schizophrenia subtype with
        florid delusions and relatively spared cognition. Mol Psychiatry. (2011) 16(8): 860-6.
35.     Kim, H. J., et al. Beclin-1-interacting autophagy protein Atg14L targets the SNARE-associated
        protein Snapin to coordinate endocytic trafficking. J Cell Sci. (2012) 125(Pt 20): 4740-50.
36.     Jenkins, A. K., et al. Neurexin 1 (NRXN1) splice isoform expression during human neocortical
        development and aging. Mol Psychiatry. (2015) Jul 28. doi: 10.1038/mp.2015.107. [Epub ahead of
        print]
37.     Ouyang, Y. B., et al. miR-181 targets multiple Bcl-2 family members and influences apoptosis and
        mitochondrial function in astrocytes. Mitochondrion. (2012) 12(2): 213-9.
38.     Akarsu, S., et al. Mitochondrial complex I and III mRNA levels in bipolar disorder. J Affect
        Disord. (2015) 15; 184: 160-3.
39.     Bemben, M. A., et al. Autism-associated mutation inhibits protein kinase C-mediated neuroligin-
        4X enhancement of excitatory synapses. Proc Natl Acad Sci USA. (2015) 112(8): 2551-6.
40.     Saito, T., et al. Mutation analysis of SYNJ1: a possible candidate gene for chromosome 21q22-
        linked bipolar disorder. Mol Psychiatry. (2001) 6(4): 387-95.
41.     Volk, D., et al. GABA transporter-1 mRNA in the prefrontal cortex in schizophrenia: decreased
        expression in a subset of neurons. Am J Psychiatry. (2001) 158(2): 256-65.
42.     Shelton, M. A., et al. Loss of Microtubule-Associated Protein 2 Immunoreactivity Linked to
        Dendritic Spine Loss in Schizophrenia. Biol Psychiatry. (2015) Jan 30. pii: S0006-3223(15)00073-
        6. doi: 10.1016/j.biopsych.2014.12.029. [Epub ahead of print]
43.     Yoo, H. J., et al. Genetic association analyses of neuregulin 1 gene polymorphism with
        endopheontype for sociality of Korean autism spectrum disorders family. Psychiatry Res. (2015)
        227(2-3): 366-8.
44.     Jajodia, A., et al. Evidence for schizophrenia susceptibility alleles in the Indian population: An
        association of neurodevelopmental genes in case-control and familial samples. Schizophr Res.
        (2015) 162(1-3): 112-7.
45.     Eltoweissy, M., et al. Proteomics analysis identifies PARK7 as an important player for renal cell
        resistance and survival under oxidative stress. Mol Biosyst. (2011) 7(4): 1277-88.
46.     Igarashi, K., Sun, J. The heme-Bach1 pathway in the regulation of oxidative stress response and
        erythroid differentiation. Antioxid Redox Signal. (2006) 8(1-2): 107-18.
47.     Yuan, A., et al. Association between DRD2/ANKK1 TaqIA polymorphism and susceptibility with
        Tourette syndrome: A meta-analysis. PLoS One. (2015) 10(6): e0131060.
48.     Mignini, F., et al. DRD2/ANKK1 TaqIA and SLC6A3 VNTR polymorphisms in alcohol
        dependence: association and gene-gene interaction study in a population of Central Italy. Neurosci
        Lett. (2012) 522(2): 103-7.
49.     Sweatt JD1 Pitt-Hopkins Syndrome: intellectual disability due to loss of TCF4-regulated gene
        transcription. Exp Mol Med. (2013) 45: e21.
50.     Genestine, M., et al. Engrailed-2 (En2) deletion produces multiple neurodevelopmental defects in
        monoamine systems, forebrain structures and neurogenesis, and behavior. Hum Mol Genet. (2015)
        Jul 28. pii: ddv301. [Epub ahead of print]
51.     Mariani, J., et al. FOXG1-dependent dysregulation of GABA/glutamate neuron differentiation in
        autism spectrum disorders. Cell. (2015) 162(2): 375-90.
52.     Hu, V. W., et al. Investigation of sex differences in the expression of RORA and its transcriptional
        targets in the brain as a potential contributor to the sex bias in autism. Mol Autism. (2015) 6: 7.
        doi: 10.1186/2040-2392-6-7.

TABLE 1-continued

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

| 53. | Li, W., et al. MicroRNA-137 is a novel hypoxia-responsive microRNA that inhibits mitophagy via regulation of two mitophagy receptors FUNDC1 and NIX. J Biol Chem. (2014) 289(15): 10691-701. |
|---|---|
| 54. | Wang, L., et al. Effects of downregulation of microRNA-181a on H2O2-induced H9c2 cell apoptosis via the mitochondrial apoptotic pathway. Oxid Med Cell Longev. (2014) 2014: 960362. |
| 55. | Sun, Q., et al. MiR-200c inhibits autophagy and enhances radiosensitivity in breast cancer cells by targeting UBQLN1. Int J Cancer. (2015) 136(5): 1003-12. |
| 56. | Zuo, L., et al. Gene-based and pathway-based genome-wide association study of alcohol dependence. Shanghai Arch Psychiatry. (2015) 27(2): 111-8. |
| 57. | Plemenitaš, A., et al. Genetic variability in tryptophan hydroxylase 2 gene in alcohol dependence and alcohol-related psychopathological symptoms. Neurosci Lett. (2015) pii: S0304-3940(15)30057-4. doi: 10.1016/j.neulet.2015.07.037. [Epub ahead of print] |
| 58. | Jacobsen, K. K. et al. Epistatic and gene wide effects in YWHA and aromatic amino hydroxylase genes across ADHD and other common neuropsychiatric disorders: Association with YWHAE. Am J Med Genet B Neuropsychiatr Genet. (2015) doi: 10.1002/ajmg.b.32339. [Epub ahead of print] |
| 59. | Chourasia, A. H., et al. Mitophagy defects arising from BNip3 loss promote mammary tumor progression to metastasis. EMBO Rep. (2015) pii: e201540759. [Epub ahead of print] |
| 60. | Jeong, K., et al. Dual attenuation of proteasomal and autophagic BMAL1 degradation in ClockΔ19/+ mice contributes to improved glucose homeostasis. Sci Rep. (2015) 5: 12801. doi: 10.1038/srep12801. |
| 61. | Frank, B., et al. Autophagic digestion of Leishmania major by host macrophages is associated with differential expression of BNIP3, CTSE, and the miRNAs miR-101c, miR-129, and miR-210. Parasit Vectors. (2015) 8(1): 404. |
| 62. | Salatino-Oliveira, A., et al. MAP1B and NOS1 genes are associated with working memory in youths with attention-deficit/hyperactivity disorder. Eur Arch Psychiatry Clin Neurosci. (2015) [Epub ahead of print] |
| 63. | Moey, C., et al. Xp11.2 microduplications including IQSEC2, TSPYL2 and KDM5C genes in patients with neurodevelopmental disorders. Eur J Hum Genet. (2015) doi: 10.1038/ejhg.2015.123. [Epub ahead of print] |
| 64. | Gregor, A., et al. Expanding the clinical spectrum associated with defects in CNTNAP2 and NRXN1. BMC Med Genet. (2011) 12: 106 |
| 65. | Gomez L., et al. Association of the KCNJ5 gene with Tourette Syndrome and Attention-Deficit/Hyperactivity Disorder. Genes Brain Behav. (2014) 13(6): 535-42. |
| 66. | Congiu, C., et al. The role of the potassium channel gene KCNK2 in major depressive disorder. Psychiatry Res. (2015) 225(3): 489-92. |
| 67. | Zuo L., et al. A New Genomewide Association Meta-Analysis of Alcohol Dependence. Alcohol Clin Exp Res. (2015) 39(8): 1388-95. |
| 68. | Xu, J., et al. NOTCH reprograms mitochondrial metabolism for proinflammatory macrophage activation. J Clin Invest. (2015) 125(4): 1579-90. |
| 69. | Nilsson, P., et al. Autophagy-related protein 7 deficiency in amyloid β (Aβ) precursor protein transgenic mice decreases Aβ in the multivesicular bodies and induces Aβ accumulation in the Golgi. Am J Pathol. (2015) 185(2): 305-13. |
| 70. | Keszler, G., et al. Association of the tumor necrosis factor -308 A/G promoter polymorphism with Tourette syndrome. Int J Immunogenet. (2014) 41(6): 493-8. |
| 71. | Grados, M., et al. Genetic findings in obsessive-compulsive disorder connect to brain-derived neutrophic factor and mammalian target of rapamycin pathways: implications for drug development. Drug Dev Res. (2014) 75(6): 372-83. |
| 72. | Li, J., et al. An association study between DLGAP1 rs11081062 and EFNA5 rs26728 polymorphisms with obsessive-compulsive disorder in a Chinese Han population. Neuropsychiatr Dis Treat. (2015) 11: 897-905. |
| 73. | Ross, J., et al. Genomewide linkage analysis in Costa Rican families implicates chromosome 15q14 as a candidate region for OCD. Hum Genet. (2011) 130(6): 795-805. |
| 74. | Nestadt, G., et al. Homeobox genes in obsessive-compulsive disorder. Am J Med Genet B Neuropsychiatr Genet. (2012) 159B(1): 53-60. |
| 75. | Shang, L., et al. Mutations in ARID2 are associated with intellectual disabilities. Neurogenetics. (2015) Aug 4. [Epub ahead of print] |
| 76. | Mota, N. R., et al. NCAM1-TTC12-ANKK1-DRD2 gene cluster and the clinical and genetic heterogeneity of adults with ADHD. Am J Med Genet B Neuropsychiatr Genet. (2015) doi: 10.1002/ajmg.b.32317. [Epub ahead of print] |
| 77. | Cho C H., et al. CDH13 and HCRTR2 May Be Associated with Hypersomnia Symptom of Bipolar Depression: A Genome-Wide Functional Enrichment Pathway Analysis. Psychiatry Investig. (2015) 12(3): 402-7. |
| 78. | Gao, L., et al. Microarray Analysis of the Major Depressive Disorder mRNA Profile Data. Psychiatry Investig. (2015) 12(3): 388-96. |
| 79. | Qin H., et al. Whole-genome association analysis of treatment response in obsessive-compulsive disorder. Mol Psychiatry. (2015) Mar 31. doi: 10.1038/mp.2015.32. [Epub ahead of print] |
| 80. | Marco, C., et al. Genes involved in pruning and inflammation are enriched in a large mega-sample of patients affected by Schizophrenia and Bipolar Disorder and controls. Psychiatry Res. (2015) pii: S0165-1781(15)00359-5. doi: 10.1016/j.psychres.2015.06.013. [Epub ahead of print] |
| 81. | Keyes K., et al. The role of allelic variation in estrogen receptor genes and major depression in the Nurses Health Study. Soc Psychiatry Psychiatr Epidemiol. (2015) Jul 14. [Epub ahead of print] |
| 82. | Gray, A. L., et al. Sex differences in glutamate receptor gene expression in major depression and suicide. Mol Psychiatry. (2015) doi: 10.1038/mp.2015.91. [Epub ahead of print] |

TABLE 1-continued

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

| | |
|---|---|
| 83. | van der Voet, M., et al. ADHD-associated dopamine transporter, latrophilin and neurofibromin share a dopamine-related locomotor signature in Drosophila. Mol Psychiatry. (2015) doi: 10.1038/mp.2015.55. [Epub ahead of print] |
| 84. | Tekirdag, K. A., et al. MIR181A regulates starvation- and rapamycin-induced autophagy through targeting of ATG5. Autophagy. (2013) 9(3): 374-85. |
| 85. | Gao., Q., et al. Synaptosome-related (SNARE) genes and their interactions contribute to the susceptibility and working memory of attention-deficit/hyperactivity disorder in males. Prog Neuropsychopharmacol Biol Psychiatry. (2015) Mar 3; 57: 132-9. doi: 10.1016/j.pnpbp.2014.11.001. Epub 2014 Nov. 13. |
| 86. | Prontera P., et al. DPP6 gene disruption in a family with Gilles de la Tourette syndrome. Neurogenetics. (2014) 15(4): 237-42. |
| 87. | Mitjans, M., et al. Exploring genetic variability at PI, GSK3, HPA, and glutamatergic pathways in lithium response: association with IMPA2, INPP1, and GSK3B genes. J Clin Psychopharmacol. (2015) Aug 11. [Epub ahead of print] |
| 88. | Chen, X., et al. A novel relationship for schizophrenia, bipolar and major depressive disorder Part 7: A hint from chromosome 7 high density association screen. Behav Brain Res. (2015) 293: 241-251. |
| 89. | Ovadia, G., Shifman, S. The genetic variation of RELN expression in schizophrenia and bipolar disorder. PLoS One. (2011) 6(5): e19955. |
| 90. | Xiang Y., et al. Ethanol Upregulates NMDA Receptor Subunit Gene Expression in Human Embryonic Stem Cell-Derived Cortical Neurons. PLoS One. (2015) 10(8): e0134907 |
| 91. | Padula A E., et al. KCNN Genes that Encode Small-Conductance Ca2+-Activated K+ Channels Influence Alcohol and Drug Addiction. Neuropsychopharmacology. (2015) 40(8): 1928-39. |
| 92. | Gassó, P., et al. Association between genetic variants related to glutamatergic, dopaminergic and neurodevelopment pathways and white matter microstructure in child and adolescent patients with obsessive-compulsive disorder. J Affect Disord. (2015) 186: 284-292. |
| 93. | Yu D., et al. Cross-disorder genome-wide analyses suggest a complex genetic relationship between Tourette's syndrome and OCD. Am J Psychiatry. (2015) 172(1): 82-93. |

| (F) | Table 1 Gene Names |
|---|---|

AP4M1, Adaptor-Related Protein Complex 4, Mu 1 Subunit
ARIN2, AT Rich Interactive Domain 2 (ARID, RFX-Like)
ARNTL (BMAL1), Aryl Hydrocarbon Receptor Nuclear Translocator-Like
ATG5, Autophagy Related 5
ATG14, Autophagy Related 14
ATP9A, ATPase, Class II, Type 9A
BCL2, B-Cell CLL/Lymphoma 2
BNIP3 (NIP3), BCL2/Adenovirus E1B 19 kDa Interacting Protein 3
BNIP3L (NIX), BCL2/Adenovirus E1B 19 kDa Interacting Protein 3-Like
BRD1, Bromodomain Containing 1
CACNA1C, Calcium Channel, Voltage-Dependent, L Type, Alpha 1C Subunit
CDH13, Cadherin 13
CHGA, Chromogranin A
CLN5, Ceroid-Lipofuscinosis, Neuronal 5
CNTNAP2, Contactin Associated Protein-Like 2
CSMD1, CUB and Sushi Multiple Domains 1
CTSE, Cathepsin E
DDX3X, DEAD (Asp-Glu-Ala-Asp) Box Helicase 3, X-Linked
DLGAP1, Discs, Large (Drosophila) Homolog-Associated Protein 1
DPP6, Dipeptidyl-Peptidase 6
DRD2, Dopamine Receptor D2
EN2, Engrailed-2
Erbb4, Erb-B2 Receptor Tyrosine Kinase 4
ESR1, Estrogen Receptor 1
FOXG1, Forkhead Box G1
FUNDC1, FUN14 Domain Containing 1
GABRA1, Gamma-Aminobutyric Acid (GABA) A Receptor, Alpha 1
GNAI2, Guanine Nucleotide Binding Protein (G Protein), Alpha Inhibiting Activity Polypeptide 2
GPC6, Glypican 6
GPX1, Glutathione Peroxidase 1
GPX7, Glutathione peroxidase 7
GRIA2, Glutamate Receptor, Ionotropic, AMPA 2
GRIN2A, Glutamate Receptor, Ionotropic, N-Methyl D-Aspartate 2A
GRIN2B, Glutamate Receptor, Ionotropic, N-Methyl D-Aspartate 2B
GRM1, Glutamate Receptor, Metabotropic 1
GRM5, Glutamate Receptor, Metabotropic 5
GRM7, Glutamate Receptor, Metabotropic 7
GSK3B, Glycogen Synthase Kinase 3 Beta
HLA-C, Major Histocompatibility Complex, Class I, C
HLA-DRA, Major Histocompatibility Complex, Class II, DR Alpha
HTR2C, 5-Hydroxytryptamine (Serotonin) Receptor 2C, G Protein-Coupled
HYOU1, Hypoxia Up-Regulated 1
IMPA2, Inositol(Myo)-1(Or 4)-Monophosphatase 2
KCNJ5, Potassium Channel, Inwardly Rectifying Subfamily J, Member 5
KCNK2, Potassium Channel, Two Pore Domain Subfamily K, Member 2

TABLE 1-continued

Data mining for predicted targets of miRNAs implicated in neurodevelopmental and neuropsychiatric disorders.
A) and B): neurodevelopmental and neuropsychiatric disorders listed alphabetically; C) major neuropathology;
D) Footnotes for Table 1; E) References cited in Table 1; F) Gene names for Table 1.

KCNN3, Potassium Channel, Calcium Activated Intermediate/Small Conductance
Subfamily N Alpha, Member 3
KDM5C, Lysine (K)-Specific Demethylase 5C
KLAA0040, KIAA0040
IL1A, Interleukin 1, Alpha
IQSEC2, IQ Motif and Sec7 Domain 2
LMX1A, LIM Homeobox Transcription Factor 1, Alpha
LSAMP, Limbic System-Associated Membrane Protein
MAF, V-Maf Avian Musculoaponeurotic Fibrosarcoma Oncogene Homolog
MAP1B, Microtubule-Associated Protein 1B
MAP2, Microtubule-Associated Protein 2
MCL-1, Myeloid Cell Leukemia 1
MEIS2, Meis Homeobox 2
MMP14, Matrix Metallopeptidase 14 (Membrane-Inserted)
MTFR1, Mitochondrial Fission Regulator 1
MYCBP2, MYC Binding Protein 2, E3 Ubiquitin Protein Ligase
NCAM1, Neural Cell Adhesion Molecule 1
NDUFS1, NADH Dehydrogenase (Ubiquinone) Fe—S Protein 1, 75 kDa (NADH-Coenzyme Q Reductase)
NEUROD1, Neuronal Differentiation 1
NFATC2, Nuclear Factor of Activated T-Cells, Cytoplasmic, Calcineurin-Dependent 2
NF1, Neurofibromin 1
NGFR, Nerve Growth Factor Receptor
NLGN4X, Neuroligin 4, X-linked
NOTCH1, Notch1
NRG1, Neuregulin 1
NRG2, Neuregulin 2
NRG3, Neuregulin 3
NRXN1, Neurexin 1
NRXN3, Neurexin 3
OFCC1, Orofacial Cleft 1 Candidate 1
PARK7, Parkinson Protein 7
PBX1, Pre-B-Cell Leukemia Homeobox 1
PHF3, PHD Finger Protein 3
PPARD, Peroxisome Proliferator-Activated Receptor Delta
PSEN1, Presenilin 1
PTK2, Protein Tyrosine Kinase 2
PTP4A1, Protein Tyrosine Phosphatase Type IVA, Member 1
PVRL1, Poliovirus Receptor-Related 1 (Herpesvirus Entry Mediator C)
PXN, Paxillin
RARA, Retinoic Acid Receptor, Alpha
RELN, Reelin
RGS6, Regulator of G-Protein Signaling 6
RORA, RAR-Related Orphan Receptor A
RYR3, Ryanodine Receptor 3
SERP1, Stress-associated endoplasmic reticulum protein 1
SIN3, SIN3 Transcription Regulator Family Member A
SIRT1, Sirtuin 1
SLC6A1, Solute Carrier Family 6 (Neurotransmitter Transporter), Member 1
SLC6A11, Solute Carrier Family 6 (Neurotransmitter Transporter), Member 11
SLIT3, Slit Homolog 3 (*Drosophila*)
SNAP25, Synaptosomal-Associated Protein 25 kDa
STK40, Serine/Threonine Kinase 40
STX1A, Syntaxin 1A
STXBP5, Syntaxin Binding Protein 5 (Tomosyn)
SYNJ1, Synaptojanin 1
TCF4, Transcription Factor 4
TNFA, Tumor Necrosis Factor-Alpha
TPH2, Tryptophan Hydroxylase 2
UBQLIN1, Ubiquilin 1
WDR7, WD Repeat Domain 7
WDR60, WD Repeat Domain 60
YWHAB, Tyrosine 3-Monooxygenase/Tryptophan 5-Monooxygenase Activation Protein, Beta
YWHAG, Tyrosine 3-Monooxygenase/Tryptophan 5-Monooxygenase Activation Protein, Gamma
YWHAQ, Tyrosine 3-Monooxygenase/Tryptophan 5-Monooxygenase Activation Protein, Theta
YWHAZ, Tyrosine 3-Monooxygenase/Tryptophan 5-Monooxygenase Activation Protein, Zeta
ZNF804A, Zinc Finger Protein 804A MnSOD mRNA expression levels in the PFC, STM and SN of the GFAP.HMOX1 mice were significantly augmented in comparison to the WT counterparts. Furthermore, glutathione reserves were depleted in the HC and STM of TG brains, as evidenced by diminished GSH concentrations and/or low GSH:GSSG ratios relative to WT preparations. These finding further corroborate the contention that oxida-tive stress downstream from sustained or repeated over-expression of HO-1 in astrocytes may be a pivotal player leading to neuronal dysfunction in a host of developmental and degenerative brain disorders.

A major finding of these experiments was that Immunocal treatment attenuated many of the behavioural, neurochemi-cal and redox abnormalities characteristic of the GFAP.HMOX1 mouse. These observations are consistent with previous reports of symptom amelioration in human SCZ patients and animal models of the disease following the administration of glutathione precursors[14]. In GFAP.HMOX1 mice of both sexes, Immunocal supplementation restored redox homeostasis by significantly increasing GSH concentrations and GSH:GSSG ratios in whole brain and in discrete regions (PFC, HC, STM) implicated in the etiopathogenesis of SCZ. The restoration of brain GSH homeostasis in the GFAP.HMOX1 mice by exposure to Immunocal was sufficient to alleviate cellular oxidative stress as evidenced by normalization of MnSOD mRNA expression in the transgenic PFC and STM. Immunocal also bolstered GSH reserves in the brains of WT animals relative to the casein-treated controls. Thus, by serving as a source of bioavailable cysteine, believed to be the rate-limiting amino acid required for GSH biosynthesis, results herein indicate that whey protein consumption augments GSH stores and antioxidant defenses in the healthy and diseased mammalian CNS.

Immunocal treatment significantly ameliorated the hyperlocomotion and stereotypy in male GFAP.HMOX1 mice and improved PPI in the transgenic females. Without wishing to be bound by theory, these benefits may be attributed to the positive impact of Immunocal exposure on aberrant monoaminergic neurotransmission observed in the TG mice. All HMOX1-related changes in brain dopamine, dopamine metabolites, serotonin, norepinephrine and epinephrine were improved by Immunocal supplementation. An interesting neurotransmitter profile was observed in the PFC of Immunocal-treated TG mice where Immunocal not only restored excessive serotonin levels and deficient DOPAC/DA ratios to WT values, but also concurrently augmented norepinephrine and dopamine concentrations in this brain region. Without wishing to be bound by theory, it is thought that by normalizing serotonin content in the TG PFC, Immunocal may have released the local dopamine system from serotonergic inhibition (as evidenced by the increased dopamine turnover and enhanced dopamine content)[74], thereby correcting the PFC hypodopaminergia. Additionally, the Immunocal-mediated increase in NE may have exerted an additive effect on DA release in the TG PFC, in keeping with the previously reported positive regulation of DA by NE in rat PFC[79].

Data sets indicate further that these beneficial effects of whey protein supplementation on dopaminergic tone are mediated, at least in part, by correction of deviant mRNA and miRNA expression profiles known to regulate the growth, function and maintenance of catecholaminergic circuitry in the developing mammalian CNS. Noteworthy in this regard is the full or partial normalization of mRNA expression profiles for neural reelin (RELN), GAD67, Nrxn1, Nlgn2 and several of their targeting miRNAs in salient regions of the GFAP.HMOX1 brain. PFC hypodopaminergia is thought to underlie the 'negative' symptoms of schizophrenia (apathy, social withdrawal, etc.)[74].

As previously reported, the wild-type and GFAP.HMOX1 mice exhibited several sex-specific differences on behavioural testing. Thus. PPI was more robust in males than females (as seen in human schizophrenia[39]) as was hyperlocomotor activity. Interestingly, Immunocal treatment significantly suppressed hyperlocomotion in male GFAP.HMOX1 mice, whereas in female VT mice certain indices of locomotor activity were enhanced by whey protein exposure. These results suggest that the development of nutrition-based strategies may allow for the management of neuropsychiatric disorders in a more nuanced, gender-specific fashion.

Immunocal supplementation in these mouse model studies exerted no appreciable effects on the dysgenesis of the hippocampal dentate gyrus and ventriculomegaly which characterize the GFAP.HMOX1 mouse[9] and human SCZ brain[81,82]. This outcome is not surprising inasmuch as these midline brain defects are established during neurodevelopment prior to the Immunocal treatment window and are likely to be irreversible. It is hypothesized that these structural anomalies may be obviated by Immunocal treatment of pregnant GFAP.HMOX1 dams and prepubertal transgenic pups. Such findings would suggest whey protein supplementation as a potential safe and effective intervention for diminishing the likelihood of SCZ in persons at-risk for this disease[83,84].

One study analyzing reelin levels in different brain regions of schizophrenia subjects found a significant decrease in reelin in 5 key brain regions, namely the prefrontal cortex (PFC), the striatum (STM), hippocampus (HC), temporal cortex, and cerebellum, compared to control subjects (Inpagnatiello et al., 1998, A decrease of reelin expression as a putative vulnerability factor in schizophrenia, *Proc. Natl. Acad. Sci.*, USA, vol. 95: pp. 15718-15723; herein incorporated by reference in its entirety). In GFAP.HMOX1 mouse model of schizophrenia, a significant decline in reelin protein immunoreactivity in the PFC, STM (caudate-putamen), and HC has been observed (Song et al. J Neurosci 32:10841-10853, 2012).

As described hereinabove, reelin (RELN) mRNA was analyzed in 3 brain regions relevant to schizophrenia in younger GFAP.HMOX1 mice: the PFC, STM and the substantia nigra (SN). Immunocal treatment induced a statistically significant increase in RELN, as observed in the PFC. Moreover, mRNA expression levels of GAD67, a gene acting downstream of RELN, were significantly increased in the STM and SN after Immunocal treatment. Without wishing to be bound by theory, these data suggest that Immunocal treatment may have salutary effects in schizophrenia and related neurodevelopmental disorders (e.g. autism) by enhancing brain reelin/GAD67 expression. The STM and SN are also key loci of pathology in Parkinson's disease and other extrapyramidal disorders; therefore it is contemplated that Immunocal-mediated upregulation of GAD67 in these regions may ameliorate such conditions as well. Again, without wishing to be bound by theory, upregulation of reelin/GAD67 in the PFC and HC may also benefit Alzheimer's dementia since degeneration in these brain regions is believed to be important, respectively, for the executive dysfunction and memory deficits characteristic of this condition. The role of reelin/GAD67 and Immunocal supplementation in Alzheimer disease could be further investigated in, for example, APPswe/PS1ΔE9 double-transgenic mice (e.g. J Neurochem 131: 778-790, 2014; herein incorporated by reference in its entirety) and other established rodent models of Alzheimer disease.

Without wishing to be bound by theory, Immunocal treatment may confer neuroprotection in human neurodegenerative disorders at least in part because (i) the glial HO-1 response is an important transducer of environmental and endogenous stressors into patterns of neural damage (pathological iron deposition, mitochondrial injury, mitophagy, etc.) characteristic of Alzheimer's disease and Parkinson's disease (Schipper H M, Song W. A Heme Oxygenase-1 Transducer Model of Degenerative and Developmental Brain Disorders. *International journal of molecu-*

*lar sciences* 2015; 16:5400-5419), (ii) central oxidative stress and glutathione deficiency figure prominently in the pathophysiology of the latter conditions (Gu M, Owen A D, Toffa S E, et al. Mitochondrial function, GSH and iron in neurodegeneration and Lewy body diseases. *Journal of the neurological sciences* 1998; 158:24-29; Jomova K, Vondra-kova D, Lawson M. Valko M. Metals, oxidative stress and neurodegenerative disorders. *Mol Cell Biochem* 2010; 345: 91-104; Mandal P K, Saharan S. Tripathi M, Murari G. Brain Glutathione Levels—A Novel Biomarker for Mild Cogni-tive Impairment and Alzheimer's Disease. Biological psy-chiatry 2015; and Schulz J B, Lindenau J, Seyfried J, Dichgans J. Glutathione, oxidative stress and neurodegen-eration. *Eur J Biochem* 2000; 267:4904-4911) and, (iii) as documented herein, Immunocal administered orally mark-edly improved GSH homeostasis in the brains of GFAP.HMOX1 mice.

The results obtained in these experiments indicate that compositions comprising whey protein isolate and/or whey protein concentrate, such as Immunocal®, may be used for treating, ameliorating, or preventing neurological or neuro-degenerative diseases or conditions in a subject. It has been found that, as described in detail herein, compositions comprising whey protein isolate and/or whey protein con-centrate may be used for restoration of neuronal reelin (RELN) levels. The effects of treatment with such compo-sitions were not limited to increasing or restoring RELN levels, indicating that such compositions may also, or alter-natively, be used to correct a number of other neurological imbalances, dysregulations, or abnormalities occurring in a subject as described hereinabove. Subjects suffering from neuropsychiatric or neurodegenerative diseases may particu-larly benefit from treatment with such compositions, how-ever other subjects may also benefit from such treatment with whey protein isolate.

Example 2—Whey Characteristics and Whey Protein Isolate Production

An example of whey protein isolate production is pro-vided below for illustrative purposes intended for the person of skill in the art.

As will be understood, whey may be considered as a by-product of cheese or of casein manufacture. Whey typi-cally contains soluble proteins of milk, so-called whey proteins. Cheese whey, for example, typically contains 5-8 g/l of proteins (N×6.38), among which β-lactoglobulin (β-lg) and α-lactalbumin (α-la) are the most abundant (accounting for 50-55% and 15-20% of total whey proteins, respectively) and bovine serum albumin (BSA), lactoferrin (LF) and immunoglobulins (IgG) are considered as minor whey proteins (accounting each for 3-5%). Whey may also comprise protein fragments or polypeptides such as so-called proteose-peptones (PP-4, PP-5, PP-8f) resulting from proteolysis of milk proteins by lactic starters in cheesemak-ing or by psychrotrophic bacteria during cold storage of raw milk. These proteinaceous compounds are not completely characterized, and their concentration in whey is highly variable. Finally, non-protein nitrogen (NPN) group may comprise a large number of molecules in whey, among which urea may account for 50-60%.

For illustrative purposes, Table 2 below provides some characteristics of some of the major proteins and polypep-tides found in an exemplary whey sample (in this case, bovine sweet whey).

TABLE 2

| Some Characteristics of Major Proteins and Polypeptides in an Exemplary Whey Sample | | |
| --- | --- | --- |
| Protein or polypeptide | Weight contribution (g/l) (approx.) | Molecular weight |
| β-lactoglobulin | 3.0 | 18 400 |
| α-lactalbumin | 1.2 | 14 200 |
| BSA | 0.3 | 69 000 |
| Lactoferrin | 0.2 | 77 000 |
| IgG | 0.2 | 160 000 |
| PP-3 | 0.6 | 22 000 |
| PP-5 | | 14 300 |
| PP-8f | | 4 100 |
| NPN | 1.6 | |

In this example, whey protein isolate may be obtained from whey, such as the whey exemplified above in Table 2. As will be understood, process steps involved in the manu-facture of whey protein isolate (WPI) may lead to compo-sitional differences in terms of protein profile between whey protein isolates. Thus, the specific components and their abundance are not meant to be considered limiting in any manner. Factors influencing whey protein isolate character-istics may include, for example:

[1] Source of the whey proteins: For example, sweet- or acid-whey may be used as starting material for the manufacture of WPI;

[2] Pasteurization: For example, the proteins in cheese whey-derived ingredients may be submitted to two (2) pasteurization (i.e. 72-75° C.—12-16 sec.) treatments at a cheese plant where milk is pasteurized (Canada and US regulation) before cheesemaking, or at the ingre-dient manufacturing plant, or before transportation of drained whey to this plant, in order to reduce bacterial count before membrane processing or ion exchange chromatography: and

[3] Defatting: For example, centrifugal clarification is typically used to reduce the fat content of whey to 0.8-1.2%. However, an additional defatting step is often performed to further decrease the fat content to 0.3-0.5% in order to increase membrane separation performance or to prevent an irreversible fouling or clugging of ion-exchange resins with polar lipids. Defatting typically involves holding whey at 50-55° C. for 30 to 90 min. in order to promote aggregation of fat particles (optionally in the presence of added $CaCl_2$)). The product will thereafter be submitted to centrifugal separation or MF in order to remove the agglomerated material.

In this example, high-protein concentration (>90% dry basis) whey protein isolate may typically be prepared from whey such as that exemplified in Table 2 by either of two methods: membrane processing or ion-exchange chroma-tography. In membrane processing, microfiltration (MF) and/or ultrafiltration (UF) membranes may be used for concentrating whey. In ion-exchange chromatography, cat-ionic- and/or anionic-exchange chromatography may be used to purify whey proteins.

In this example, obtained samples may be submitted to spray drying conditions. Where a substantially undenatured isolate is to be prepared, the obtained concentrated liquid may be, for example, sprayed in a hot air current (inlet T°: 180-200° C., outlet T°: 80-100° C.) circulating in a spray drying tower. A combination of dehydration and gravity may allow the collection of dry particles (4-8% humidity) at the bottom of the spray dryer. Estimates obtained from mathematical modeling of such drying processes suggest that the droplet temperature does not exceed about 80-85° C. during the few seconds used for dehydration, providing for an example of low impact spray drying which may not substantially denature whey protein.

As will be understood, ingredients having high-protein contents may generally be more difficult to rehydrate (possibly because of their low lactose and minerals content). For certain applications where rapid rehydration of the powder obtained from spray drying is desired, the powder may be submitted to agglomeration. Such steps may involve a final drying of the powder (from 12-15% to 4% humidity) on a fluid bed, generating agglomerated particles having better sinkability in water. In products containing fat (which is generally not the case for high protein ingredients), lecithin may be injected during fluid bed drying. Lecithin may cover fat droplets and improve their wettability. Instantization step(s) may also be used, although such steps are generally uncommon in the manufacture of high-protein ingredients.

As a result of the above steps, an example of a whey protein isolate may be prepared from the whey protein starting material exemplified in Table 2 above. It will be understood that this example is provided for illustrative and non-limiting purposes, and that many alternative, substituted, or modified whey protein sources and/or processing steps known to the person of skill in the art having regard to the teachings herein are also contemplated.

Example 3—Effects of Whey Protein Isolate in Cell and Mouse Models of Alzheimer's Disease (AD)

As discussed above, deficits in Reelin expression and/or Reelin signaling play a pathogenic role in several nervous system disorders including schizophrenia and Alzheimer's disease (AD).

As described hereinabove, the cysteine-rich whey protein supplement, Immunocal®, rescues Reelin expression, particularly in the prefrontal cortex, of a mouse model of schizophrenia. Given that Reelin expressing neurons of the entorhinal cortex layer II are a highly vulnerable population of cells that are lost very early in AD, the presently described experiments sought to evaluate the effects of whey protein isolate on Reelin expression and signaling in vitro in hippocampal-entorhinal cortex rat brain slices and in vivo in the hAPPSweInd mutant (J20) mouse model of AD.

As discussed below, incubation of hippocampal-entorhinal cortex slices with Immunocal® increased Reelin expression at the mRNA and protein levels. In addition, immunostaining of slices revealed a striking increase in the intensity and number of neurons staining positively for Reelin within the entorhinal cortex, dentate gyrus and CA1 region of the hippocampus following Immunocal®, treatment in vitro. These studies next evaluated the effects of whey protein isolate in vivo by treating hemizygous J20 AD mice from 3 months-old to 5 months-old with Immunocal®. Reelin expression and signaling was then assessed by western blotting and immunofluorescence microscopy and cognitive function using the Barnes maze to test spatial learning and memory. Immunocal®, treatment corrected a deficit in cortical GSH levels observed in the brains of untreated hemizygous J20 mice. Western blotting of brain sections micro-dissected to enrich for the hippocampal-entorhinal cortex sub-region revealed a decrease in Reelin and GAD67 expression in untreated hemizygous J20 AD mice compared to non-carrier control mice and this effect was prevented by treatment with Immunocal®. In addition, untreated hemizygous J20 AD mice displayed a marked reduction in p-CREB immunoreactivity in the hippocampal-entorhinal cortex sub-region of the brain and this deficit was essentially rescued by treatment with Immunocal®. In a similar manner, using immunofluorescence microscopy, Reelin expression was diminished in the entorhinal cortex, dentate gyrus and CA1/CA3 regions of the hippocampus in untreated hemizygous J20 AD mice compared to non-carrier control mice. In contrast, Immunocal® treatment largely rescued these deficits in Reelin expression. In particular. Immunocal® treated J20 mice displayed robust Reelin staining in layer II of entorhinal cortex, apparently rescuing the loss of Reelin positive neurons observed in this brain region in untreated J20 AD mice. In parallel with the observed rescue in Reelin expression in J20 mice, Immunocal®, also preserved GAD67 expression in the dentate gyrus and CA3 region of the hippocampus and markedly enhanced the co-staining of Reelin and phospho-DAB1 in the CA1 of these mice. Finally, Immunocal® treatment had a statistically significant positive effect on Barnes maze performance, both during the late stages of the acquisition phase and during the probe phase, in female, hemizygous J20 AD mice. Collectively, these findings indicate that Immunocal® induces Reelin expression in vitro in hippocampal-entorhinal cortex brain slices and rescues Reelin expression and signaling in vivo within the entorhinal cortex and hippocampus in the J20 mouse model of AD.

Alzheimer's Disease: Phenotypic and Pathological Characteristics. Alzheimer's disease (AD) is the leading cause of dementia and cognitive decline with over 5 million patients currently diagnosed in the United States and approximately 500,000 new cases each year. Aging is the most significant risk factor for developing sporadic AD. According to the Alzheimer's Association, approximately 13% of people age 65 and older have AD and this fraction increases to approximately 45% of people over the age of 85. Given the demographic shift to advancing age in our population, there is predicted to be a very significant increase in the number of people diagnosed with AD in the next several decades. By 2025 the number of people age 65 and older suffering with AD is predicted to be approximately 7.7 million and this number is expected to perhaps double by 2050. The average life expectancy once a patient is diagnosed with AD is approximately 8 years and AD has risen to the 6th leading cause of death in the United States. Alzheimer's disease was first described in 1906 by Dr. Alois Alzheimer and is characterized phenotypically by progressive memory loss and cognitive decline. Pathological hallmarks of the disease include amyloid plaques consisting of insoluble deposits of amyloid beta (Aβ) peptide and neurofibrillary tangles containing hyper-phosphorylated tan protein. These plaques and tangles are found throughout the brain parenchyma and are believed to play a significant role in the neuronal loss and atrophy that are characteristic of the AD brain. Of the diverse neuronal cell types that die in AD, hippocampal pyramidal cells, cortical pyramidal cells, and basal forebrain cholinergic neurons are among the most severely affected. The death of these populations of neurons leads to profound synaptic loss and significant neurotransmitter deficits, particularly in cholinergic pathways. Although 3 genes (amyloid precursor protein (APP), presenilin 1 (PS1), and presenilin 2 (PS2)) have been shown to be mutated in early onset, autosomal dominant, familial AD, these inherited forms of the disease make up less than 5% of AD cases, with the remaining 95% of cases being sporadic in nature. Current FDA approved drugs for AD are limited to acetylcholinesterase inhibitors and the NMDA antagonist memantine. These drugs are minimally effective and treat the symptoms of AD while having no effect on the underlying etiology of the disease. As such, current therapies do not significantly delay or halt the progression of AD.

Figure 12:
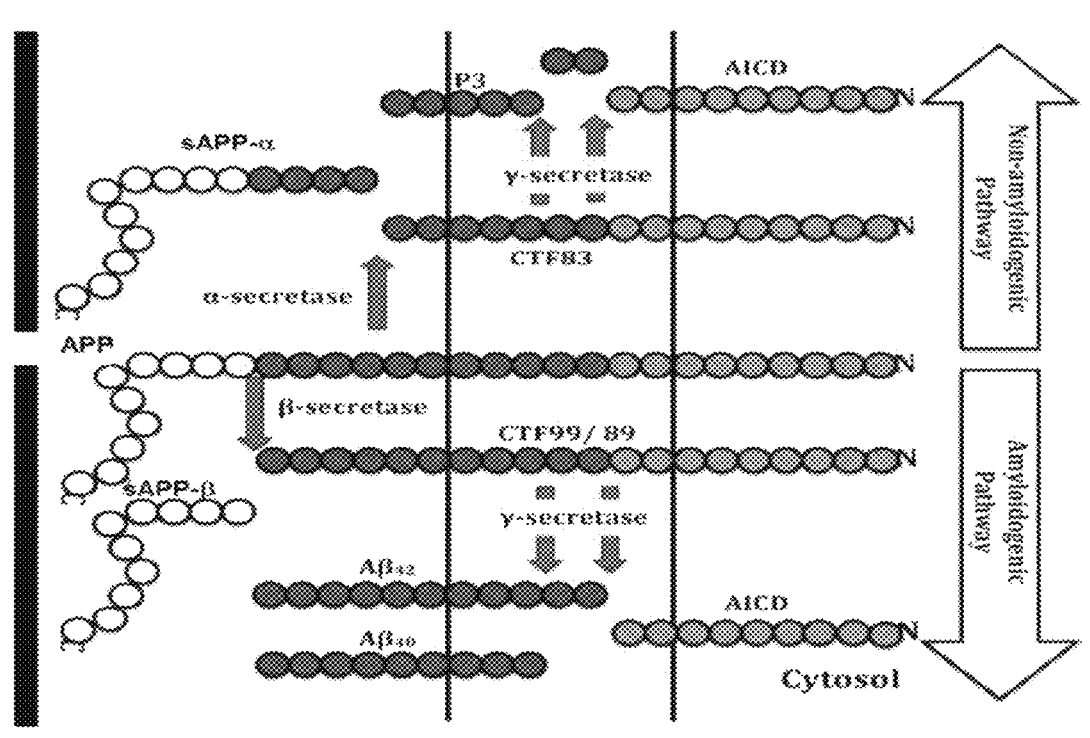
FIG. 12 shows distinct pathways of APP proteolytic processing. APP processing has two different pathways once it has been inserted into a lipid membrane. The non-amyloidogenic pathway utilizes α-secretase to produce soluble amyloid-beta precursor protein-alpha (sAPP$_\alpha$) and C-terminal fragment 83 (CTF83). γ-secretase then cleaves the CTF83 into a soluble p3 fragment and the amyloid precursor protein intracellular domain (AICD). The amyoidogenic pathway utilizes processing by β-secretase, which produces the soluble amyloid-beta precursor protein-beta (sAPP$_\beta$) and C-terminal fragment 99 or 89 (CTF99/89), depending on tissue type. γ-secretase then cleaves CTF99/89 into Aβ$_{40}$ or Aβ$_{42}$, which become extracellular, and the AICD. Figure adapted from Miller et al. (2008).

The Amyloid Cascade Hypothesis. The amyloid cascade hypothesis has dominated the field of AD research for the past two decades and is founded on the premise that deposition of Aβ peptide is the initiating event in disease pathogenesis, ultimately leading to neurofibrillary tangle formation, synaptic loss, and neuronal cell demise (Hardy and Higgins, 1992). Throughout the years, the molecular form of Aβ thought to initiate the toxic cascade responsible for AD pathology has shifted from insoluble plaques to protofibrils to soluble oligomers (Klein et al., 2001; Naylor et al., 2008; Ferreira and Klein, 2011: Larson and Lesne, 2012). Regardless of which particular form(s) of Aβ leads to disease pathology, for more than a decade, the amyloidogenic processing of APP to form Aβ has been recognized as a viable molecular target for AD therapeutic development (Vassar, 2001: Evin et al., 2006). The amyloidogenic pathway generates beta amyloid peptide (of which the $A\beta_{1-42}$ form (here referred to simply as Aβ) is commonly regarded as the most likely toxic species) through the sequential cleavage of APP by the beta-site APP cleaving enzyme (BACE; also known as β-secretase) and γ-secretase (FIG. 12). Alternatively, the sequential cleavage of APP by α-secretase and γ-secretase is considered non-amyloidogenic and primarily produces a soluble non-aggregating form of APP (sAPPα). Based largely on the amyloid cascade hypothesis and more recent studies showing that soluble Aβ oligomers are intrinsically neurotoxic, selective inhibitors of BACE and γ-secretase have been developed as drugs to decrease the tissue load of Aβ in AD brain (Vassar et al., 2009; D'Onofrio et al., 2012). The development of selective BACE inhibitors that are orally bioavailable and penetrate the blood brain barrier has been slow; however, this class of compounds has recently begun clinical testing in AD (Ghosh et al., 2012). The Merck compound, MK-8931 (verubecestat), initially completed Phase I testing and reportedly was capable of reducing cerebral spinal fluid amyloid levels by up to 90% in rats, monkeys, healthy human volunteers, and AD patients (Menting and Claassen, 2014; Kennedy et al., 2016). A Phase II/III clinical trial of this drug (EPOCH) completed enrollment in early 2016 in a population of patients with mild-to-moderate AD. Unfortunately, in February of 2017, Merck announced that it was terminating the trial after an interim analysis suggested little chance of discerning any positive therapeutic benefit. This was a significant setback for the AD field; however, Merck has continued another trial of verubecestat in patients with prodromal AD (APECS). In a similar manner to the recent failure of BACE inhibitors, γ-secretase inhibitors have been largely disappointing in the clinic. Most notably, two large Phase III clinical trials of the Eli Lilly compound, semagacestat, in mild-to-moderate AD patients were terminated early due to a statistically significant worsening of clinical measures of cognition and ability to perform activities associated with daily living (D'Onofrio et al., 2012). It is presently unclear why this compound failed clinically but it may be an off target effect related to modulation of Notch signaling as Notch is also a substrate for γ-secretase-mediated cleavage. Thus, Notch-sparing γ-secretase inhibitors are currently under development in hopes of circumventing possible toxic effects of this class of drugs (Augelli-Szafran et al., 2010). As a result of these recent clinical disappointments, and due to the observation that brain amyloid load does not necessarily correlate with the severity of cognitive deficits in AD (as well as other findings contrary to an amyloid-centric view), some have begun to question whether the amyloid cascade hypothesis is sufficient to explain the underlying pathogenesis of late onset, sporadic AD (Giannakopoulos et al., 2003; Pimplikar et al., 2010; Castellani and Smith, 2011; Karran et al., 2011: Mullane and Williams, 2013; Karran and De Strooper, 2016; Swerdlow et al., 2017; Tse and Herrup, 2017).

The Complex Role Of Reelin In Alzheimer's Disease. Reelin is a large glycoprotein secreted by specific cells within the central nervous system that plays a key role in patterning and layering of the cerebral cortex and other regions of the brain during development. In adults, Reelin plays a central role in processes that influence synapse formation and neuronal plasticity required for learning and memory, such as the regulation of dendritic spine architecture and the maintenance of long term potentiation (Niu et al., 2004; Beffertt al., 2006; Kim et al., 2015; Bosch et al., 2016). Alzheimer's disease is the most prevalent cognitive disorder in adults and is characterized by substantial deficits in learning and memory. The pathological basis of AD is complex and is characterized by the formation of senile plaques made up of misfolded AP protein and neurofibrillary tangles consisting of hyper-phosphorylated tau protein. Specific populations of neurons in the brain die in AD including most prominently, forebrain cholinergic neurons, hippocampal neurons, and cortical pyramidal neurons. In particular, neurons of the entorhinal cortex project to the hippocampus and are involved in declarative memory formation and consolidation. Entorhinal cortex layer II neurons provide the principal excitatory glutamatergic input to the dentate gyrus of the hippocampus. The entorhinal cortex layer H neurons are one of the first neuronal populations to die in AD, resulting in a severe loss of synaptic contacts to the dentate gyrus. Many of the entorhinal cortex layer II neurons express Reelin and these Reelin-expressing cells are significantly reduced in the brains of human amyloid precursor protein (hAPP) transgenic mice expressing the Swedish and Indiana mutant form of the hAPP gene (J20 strain). In accordance with the loss of these Reelin-expressing entorhinal cortex layer II neurons, Reelin levels in the hippocampus of J20 mice are also significantly reduced, compared to nontransgenic controls (Chin et al., 2007). Similar loss of Reelin-expressing entorhinal cortex layer II neurons is also observed in the brains of patients with AD (Chin et al., 2007; Herring et al., 2012). Finally, in a transgenic rat model of AD (McGill-R-Thy1-APP strain), Reelin-expressing neurons of the entorhinal cortex layer II were found to selectively express increased levels of soluble intracellular Aβ early in disease, prior to the deposition of amyloid plaques (Kobro-Flatmoen et al., 2016). Collectively, these studies suggest that Reelin-expressing neurons of entorhinal cortex layer II play a central role in the early pathogenic changes in AD and loss of these Reelin-expressing cells and their synaptic projections to the hippocampus are early markers of disease (Krstic et al., 2013). Thus deficits in Reelin signaling to the hippocampus likely underlie some of the cognitive deficits observed in patients with AD (Cuchillo-Ibañez et al., 2016; Yu et al., 2016).

A Brief Overview Of Reelin Signaling. Reelin is secreted into the extracellular space where it interacts with one of two cell surface receptors on target cells, either the very low density lipoprotein receptor (VLDLR) or the apolipoprotein E receptor-2 (ApoER2). Upon binding its receptor, Reelin induces tyrosine phosphorylation of the adapter protein. Disabled-1 (DAB1), via the nonreceptor tyrosine kinases, Src or Fyn. Phosphorylated DAB1 acts as a docking site to initiate multiple downstream signal transduction cascades such as those involved in cell survival (PI3K/AKT) and regulation of actin assembly (Cdc42/PAK/cofilin) (FIG. 13) (Wasser and Herz, 2017).

Figure 13:
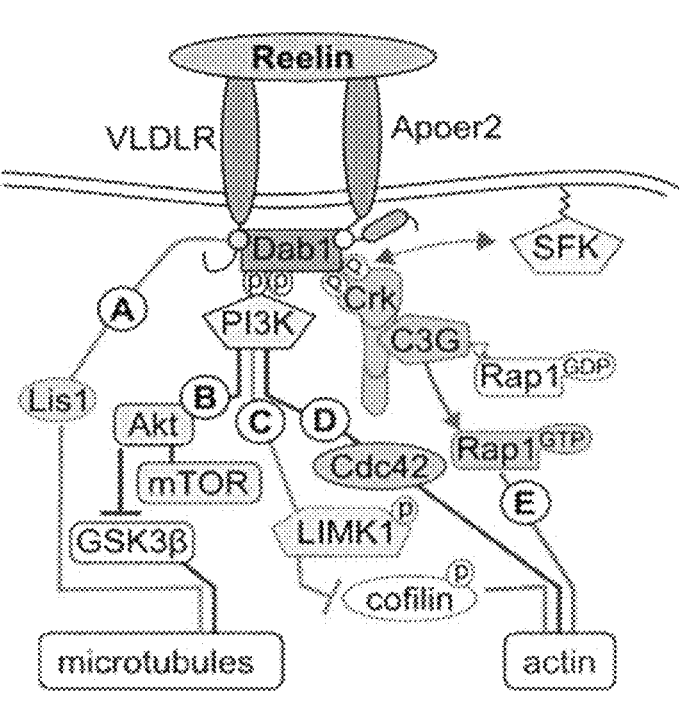
FIG. 13 shows the canonical Reelin signaling pathway. Reelin binds to one of two cell surface receptors, VLDLR or Apoer2, and induces tyrosine phosphorylation of the adapter protein, Dab1, via Src family kinase (SFK) activity. Phosphorylated Dab1 acts as a docking site to initiate multiple downstream signaling cascades. Figure adapted from Wasser and Herz (2017).

The pathway shown in FIG. 13 represents the canonical Reelin signaling pathway and is the one most commonly attributed to Reelin's actions in the central nervous system. However, other (non-canonical) Reelin signaling pathways do exist, as well as additional Reelin receptors (Bock and May, 2016; Lee and D'Arcangelo, 2016).

Modulation Of Reelin Expression And Signaling As A Means Of Altering The Course Of Alzheimer's Disease. As noted above, Reelin-expressing cells of the entorhinal cortex layer II are significantly reduced in the brains of hAPP transgenic mice expressing the Swedish and Indiana mutant form of the hAPP gene (J20 strain). In accordance with the loss of these Reelin-expressing entorhinal cortex layer II neurons, Reelin levels in the hippocampus of J20 mice are also significantly reduced, compared to nontransgenic controls. Moreover, further reducing Reelin in these mice by crossing J20 AD model mice with heterozygous reeler mice accelerates amyloid plaque formation and tau pathology (Kocherhans et al., 2010). On the other hand, Reelin overexpression in J20 AD model mice significantly delays Aβ fibril formation and rescues cognitive deficits in these mice (Pujadas et al., 2014). Thus, J20 mice are an established model of familial AD and the disease course of these mice is significantly impacted by alterations in Reelin expression, making this an excellent model system to investigate the effects of Immunocal® on these processes. The whey protein supplement, Immunocal®, is a rich source of the glutathione precursor, cysteine, and is known to boost antioxidant levels in vivo. In addition, as described in detail hereinabove, in a schizophrenia mouse model characterized by low Reelin levels, Immunocal® elevated Reelin in the brain.

Loss of Reelin-expressing entorhinal cortex layer II neurons has also been observed in the brains of patients with AD, and therefor studies investigating whether Immunocal® elevates Reelin expression and signaling in the entorhinal cortex-hippocampus of J20 mice and mitigates cognitive dysfunction in these animals, was performed as described herein.

The present studies have been performed determine if supplementation with a whey protein isolate such as Immunocal® increases Reelin expression in vitro in a hippocampal-entorhinal cortex slice model and in vivo within the brain of an Alzheimer's disease mouse model (J20 strain). In addition, Immunocal® administration to J20 AD model mice studies were performed to determine whether enhanced cognitive function and diminished amyloid load would be observed when compared to untreated mice.

Experimental Methods and Results

I. In Vitro Studies

Experimental model: The effects of Immunocal® on Reelin expression in vitro were investigated. Organotypic hippocampal-entorhinal cortex slices prepared from postnatal day 25 rats were utilized. Brain slices were prepared using a vibrating microtome essentially as described by Leutgeb et al. (2003).

Treatment and analysis of brain slices: Hippocampal-entorhinal cortex slices (~400 micron thickness) were cultured in a humidified incubator in tissue culture medium with 5% $CO_2$/95% air at 37° C. After equilibration overnight, slices were subsequently treated with either culture medium alone or containing Immunocal® (3.3% w/v) for 24 h, followed by measurement of Reelin expression assessed at the mRNA level using quantitative real-time polymerase chain reaction (qPCR) and at the protein level using western blotting. In addition, the expression of Reelin within entorhinal cortex layer II neurons was evaluated specifically using immunofluorescence microscopy after co-staining slices for Reelin and NeuN. As a control to assess viability of the slices and functionality of the Reelin signaling pathway, DAB1 was immunoprecipitated and tyrosine phosphorylation of this adapter protein was measured by western blotting following incubation with recombinant Reelin.

Figure 15:
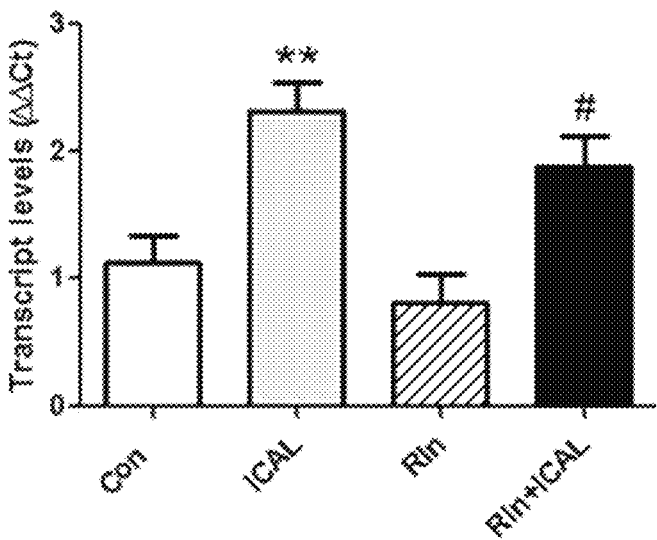
FIG. 15 shows results of studies in which Immunocal® treatment increased Reelin mRNA expression in vitro in hippocampal-entorhinal cortex slices. Brain slices were incubated for 24 h in either control medium (Con), medium containing Immunocal® (ICAL), recombinant Reelin protein (Rln), or a combination of the two. Total RNA was extracted from the slices, cDNA was prepared and subjected to qPCR using primers and probes for rat Reelin and GAPDH (as a control housekeeping gene). Data are expressed as the ΔΔCt levels of the Reelin transcript normalized to GAPDH. **p<0.01 compared to Con; #p<0.05 versus Rln alone (n=5 independent rat brain slice preparations).

Results: Incubation of hippocampal-entorhinal cortex slices with recombinant Reelin for 24 h induced a marked increase in the tyrosine phosphorylation of the adapter protein DAB1 (FIG. 14A). This result demonstrates two points; first, the brain slices were viable under the incubation conditions used and second, the Reelin signaling pathway is intact in the slice culture as addition of recombinant Reelin stimulated (Src/Fyn-dependent) tyrosine phosphorylation of DAB1 via binding to its cell surface receptors. Next, hippocampal-entorhinal cortex slices were incubated for 24 h in either tissue culture medium alone or containing Immunocal®. Immunocal® treatment induced an increase in the full length Reelin protein (388 kDa) and in two prominent Reelin cleavage products (310 kDa and 180 kDa) (FIG. 14B). In addition, the Reelin transcript was measured by qPCR after incubation of brain slices in control medium, medium containing Immunocal®, recombinant Reelin, or a combination of the two. Incubation with Immunocal® induced a statistically significant, approximately two-fold increase in Reelin mRNA transcript levels in either the absence or presence of recombinant Reelin protein (FIG. 15). Incubation with recombinant Reelin protein alone had no significant effect on the amount of Reelin transcript detected in the slices, although a trend towards decreased Reelin mRNA levels was observed under these conditions.

Next, the effects of Immunocal® treatment on Reelin expression were assessed in hippocampal-entorhinal cortex slices by co-staining for Reelin and NeuN using specific antibodies and immunofluorescence microscopy. Incubation of brain slices with Immunocal® induced a striking increase in Reelin immunoreactivity in the entorhinal cortex, dentate gyrus, and CA1 region of the hippocampus (FIG. 16). Some, but not all, of the Reelin positive cells also co-stained for NeuN.

II. In Vivo Studies

Experimental model: To investigate the effects of Immunocal® on Reelin expression in vivo, the hAPP(Swe/Ind) mutant transgenic mouse model of AD (J20 strain) was utilized. This mouse model is commercially available from Jackson Laboratories (B6.Cg-Tg(PDGFB-APPSwInd) 20 Lms/2Mmjax) and displays significant brain pathology, amyloid plaques, and cognitive deficits that recapitulates multiple aspects of AD in humans (Mucke et al., 2000: Karl et al., 2012: Diaz-Hernandez et al., 2012). According to previous reports, these transgenic mice typically show significant cognitive deficits, diminished numbers of Reelin-positive, entorhinal cortex layer II neurons, and decreased Reelin expression in the hippocampus by approximately 4-5 months of age. Amyloid plaques are visible in the brains of these mice by around 12 months of age. All animal studies were conducted in accordance with a protocol approved by the University of Denver Institutional Animal Care and Use Committee.

Studies were performed to determine whether Immunocal® treatment would rescue the Reelin-expressing neurons of the entorhinal cortex layer II and as a result, enhance Reelin expression and signaling in the hippocampus of J20

AD model mice. As well, studies were performed to investigate whether Immunocal® treatment corrects or delays the cognitive deficits observed in J20 AD model mice.

Immunocal® treatment: To perform these studies, three groups of mice were used: hAPP(Swe/Ind) mutant hemizygous mice (J20 strain) treated with Immunocal® (3.3% w/v in drinking water ad libitum, as previously described by Ross et al., 2014), untreated hemizygous J20 mice, and untreated nontransgenic (non-carrier) control mice. Immunocal® treatment was initiated at 3 months-old and continued until the mice were 5 months-old.

Behavioral cognitive testing: During the final week of treatment, mice were evaluated for spatial learning and memory performance using the Barnes maze (FIG. 17). The mice were subjected to a six-day acquisition phase followed by a single day of probe testing, as previously described by Mouzon et al. (2012).

Figure 18:
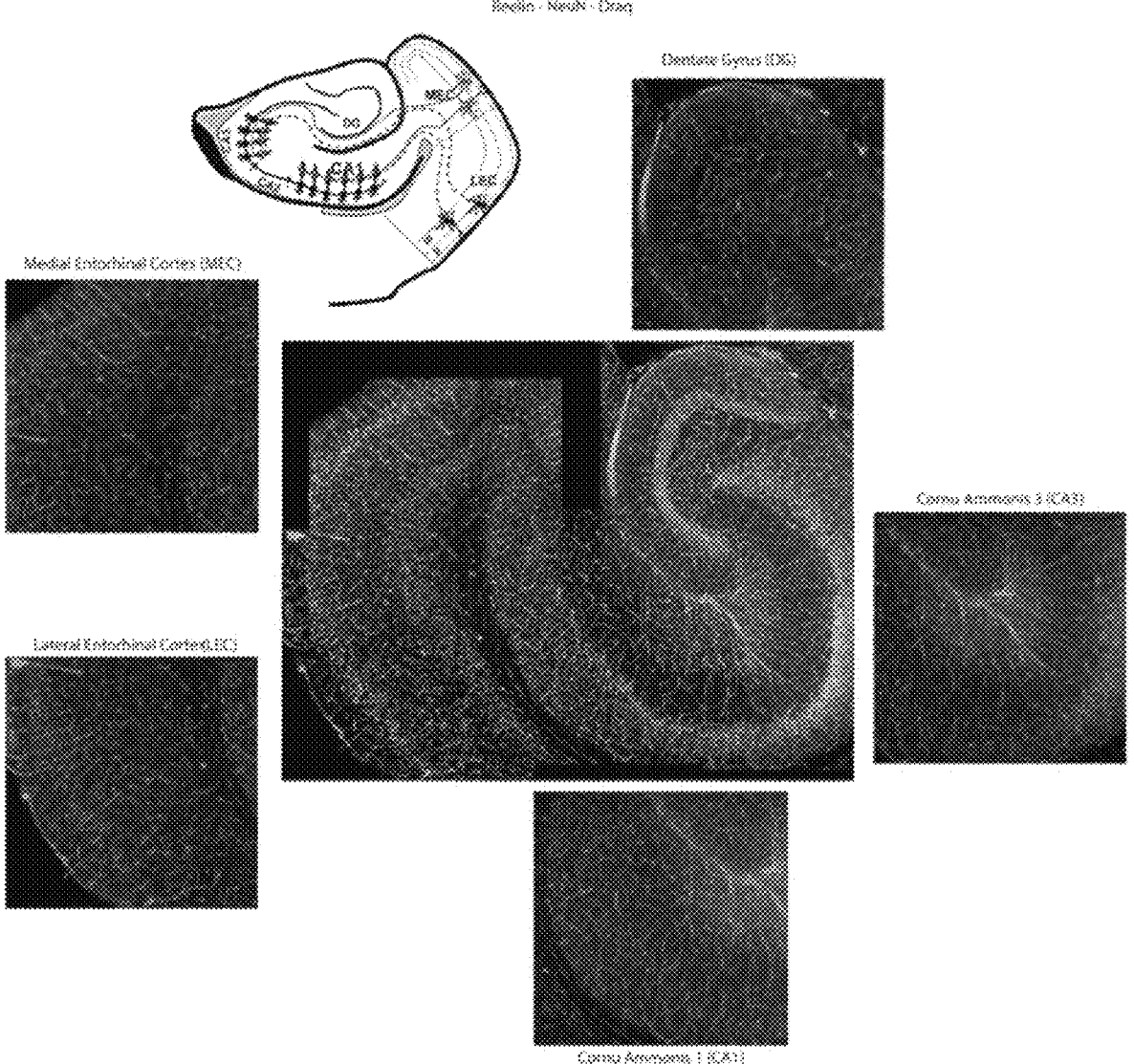
FIG. 18 shows cyto-architecture of the hippocampal-entorhinal cortex region of mouse brain. A control (non-carrier) mouse brain was co-stained for Reelin (shown in green), NeuN (shown in red), and Draq (a nuclear marker, shown in blue). The cartoon at top left shows the cyto-architecture of this region schematically.

Immunostaining and western blotting for Reelin and its signaling pathway components: Following behavioral testing, mice were euthanized and biochemical and immuno-histochemical analysis was conducted on brain tissue to evaluate Reelin-expressing neurons in the entorhinal cortex layer II and Reelin expression and signaling in the dentate gyrus, CA1, and CA3 of the hippocampus. For western blotting, brains were micro-dissected to obtain tissue samples enriched for the hippocampal-entorhinal cortex architecture. For immunofluorescence staining of brain tissue, a composite of several sections from a single non-carrier control mouse stained for Reelin, NeuN, and Draq (a nuclear stain) is shown in FIG. 18 to demonstrate the type of staining that was obtained and to orient the reader to the architecture of the hippocampal-entorhinal cortex region.

Analysis of Brain GSH by HPLC with Electrochemical Detection (HPLC-ECD):

Tissue Processing

Cortical tissue was obtained from mice and immediately frozen in liquid nitrogen. For HPLC-ECD analysis, 2.5M perchloric acid was added and the brains were roughly chopped using pointed surgical scissors. Samples were then sonicated 3 times for 15 s intervals. Samples were then centrifuged for 5 min at 13,000 rpm and the supernatant was removed. A 20 µL aliquot of the supernatant was used for a BCA protein assay. The remainder of each solution was neutralized with 500 µL of 4M KOH and vortexed thoroughly. Samples were then centrifuged for 15 min at 13,000 rpm, and stored at −80° C. until separation and analysis by HPLC-ECD.

HPLC-ECD

GSH in samples and known standards were separated by reversed-phase HPLC on a C18 bonded silica column at 35° C. (5 µm, 4.6×250 mm) from Dionex, Inc. (Sunnyvale, CA). Analytes were detected using a CoulArray® detector (model 5600, ESA) on three coulometric array cells in series; electrochemical detectors were set between 0 and 900 mV at increments of 75 mV. Concentrations were determined with a standard curve of each identified analyte. Mobile phase consisted of 50 mM lithium acetate and 1% acetonitrile in water, pH 3.8. The flow rate was set to 0.4 mL/min for all samples. CoulArray® software was used for baseline correction and peak analysis.

Figure 19:
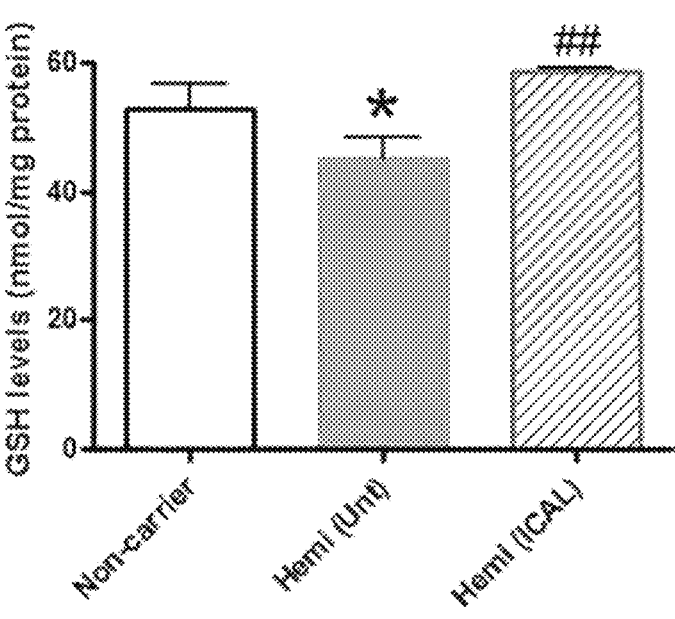
FIG. 19 shows results of studies in which Immunocal® treatment preserved brain GSH in J20 AD model mice. Brain (cortical) tissue was harvested from 5 month-old hemizygous J20 AD mice (either untreated (Unt) or treated with Immunocal® (ICAL) for 2 months) and non-carrier control mice. Tissue was extracted and reduced GSH was measured by HPLC with electrochemical detection. Values are normalized to protein content and represent the mean±SEM for n=3 mice per group. Statistical differences were calculated by one-way ANOVA with a post hoc Tukey's test. *significantly different than non-carrier at p<0.05. ##significantly different than Hemi (Unt) at p<0.01.

Results: First, the brain levels of reduced GSH in cortical tissue from the mice were measured using HPLC-ECD. Untreated hemizygous J20 mice displayed a statistically significant decrease in cortical GSH at 5 months-old when compared to non-carrier control mice (FIG. 19). However, hemizygous J20 mice treated with Immunocal® from 3 months-old to 5 months-old showed a complete preservation of cortical GSH which was statistically significantly greater than the levels observed in untreated hemizygous mice (FIG. 19). Thus, Immunocal® treatment corrected a deficit in brain GSH observed in AD model mice.

Figure 20:
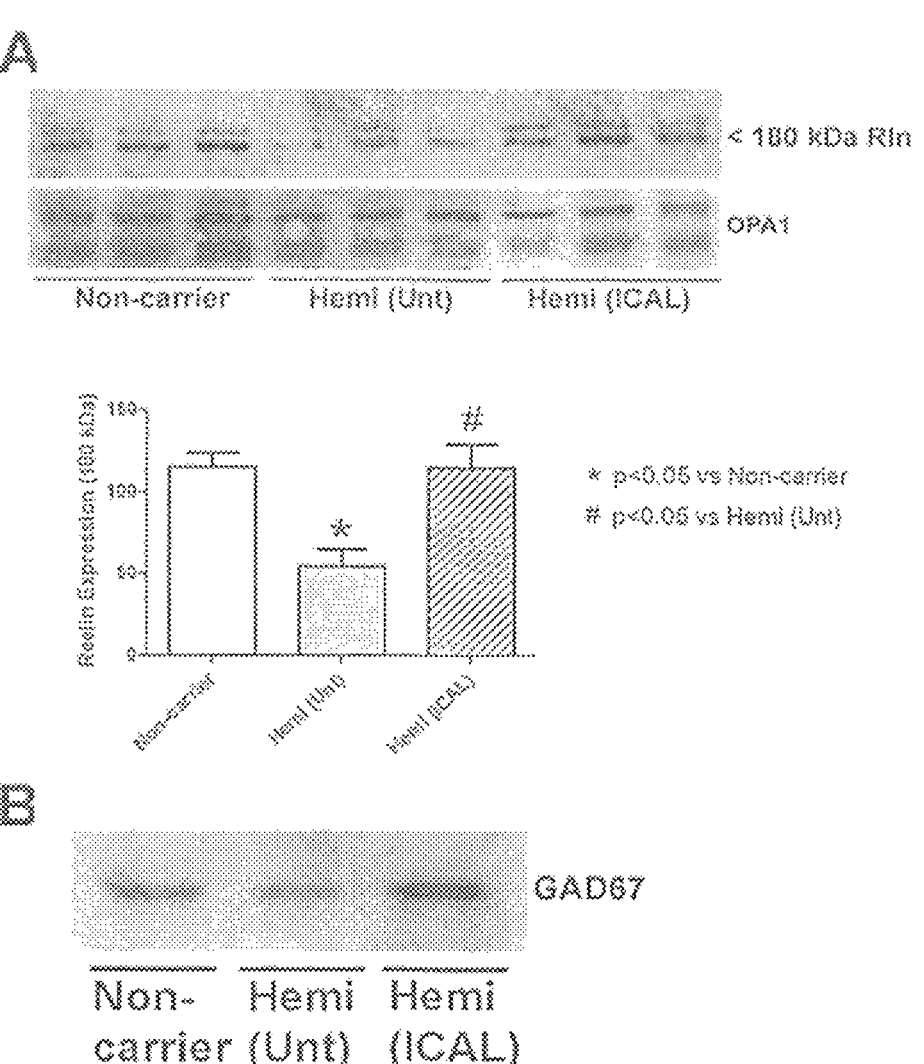
FIG. 20 shows results of studies in which Immunocal® treatment rescued Reelin expression and increased GAD67 expression in J20 AD model mice. Brain tissue was harvested from 5 month-old hemizygous J20 AD mice (either untreated (Unt) or treated with Immunocal® (ICAL) for 2 months) and non-carrier control mice. Tissue was micro-dissected to enrich for the hippocampal-entorhinal cortex sub-region. Brain lysates were resolved by SDS-PAGE and immunoblotted for (A) Reelin (Rln) and (B) GAD67. The Reelin blot was stripped and reprobed for OPA1. The graph shows the densitometric analysis of the 180 kDa Reelin bands in arbitrary units (n=3 mice per group). Statistical differences were calculated by one-way ANOVA with a post hoc Tukey's test.

The expression of Reelin and the glutamic acid decarboxylase protein (GAD67) was next evaluated by western blotting of mouse brain lysates. GAD67 is expressed in GABAergic neurons and its expression is regulated in a manner parallel with Reelin. For example, both Reelin and GAD67 expression are significantly decreased in the pre-frontal cortex of patients with schizophrenia and both gene promoters are similarly regulated by drugs that influence epigenetic modifications such as DNA methyltransferase inhibitors and histone deacetylase inhibitors (Guidotti et al., 2000; Kundakovic et al., 2009). Brain lysates enriched for the hippocampal-entorhinal cortex sub-region were immunoblotted for Reelin and GAD67. Reelin expression was significantly reduced in untreated hemizygous J20 AD mice compared to non-carrier controls and Immunocal® treatment largely corrected this deficiency (FIG. 20A). Only the 180 kDa cleavage fragment of Reelin was detected in these mouse brain lysates. Quantitative densitometric analysis of the 180 kDa Reelin baud revealed an approximate 50% reduction in Reelin protein expression in hemizygous untreated AD mice compared to non-carrier controls, and a complete preservation of Reelin expression in Immunocal®-treated mice (FIG. 20A, graph). The Reelin blots were stripped and reprobed for the inner mitochondrial membrane protein, OPA1, initially as a loading control. Interestingly, OPA1 levels were substantially reduced in 5-month-old hemizygous J20 mice when compared to non-carrier control mice. We have previously shown OPA1 to be susceptible to cleavage and degradation in the brains of old mice and rats (Gray et al., 2013). Nonetheless, Immunocal®® treatment did not appear to rescue OPA1 levels in the brains of hemizygous J20 mice as evidenced by both untreated and Immunocal®-treated hemizygous mice displaying equivalent amounts of this mitochondrial protein in brain lysates (FIG. 20A). Thus, the changes observed in Reelin expression in these same brain lysates were not due to discrepancies in protein loading. The expression of GAD67 was somewhat variable between untreated hemizygous AD mice and non-carrier control mice; however, Immunocal® treatment of hemizygous mice markedly increased GAD67 protein levels (FIG. 20B).

Figure 21:
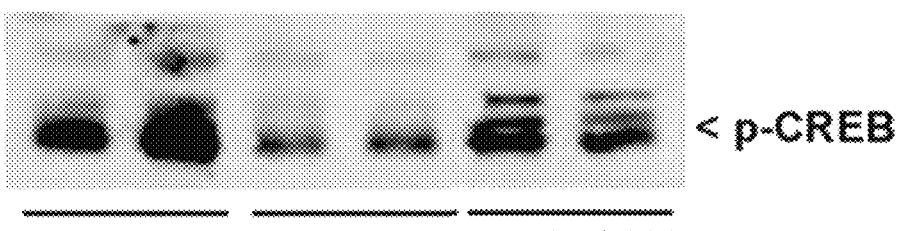
FIG. 21 shows results of studies in which Immunocal® treatment preserved brain p-CREB in J20 AD model mice. Brain tissue was harvested from 5 month-old hemizygous J20 AD mice (either untreated (Unt) or treated with Immunocal® (ICAL) for 2 months) and non-carrier control mice. Tissue was micro-dissected to enrich for the hippocampal-entorhinal cortex sub-region. Brain lysates were resolved by SDS-PAGE and immunoblotted for CREB phosphorylated on Ser133 (p-CREB). Brain lysates from two mice per treatment group are shown.

One of the principal transcription factors known to regulate Reelin expression is the cAMP response element-binding protein (CREB) (Grayson et al., 2006). Therefore, the phosphorylation of CREB on Ser133 (p-CREB) which is necessary for its transcriptional activity was evaluated. Brain lysates enriched for the hippocampal-entorhinal cortex sub-region were immunoblotted for p-CREB. Phosphorylation of CREB on Ser133 was relatively high in non-carrier control mice but was dramatically reduced in hemizygous untreated J20 AD mice (FIG. 21). Treatment of hemizygous J20 mice with Immunocal® from 3 months-old to 5 months-old resulted in a nearly complete preservation of p-CREB expression in the hippocampal-entorhinal cortex sub-region (FIG. 21). Thus, Immunocal®, treatment corrected a major deficiency in brain p-CREB observed in AD model mice.

Figure 22:
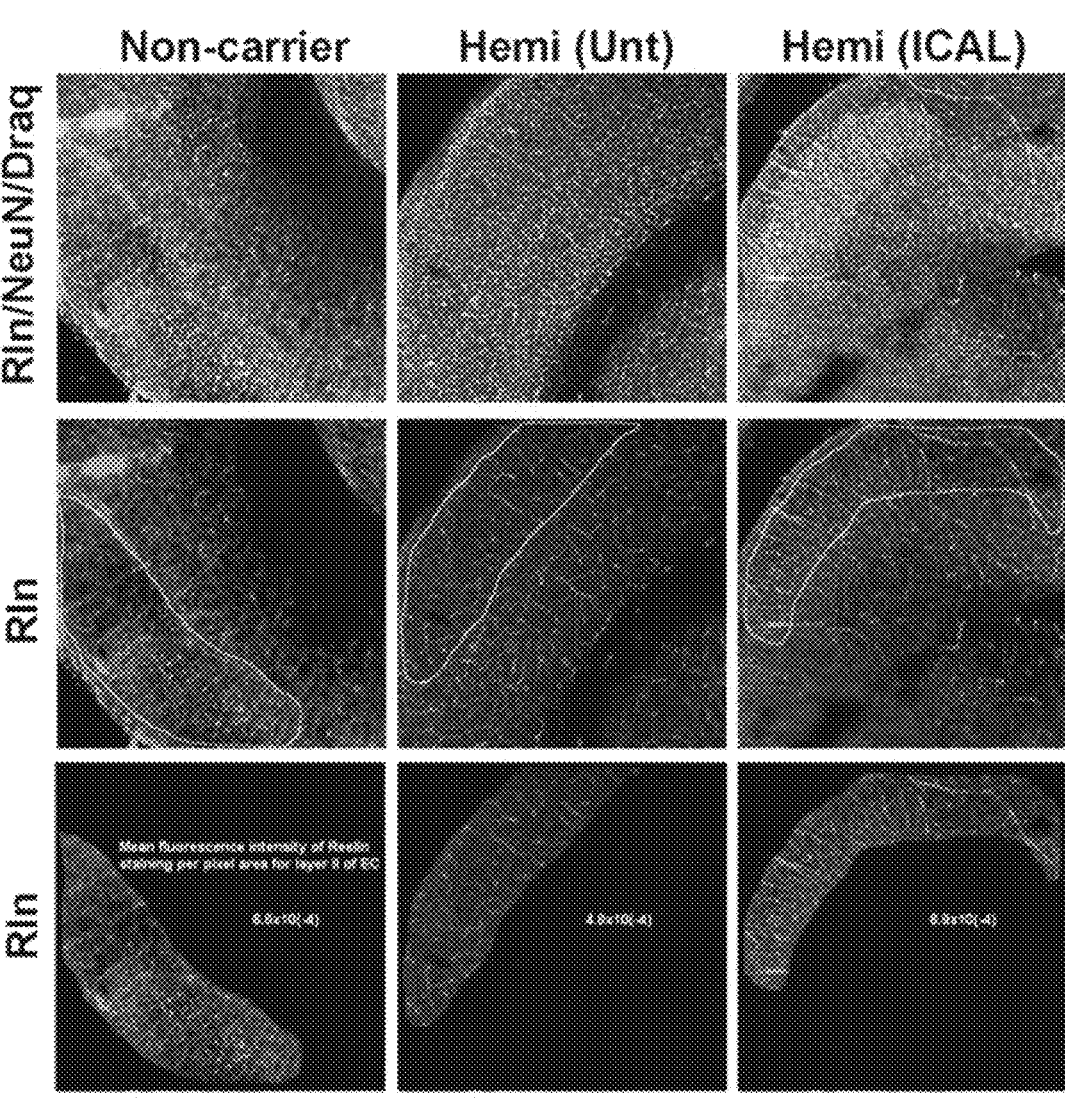
FIG. 22 shows results of studies in which Immunocal® treatment rescued Reelin expression in entorhinal cortex layer II of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to Reelin (Rln, shown in green) and NeuN (shown in red), along with Draq (nuclear stain, shown in blue). The demarcated areas in the middle panels encompass an approximation of layer II of entorhinal cortex and are represented in the lower panels. The mean fluorescence intensity (per pixel area) of Reelin staining in this region was calculated using Adobe Photoshop. The untreated hemizygous J20 AD mouse showed an approximately 30% reduction in Reelin staining in layer II of entorhinal cortex compared to the non-carrier control. This deficit was prevented by treatment with Immunocal®. Similar results were observed in four independent sets of mice consisting of a non-carrier control, hemizygous untreated and hemizygous Immunocal®-treated.

Next, immunofluorescence microscopy was used to evaluate Reelin expression in the entorhinal cortex, dentate gyrus, and CA1/CA3 regions of the hippocampus in J20 AD model mice. The entorhinal cortex of non-carrier control mice showed significant Reelin immunoreactivity, particularly in layer II, the area demarcated in the middle panels of FIG. 22 and reproduced in the lower panels. In comparison to the non-carrier control, untreated hemizygous J20 AD mice displayed a marked (~30%) reduction in Reelin immunoreactivity in layer 11 of entorhinal cortex. The measured reduction in Reelin immunoreactivity is comparable to previously reported reductions in Reelin positive layer II neurons in 6-7 month-old J20 mice (Chin et al., 2007). Intriguingly, treatment with Immunocal® from 3 months-old to 5 months-old essentially rescued this deficit in Reelin expression within layer II of the entorhinal cortex of J20 AD mice (FIG. 22).

Figure 23:
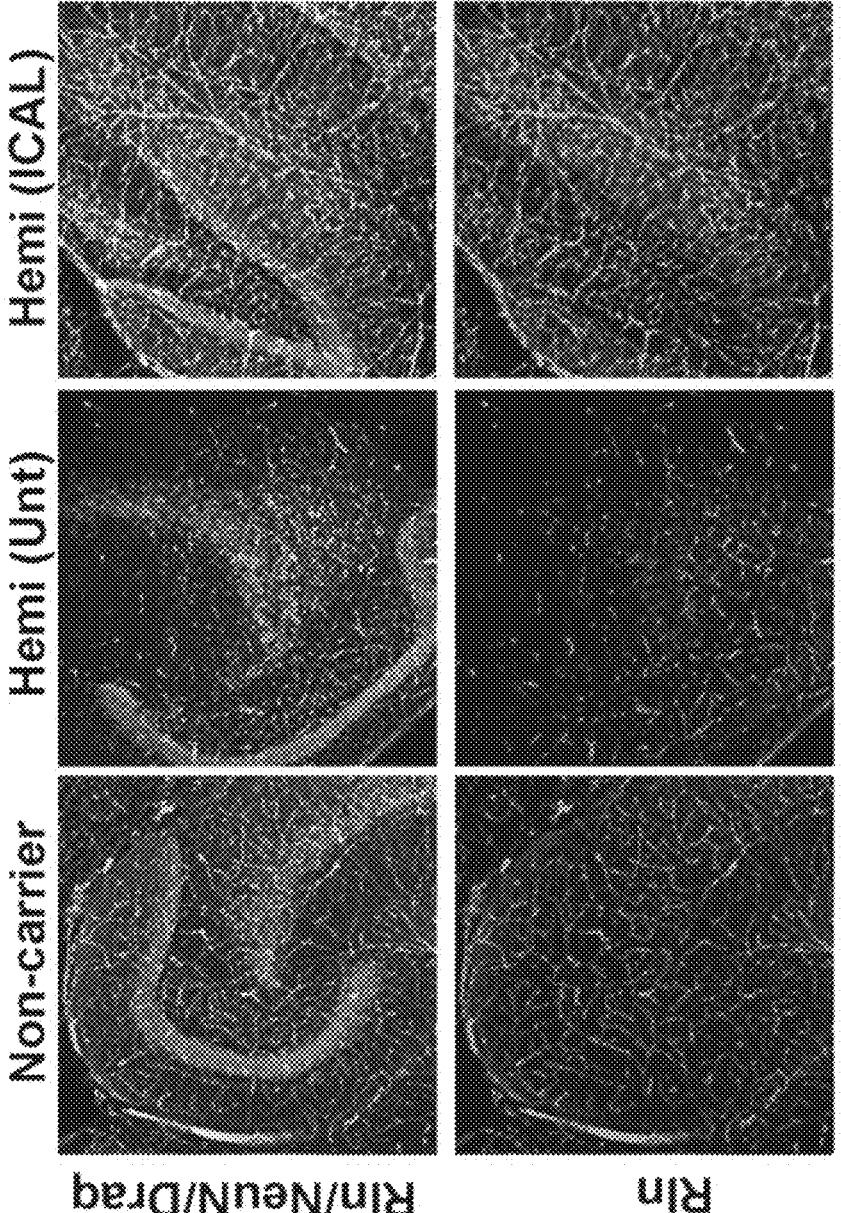
FIG. 23 shows results of studies in which Immunocal® treatment increased Reelin expression in dentate gyrus of J20 AD model mice. Brain tissue was harvested from 5 month-old hemizygous (Hemi) J20 AD mice (either untreated (Unt) or treated with Immunocal® (ICAL) for 2 months) and non-carrier control mice. Formalin-fixed sections were co-stained with antibodies to Reelin (Rln, shown in green) and NeuN (shown in red), along with Draq (nuclear stain, shown in blue).

Next, Reelin staining in the dentate gyrus and CA1/CA3 regions of the hippocampus in J20 AD model mice was assessed. In the dentate gyrus, Reelin expression was diffuse and moderate in intensity in non-carrier control mice (FIG. 23). Untreated hemizygous J20 AD mice showed a slight overall reduction in Reelin staining in the dentate gyrus, whereas Immunocal®-treated hemizygous J20 mice displayed a striking increase in the intensity of Reelin staining in this brain region (FIG. 23).

In the CA1 region of the hippocampus, Reelin expression was very high in non-carrier control mice and was markedly reduced in untreated hemizygous J20 AD mice (FIG. 24). Notably, this deficit in Reelin staining was essentially prevented by treatment of hemizygous J20 mice with Immunocal® for 2 months (FIG. 24). A very similar effect on Reelin expression was observed in the CA3 region of the hippocampus. In particular, Reelin expressing neurons in the middle section of this sub-region were particularly evident in non-carrier control mice, essentially absent in untreated hemizygous J20 AD mice, and largely preserved in Immunocal®-treated J20 mice (FIG. 25).

Next, GAD67 staining and Reelin co-staining with phospho-DAB1 in the dentate gyrus and CA1/CA3 regions of the hippocampus in J20 AD model mice was evaluated. GAD67 staining in the dentate gyrus of non-carrier control mice was relatively diffuse and the overall intensity was somewhat diminished in untreated hemizygous J20 AD mice (FIG. 26). In contrast, GAD67 staining was markedly increased in the dentate gyrus of hemizygous J20 mice which had been treated with Immunocal® (FIG. 26). A similar pattern of GAD67 staining in the CA3 region of the hippocampus was observed. In particular, there were several prominent GAD67 expressing neurons clearly visible in the middle section of the CA3 region of non-carrier control mice (FIG. 27). These GAD67-positive cells were essentially absent from the CA3 of untreated hemizygous J20 AD mice, while Immunocal treatment largely rescued GAD67 expression in this region (FIG. 27). Finally, co-staining of Reelin and phospho-DAB1 (pTyr232; a Src/Fyn phosphorylation site) in the CA1 region of the hippocampus in J20 AD model mice was evaluated. Compared to non-carrier control mice, untreated hemizygous J20 AD mice displayed a subtle decrease in the intensity of Reelin and phospho-DAB1 co-staining in the CA1 (FIG. 28). In contrast, Immunocal® treatment for two months induced a marked increase in Reelin and phospho-DAB1 co-staining in this region of the hippocampus of hemizygous J20 mice (FIG. 28).

Finally, the effects of Immunocal® treatment were evaluated for two months on cognitive function in J20 AD model mice at approximately 5 months of age. In particular, the Barnes maze was utilized to test for spatial learning and memory performance. During the six-day acquisition phase, mice in all groups progressively learned to find the escape pod on the maze. No significant differences were observed between groups in the time delay to find the escape pod on days 1-4 of the acquisition phase. However, on days 5 and 6 of the acquisition phase (combined), the Immunocal®-treated, hemizygous J20 female mice were significantly quicker at finding the escape pod than the untreated hemizygous female group (FIG. 29A). Moreover, during the probe phase, the untreated hemizygous female mice were significantly slower than the non-carrier female group at finding the escape pod and this deficit was corrected in the Immunocal® treated hemizygous female group (FIG. 29B).

Previous work has shown that deficits in Reelin expression and/or Reelin signaling play a pathogenic role in several nervous system disorders including schizophrenia and AD. Thus, strategies aimed at correcting these deficits are desirable in this field of study. The cysteine-rich, whey protein supplement, Immunocal®, has been shown to elevate glutathione in the brain and spinal cord, and is neuroprotective and therapeutically efficacious in mouse models of schizophrenia and amyotrophic lateral sclerosis (Ross et al., 2014; examples above). As described hereinabove, Immunocal® treatment is shown to rescue Reelin expression at the mRNA and protein level in the prefrontal cortex of a mouse model of schizophrenia. Given that Reelin expressing neurons of the entorhinal cortex layer II are a highly vulnerable population of cells that are lost very early in AD, the effects of Immunocal® on Reelin expression and signaling in vitro in hippocampal-entorhinal cortex rat brain slices and in vivo in the hAPPSweInd mutant (J20) mouse model of AD was investigated in the experiments provided herein.

Incubation of hippocampal-entorhinal cortex slices with Immunocal® increased Reelin expression at the mRNA and protein levels, as assessed by qPCR and western blotting. In addition, immunostaining of slices revealed a striking increase in the intensity and number of neurons staining positively for Reelin within the entorhinal cortex, dentate gyrus and CA1 region of the hippocampus following Immunocal® treatment in vitro.

The effects of Immunocal® treatment in vivo was next evaluated by treating hemizygous J20 AD mice from 3 months-old to 5 months-old. Reelin expression and signaling was assessed by western blotting and immunofluorescence microscopy and cognitive function using the Barnes maze was also measured to test spatial learning and memory. In the studies described herein, Immunocal® treatment corrected a deficit in cortical GSH levels observed in the brains of untreated hemizygous J20 mice. Western blotting of brain sections micro-dissected to enrich for the hippocampal-entorhinal cortex sub-region revealed a decrease in Reelin and GAD67 expression in untreated hemizygous J20 AD mice compared to non-carrier control mice and these effects were prevented by treatment with Immunocal®. In addition, untreated hemizygous J20 AD mice displayed a marked reduction in p-CREB immunoreactivity in the hippocampal-entorhinal cortex sub-region of the brain and this deficit was essentially rescued by treatment with Immunocal®. In a similar manner, using immunofluorescence microscopy, Reelin expression was diminished in the entorhinal cortex, dentate gyrus and CA1/CA3 regions of the hippocampus in untreated hemizygous J20 AD mice compared to non-carrier control mice. In contrast, Immunocal® treatment largely rescued these deficits in Reelin expression and in some cases, markedly increased the expression of Reelin even above what was observed in the non-carrier control mice. In particular. Immunocal® treated J20 mice displayed robust Reelin staining in layer II of entorhinal cortex, apparently rescuing the loss of Reelin positive neurons observed in this brain region in untreated J20 AD mice. In parallel with the observed rescue of Reelin expression in the hippocampus-entorhinal cortex of J20 mice, Immuno-cal® also preserved GAD67 expression in the dentate gyrus and CA3 region of the hippocampus and markedly enhanced the co-staining of Reelin and phospho-DAB1 in the CA1 of these mice.

Further, Immunocal® treatment had a statistically significant positive effect on Barnes maze performance, both during the late stages of the acquisition phase and during the probe phase, in female, hemizygous J20 AD mice. Collectively, these findings indicate that treatment with Immuno-cal® induces Reelin expression in vitro in hippocampal-entorhinal cortex brain slices and rescues Reelin expression and signaling in vivo within the entorhinal cortex and hippocampus of the J20 mouse model of AD in these studies.

TABLE 3

| References Cited in Example 3 |
| --- |

Augelli-Szafran, C. E., H. X. Wei, D. Lu, J. Zhang, Y. Gu, T. Yang, P. Osenkowski, W. Ye, M. S. Wolfe (2010). "Discovery of notch-sparing gamma-secretase inhibitors." Curr Alzheimer Res 7(3): 207-209.

Beffert U., A. Durudas, E. J. Weeber, P. C. Stolt, K. M. Giehl, J. D. Sweatt, R. E. Hammer, J. Herz (2006). "Functional dissection of Reelin signalizing by site-directed disruption of Disabled-1 adaptor binding to apolipoprotein E receptor 2: distinct roles in development and synaptic plasticity." J Neurosci 26(7): 2041-2052.

Bock H. H, P. May (2016). "Canonical and non-canonical reelin signaling." Front Cell Neurosci 10: 166.

Bosch, C., N. Masachs, D. Expsosito-Alsonso, A. Martinez, C. M. Teixeira, I. Fernaud, L. Pujadas, F. Ulloa, J. X. Comella, J. DeFelipe, A. Merchan-Pérez, E. Soriano (2016). "Reelin regulates the maturation of dendritic spine, synaptogenesis and glial ensheathment of newborn granule cells." Cereb Cortex 26(11): 4282-4298.

Castellani, R. J., M. A. Smith (2011). "Compounding artefacts with uncertainty, and an amyloid cascade hypothesis that is 'too big to fail'." J Pathol 224(2): 147-152.

Chin, J., C. M. Massaro, J. J. Palop, M. T. Thwin, G. Q. Yu, N. Bien-Lv, A. Bender, L. Mucke (2007). "Reelin depletion in the entorhinal cortex of human amyloid precursor protein transgenic mice and humans with Alzheimer's disease." J Neurosci 27(11): 2727-2733.

Cuchillo-Ibañez, I., V. Balmaceda, T. Mata-Balaguer (2016). "Reelin in Alzheimer's disease, increased levels but impaired signaling: when more is less." J Alz Dis 52: 403-416.

Diaz-Hernandez, J. I., R. Gomez-Villafuertes, M. León-Otegui, L. Hontecillas-Prieto, A. Del Puerto, J. L. Trejo, J. J. Lucas, J. J. Garrido, J. Gualix, M. T. Miras-Portugal, M. Diaz-Hernandez (2012). "In vivo P2X7 inhibition reduces amyloid plaques in Alzheimer's disease through GSK3☐ and secretases." Neurobiol Aging 33(8): 1816-1828.

D'Onofrio, G., F. Panza, V. Frisardi, V. Solfrizzi, B. P. Imbimbo, G. Paroni, L. Cascavilla, D. Seripa, A. Pilotto (2012). "Advances in the identification of gamma-secretase inhibitors for the treatment of Alzheimer's disease." Expert Opin Drug Discov 7(1): 19-37.

Evin, G., M. F. Sernee, C. L. Masters (2006). "Inhibition of gamma-secretase as a therapeutic intervention for Alzheimer's disease: prospects, limitations and strategies." CNS Drugs 20(5): 351-372.

Ferreira, S. T., W. L. Klein (2011). "The Abeta oligomer hypothesis for synapse failure and memory loss in Alzheimer's disease." Neurobiol Learn Mem 96(4): 529-543.

Ghosh, A. K., M. Brindisi, J. Tang (2012). "Developing beta-secretase inhibitors for treatment of Alzheimer's disease." J Neurochem 120 Suppl 1: 71-83.

Giannakopoulos, P., F. R. Herrmann, T. Bussiere, C. Bouras, E. Kovari, D. P. Perl, J. H. Morrison, G. Gold, P. R. Hof (2003). "Tangle and neuron numbers, but not amyloid load, predict cognitive status in Alzheimer's disease." Neurology 60(9): 1495-1500.

Gray, J. J., A. E. Zommer, R. J. Bouchard, N. Duval, C. Blackstone, D. A. Linseman (2013). "N-terminal cleavage of the mitochondrial fusion GTPase OPA1 occurs via a caspase-independent mechanism in cerebellar granule neurons exposed to oxidative or nitrosative stress." Brain Res 1494: 28-43.

Grayson, D. R., C. Ying, E. Costa, E. Doug, A. Guidotti, M. Kundakovic, R. P. Sharma (2006). "The human reelin gene: Transcription factors (+), repressors (−) and the methylation switch (+/−) in schizophrenia." Pharmacol & Therap 111: 272-286.

Guidotti, A., J. Auta, J. M. Davis, V. D. Gerevini, Y. Dwivedi, D. R. Grayson, F. Impagnatiello, G. Pandey, C. Pesold, R. Sharma, D. Uzunov, E. Costa (2000). "Decrease in reelin and glutamic acid decarboxylase67 (GAD67) expression in schizophrenia and bipolar disorder." Arch Gen Psychiatry 57: 1061-1069.

Hardy, J. A., G. A. Higgins. (1992). "Alzheimer's disease: the amyloid cascade hypothesis." Science 256(5054): 184-185.

Herring, A., A. Donath, K. M. Steiner, M. P. Widera, S. Hamzehian, D. Kanakis, K. Kolble, A. ElAli, D. M. Hermann, W. Paulus W, K. Keyvani (2012). "Reelin depletion is an early phenomenon of Alzheimer's pathology." J Alz Dis 30(4): 963-979.

Karl, T., S. Bhatia, D. Cheng, W. S. Kim, B. Garner (2012). "Cognitive phenotyping of amyloid precursor protein transgenic J20 mice." Behav Brain Res 228(2): 392-397.

Karran, E., M. Mercken, B. De Strooper (2011). "The amyloid cascade hypothesis for Alzheimer's disease: an appraisal for the development of therapeutics." Nat Rev Drug Discov 10(9): 698-712.

Karran, E., B. De Strooper (2016). "The amyloid cascade hypothesis: are we poised for success or failure?" J Neurochem 139 Suppl 2: 237-252.

Kennedy, M. E., A. W. Stamford, X. Chen, K. Cox, J. N. Cumming, M. F. Dockendorf, M. Egan, L. Ereshefsky, R. A. Hodgson, L. A. Hyde, S. Jhee, H. J. Kleijn, R. Kuvelkar, W. Li, B. A. Mattson, H. Mei, J. Palcza, J. D. Scott, M. Tanen, M. D. Trover, J. L. Tseng, J. A. Stone, E. M. Parker, M. S. Forman (2016). "The BACE1 inhibitor verubecestat (MK-8931) reduces CNS ☐-amyloid in animal models and in Alzheimer's disease patients." Sci Transl Med 8(363): 363ra150.

TABLE 3-continued

References Cited in Example 3

Kim M., Y. Jeong, Y. C. Chang (2015). "Extracellular matrix protein reelin regulate dendritic spine density through CaMKII☐." Neurosci Lett 599: 97-101.

Klein, W. L., G. A. Krafft, C. E. Finch (2001). "Targeting small Abeta oligomers: the solution to an Alzheimer's disease conundrum?" Trends Neurosci 24(4): 219-224.

Kobro-Flatmoen, A., A. Nagelhus, M. P. Witter (2016). "Reelin-immunoreactive neurons in entorhinal cortex layer II selectively express intracellular amyloid in early Alzheimer's disease." Neurobiol Dis 93: 172-183.

Kocherhans, S., A. Madhusudan, J. Doehner, K. S. Breu, R. M. Nitsch, J. M. Fritschy, I. Knuesel (2010). "Reduced Reelin expression accelerates amyloid-beta plaque formation and tau pathology in transgenic Alzheimer's disease mice." J Neurosci 30(27): 9228-9240.

Krstic, D., S. Pfister, T. Notter, I. Knuesel (2013). "Decisive role of Reelin signaling during early stages of Alzheimer's disease." Neuroscience 246: 108-116.

Kundakovic, M. Y. Chen, A. Guidotti, D. R. Grayson (2009). "The reelin and GAD67 promoters are activated by epigenetic drugs that facilitate the disruption of local repressor complexes." Mol Pharmacol 75(2): 342-345.

Larson, M. E. S. E. Lesne (2012). "Soluble Abeta oligomer production and toxicity." J Neurochem 120 Suppl 1: 125-139.

Lee G. H., G. D'Arcangelo (2016). "New insights into reelin-mediated signaling pathways." Front Cell Neurosci 10: 122.

Leutgeb, J. K., J. U. Frey, T. Behnisch (2003). "LTP in cultured hippocampal-entorhinal cortex slices from young adult (P25-30) rats." J Neurosci Meth 130: 19-32.

Menting, K. W., J. A. Claassen (2014). "☐-secretase inhibitor; a promising novel therapeutic drug in Alzheimer's disease." Front Aging Neurosci 6: 165.

Mouzon, B., H. Chaytow, G. Crynen, C. Bachmeier, J. Stewart, M. Mullan, W. Stewart, F. Crawford (2012). "Repetitive mild traumatic brain injury in a mouse model produces learning and memory deficits accompanied by histological changes." J Neurotrauma 29(18): 2761-2773.

Mucke, L., E. Masliah, G. Q. Yu, M. Mallory, E. M. Rockenstein, G. Tatsuno, K. Hu, D. Kholodenko, K. Johnson-Wood, L. McConlogue (2000). "High-level neuronal expression of abeta 1-42 in wild-type human amyloid protein precursor transgenic mice: synaptotoxicity without plaque formation." J Neurosci 20(11): 4050-4058.

Mullane, K., M. Williams (2013). "Alzheimer's therapeutics: continued clinical failures question the validity of the amyloid hypothesis-but what lies beyond?" Biochem Pharmacol 85(3): 289-305.

Muller T., H. E. Meyer, R. Egensperger, K. Marcus (2008). "The amyloid precursor protein intracellular domain (AICD) as modulator of gene expression, apoptosis, and cytoskeletal dynamics-relevance for Alzheimer's disease." Prog Neurobiol 85(4): 393-406.

Naylor, R., A. F. Hill, K. J. Barnham (2008). "Is covalently crosslinked Abeta responsible for synaptotoxicity in Alzheimer's disease?" Curr Alzheimer Res 5(6): 533-539.

Niu, S., A. Renfro, C. C. Quattrocchi, M. Sheldon, G. D'Arcangelo (2004). "Reelin promotes hippocampal dendrite development through VLDLR/ApoER2-Dab1 pathway." Neuron 41(1): 71-84.

Pimplikar, S. W., R. A. Nixon, N. K. Robakis, J. Shen, L. H. Tsai (2010). "Amyloid-independent mechanisms in Alzheimer's disease pathogenesis." J Neurosci 30(45): 14946-14954.

Pujadas, L., D. Rossi, R. Andrés, C. M. Teixeira, B. Serra-Vidal, A. Parcerisas, R. Maldonado, E. Giralt, N. Carulla, E. Soriano (2014). "Reelin delays amyloid-beta fibril formation and rescues cognitive deficits in a model of Alzheimer's disease." Nat Commun 5: 3443.

Ross, E. K., A. N. Winter, H. M. Wilkins, W. A. Sumner, N. Duval, D. Patterson, D. A. Linseman (2014). "A cystine-rich whey supplement (Immunocal ®) delays disease onset and prevents spinal cord glutathione depletion in the hSOD1(G93A) mouse model of amyotrophic lateral sclerosis." Antioxidants 3(4): 843-865.

Swerdlow R. H., S. Koppel, I. Weidling, C. Hayley, Y. Ji, H. M. Wilkins (2017). "Mitochondria, cybrids, aging, and Alzheimer's Disease." Prog Mol Biol Transl Sci 146: 259-302.

Tse K. H., K. Herrup (2017). "Re-imagining Alzheimer's disease - the diminishing importance of amyloid and a glimpse of what lies ahead." J Neurochem epub ahead of print.

Vassar, R. (2001). "The beta-secretase, BACE: a prime drug target for Alzheimer's disease." J Mol Neurosci 17(2): 157-170.

Vassar, R., D. M. Kovacs, R. Yan, P. C. Wong (2009). "The beta-secretase enzyme BACE in health and Alzheimer's disease: regulation, cell biology, function, and therapeutic potential." J Neurosci 29(41): 12787-12794.

Wasser, C. R., J. Herz (2017). "Reelin: neurodevelopmental architect and homeostatic regulator of excitatory synapses." J Biol Chem 292(4): 1330-1338.

Yu N. N., M. S. Tan, J. T. Yu, A. M. Xie, L. Tan (2016). "The role of reelin signaling in Alzheimer's disease." Mol Neurobiol 53(8): 5692-5700.

References cited in Table 3 above, and those cited elsewhere herein, are herein incorporated by reference in their entireties.

REFERENCES

1. Albayrak Y, Akyol E S, Beyazyuz M, Baykal S, Kuloglu M. Neurological soft signs might be endophenotype candidates for patients with deficit syndrome schizophrenia. Neuropsychiatr Dis Treat 2015; 11:2825-2831.

2. Waxman J, Van Lieshout R J, Schmidt L A. Early adversity and mental health: linking extremely low birth weight, emotion regulation, and internalizing disorders. Curr Pediatr Rev 2014; 10:208-215.

3. Provencal N, Binder E B. The effects of early life stress on the epigenome: From the womb to adulthood and even before. Experimental neurology 2014; 268:10-20.

4. Do K Q, Cuenod M, Hensch T K. Targeting Oxidative Stress and Aberrant Critical Period Plasticity in the Developmental Trajectory to Schizophrenia. Schizophr Bull 2015; 41:835-846.

5. Meyer U, Feldon J, Schedlowski M, Yee B K. Immunological stress at the maternal-foetal interface: a link between neurodevelopment and adult psychopathology. Brain Behav Immun 2006; 20:378-388.

6. Kirsten T B, Chaves-Kirsten G P, Bernardes S, et al. Lipopolysaccharide Exposure Induces Maternal Hypozincemia, and Prenatal Zinc Treatment Prevents Autistic-Like Behaviors and Disturbances in the Striatal Dopaminergic and mTOR Systems of Offspring. PLoS One 2015: 10:e0134565.

7. Galvao M C, Chaves-Kirsten G P, Queiroz-Hazarbassanov N, Carvalho V M, Bernardi M M, Kirsten T B. Prenatal zinc reduces stress response in adult rat offspring exposed to lipopolysaccharide during gestation. Life Sci 2014; 120:54-60.

8. Zappitelli M, Pinto T, Grizenko N. Pre-, peri-, and postnatal trauma in subjects with attention-deficit hyperactivity disorder. Can J Psychiatry 2001:46:542-548.

9. Song W, Zukor H, Lin S H. et al. Schizophrenia-like features in transgenic mice overexpressing human HO-1 in the astrocytic compartment. The Journal of neuroscience: the official journal of the Society for Neuroscience 2012:32:10841-10853.

10. Song W, Zukor H, Lin S H, et al. Unregulated brain iron deposition in transgenic mice over-expressing HMOX1 in the astrocytic compartment. J Neurochem 2012; 123:325-336.

11. Koga M, Serritella A V, Sawa A, Sedlak T W. Implications for reactive oxygen species in schizophrenia pathogenesis. Schizophr Res 2015.

12. Magalhaes P V, Dean O, Andreazza A C, Berk M, Kapczinski F. Antioxidant treatments for schizophrenia. Cochrane Database Syst Rev 2016; 2:CD008919.

13. Corcoba A, Steullet P, Duarte J M, et al. Glutathione Deficit Affects the Integrity and Function of the Fimbria/Fornix and Anterior Commissure in Mice: Relevance for Schizophrenia. Int J Neuropsychopharmacol 2015.

14. Yao J K, Keshavan M S. Antioxidants, redox signaling, and pathophysiology in schizophrenia: an integrative view. Antioxid Redox Signal 2011; 15:2011-2035.

15. Micke P, Beeh K M, Buhl R. Effects of long-term supplementation with whey proteins on plasma glutathione levels of HIV-infected patients. Eur J Nutr 2002; 41:12-18.

16. Micke P, Beeh K M, Schlaak J F, Buhl R. Oral supplementation with whey proteins increases plasma glutathione levels of HIV-infected patients. Eur J Clin Invest 2001; 31:171-178.

17. Kelly K M. Bringing evidence to complementary and alternative medicine in children with cancer: Focus on nutrition-related therapies. Pediatr Blood Cancer 2008; 50:490-493; discussion 498.

18. Grey V, Mohammed S R, Smountas A A, Bahlool R, Lands L C. Improved glutathione status in young adult patients with cystic fibrosis supplemented with whey protein. J Cyst Fibros 2003:2:195-198.

19. Bounous G, Letourneau L, Kongshavn P A. Influence of dietary protein type on the immune system of mice. The Journal of nutrition 1983; 113:1415-1421.

20. Wong C W. Watson D L. Immunomodulatory effects of dietary whey proteins in mice. The Journal of dairy research 1995; 62:359-368.

21. Low P P, Rutherfurd K J, Gill H S, Cross M L. Effect of dietary whey protein concentrate on primary and secondary antibody responses in immunized BALB/c mice. International immunopharmacology 2003; 3:393-401.

22. Karelis A D. Messier V, Suppere C, Briand P, Rabasa-Lhoret R. Effect of cysteine-rich whey protein (Immunocal®) supplementation in combination with resistance training on muscle strength and lean body mass in non-frail elderly subjects: a randomized, double-blind controlled study. The journal of nutrition, health & aging 2015:19:531-536.

23. Lands L C, Grey V L, Smountas A A. Effect of supplementation with a cysteine donor on muscular performance. Journal of applied physiology 1999; 87:1381-1385.

24. Ross E K. Gray J J, Winter A N, Linseman D A. Immunocal® and preservation of glutathione as a novel neuroprotective strategy for degenerative disorders of the nervous system. Recent patents on CNS drug discovery 2012:7:230-235.

25. Pinna G. Agis-Balboa R C, Zhubi A, et al. Imidazenil and diazepam increase locomotor activity in mice exposed to protracted social isolation. Proc Natl Acad Sci USA 2006; 103:4275-4280.

26. Wood G K. Tomasiewicz H, Rutishauser U, et al. NCAM-180 knockout mice display increased lateral ventricle size and reduced prepulse inhibition of startle. Neuroreport 1998:9:461-466.

27. Fenton H, Finch P W, Rubin J S, et al. Hepatocyte growth factor (HGF/SF) in Alzheimer's disease. Brain Res 1998; 779:262-270.

28. Laplante F, Srivastava L K, Quirion R. Alterations in dopaminergic modulation of prefrontal cortical acetylcholine release in post-pubertal rats with neonatal ventral hippocampal lesions. J Neurochem 2004; 89:314-323.

29. Sauz-Alfayate G, Obeso A, Agapito M T, Gonzalez C. Reduced to oxidized glutathione ratios and oxygen sensing in calf and rabbit carotid body chemoreceptor cells. J Physiol 2001; 537:209-220.

30. Palkovits M. Isolated removal of hypothalamic or other brain nuclei of the rat. Brain Res 1973; 59:449-450.

31. Kilts C D. Anderson C M. The simultaneous quantification of dopamine, norepinephrine and epinephrine in micropunched rat brain nuclei by on-line trace enrichment HPLC with electrochemical detection: Distribution of catecholamines in the limbic system. Neurochem Int 1986; 9:437-445.

32. Gratton A, Hoffer B J, Gerhardt G A. In vivo electrochemical studies of monoamine release in the medial prefrontal cortex of the rat. Neuroscience 1989; 29:57-64.

33. Hibbeler S, Scharsack J P, Becker S. Housekeeping genes for quantitative expression studies in the three-spined stickleback Gasterosteus aculeatus. BMC Mol Biol 2008; 9:18.

34. Mak S K, McCormack A L, Langston J W. Kordower J H, Di Monte D A. Decreased alpha-synuclein expression in the aging mouse substantia nigra. Experimental neurology 2009; 220:359-365.

35. Humphreys D T, Hynes C J, Patel H R, et al. Complexity of murine cardiomyocyte miRNA biogenesis, sequence variant expression and function. PLoS One 2012; 7:e30933.

36. Livak K J, Schmittgen T D. Analysis of relative gene expression data using real-time quantitative PCR and the 2(-Delta Delta C(T)) Method. Methods 2001; 25:402-408.

37. Griffiths-Jones S, Saini H K, van Dongen S, Enright A J. miRBase: tools for microRNA genomics. Nucleic Acids Res 2008; 36:D154-158.

38. Franklin K B J, Paxinos G. Paxinos and Franklin's The mouse brain in stereotaxic coordinates, Fourth edition. ed. Amsterdam: Academic Press, an imprint of Elsevier, 2013.

39. Aasen L Kolli L, Kumari V. Sex effects in prepulse inhibition and facilitation of the acoustic startle response: implications for pharmacological and treatment studies. J Psychopharmacol 2005; 19:39-45.

40. Braff D L, Light G A, Ellwanger J, Sprock J, Swerdlow N R. Female schizophrenia patients have prepulse inhibition deficits. Biological psychiatry 2005; 57:817-820.

41. Suddath R L, Christison G W, Torrey E F, Casanova M F, Weinberger D R. Anatomical abnormalities in the brains of monozygotic twins discordant for schizophrenia. The New England journal of medicine 1990; 322:789-794.

42. Scheibel A B, Conrad A S. Hippocampal dysgenesis in mutant mouse and schizophrenic man: is there a relationship? Schizophr Bull 1993:19:21-33.

43. Jakob H, Beckmann H. Prenatal developmental disturbances in the limbic allocortex in schizophrenics. J Neural Transm 1986; 65:303-326.

44. Magdaleno S M, Curran T. Brain development: integrins and the Reelin pathway. Curr Biol 2001; 11:R1032-1035.

45. Kundakovic M, Chen Y, Guidotti A, Grayson D R. The reelin and GAD67 promoters are activated by epigenetic drugs that facilitate the disruption of local repressor complexes. Mol Pharmacol 2009; 75:342-354.

46. Kirov G. Rujescu D, Ingason A, Collier D A, O'Donovan M C, Owen M J. Neurexin 1 (NRXN1) deletions in schizophrenia. Schizophr Bull 2009; 35:851-854.

47. Kumar R A, Christian S L. Genetics of autism spectrum disorders. Curr Neurol Neurosci Rep 2009; 9:188-197.

48. Morrow E M. Yoo S Y, Flavell S W, et al. Identifying autism loci and genes by tracing recent shared ancestry. Science 2008; 321:218-223.

49. Kim H G, Kishikawa S, Higgins A W, et al. Disruption of neurexin 1 associated with autism spectrum disorder. Am J Hum Genet 2008; 82:199-207.

50. Marshall C R, Noor A, Vincent J B. et al. Structural variation of chromosomes in autism spectrum disorder. Am J Hum Genet 2008; 82:477-488.

51. Weiss L A, Shen Y, Kom J M, et al. Association between microdeletion and microduplication at 16p11.2 and autism. The New England journal of medicine 2008:358:667-675.

52. Sun C, Cheng M C. Qin R. et al. Identification and functional characterization of rare mutations of the neuroligin-2 gene (NLGN2) associated with schizophrenia. Hum Mol Genet 2011:20:3042-3051.

53. Yin J, Lin J, Luo X, et al. miR-137: a new player in schizophrenia. International journal of molecular sciences 2014; 15:3262-3271.

54. Saba R, Storchel P H, Aksoy-Aksel A, et al. Dopamine-regulated microRNA MiR-181a controls GluA2 surface expression in hippocampal neurons. Mol Cell Biol 2012; 32:619-632.

55. Kim A H, Reimers M, Maher B, et al. MicroRNA expression profiling in the prefrontal cortex of individuals affected with schizophrenia and bipolar disorders. Schizophr Res 2010; 124:183-191.

56. Moreau M P, Bruse S E, David-Rus R, Buyske S, Brzustowicz L M. Altered microRNA expression profiles in postmortem brain samples from individuals with schizophrenia and bipolar disorder. Biological psychiatry 2011; 69:188-193.

57. Lin S H, Song W, Cressatti M, Zukor H, Wang E, Schipper H M. Heme oxygenase-1 modulates microRNA expression in cultured astroglia: implications for chronic brain disorders. Glia 2015:63:1270-1284.

58. Adlakha Y K, Saini N. Brain microRNAs and insights into biological functions and therapeutic potential of brain enriched miRNA-128. Mol Cancer 2014; 13:33.

59. Beveridge N J. Cairns M J. MicroRNA dysregulation in schizophrenia. Neurobiol Dis 2012; 46:263-271.

60. Magenta A, Cencioni C, Fasanaro P, et al. miR-200c is upregulated by oxidative stress and induces endothelial cell apoptosis and senescence via ZEB1 inhibition. Cell Death Differ 2011; 18:1628-1639.

61. Stary C M, Xu L, Sun X, et al. MicroRNA-200c contributes to injury from transient focal cerebral ischemia by targeting Reelin. Stroke; a journal of cerebral circulation 2015; 46:551-556.

62. Flurkey K, Currer J M. Harrison D E. The Mouse in Aging Research. In: Fox J G, ed. The Mouse in Biomedical Research 2nd Edition. Burlington: Elsevier, 2007: 637-672.

63. Szymanski S, Lieberman J A, Alvir J M, et al. Gender differences in onset of illness, treatment response, course, and biologic indexes in first-episode schizophrenic patients. Am J Psychiatry 1995; 152:698-703.

64. Innamorato N G, Jazwa A, Rojo A I, et al. Different susceptibility to the Parkinson's toxin MPTP in mice lacking the redox master regulator Nrf2 or its target gene heme oxygenase-1. PLoS One 2010; 5:e11838.

65. Van Der Heyden J C, Rotteveel J J, Wevers R A. Decreased homovanillic acid concentrations in cerebrospinal fluid in children without a known defect in dopamine metabolism. Eur J Paediatr Neurol 2003; 7:31-37.

66. Lambert G W. Eisenhofer G, Jennings G L, Esler M D. Regional homovanillic acid production in humans. Life Sci 1993:53:63-75.

67. Hamson P J. The hippocampus in schizophrenia: a review of the neuropathological evidence and its pathophysiological implications. Psychopharmacology (Berl) 2004; 174:151-162.

68. Robbins T W, Jones G H, Wilkinson L S. Behavioural and neurochemical effects of early social deprivation in the rat. J Psychopharmacol 1996:10:3947.

69. Slifstein M, van de Giessen E, Van Snellenberg J, et al. Deficits in prefrontal cortical and extrastriatal dopamine release in schizophrenia: A positron emission tomographic functional magnetic resonance imaging study. JAMA Psychiatry 2015:72:316-324.

70. Wearne T A, Mirzaei M, Franklin J L, Goodchild A K, Haynes P A, Cornish J L. Methamphetanine-induced sensitization is associated with alterations to the proteome of the prefrontal cortex: implications for the maintenance of psychotic disorders. J Proteome Res 2014.

71. Edwards B G, Barch D M, Braver T S. Improving prefrontal cortex function in schizophrenia through focused training of cognitive control. Front Hum Neurosci 2010; 4:32.

72. Sumiyoshi T, Stockmeier C A, Overholser J C, Dilley G E, Meltzer H Y. Serotonin1A receptors are increased in postmortem prefrontal cortex in schizophrenia. Brain research 1996; 708:209-214.

73. Hashimoto T, Nishino N, Nakai H, Tanaka C. Increase in serotonin 5-HT1A receptors in prefrontal and temporal cortices of brains from patients with chronic schizophrenia. Life sciences 1991; 48:355-363.

74. Kapur S, Remington G. Serotonin-dopamine interaction and its relevance to schizophrenia. Am J Psychiatry 1996:153:466-476.
75. Torrey E F, Barci B M, Webster M J, Bartko J J. Meador-Woodruff J H, Knable M B. Neurochemical markers for schizophrenia, bipolar disorder, and major depression in postmortem brains. Biological psychiatry 2005; 57:252-260.
76. Wright C, Turner J A. Calhoun V D, Perrone-Bizzozero N. Potential Impact of miR-137 and Its Targets in Schizophrenia. Front Genet 2013; 4:58.
77. Abu-Elneel K. Liu T, Gazzaniga F S, et al. Heterogeneous dysregulation of microRNAs across the autism spectrum. Neurogenetics 2008; 9:153-161.
78. Schipper H M, Song W. A Heme Oxygenase-1 Transducer Model of Degenerative and Developmental Brain Disorders. International journal of molecular sciences 2015; 16:5400-5419.
79. Gresch P J, Sved A F, Zigmond M J, Finlay J M. Local Influence of Endogenous Norepinephrine on Extracellular Dopamine in Rat Medial Prefrontal Cortex. Journal of neurochemistry 1995; 65:111-116.
80. Fusar-Poli P, Papanastasiou E, Stahl D, et al. Treatments of Negative Symptoms in Schizophrenia: Meta-Analysis

66 of 168 Randomized Placebo-Controlled Trials. Schizophrenia bulletin 2015; 41:892-899.
81. Tamminga C A, Stan A D, Wagner A D. The hippocampal formation in schizophrenia. Am J Psychiatry 2010; 167: 1178-1193.
82. Walton N M, Zhou Y, Kogan J H, et al. Detection of an immature dentate gyrus feature in human schizophrenia/bipolar patients. Translational psychiatry 2012:2:e135.
83. Brown A S. The environment and susceptibility to schizophrenia. Prog Neurobiol 2011; 93:23-58.
84. King S, St-Hilaire A, Heidkamp D. Prenatal Factors in Schizophrenia. Current Directions in Psychological Science 2010:19:209-213.
85. Igarashi K, Sun J. The heme-Bach1 pathway in the regulation of oxidative stress response and erythroid differentiation. Antioxid Redox Signal 2006; 8:107-118.
86. Nestadt G. Wang Y, Grados M A, et al. Homeobox genes in obsessive-compulsive disorder. Am J Med Genet B Neuropsychiatr Genet 2012; 159B:53-60.

All references cited herein, cited in Tables 1 and 3, and cited elsewhere in the specification are herein incorporated by reference in their entirety.

What is claimed is:

1. A method for increasing reelin (RELN) levels in the prefrontal cortex (PFC) of a brain of a subject with schizophrenia, said method comprising:

a) performing a biopsy of the PFC of said subject; determining the initial RELN level in the PFC from said biopsy; and b) administering a composition comprising whey protein concentrate and/or whey protein isolate to said subject for 4-6 weeks;

performing a biopsy of the PFC of said subject;

determining RELN level in the PFC from said biopsy;

wherein the measured RELN level from b) is greater than the measured initial RELN level from a).

2. The method of claim 1, wherein the whey protein isolate or whey protein concentrate is undenatured whey protein isolate or whey protein concentrate.

\* \* \* \* \*

SEQUENCE LISTING

<160> NUMBER OF SEQ ID NOS: 24

<210> SEQ ID NO 1
<211> LENGTH: 11580
<212> TYPE: DNA
<213> ORGANISM: homo sapien

<400> SEQUENCE: 1

```
cacgcgtggg ctcggcgggg gcccgctccc aggcccgctc ccgagcccgt tccgctcccg      60
tccgccttct tctcgccttc tctccgcgtg gctcctccgt cccggcgtct ccaaaactga     120
atgagcgagc ggcgcgtagg gcgscggcgg cggcggcggc ggcggcggcg gcggcatgga     180
gcgcagtggc tgggcccggc agactttcct cctagcgctg ttgctggggg cgacgctgag     240
ggcgcgcgcg gcggctggct attacccccg cttttcgccc ttcttttcc tgtgcaccca     300
ccacggggag ctggaagggg atggggagca gggcgaggtg ctcatttccc tgcatattgc     360
gggcaacccc acctactacg ttccgggaca agaataccat gtgacaattt caacaagcac     420
cttttttgac ggcttgctgg tgacaggact atacacatct acaagtgttc aggcatcaca     480
gagcattgga ggttccagtg ctttcggatt tgggatcatg tctgaccacc agtttggtaa     540
ccagtttatg tgcagtgtgg tagcctctca cgtgagtcac ctgcccacaa ccaacctcag     600
tttcatctgg attgctccac ctgcgggcac aggctgtgtg aatttcatgg ctacagcaac     660
acaccggggc caggttattt tcaaagatgc tttagcccag cagttgtgtg aacaaggagc     720
tccaacagat gtcactgtgc acccacatct agctgaaata catagtgaca gcattatcct     780
gagagatgac tttgactcct accaccaact gcaattaaat ccaaatatat gggttgaatg     840
taacaactgt gagactggag aacagtgtgg cgcgattatg catggcaatg ccgtcacctt     900
ctgtgaacca tatggcccac gagaactgat taccacaggc cttaatacaa caacagcttc     960
tgtcctccaa ttttccattg ggtcaggttc atgtcgcttt agttattcag accccagcat    1020
catcgtgtta tatgccaaga ataactctgc ggactggatt cagctagaga aaattagagc    1080
cccttccaat gtcagcacaa tcatccatat cctctacctt cctgaggacg ccaaagggga    1140
gaatgtccaa tttcagtgga agcaggaaaa tcttcgtgta ggtgaagtgt atgaagcctg    1200
```

-continued

```
ctgggcctta gataacatct tgatcatcaa ttcagctcac agacaagtcg ttttagaaga    1260
tagtctcgac ccagtggaca caggcaactg gcttttcttc ccaggagcta cagttaagca    1320
tagctgtcag tcagatggga actccattta tttccatgga aatgaaggca gcgagttcaa    1380
ttttgccacc accagggatg tagatctttc cacagaagat attcaagagc aatggtcaga    1440
agaatttgag agccagccta caggatggga tgtcttggga gctgtcattg gtacagaatg    1500
tggaacgata gaatcaggct tatcaatggt cttcctcaaa gatggagaga ggaaattatg    1560
cactccatcc atggacacta ccggttatgg gaacctgagg ttttactttg tgatgggagg    1620
aatttgtgac cctggaaatt ctcatgaaaa tgacataatc ctgtatgcaa aaattgaagg    1680
aagaaaagag catataacac tggataccct ttcctattcc tcatataagg ttccgtcttt    1740
ggtttctgtg gtcatcaatc ctgaacttca gactcctgct accaaatttt gtctcaggca    1800
aaagaaccat caaggacata ataggaatgt ctgggctgta gactttttcc atgtcttgcc    1860
tgttctccct tctacaatgt ctcacatgat acagttttcc atcaatctgg gatgtggaac    1920
gcatcagcct ggtaacagtg tcagcttgga attttctacc aaccatgggc gctcctggtc    1980
cctccttcac actgaatgct tacctgagat ctgtgctgga ccccacctcc cccacagcac    2040
tgtctactcc tctgaaaact acagtgggtg gaaccgaata acaattcccc ttcctaacgc    2100
agcactaacc cggaacacca ggattcgctg gagacaaaca ggaccaatcc ttggaaacat    2160
gtgggcaatt gataatgttt atattggccc gtcatgtctc aaattctgtt ctggcagagg    2220
acagtgcact agacatggtt gcaagtgtga ccctggattt tctggcccag cttgtgagat    2280
ggcatcccag acattcccaa tgtttatttc tgaaagcttt ggcagttcca ggctctcctc    2340
ttaccataac tttttactcta tccgtggtgc tgaagtcagc tttggttgtg gtgtcttggc    2400
cagtggtaag gccctggttt tcaacaaaga agggcggcgt cagctaatta catctttcct    2460
tgacagctca caatccaggt ttctccagtt cacactgaga ctggggagca aatctgttct    2520
gagcacgtgc agagcccctg atcagcctgg tgaaggagtt ttgctgcatt attcttatga    2580
taatgggata acttggaaac tcctggagca ttattcatat ctcagctatc atgagcccag    2640
aataatctcc gtagaactac caggtgatgc aaagcagttt ggaattcagt tcagatggtg    2700
gcaaccgtat cattcttccc agagagaaga tgtatgggct attgatgaga ttatcatgac    2760
atctgtgctt ttcaacagca ttagtcttga ctttaccaat cttgtggagg tcactcagtc    2820
tctgggattc taccttggaa atgttcagcc atactgtggc cacgactgga cccttttgtttt    2880 tacaggagat tctaaacttg cctcaagtat gcgctatgtg gaaacacaat caatgcagat    2940
aggagcatcc tatatgattc agttcagttt ggtgatggga tgtggccaga aatacacccc    3000
acacatggac aaccaggtga agctggagta ctcaaccaac cacggcctta cctggcacct    3060
cgtccaagaa gaatgccttc aagtatgcc aagttgtcag gaatttacat cagcaagtat    3120
ttaccatgcc agtgagttta cacagtggag gagagtcata gtgcttcttc cccagaaaac    3180
ttggtccagt gctacccgtt tccgctggag ccagagctat tacacagctc aagacgagtg    3240
ggctttggac agcatttaca ttgggcagca gtgccccaac atgtgcagtg gcatggctc    3300 atgcgatcat ggcatatgca ggtgtgacca ggggtaccaa ggcactgaat gccacccaga    3360
agctgccctt ccgtccacaa ttatgtcaga ttttgagaac cagaatggct gggagtctga    3420
ctggcaagaa gttattgggg gagaaaattgt aaaaccagaa caagggtgtg gtgtcatctc    3480
ttctggatca tctctgtact tcagcaaggc tgggaaaaga cagctggtga gttgggacct    3540
```

```
ggatacttct tgggtggact ttgtccagtt ctacatccag ataggcggag agagtgcttc    3600
atgcaacaag cctgacagca gagaggaggg cgtcctcctt cagtacagca acaatggggg    3660
catccagtgg cacctgctag cagagatgta ctttttcagac ttcagcaaac ccagatttgt    3720
ctatctggag cttccagctg ctgccaagac cccttgcacc aggttccgct ggtggcagcc    3780
cgtgttctca ggggaggact atgaccagtg ggcagtcgat gacatcatca ttctgtccga    3840
gaagcagaag cagatcatcc cagttatcaa tccaactta cctcagaact tttatgagaa    3900
gccagctttt gattacccta tgaatcagat gagtgtgtgg ttgatgttgg ctaatgaagg    3960
aatggttaaa aatgaaacct tctgtgctgc cacaccatca gcaatgatat ttggaaaatc    4020
agatggagat cgatttgcag taactcgaga tttgaccctg aaacctggat atgtgctaca    4080
gttcaagcta aacataggtt gtgccaatca attcagcagt actgctccag ttcttcttca    4140
gtactctcat gatgctggta tgtcctggtt tctggtgaaa gaaggctgtt acccggcttc    4200
tgcaggcaaa ggatgcgaag gaaactccag agaactaagt gagcccacca tgtatcacac    4260
aggggacttt gaagaatgga caagaatcac cattgttatt ccaaggtctc ttgcatccag    4320
caagaccaga ttccgatgga tccaggagag cagctcacag aaaaacgtgc ctccatttgg    4380
tttagatgga gtgtacatat ccgagccttg tcccagttac tgcagtggcc atggggactg    4440
catttcagga gtgtgtttct gtgacctggg atatactgct gcacaaggaa cctgtgtgtc    4500
aaatgtcccc aatcacaatg agatgttcga taggtttgag gggaagctca gccctctgtg    4560
gtacaagata acaggtgccc aggttggaac tggctgtgga acacttaacg atggcaaatc    4620
tctctacttc aatggccctg ggaaaaggga agcccggacg gtccctctgg acaccaggaa    4680
tatcagactt gttcaatttt atatacaaat ggaagcaaa acttcaggca ttacctgcat    4740
caaaccaaga actagaaatg aagggcttat tgttcagtat tcaaatgaca atgggatact    4800
ctggcatttg cttcgagagt tggacttcat gtccttcctg gaaccacaga tcatttccat    4860
tgacctgcca caggacgcga agacacctgc aacggcattt cgatggtggc aaccgcaaca    4920
tgggaagcat tcagcccagt gggctttgga tgatgttctt ataggaatga atgacagctc    4980
tcaaactgga tttcaagaca aatttgatgg ctctatagat ttgcaagcca actggtatcg    5040
aatccaagga ggtcaagttg atattgactg tctctctatg gatactgctc tgatattcac    5100
tgaaaacata ggaaaacctc gttatgctga acctgggatt tttcatgtgt cagcatctac    5160
ctttttgcag tttgaaatga gcatgggctg tagcaagccc ttcagcaact cccacagtgt    5220
acagctccag tattctctga acaatggcaa ggactggcat cttgtcaccg aagagtgtgt    5280
tcctccaacc attggctgtc tgcattacac ggaaagttca atttacacct cggaaagatt    5340
ccagaattgg aagcggatca ctgtctacct tccactctcc accatttctc ccaggacccg    5400
gttcagatgg attcaggcca actacactgt gggggctgat tcctgggcga ttgataatgt    5460
tgtactggcc tcagggtgcc cttggatgtg ctcaggacga gggatttgtg atgctggacg    5520
ctgtgtgtgt gaccggggct ttggtggacc ctattgtgtt cctgttgttc ctctgccctc    5580
gattcttaaa gacgatttca atgggaattt acatcctgac ctttggcctg aagtgtatgg    5640
tgcagagagg gggaatctga atggtgaaac catcaaatct ggaacatctc taattttaa    5700 aggggaagga ctaaggatgc ttatttcaag agatctagat tgtacaaata caatgtatgt    5760
ccagttttca cttagattta tagcaaaaag tacccagag agatctcact ctattctgtt    5820
acaattctcc atcagtggag gaatcacttg gcacctgatg gatgaatttt actttcctca    5880
aacaacgaat atacttttca tcaatgttcc cttgccatac actgcccaaa ccaatgctac    5940
```

-continued

```
aagattcaga ctctggcaac cttataataa cggtaagaaa gaagaaatct ggattgttga    6000
tgacttcatt atcgatggaa ataatgtaaa caaccctgtg atgctcttgg atacatttga    6060
ttttgggccc agagaagaca attggttttt ctatcctggt ggtaacatcg gtctttattg    6120
tccatattct tcaaaggggg cacctgaaga agattcagct atggtgtttg tttcaaatga    6180
agttggtgag cattccatta ccacccgtga cctaaatgtg aatgagaaca ccatcataca    6240
atttgagatc aacgttggct gttcgactga tagctcatcc gcggatccag tgagactgga    6300
attttcaagg gacttcgggg cgacctggca ccttctgctg cccctctgct accacagcag    6360
cagccacgtc agctctttat gctccaccga gcaccacccc agcagcacct actacgcagg    6420
aaccatgcag ggctggagga gggaggtcgt gcactttggg aagctgcacc tttgtggatc    6480
tgtccgtttc agatggtacc agggatttta ccctgccggc tctcagccag tgacatgggc    6540
cattgataat gtctacatcg gtccccagtg tgaggagatg tgtaatggac aggggagctg    6600
tatcaatgga accaaatgta tatgtgaccc tggctactca ggtccaacct gtaaaataag    6660
caccaaaaat cctgattttc tcaaagatga tttcgaaggt cagctagaat ctgatagatt    6720
cttattaatg agtggtggga aaccatctcg aaagtgtgga atcctttcta gtggaaacaa    6780
cctctttttc aatgaagatg gcttgcgcat gttgatgaca cgagacctgg atttatcaca    6840
tgctagattt gtgcagttct tcatgagact gggatgtggt aaaggcgttc ctgacccccag    6900 gagtcaaccc gtgctcctac agtattctct caacggtggc ctctcgtgga gtcttcttca    6960
ggagttcctt ttcagcaatt ccagcaatgt gggcaggtac attgccctgg agataccctt    7020
gaaagcccgt tctggttcta ctcgccttcg ctggtggcaa ccgtctgaga atgggcactt    7080
ctacagcccc tgggttatcg atcagattct tattggagga aatatttctg gtaatacggt    7140
cttggaagat gatttcacaa cccttgatag taggaaatgg ctgcttcacc caggaggcac    7200
caagatgccc gtgtgtggct ctactggtga tgccctggtc ttcattgaaa aggccagcac    7260
ccgttacgtg gtcagcacag acgttgccgt gaatgaggat tccttcctac agatagactt    7320
cgctgcctcc tgctcagtca cagactcttg ttatgcgatt gaattggaat actcagtaga    7380
tcttggattg tcatggcacc cattggtaag ggactgtctg cctaccaatg tggaatgcag    7440
tcgctatcat ctgcaacgga tcctggtgtc agacactttc aacaagtgga ctagaatcac    7500
tctgcctctc cctccttata ccaggtccca agccactcgt ttccgttggc atcaaccagc    7560
tccttttgac aagcagcaga catgggcaat agataatgtc tatatcgggg atggctgcat    7620
agacatgtgc agtggccatg ggagatgcat ccagggaaac tgcgtctgtg atgaacagtg    7680
gggtggcctg tactgtgatg accccgagac ctctcttcca acccaactca aagacaactt    7740
caatcgagct ccatccagtc agaactggct gactgtgaac ggagggaaat tgagtacagt    7800
gtgtggagcc gtggcgtcgg gaatggctct ccatttcagt gggggttgta gtcgattatt    7860
agtcactgtg gatctaaacc tcactaatgc tgagttcatc caattttact tcatgtatgg    7920
gtgcctgatt acaccaaaca accgtaacca aggtgttctc ttggaatatt ctgtcaatgg    7980
aggcattacc tggaacctgc tcatggagat tttctatgac cagtacagta agcccggatt    8040
tgtgaatatc cttctccctc ctgatgctaa agagattgcc actcgcttcc gctggtggca    8100
gccaagacat gacggcctgg atcagaacga ctgggccatt gacaatgtcc tcatctcagg    8160
ctctgctgac caaaggaccg ttatgctgga caccttcagc agcgccccag taccccagca    8220
cgagcgctcc cctgcagatg ccggccctgt cgggaggatc gcctttgaca tgtttatgga    8280
```

-continued

```
agacaaaact tcagtgaatg agcactggct attccatgat gattgtacag tagaaagatt      8340
ctgtgactcc cctgatggtg tgatgctctg tggcagtcat gatggacggg aggtgtatgc      8400
agtgacccat gacctgactc ccactgaagg ctggattatg caattcaaga tctcagttgg      8460
atgtaaggtg tctgaaaaaa ttgcccagaa tcaaattcat gtgcagtatt ctactgactt      8520
cggtgtgagt tggaattatc tggtccctca gtgcttgcct gctgacccaa aatgctctgg      8580
aagtgtttct cagccatctg tattctttcc aactaaaggg tggaaaagga tcacctaccc      8640
acttcctgaa agcttagtgg gaaatccggt aaggtttagg ttctatcaga agtactcaga      8700
catgcagtgg gcaatcgata atttctacct gggccctgga tgcttggaca actgcagggg      8760
ccatggagat tgcttaaggg aacagtgcat ctgtgatccg ggatactcag ggccaaactg      8820
ctacttgacc cacactctga agactttcct gaaggaacgc tttgacagtg aagaaatcaa      8880
acctgactta tggatgtcct tagaaggtgg aagtacttgc actgagtgtg gaattcttgc      8940
cgaggacact gcactctatt ttgggggatc cactgtgaga caagcggtta cacaagattt      9000
ggatcttcga ggtgcaaagt tcctgcaata ctgggggcgc atcggtagtg agaacaacat      9060
gacctcttgc catcgtccca tctgccggaa ggaaggcgtg ctgttggact actctaccga      9120
tggaggaatt acctggactt tgctccatga gatggattac cagaaataca tttctgttag      9180
acacgactac atacttcttc ctgaagatgc cctcaccaac acaactcgac ttcgctggtg      9240
gcagcctttt gtgatcagca atggaattgt ggtctctggg gtggagcgtg ctcagtgggc      9300
actggacaac attttgattg gtggagcaga aatcaatccc agccaattgg tggacacttt      9360
tgatgatgaa ggcacttccc atgaagaaaa ctggagtttt taccctaatg ctgtaaggac      9420
agcaggattt tgtggcaatc catcctttca cctctattgg ccaaataaaa agaaggacaa      9480
gactcacaat gctctctcct cccgagaact cattatacag ccaggataca tgatgcagtt      9540
taaaattgtg gtgggttgtg aagccacttc ttgtggtgac cttcattccg taatgctgga      9600
atacactaag gatgcaagat cggattcctg gcagctcgta cagacccagt gccttccttc      9660
ctcttctaac agcattggct gctcccctt ccagttccat gaagccacca tctacaactc      9720
tgtcaacagc tcaagctgga aaagaatcac catccagctg cctgaccatg tctcctctag      9780
tgcaacacag ttccgctgga tccagaaggg agaagaaact gagaagcaaa gctgggcaat      9840
tgaccacgtg tacattggag aggcttgccc caagctctgc agcggcacg gatactgcac       9900 gaccggtgcc atctgcatct cgacgagag cttccaaggt gatgactgct ctgttttcag       9960
tcacgacctt cccagttata ttaaagataa ttttgagtcc gcaagagtca ccgaggcaaa    10020
ctgggagacc attcaaggtg gagtcatagg aagtggctgt gggcagctgg cccctacgc     10080 ccatggagac tcactgtact ttaatggctg tcagatcagg caagcagcta ccaagcctct    10140
ggatctcact cgagcaagca aaatcatgtt tgttttgcaa attgggagca tgtcgcagac    10200
ggacagctgc aacagtgacc tgagtggccc ccacgctgtg gacaaggcgg tgctgctgca    10260
atacagcgtc aacaacggga tcacctggca tgtcatcgcc cagcaccagc caaaggactt    10320
cacacaagct cagagagtgt cttacaatgt cccctggag gcacggatga aaggagtctt     10380
actgcgctgg tggcaaccac gccacaatgg aacaggtcat gatcaatggg ctttggacca    10440
tgtggaggtc gtcctagtaa gcactcgcaa acaaaattac atgatgaatt tttcacgaca    10500
acatgggctc agacatttct acaacagaag acgaaggtca cttaggcgat acccatgaag    10560
aatcaaaaag tttattttttt ttcttccaac atgtgatgtg ttgctctcca ttcttttaaa   10620
tctcgcacta catctgatat caggaaatat ctgtgaagga cttggtgatt acctgaaagc    10680
```

-continued

```
ccttctcaag accgagtgta caccactttc ccacactgtg aactaatgac aagtgactta   10740
tttgctcata agtaaatgtc ttcatgttga tgtgtccgtg aaagttgtga tctgttgtaa   10800
tatcagttac agtggcagta ttgacaataa gaaacagttt aacagaaaaa tgaaatttaa   10860
gcacaaaaaa tttaagagat tttatgttta aaatggcatt tagcacagta tttaacattc   10920
ttggtcacaa agctatttaa gtggactgta tttcagctat gtctcatgtt ttatatgatt   10980
aaattatcat tgtttgtcct ttatgtattc tcttctacaa tacaacacat tgaaactgta   11040
tttacttgtt atgttgtaat attttgctgc tgaatttggg gctacttata ttctgcagaa   11100
aattaattga aatacctatt caagaagata gttgtaaaga tattgtatct cctttaatat   11160
actccttaaa aatgtatgtt ggtttagcgt tgttttgtgg ataagaaaaa tgcttgaccc   11220
tgaaatattt tctactttaa attgtggatg aagaccctat ctcccacaaa taagttccca   11280
tttccttgtc taaagatctt tttttaagtg ttctgtggct gatttactaa cagtaactgc   11340
cattttttgt ctgtgataac agagtgattt gtaaaacagt ggttgttttt tcattgtgtt   11400
ttcttcgtgg attgtttttt ctgcgggtca tattcatacc ttctgatgaa gttgtacaac   11460
accagcaaca ttataatggc cctgtagctc tgaatgctat ttgtgtaact gaaaggttgc   11520
actctagggt gaaccaagct ataaaagccc atgcttaaat aaaaattatg tccaaaagcc   11580
```

```
<210> SEQ ID NO 2
<211> LENGTH: 3460
<212> TYPE: PRT
<213> ORGANISM: homo sapien

<400> SEQUENCE: 2

Met Glu Arg Ser Gly Trp Ala Arg Gln Thr Phe Leu Leu Ala Leu Leu
1               5                   10                  15

Leu Gly Ala Thr Leu Arg Ala Arg Ala Ala Ala Gly Tyr Tyr Pro Arg
                20                  25                  30

Phe Ser Pro Phe Phe Phe Leu Cys Thr His His Gly Glu Leu Glu Gly
            35                  40                  45

Asp Gly Glu Gln Gly Glu Val Leu Ile Ser Leu His Ile Ala Gly Asn
        50                  55                  60

Pro Thr Tyr Tyr Val Pro Gly Gln Glu Tyr His Val Thr Ile Ser Thr
65                  70                  75                  80

Ser Thr Phe Phe Asp Gly Leu Leu Val Thr Gly Leu Tyr Thr Ser Thr
                85                  90                  95

Ser Val Gln Ala Ser Gln Ser Ile Gly Gly Ser Ser Ala Phe Gly Phe
            100                 105                 110

Gly Ile Met Ser Asp His Gln Phe Gly Asn Gln Phe Met Cys Ser Val
        115                 120                 125

Val Ala Ser His Val Ser His Leu Pro Thr Thr Asn Leu Ser Phe Ile
    130                 135                 140

Trp Ile Ala Pro Pro Ala Gly Thr Gly Cys Val Asn Phe Met Ala Thr
145                 150                 155                 160

Ala Thr His Arg Gly Gln Val Ile Phe Lys Asp Ala Leu Ala Gln Gln
                165                 170                 175

Leu Cys Glu Gln Gly Ala Pro Thr Asp Val Thr Val His Pro His Leu
            180                 185                 190

Ala Glu Ile His Ser Asp Ser Ile Ile Leu Arg Asp Asp Phe Asp Ser
        195                 200                 205

Tyr His Gln Leu Gln Leu Asn Pro Asn Ile Trp Val Glu Cys Asn Asn
```

```
            210                 215                 220

Cys Glu Thr Gly Glu Gln Cys Gly Ala Ile Met His Gly Asn Ala Val
225                 230                 235                 240

Thr Phe Cys Glu Pro Tyr Gly Pro Arg Glu Leu Ile Thr Thr Gly Leu
                245                 250                 255

Asn Thr Thr Thr Ala Ser Val Leu Gln Phe Ser Ile Gly Ser Gly Ser
                260                 265                 270

Cys Arg Phe Ser Tyr Ser Asp Pro Ser Ile Ile Val Leu Tyr Ala Lys
            275                 280                 285

Asn Asn Ser Ala Asp Trp Ile Gln Leu Glu Lys Ile Arg Ala Pro Ser
        290                 295                 300

Asn Val Ser Thr Ile Ile His Ile Leu Tyr Leu Pro Glu Asp Ala Lys
305                 310                 315                 320

Gly Glu Asn Val Gln Phe Gln Trp Lys Gln Glu Asn Leu Arg Val Gly
                325                 330                 335

Glu Val Tyr Glu Ala Cys Trp Ala Leu Asp Asn Ile Leu Ile Ile Asn
                340                 345                 350

Ser Ala His Arg Gln Val Val Leu Glu Asp Ser Leu Asp Pro Val Asp
            355                 360                 365

Thr Gly Asn Trp Leu Phe Phe Pro Gly Ala Thr Val Lys His Ser Cys
        370                 375                 380

Gln Ser Asp Gly Asn Ser Ile Tyr Phe His Gly Asn Glu Gly Ser Glu
385                 390                 395                 400

Phe Asn Phe Ala Thr Thr Arg Asp Val Asp Leu Ser Thr Glu Asp Ile
                405                 410                 415

Gln Glu Gln Trp Ser Glu Glu Phe Glu Ser Gln Pro Thr Gly Trp Asp
                420                 425                 430

Val Leu Gly Ala Val Ile Gly Thr Glu Cys Gly Thr Ile Glu Ser Gly
            435                 440                 445

Leu Ser Met Val Phe Leu Lys Asp Gly Glu Arg Lys Leu Cys Thr Pro
        450                 455                 460

Ser Met Asp Thr Thr Gly Tyr Gly Asn Leu Arg Phe Tyr Phe Val Met
465                 470                 475                 480

Gly Gly Ile Cys Asp Pro Gly Asn Ser His Glu Asn Asp Ile Ile Leu
                485                 490                 495

Tyr Ala Lys Ile Glu Gly Arg Lys Glu His Ile Thr Leu Asp Thr Leu
            500                 505                 510

Ser Tyr Ser Ser Tyr Lys Val Pro Ser Leu Val Ser Val Val Ile Asn
            515                 520                 525

Pro Glu Leu Gln Thr Pro Ala Thr Lys Phe Cys Leu Arg Gln Lys Asn
        530                 535                 540

His Gln Gly His Asn Arg Asn Val Trp Ala Val Asp Phe Phe His Val
545                 550                 555                 560

Leu Pro Val Leu Pro Ser Thr Met Ser His Met Ile Gln Phe Ser Ile
                565                 570                 575

Asn Leu Gly Cys Gly Thr His Gln Pro Gly Asn Ser Val Ser Leu Glu
            580                 585                 590

Phe Ser Thr Asn His Gly Arg Ser Trp Ser Leu Leu His Thr Glu Cys
            595                 600                 605

Leu Pro Glu Ile Cys Ala Gly Pro His Leu Pro His Ser Thr Val Tyr
        610                 615                 620

Ser Ser Glu Asn Tyr Ser Gly Trp Asn Arg Ile Thr Ile Pro Leu Pro
625                 630                 635                 640
```

```
Asn Ala Ala Leu Thr Arg Asn Thr Arg Ile Arg Trp Arg Gln Thr Gly
                645                 650                 655

Pro Ile Leu Gly Asn Met Trp Ala Ile Asp Asn Val Tyr Ile Gly Pro
                660                 665                 670

Ser Cys Leu Lys Phe Cys Ser Gly Arg Gly Gln Cys Thr Arg His Gly
                675                 680                 685

Cys Lys Cys Asp Pro Gly Phe Ser Gly Pro Ala Cys Glu Met Ala Ser
            690                 695                 700

Gln Thr Phe Pro Met Phe Ile Ser Glu Ser Phe Gly Ser Ser Arg Leu
705                 710                 715                 720

Ser Ser Tyr His Asn Phe Tyr Ser Ile Arg Gly Ala Glu Val Ser Phe
                725                 730                 735

Gly Cys Gly Val Leu Ala Ser Gly Lys Ala Leu Val Phe Asn Lys Glu
            740                 745                 750

Gly Arg Arg Gln Leu Ile Thr Ser Phe Leu Asp Ser Ser Gln Ser Arg
            755                 760                 765

Phe Leu Gln Phe Thr Leu Arg Leu Gly Ser Lys Ser Val Leu Ser Thr
770                 775                 780

Cys Arg Ala Pro Asp Gln Pro Gly Glu Gly Val Leu Leu His Tyr Ser
785                 790                 795                 800

Tyr Asp Asn Gly Ile Thr Trp Lys Leu Leu Glu His Tyr Ser Tyr Leu
            805                 810                 815

Ser Tyr His Glu Pro Arg Ile Ile Ser Val Glu Leu Pro Gly Asp Ala
            820                 825                 830

Lys Gln Phe Gly Ile Gln Phe Arg Trp Trp Gln Pro Tyr His Ser Ser
            835                 840                 845

Gln Arg Glu Asp Val Trp Ala Ile Asp Glu Ile Ile Met Thr Ser Val
    850                 855                 860

Leu Phe Asn Ser Ile Ser Leu Asp Phe Thr Asn Leu Val Glu Val Thr
865                 870                 875                 880

Gln Ser Leu Gly Phe Tyr Leu Gly Asn Val Gln Pro Tyr Cys Gly His
                885                 890                 895

Asp Trp Thr Leu Cys Phe Thr Gly Asp Ser Lys Leu Ala Ser Ser Met
            900                 905                 910

Arg Tyr Val Glu Thr Gln Ser Met Gln Ile Gly Ala Ser Tyr Met Ile
            915                 920                 925

Gln Phe Ser Leu Val Met Gly Cys Gly Gln Lys Tyr Thr Pro His Met
    930                 935                 940

Asp Asn Gln Val Lys Leu Glu Tyr Ser Thr Asn His Gly Leu Thr Trp
945                 950                 955                 960

His Leu Val Gln Glu Glu Cys Leu Pro Ser Met Pro Ser Cys Gln Glu
                965                 970                 975

Phe Thr Ser Ala Ser Ile Tyr His Ala Ser Glu Phe Thr Gln Trp Arg
            980                 985                 990

Arg Val Ile Val Leu Leu Pro Gln  Lys Thr Trp Ser Ser  Ala Thr Arg
            995                 1000                1005

Phe Arg  Trp Ser Gln Ser Tyr  Tyr Thr Ala Gln Asp  Glu Trp Ala
    1010                1015                1020

Leu Asp  Ser Ile Tyr Ile Gly  Gln Gln Cys Pro Asn  Met Cys Ser
    1025                1030                1035

Gly His  Gly Ser Cys Asp His  Gly Ile Cys Arg Cys  Asp Gln Gly
    1040                1045                1050
```

Tyr Gln Gly Thr Glu Cys His Pro Glu Ala Ala Leu Pro Ser Thr
    1055            1060            1065

Ile Met Ser Asp Phe Glu Asn Gln Asn Gly Trp Glu Ser Asp Trp
    1070            1075            1080

Gln Glu Val Ile Gly Gly Glu Ile Val Lys Pro Glu Gln Gly Cys
    1085            1090            1095

Gly Val Ile Ser Ser Gly Ser Ser Leu Tyr Phe Ser Lys Ala Gly
    1100            1105            1110

Lys Arg Gln Leu Val Ser Trp Asp Leu Asp Thr Ser Trp Val Asp
    1115            1120            1125

Phe Val Gln Phe Tyr Ile Gln Ile Gly Gly Glu Ser Ala Ser Cys
    1130            1135            1140

Asn Lys Pro Asp Ser Arg Glu Glu Gly Val Leu Leu Gln Tyr Ser
    1145            1150            1155

Asn Asn Gly Gly Ile Gln Trp His Leu Leu Ala Glu Met Tyr Phe
    1160            1165            1170

Ser Asp Phe Ser Lys Pro Arg Phe Val Tyr Leu Glu Leu Pro Ala
    1175            1180            1185

Ala Ala Lys Thr Pro Cys Thr Arg Phe Arg Trp Trp Gln Pro Val
    1190            1195            1200

Phe Ser Gly Glu Asp Tyr Asp Gln Trp Ala Val Asp Asp Ile Ile
    1205            1210            1215

Ile Leu Ser Glu Lys Gln Lys Gln Ile Ile Pro Val Ile Asn Pro
    1220            1225            1230

Thr Leu Pro Gln Asn Phe Tyr Glu Lys Pro Ala Phe Asp Tyr Pro
    1235            1240            1245

Met Asn Gln Met Ser Val Trp Leu Met Leu Ala Asn Glu Gly Met
    1250            1255            1260

Val Lys Asn Glu Thr Phe Cys Ala Ala Thr Pro Ser Ala Met Ile
    1265            1270            1275

Phe Gly Lys Ser Asp Gly Asp Arg Phe Ala Val Thr Arg Asp Leu
    1280            1285            1290

Thr Leu Lys Pro Gly Tyr Val Leu Gln Phe Lys Leu Asn Ile Gly
    1295            1300            1305

Cys Ala Asn Gln Phe Ser Ser Thr Ala Pro Val Leu Leu Gln Tyr
    1310            1315            1320

Ser His Asp Ala Gly Met Ser Trp Phe Leu Val Lys Glu Gly Cys
    1325            1330            1335

Tyr Pro Ala Ser Ala Gly Lys Gly Cys Glu Gly Asn Ser Arg Glu
    1340            1345            1350

Leu Ser Glu Pro Thr Met Tyr His Thr Gly Asp Phe Glu Glu Trp
    1355            1360            1365

Thr Arg Ile Thr Ile Val Ile Pro Arg Ser Leu Ala Ser Ser Lys
    1370            1375            1380

Thr Arg Phe Arg Trp Ile Gln Glu Ser Ser Ser Gln Lys Asn Val
    1385            1390            1395

Pro Pro Phe Gly Leu Asp Gly Val Tyr Ile Ser Glu Pro Cys Pro
    1400            1405            1410

Ser Tyr Cys Ser Gly His Gly Asp Cys Ile Ser Gly Val Cys Phe
    1415            1420            1425

Cys Asp Leu Gly Tyr Thr Ala Ala Gln Gly Thr Cys Val Ser Asn
    1430            1435            1440

Val Pro Asn His Asn Glu Met Phe Asp Arg Phe Glu Gly Lys Leu

-continued

```
          1445                1450                1455

Ser Pro  Leu Trp Tyr Lys Ile  Thr Gly Ala Gln Val  Gly Thr Gly
     1460                1465                1470

Cys Gly  Thr Leu Asn Asp Gly  Lys Ser Leu Tyr Phe  Asn Gly Pro
     1475                1480                1485

Gly Lys  Arg Glu Ala Arg Thr  Val Pro Leu Asp Thr  Arg Asn Ile
     1490                1495                1500

Arg Leu  Val Gln Phe Tyr Ile  Gln Ile Gly Ser Lys  Thr Ser Gly
     1505                1510                1515

Ile Thr  Cys Ile Lys Pro Arg  Thr Arg Asn Glu Gly  Leu Ile Val
     1520                1525                1530

Gln Tyr  Ser Asn Asp Asn Gly  Ile Leu Trp His Leu  Leu Arg Glu
     1535                1540                1545

Leu Asp  Phe Met Ser Phe Leu  Glu Pro Gln Ile Ile  Ser Ile Asp
     1550                1555                1560

Leu Pro  Gln Asp Ala Lys Thr  Pro Ala Thr Ala Phe  Arg Trp Trp
     1565                1570                1575

Gln Pro  Gln His Gly Lys His  Ser Ala Gln Trp Ala  Leu Asp Asp
     1580                1585                1590

Val Leu  Ile Gly Met Asn Asp  Ser Ser Gln Thr Gly  Phe Gln Asp
     1595                1600                1605

Lys Phe  Asp Gly Ser Ile Asp  Leu Gln Ala Asn Trp  Tyr Arg Ile
     1610                1615                1620

Gln Gly  Gly Gln Val Asp Ile  Asp Cys Leu Ser Met  Asp Thr Ala
     1625                1630                1635

Leu Ile  Phe Thr Glu Asn Ile  Gly Lys Pro Arg Tyr  Ala Glu Thr
     1640                1645                1650

Trp Asp  Phe His Val Ser Ala  Ser Thr Phe Leu Gln  Phe Glu Met
     1655                1660                1665

Ser Met  Gly Cys Ser Lys Pro  Phe Ser Asn Ser His  Ser Val Gln
     1670                1675                1680

Leu Gln  Tyr Ser Leu Asn Asn  Gly Lys Asp Trp His  Leu Val Thr
     1685                1690                1695

Glu Glu  Cys Val Pro Pro Thr  Ile Gly Cys Leu His  Tyr Thr Glu
     1700                1705                1710

Ser Ser  Ile Tyr Thr Ser Glu  Arg Phe Gln Asn Trp  Lys Arg Ile
     1715                1720                1725

Thr Val  Tyr Leu Pro Leu Ser  Thr Ile Ser Pro Arg  Thr Arg Phe
     1730                1735                1740

Arg Trp  Ile Gln Ala Asn Tyr  Thr Val Gly Ala Asp  Ser Trp Ala
     1745                1750                1755

Ile Asp  Asn Val Val Leu Ala  Ser Gly Cys Pro Trp  Met Cys Ser
     1760                1765                1770

Gly Arg  Gly Ile Cys Asp Ala  Gly Arg Cys Val Cys  Asp Arg Gly
     1775                1780                1785

Phe Gly  Gly Pro Tyr Cys Val  Pro Val Val Pro Leu  Pro Ser Ile
     1790                1795                1800

Leu Lys  Asp Asp Phe Asn Gly  Asn Leu His Pro Asp  Leu Trp Pro
     1805                1810                1815

Glu Val  Tyr Gly Ala Glu Arg  Gly Asn Leu Asn Gly  Glu Thr Ile
     1820                1825                1830

Lys Ser  Gly Thr Ser Leu Ile  Phe Lys Gly Glu Gly  Leu Arg Met
     1835                1840                1845
```

-continued

```
Leu Ile  Ser Arg Asp Leu Asp  Cys Thr Asn Thr Met  Tyr Val Gln
    1850             1855              1860

Phe Ser  Leu Arg Phe Ile Ala  Lys Ser Thr Pro Glu  Arg Ser His
    1865             1870              1875

Ser Ile  Leu Leu Gln Phe Ser  Ile Ser Gly Gly Ile  Thr Trp His
    1880             1885              1890

Leu Met  Asp Glu Phe Tyr Phe  Pro Gln Thr Thr Asn  Ile Leu Phe
    1895             1900              1905

Ile Asn  Val Pro Leu Pro Tyr  Thr Ala Gln Thr Asn  Ala Thr Arg
    1910             1915              1920

Phe Arg  Leu Trp Gln Pro Tyr  Asn Asn Gly Lys Lys  Glu Glu Ile
    1925             1930              1935

Trp Ile  Val Asp Asp Phe Ile  Ile Asp Gly Asn Asn  Val Asn Asn
    1940             1945              1950

Pro Val  Met Leu Leu Asp Thr  Phe Asp Phe Gly Pro  Arg Glu Asp
    1955             1960              1965

Asn Trp  Phe Phe Tyr Pro Gly  Gly Asn Ile Gly Leu  Tyr Cys Pro
    1970             1975              1980

Tyr Ser  Ser Lys Gly Ala Pro  Glu Glu Asp Ser Ala  Met Val Phe
    1985             1990              1995

Val Ser  Asn Glu Val Gly Glu  His Ser Ile Thr Thr  Arg Asp Leu
    2000             2005              2010

Asn Val  Asn Glu Asn Thr Ile  Ile Gln Phe Glu Ile  Asn Val Gly
    2015             2020              2025

Cys Ser  Thr Asp Ser Ser Ser  Ala Asp Pro Val Arg  Leu Glu Phe
    2030             2035              2040

Ser Arg  Asp Phe Gly Ala Thr  Trp His Leu Leu Leu  Pro Leu Cys
    2045             2050              2055

Tyr His  Ser Ser Ser His Val  Ser Ser Leu Cys Ser  Thr Glu His
    2060             2065              2070

His Pro  Ser Ser Thr Tyr Tyr  Ala Gly Thr Met Gln  Gly Trp Arg
    2075             2080              2085

Arg Glu  Val Val His Phe Gly  Lys Leu His Leu Cys  Gly Ser Val
    2090             2095              2100

Arg Phe  Arg Trp Tyr Gln Gly  Phe Tyr Pro Ala Gly  Ser Gln Pro
    2105             2110              2115

Val Thr  Trp Ala Ile Asp Asn  Val Tyr Ile Gly Pro  Gln Cys Glu
    2120             2125              2130

Glu Met  Cys Asn Gly Gln Gly  Ser Cys Ile Asn Gly  Thr Lys Cys
    2135             2140              2145

Ile Cys  Asp Pro Gly Tyr Ser  Gly Pro Thr Cys Lys  Ile Ser Thr
    2150             2155              2160

Lys Asn  Pro Asp Phe Leu Lys  Asp Asp Phe Glu Gly  Gln Leu Glu
    2165             2170              2175

Ser Asp  Arg Phe Leu Leu Met  Ser Gly Gly Lys Pro  Ser Arg Lys
    2180             2185              2190

Cys Gly  Ile Leu Ser Ser Gly  Asn Asn Leu Phe Phe  Asn Glu Asp
    2195             2200              2205

Gly Leu  Arg Met Leu Met Thr  Arg Asp Leu Asp Leu  Ser His Ala
    2210             2215              2220

Arg Phe  Val Gln Phe Phe Met  Arg Leu Gly Cys Gly  Lys Gly Val
    2225             2230              2235
```

```
Pro Asp Pro Arg Ser Gln Pro  Val Leu Leu Gln Tyr  Ser Leu Asn
    2240                 2245              2250

Gly Gly Leu Ser Trp Ser Leu  Leu Gln Glu Phe Leu  Phe Ser Asn
    2255                 2260              2265

Ser Ser Asn Val Gly Arg Tyr  Ile Ala Leu Glu Ile  Pro Leu Lys
    2270                 2275              2280

Ala Arg Ser Gly Ser Thr Arg  Leu Arg Trp Trp Gln  Pro Ser Glu
    2285                 2290              2295

Asn Gly His Phe Tyr Ser Pro  Trp Val Ile Asp Gln  Ile Leu Ile
    2300                 2305              2310

Gly Gly Asn Ile Ser Gly Asn  Thr Val Leu Glu Asp  Asp Phe Thr
    2315                 2320              2325

Thr Leu Asp Ser Arg Lys Trp  Leu Leu His Pro Gly  Gly Thr Lys
    2330                 2335              2340

Met Pro Val Cys Gly Ser Thr  Gly Asp Ala Leu Val  Phe Ile Glu
    2345                 2350              2355

Lys Ala Ser Thr Arg Tyr Val  Val Ser Thr Asp Val  Ala Val Asn
    2360                 2365              2370

Glu Asp Ser Phe Leu Gln Ile  Asp Phe Ala Ala Ser  Cys Ser Val
    2375                 2380              2385

Thr Asp Ser Cys Tyr Ala Ile  Glu Leu Glu Tyr Ser  Val Asp Leu
    2390                 2395              2400

Gly Leu Ser Trp His Pro Leu  Val Arg Asp Cys Leu  Pro Thr Asn
    2405                 2410              2415

Val Glu Cys Ser Arg Tyr His  Leu Gln Arg Ile Leu  Val Ser Asp
    2420                 2425              2430

Thr Phe Asn Lys Trp Thr Arg  Ile Thr Leu Pro Leu  Pro Pro Tyr
    2435                 2440              2445

Thr Arg Ser Gln Ala Thr Arg  Phe Arg Trp His Gln  Pro Ala Pro
    2450                 2455              2460

Phe Asp Lys Gln Gln Thr Trp  Ala Ile Asp Asn Val  Tyr Ile Gly
    2465                 2470              2475

Asp Gly Cys Ile Asp Met Cys  Ser Gly His Gly Arg  Cys Ile Gln
    2480                 2485              2490

Gly Asn Cys Val Cys Asp Glu  Gln Trp Gly Gly Leu  Tyr Cys Asp
    2495                 2500              2505

Asp Pro Glu Thr Ser Leu Pro  Thr Gln Leu Lys Asp  Asn Phe Asn
    2510                 2515              2520

Arg Ala Pro Ser Ser Gln Asn  Trp Leu Thr Val Asn  Gly Gly Lys
    2525                 2530              2535

Leu Ser Thr Val Cys Gly Ala  Val Ala Ser Gly Met  Ala Leu His
    2540                 2545              2550

Phe Ser Gly Gly Cys Ser Arg  Leu Leu Val Thr Val  Asp Leu Asn
    2555                 2560              2565

Leu Thr Asn Ala Glu Phe Ile  Gln Phe Tyr Phe Met  Tyr Gly Cys
    2570                 2575              2580

Leu Ile Thr Pro Asn Asn Arg  Asn Gln Gly Val Leu  Leu Glu Tyr
    2585                 2590              2595

Ser Val Asn Gly Gly Ile Thr  Trp Asn Leu Leu Met  Glu Ile Phe
    2600                 2605              2610

Tyr Asp Gln Tyr Ser Lys Pro  Gly Phe Val Asn Ile  Leu Leu Pro
    2615                 2620              2625

Pro Asp Ala Lys Glu Ile Ala  Thr Arg Phe Arg Trp  Trp Gln Pro
```

```
          2630                    2635                    2640

Arg His  Asp Gly Leu Asp Gln  Asn Asp Trp Ala Ile  Asp Asn Val
    2645                    2650                    2655

Leu Ile  Ser Gly Ser Ala Asp  Gln Arg Thr Val Met  Leu Asp Thr
    2660                    2665                    2670

Phe Ser  Ser Ala Pro Val Pro  Gln His Glu Arg Ser  Pro Ala Asp
    2675                    2680                    2685

Ala Gly  Pro Val Gly Arg Ile  Ala Phe Asp Met Phe  Met Glu Asp
    2690                    2695                    2700

Lys Thr  Ser Val Asn Glu His  Trp Leu Phe His Asp  Asp Cys Thr
    2705                    2710                    2715

Val Glu  Arg Phe Cys Asp Ser  Pro Asp Gly Val Met  Leu Cys Gly
    2720                    2725                    2730

Ser His  Asp Gly Arg Glu Val  Tyr Ala Val Thr His  Asp Leu Thr
    2735                    2740                    2745

Pro Thr  Glu Gly Trp Ile Met  Gln Phe Lys Ile Ser  Val Gly Cys
    2750                    2755                    2760

Lys Val  Ser Glu Lys Ile Ala  Gln Asn Gln Ile His  Val Gln Tyr
    2765                    2770                    2775

Ser Thr  Asp Phe Gly Val Ser  Trp Asn Tyr Leu Val  Pro Gln Cys
    2780                    2785                    2790

Leu Pro  Ala Asp Pro Lys Cys  Ser Gly Ser Val Ser  Gln Pro Ser
    2795                    2800                    2805

Val Phe  Phe Pro Thr Lys Gly  Trp Lys Arg Ile Thr  Tyr Pro Leu
    2810                    2815                    2820

Pro Glu  Ser Leu Val Gly Asn  Pro Val Arg Phe Arg  Phe Tyr Gln
    2825                    2830                    2835

Lys Tyr  Ser Asp Met Gln Trp  Ala Ile Asp Asn Phe  Tyr Leu Gly
    2840                    2845                    2850

Pro Gly  Cys Leu Asp Asn Cys  Arg Gly His Gly Asp  Cys Leu Arg
    2855                    2860                    2865

Glu Gln  Cys Ile Cys Asp Pro  Gly Tyr Ser Gly Pro  Asn Cys Tyr
    2870                    2875                    2880

Leu Thr  His Thr Leu Lys Thr  Phe Leu Lys Glu Arg  Phe Asp Ser
    2885                    2890                    2895

Glu Glu  Ile Lys Pro Asp Leu  Trp Met Ser Leu Glu  Gly Gly Ser
    2900                    2905                    2910

Thr Cys  Thr Glu Cys Gly Ile  Leu Ala Glu Asp Thr  Ala Leu Tyr
    2915                    2920                    2925

Phe Gly  Gly Ser Thr Val Arg  Gln Ala Val Thr Gln  Asp Leu Asp
    2930                    2935                    2940

Leu Arg  Gly Ala Lys Phe Leu  Gln Tyr Trp Gly Arg  Ile Gly Ser
    2945                    2950                    2955

Glu Asn  Asn Met Thr Ser Cys  His Arg Pro Ile Cys  Arg Lys Glu
    2960                    2965                    2970

Gly Val  Leu Leu Asp Tyr Ser  Thr Asp Gly Gly Ile  Thr Trp Thr
    2975                    2980                    2985

Leu Leu  His Glu Met Asp Tyr  Gln Lys Tyr Ile Ser  Val Arg His
    2990                    2995                    3000

Asp Tyr  Ile Leu Leu Pro Glu  Asp Ala Leu Thr Asn  Thr Thr Arg
    3005                    3010                    3015

Leu Arg  Trp Trp Gln Pro Phe  Val Ile Ser Asn Gly  Ile Val Val
    3020                    3025                    3030
```

-continued

```
Ser Gly Val Glu Arg Ala Gln  Trp Ala Leu Asp Asn  Ile Leu Ile
3035                3040                3045

Gly Gly Ala Glu Ile Asn Pro  Ser Gln Leu Val Asp  Thr Phe Asp
3050                3055                3060

Asp Glu Gly Thr Ser His Glu  Glu Asn Trp Ser Phe  Tyr Pro Asn
3065                3070                3075

Ala Val Arg Thr Ala Gly Phe  Cys Gly Asn Pro Ser  Phe His Leu
3080                3085                3090

Tyr Trp Pro Asn Lys Lys Lys  Asp Lys Thr His Asn  Ala Leu Ser
3095                3100                3105

Ser Arg Glu Leu Ile Ile Gln  Pro Gly Tyr Met Met  Gln Phe Lys
3110                3115                3120

Ile Val Val Gly Cys Glu Ala  Thr Ser Cys Gly Asp  Leu His Ser
3125                3130                3135

Val Met Leu Glu Tyr Thr Lys  Asp Ala Arg Ser Asp  Ser Trp Gln
3140                3145                3150

Leu Val Gln Thr Gln Cys Leu  Pro Ser Ser Ser Asn  Ser Ile Gly
3155                3160                3165

Cys Ser Pro Phe Gln Phe His  Glu Ala Thr Ile Tyr  Asn Ser Val
3170                3175                3180

Asn Ser Ser Ser Trp Lys Arg  Ile Thr Ile Gln Leu  Pro Asp His
3185                3190                3195

Val Ser Ser Ser Ala Thr Gln  Phe Arg Trp Ile Gln  Lys Gly Glu
3200                3205                3210

Glu Thr Glu Lys Gln Ser Trp  Ala Ile Asp His Val  Tyr Ile Gly
3215                3220                3225

Glu Ala Cys Pro Lys Leu Cys  Ser Gly His Gly Tyr  Cys Thr Thr
3230                3235                3240

Gly Ala Ile Cys Ile Cys Asp  Glu Ser Phe Gln Gly  Asp Asp Cys
3245                3250                3255

Ser Val Phe Ser His Asp Leu  Pro Ser Tyr Ile Lys  Asp Asn Phe
3260                3265                3270

Glu Ser Ala Arg Val Thr Glu  Ala Asn Trp Glu Thr  Ile Gln Gly
3275                3280                3285

Gly Val Ile Gly Ser Gly Cys  Gly Gln Leu Ala Pro  Tyr Ala His
3290                3295                3300

Gly Asp Ser Leu Tyr Phe Asn  Gly Cys Gln Ile Arg  Gln Ala Ala
3305                3310                3315

Thr Lys Pro Leu Asp Leu Thr  Arg Ala Ser Lys Ile  Met Phe Val
3320                3325                3330

Leu Gln Ile Gly Ser Met Ser  Gln Thr Asp Ser Cys  Asn Ser Asp
3335                3340                3345

Leu Ser Gly Pro His Ala Val  Asp Lys Ala Val Leu  Leu Gln Tyr
3350                3355                3360

Ser Val Asn Asn Gly Ile Thr  Trp His Val Ile Ala  Gln His Gln
3365                3370                3375

Pro Lys Asp Phe Thr Gln Ala  Gln Arg Val Ser Tyr  Asn Val Pro
3380                3385                3390

Leu Glu Ala Arg Met Lys Gly  Val Leu Leu Arg Trp  Trp Gln Pro
3395                3400                3405

Arg His Asn Gly Thr Gly His  Asp Gln Trp Ala Leu  Asp His Val
3410                3415                3420
```

-continued

```
Glu Val  Val Leu Val Ser Thr  Arg Lys Gln Asn Tyr  Met Met Asn
    3425            3430            3435

Phe Ser  Arg Gln His Gly Leu  Arg His Phe Tyr Asn  Arg Arg Arg
    3440            3445            3450

Arg Ser  Leu Arg Arg Tyr Pro
    3455            3460

<210> SEQ ID NO 3
<211> LENGTH: 18
<212> TYPE: DNA
<213> ORGANISM: Artificial Sequence
<220> FEATURE:
<223> OTHER INFORMATION: Manganese superoxide dismutase (MnSOD) forward
      primer

<400> SEQUENCE: 3
gctgcaccac agcaagca                                                 18

<210> SEQ ID NO 4
<211> LENGTH: 19
<212> TYPE: DNA
<213> ORGANISM: Artificial Sequence
<220> FEATURE:
<223> OTHER INFORMATION: Manganese superoxide dismutase (MnSOD) reverse
      primer

<400> SEQUENCE: 4
tcggtggcgt tgagattgt                                                19

<210> SEQ ID NO 5
<211> LENGTH: 17
<212> TYPE: DNA
<213> ORGANISM: Artificial Sequence
<220> FEATURE:
<223> OTHER INFORMATION: Reelin forward primer

<400> SEQUENCE: 5
gccacgccac aatggaa                                                  17

<210> SEQ ID NO 6
<211> LENGTH: 19
<212> TYPE: DNA
<213> ORGANISM: Artificial Sequence
<220> FEATURE:
<223> OTHER INFORMATION: Reelin reverse primer

<400> SEQUENCE: 6
cgacctccac atggtccaa                                                19

<210> SEQ ID NO 7
<211> LENGTH: 22
<212> TYPE: DNA
<213> ORGANISM: Artificial Sequence
<220> FEATURE:
<223> OTHER INFORMATION: Glutamate decarboxylase 1 (Brain, 67 kDa;
      Gad-1/67) forward primer

<400> SEQUENCE: 7
cgcttggctt tggaaccgac aa                                            22

<210> SEQ ID NO 8
<211> LENGTH: 23
<212> TYPE: DNA
<213> ORGANISM: Artificial Sequence
<220> FEATURE:
<223> OTHER INFORMATION: Glutamate decarboxylase 1 (Brain, 67 kDa;
```

Gad-1/67) reverse primer

<400> SEQUENCE: 8
gaatgctccg taaacagtcg tgc                                          23

<210> SEQ ID NO 9
<211> LENGTH: 22
<212> TYPE: DNA
<213> ORGANISM: Artificial Sequence
<220> FEATURE:
<223> OTHER INFORMATION: Neurexin 1 (Nrxn1) forward primer

<400> SEQUENCE: 9
accgtgcctt agcaatcctt gc                                           22

<210> SEQ ID NO 10
<211> LENGTH: 22
<212> TYPE: DNA
<213> ORGANISM: Artificial Sequence
<220> FEATURE:
<223> OTHER INFORMATION: Neurexin 1 (Nrxn1) reverse primer

<400> SEQUENCE: 10
gtcgtagctc aaaaccgttg cc                                           22

<210> SEQ ID NO 11
<211> LENGTH: 22
<212> TYPE: DNA
<213> ORGANISM: Artificial Sequence
<220> FEATURE:
<223> OTHER INFORMATION: Neuroligin 2 (Nlgn 2) forward primer

<400> SEQUENCE: 11
cgatgtcatg ctcagcgcag ta                                           22

<210> SEQ ID NO 12
<211> LENGTH: 22
<212> TYPE: DNA
<213> ORGANISM: Artificial Sequence
<220> FEATURE:
<223> OTHER INFORMATION: Neuroligin 2 (Nlgn 2) reverse primer

<400> SEQUENCE: 12
ccacactacc tcttcaaagc gg                                           22

<210> SEQ ID NO 13
<211> LENGTH: 21
<212> TYPE: DNA
<213> ORGANISM: Artificial Sequence
<220> FEATURE:
<223> OTHER INFORMATION: Beta-Actin forward primer

<400> SEQUENCE: 13
cagcagatgt ggatcagcaa g                                            21

<210> SEQ ID NO 14
<211> LENGTH: 18
<212> TYPE: DNA
<213> ORGANISM: Artificial Sequence
<220> FEATURE:
<223> OTHER INFORMATION: Beta-Actin reverse primer

<400> SEQUENCE: 14
gcatttgcgg tggacgat                                                18

```
<210> SEQ ID NO 15
<211> LENGTH: 23
<212> TYPE: DNA
<213> ORGANISM: Artificial Sequence
<220> FEATURE:
<223> OTHER INFORMATION: mmu-miR-137-5p primer sequence

<400> SEQUENCE: 15
acgggtattc ttgggtggat aat                                              23

<210> SEQ ID NO 16
<211> LENGTH: 23
<212> TYPE: DNA
<213> ORGANISM: Artificial Sequence
<220> FEATURE:
<223> OTHER INFORMATION: mmu-miR-137-3p primer sequence

<400> SEQUENCE: 16
ttattgctta agaatacgcg tag                                              23

<210> SEQ ID NO 17
<211> LENGTH: 23
<212> TYPE: DNA
<213> ORGANISM: Artificial Sequence
<220> FEATURE:
<223> OTHER INFORMATION: mmu-miR-181a primer sequence

<400> SEQUENCE: 17
aacattcaac gctgtcggtg agt                                              23

<210> SEQ ID NO 18
<211> LENGTH: 21
<212> TYPE: DNA
<213> ORGANISM: Artificial Sequence
<220> FEATURE:
<223> OTHER INFORMATION: mmu-miR-128-1-5p primer sequence

<400> SEQUENCE: 18
cggggccgta gcactgtctg a                                                21

<210> SEQ ID NO 19
<211> LENGTH: 21
<212> TYPE: DNA
<213> ORGANISM: Artificial Sequence
<220> FEATURE:
<223> OTHER INFORMATION: mmu-miR-128-3p primer sequence

<400> SEQUENCE: 19
tcacagtgaa ccggtctctt t                                                21

<210> SEQ ID NO 20
<211> LENGTH: 23
<212> TYPE: DNA
<213> ORGANISM: Artificial Sequence
<220> FEATURE:
<223> OTHER INFORMATION: mmu-miR-138 primer sequence

<400> SEQUENCE: 20
agctggtgtt gtgaatcagg ccg                                              23

<210> SEQ ID NO 21
<211> LENGTH: 23
<212> TYPE: DNA
<213> ORGANISM: Artificial Sequence
<220> FEATURE:
<223> OTHER INFORMATION: mmu-miR-200c primer sequence
```

-continued

```
<400> SEQUENCE: 21
taatactgcc gggtaatgat gga                                          23

<210> SEQ ID NO 22
<211> LENGTH: 22
<212> TYPE: DNA
<213> ORGANISM: Artificial Sequence
<220> FEATURE:
<223> OTHER INFORMATION: small nucleolar RNA 202 (snoRNA-202) internal
      forward primer

<400> SEQUENCE: 22
agtacttttg aacccttttc ca                                           22

<210> SEQ ID NO 23
<211> LENGTH: 11673
<212> TYPE: DNA
<213> ORGANISM: Mus musculus

<400> SEQUENCE: 23
ggggcgtcgc gtgcacaccg gcggcggcgg cgctcggagg cggacgacgc gctctcggcg      60
cccgcggccc cggttccccc cgcgctctcg ctccggcggc ccaaagtaac ttcgggagcc     120
tcggtctccc gctaacttcc ccccgcgggc tcggttgccc ggacccgctc ggctcgagcc     180
cgccgccggc tcgccttccc cgcacgcggc tcctccgtgc cggtgcctcc gaaagtggat     240
gagagagcgc gcggggcgcg cggcggcacg gagcgcggcg gcatggagcg cggctgctgg     300
gcgccgcggg ctctcgtcct ggccgtgctg ctgctgctgg cgacgctgag ggcgcgcgcg     360
gccaccggct actacccgcg cttctcgcct ttctttttcc tgtgcaccca ccacgggggag    420 ctggaagggg atggggagca gggcgaggtg ctcatttccc tgcacattgc gggcaacccc     480
acctactacg taccgggaca ggaataccat gttacaattt caacaagcac cttctttgat     540
ggcttgctgg tgacgggact ctatacctcg acaagcatcc agtcttctca gagcattgga     600
ggctccagcg cctttggatt cgggatcatg tccgaccacc agtttggtaa ccagtttatg     660
tgcagtgtgg tggcctctca tgtgagtcac ctgcctacaa ccaacctcag ctttgtctgg     720
attgccccac cagctggcac aggctgtgtg aatttcatgg ctactgcaac acataggggc     780
caggtgattt tcaaagacgc actggcccag cagctgtgtg aacaaggagc tcccacagag     840
gccactgctt actcgcacct tgctgaaata cacagtgaca gtgtgatcct acgagatgac     900
tttgactcct accagcaact ggaattgaac cccaacatat gggttgaatg cagcaactgt     960
gagatgggag agcagtgtgg caccatcatg catggcaatg ctgtcacctt ctgtgagccg    1020
tacggccctc gagagctgac caccacatgc ctgaacacaa caacagcatc tgtcctccag    1080 tttttccattg ggtcaggatc atgtcgattt agttactctg accccagcat cactgtgtca    1140
tacgccaaga acaataccgc tgattggatt cagctggaga aaattagagc cccttccaat    1200
gtgagcacag tcatccacat cctgtacctc ccgaggaag ccaaaggga gagcgtgcag      1260 ttccagtgga aacaggacag cctgcgagtg ggtgaggtgt atgaggcctg ctgggccctg    1320
gataacatcc tggtcatcaa ttcagcccac agagaagtcg ttctggagga caacctcgac    1380
ccggtcgaca cgggcaactg gctcttcttc cctggagcaa cggtcaagca tagctgtcag    1440
tcagatggga actccatta tttccatgga aatgaaggca gcgagttcaa ttttgccacc    1500
acccgggatg tagatctttc tacagaggat attcaagagc agtggtcaga agaatttgag    1560
agccagccca caggatggga tatcttggga gcagtagttg gtgcagactg tggaaccgta    1620
```

```
gaatcaggac tatcactggt gttcctcaaa gatggagaga ggaagctttg cacccccctac   1680 atggatacaa ctggttatgg caacctgagg ttctacttcg ttatgggagg aatctgtgac   1740
cctggagtct ctcatgaaaa cgatatcatc ttatatgcaa agattgaagg aagaaaagaa   1800
cacattgcac tggacactct tacctattct tcctataagg ttccgtcttt ggtttctgtg   1860
gtcatcaacc ctgaacttca gacacctgcc accaaatttt gtctcaggca aaagagccac   1920
caagggtata atcggaatgt ctgggctgtg gacttcttcc atgtgctgcc cgttctccct   1980
tcaacaatgt ctcacatgat ccagttttct attaatttgg gatgcggcac acaccagcct   2040
gggaacagcg tcagcttgga gttttctact aaccatggac ggtcctggtc cctactccac   2100
actgagtgct tgccggagat ctgtgcaggc ccccacctcc cccacagcac tgtctactcc   2160
tcagaaaact acagcgggtg gaaccgaatc acgattcctc tccctaatgc agcactcacc   2220
cgagacacca ggattcgctg gagacaaaca ggcccaatcc tgggaaatat gtgggcaatt   2280
gataatgttt atataggtcc ttcgtgtctc aaattctgtt ctggcagagg acaatgcact   2340
cggcatggct gcaagtgtga cccaggattt tctggcccag cttgtgagat ggcatctcag   2400
acattcccaa tgtttatttc ggaaagcttt ggcagtgcca gactttcctc ttaccataac   2460
ttttactcta tccgtggtgc tgaagtcagc tttggttgtg gtgtcttagc cagtggtaag   2520
gctctggttt tcaacaaaga tgggaggcgg cagctaatca cgtcctttct ggacagctcg   2580
cagtccaggt ttcttcagtt tacactgagg ctggggagca agtctgtgct gagcacgtgc   2640
agagcccctg accagccggg ggagggagtc ctgctgcact attcatatga caacgggata   2700
acatggaaac tcctggagca ctattcctac gtcaactacc acgagcccag aataatctct   2760
gtagagctac cggatgatgc aagacagttt ggaatccagt tcagatggtg gcagccttac   2820
cattcttccc aaggagaaga cgtgtgggcc attgatgaga ttgtcatgac ctcagtcctg   2880
ttcaacagca tcagtctcga ctttaccaat cttgtggaag tcactcaatc cctgggattc   2940
taccttggca atgttcaacc atactgtggc catgactgga cgctttgttt tacgggagat   3000
tctaaacttg cctcaagcat gcgctatgtg gaaacacagt ccatgcagat cggagcatcc   3060
tatatgattc agttcagcct agtgatggga tgtggccaga aatacactcc tcacatggac   3120
aaccaggtga agctggagta ctcagccaac cacggcctta catggcacct tgtacaagaa   3180
gaatgccttc ccagtatgcc aagctgccag gaatttacat ctgccagcat ttaccatgcc   3240
agcgagttca cacagtggag aagagtcact gttgttcttc cccagaaaac atggtccggt   3300
gccacccgct tccgttggag tcagagctat tacacagccc aggatgagtg ggctttagac   3360
aacatttaca ttgggcagca gtgccccaac atgtgcagtg ggcatggctc atgtgaccat   3420
ggcgtgtgca ggtgtgacca gggataccag ggcactgaat gccacccaga agctgcactt   3480
ccttccacga ttatgtcaga ttttgagaac ccgagcagtt gggaatcaga ctggcaggaa   3540
gttattgggg gagaagttgt aaagcctgag caaggctgtg gagtcgtgtc ttctggatct   3600
tctctgtact tcagcaaggc tgggaagagg cagctggtga ctgggaccct ggacacatcc   3660
tgggtggact ttgtccagtt ctacatccag ataggaggag agagtgctgc atgcaacaag   3720
cctgacagca gagaggaggg cattctgctc cagtatagca caacgggggg catccagtgg   3780
cacctgctgg cagagatgta cttctcagac ttcagcaaac ccagatttgt ctacctggag   3840
ctcccagctg ctgggaagac cccttgtacc aggttccgct ggtggaagcc tgtgttctcg   3900
ggggaggact atgaccagtg ggcgttgat gatatcatca ttctgtcaga gaagcagaag   3960
caggttatcc cagttgtcaa cccaactttg ccccagaact tctatgagaa gccagctttc   4020
```

-continued

```
gattacccta tgaaccaaat gagtgtgtgg ctaatgttgg ccaatgaagg catggctaaa    4080
aacgacagct tctgtgcgac cacgccgtca gccatggtgt ttggaaagtc agatggagac    4140
cggtttgcag taactcgaga tctgaccctg aaacctggat atgtgctgca gttcaagcta    4200
aacataggct gcaccagcca gttcagcagc actgccccgg ttctcctgca gtattcacat    4260
gatgccggca tgtcgtggtt tctgttgaag gaaggatgct cccagcgtc agcagccaaa     4320 ggatgtgaag ggaactccag ggaattgagt gagcctactg tctattatac tggggacttc    4380
gaagaatgga ctagaatcac cattgccatt ccaaggtccc ttgcatccag caagaccaga    4440
ttccgatgga tccaagagag cagctctcag aagaatgtgc ccccgtttgg cttagatggg    4500
gtgtacatat ctgagccttg tcccagttac tgcagtggcc atggagactg catctcgggg    4560
gtgtgttttt gtgacctggg gtacacagct gcacaaggaa cctgtgtgtc aaacacccct    4620
aaccacagtg agatgttcga caggtttgag gggaagctaa gcccactgtg gtacaaaatc    4680
accgggggtc aggttggcac gggctgtggc accctcaatg acggcaggtc cctctacttt    4740
aatggccttg ggaaaaggga agccaggaca gtcccactgg acaccaggaa tatcagtctt    4800
gttcagtttt atatacaaat tggaagtaaa acatcaggga ttacgtacat caccccacgg    4860
gctagatatg aggggcttgt tgttcagtat tccaatgata atgggatact ttggcatttg    4920
ctgagagagt tggatttcat gtcattcctg gagccacaga tcatttccat tgacctgccc    4980
cgggaagcaa agacacctgc cacagctttc cggtggtggc agccgcagca tgggaagcat    5040
tcggcccagt gggctttggg tgatgtcctt ataggagtga atgacagctc tcaaactgga    5100
tttcaagata aattggatgg ctccatagac ttgcaagcca actggtatcg aatccaggga    5160
ggccaagttg atatcgactg cctctctatg gacactgccc ttatattcac tgaaaacata    5220
ggaaaccctc gctatgctga gacctgggac ttccatgtgt cagagtcaag cttcttacag    5280
tgggaaatga acatgggctg cagcaagcct ttcagtggtg cccacggcat acagctccag    5340
tactctctga acaacggcaa ggactggcag cttgtcaccg aagagtgtgt ccctccaacc    5400
attgggtgcg tgcactacac agagagttca acttacacat cagaaagatt ccagaactgg    5460
aggcgggtca cggtctacct gccactcgcc accaattctc ccaggactcg gttcagatgg    5520
attcagacca actatactgt tggagcagat tcctgggcta ttgataatgt catcctggcc    5580
tcgggctgtc cttggatgtg ctcaggacga gggatctgtg attcggggcg ctgtgtgtgt    5640 daccgggggct tcggtggacc cttctgtgtt cctgttgttc ctcttccctc cattctaaaa    5700
gatgatttca atgggaactt acatcctgac cttttggcctg aagtgtacgg ggcagagagg    5760
ggcaatctga atggcgaaac catcaaatcc ggaacatgtc tgatctttaa aggggaggga    5820
ctaagaatgc ttatttccag agatctagat tgtaccaata ctatgtatgt ccagttctct    5880
ctccgattta tagcgaaagg taccccagag aggtctcact ccatccttct acagttctct    5940
gtcagtggag gagtcacctg gcacctgatg gatgaattct acttccctca aacgaccagc    6000 atactttttca tcaatgttcc cttaccatac ggtgcccaaa ccaacgctac aagattcaga    6060
ctctggcaac cgtacaataa tggtaagaaa gaagaaatct ggatcattga tgactttatt    6120
attgatggaa acaatttgaa caacccccgtg ctgctgctgg acacgttcga ctttgggccc    6180
agggaagaca attggttttt ctatccgggt ggtaatatcg gactttactg cccgtattct    6240 tcaaaggggag ctcctgagga ggattcggcc atggtgtttg tttcaaacga agttggagaa    6300
cactccatta ccacacgaga cctaagtgtg aacgagaaca ccatcattca atttgagatc    6360
```

-continued

```
aatgttggct gctccactga tagttcttct gctgatccgg tcagactgga attctcaagg    6420
gactttggag ccacctggca cctgctgctg cctctctgct accacagcag cagcctcgtc    6480
agctccttat gctccactga gcatcacccg agcagcacct actacgcggg gaccacccag    6540
ggctggcggc gggaggtcgt gcacttcgga aagctgcacc tttgtggatc tgtgcgtttc    6600
cgttggtacc agggatttta tcctgctggc tctcagccgg tcacatgggc cattgacaat    6660
gtctacattg gtccccagtg tgaagagatg tgctatgggc acgggagctg catcaatgga    6720
accaagtgta tatgtgaccc gggctactct gggccaacct gtaaaataag caccaaaaat    6780
cctgattttc tcaaagacga ctttgaaggt caactggaat ccgatcgatt cttactgatg    6840
agcggtggga agccgtctcg taagtgtggc atcctttcca gtgggaacaa cctcttcttc    6900
aatgaggacg gcttgcgcat gctagtaaca cgggacctgg atttatcaca tgcaaggttt    6960
gtgcagttct tcatgagact gggatgtggt aaaggtgttc cagaccccag gagccagccc    7020
gtgcttctgc agtactccct caatggcggc ctctcctgga gtcttcttca agagttcctc    7080
ttcagcaact ccagcaatgt gggcaggtac attgccctgg aaatgcccct gaaagcccgt    7140
tctggttcga cacgcctccg ctggtggcag ccatctgaaa atgggcactt ctatagcccc    7200
tgggtgatcg accagattct tattggagga aatatctctg gtaatacagt cttagaagat    7260
gatttctcaa ctctggacag cagaaagtgg ctgcttcacc caggaggcac caagatgcct    7320
gtgtgtggct ccacaggcga tgccctggtc tttattgaaa aggccagcac ccgttacgtg    7380
gtcacgacag acatcgctgt gaatgaggac tcattcctac agatagactt tgctgcctcc    7440
tgctcagtca cagactcctg ctatgctatt gaactggagt actcggtgga tctcggtctg    7500
tcgtggcacc cgctggtgag ggactgcctg cctaccaatg ttgagtgtag tcgttaccac    7560
ctgcagcgga tcctggtgtc agatactttc aacaagtgga ccagaatcac tctgcccctg    7620
ccttcctaca ccaggtctca agccactcgt ttccgctggc atcagccagc gccttttgac    7680
aagcagcaga cctgggcaat agataatgtc tatattgggg atggttgcct agacatgtgc    7740
agtggccacg ggagatgcgt ccagggaagc tgtgtctgtg atgaacagtg gggaggcctg    7800
tactgtgatg agcctgagac ctcccttccc acccagctca aagacaactt caaccgagcc    7860
ccctccaacc agaactggct gactgtgagc ggtgggaagc tgagtacagt gtgtgggct    7920 gtggcttccg gcctggctct ccatttcagt ggggctgca gccgattgtt agtcactgtg    7980
gatctgaacc tcaccaatgc tgagtttatc cagtttact ttatgtatgg atgcctcatt    8040
acgccgagca accgtaacca gggagtcctg ctggagtact ctgtcaatgg aggcatcacc    8100
tggaacttgc tgatggagat tttctatgac cagtacagca aacctggatt tgtgaatatc    8160
cttctccctc ctgatgctaa agagattgcc actcgcttcc gatggtggca gccacgacat    8220
gatggccttg accagaatga ctgggccatt gacaatgtcc tcatctcggg ctctgcggac    8280
cagaggacag tcatgctgga cacctttagc agcgccccag taccacagca tgagcgctcc    8340
cccgcagacg ctggccctgt tggaagaatt gcttttgaaa tgttcttaga agacaaaact    8400
tcagtgaatg agaattggct cttccatgat gactgtacag tggaaagatt ctgtgactcg    8460
ccagatggtg tcatgctctg tggcagccat gatggacgag aggtgtatgc agtgactcat    8520
gacctgacgc ccactgagaa ctggatcatg cagttcaaga tctctgttgg atgcaaagtg    8580
cctgaaaaaa ttgcccagaa tcaaattcac gtgcagtttt ctactgactt tggcgtgagc    8640
tggagttatt tagtccctca gtgcttaccc gccgacccaa agtgttctgg aagcgtttct    8700
caaccgtctg tgttcttccc aactgaaggg tggaaaagga tcacctaccc gcttcctgaa    8760
```

-continued

```
agcttaacgg ggaatcctgt aagatttagg ttctaccaaa agtactcaga tgtgcagtgg    8820
gcaattgaca atttctacct tggccctgga tgtttggaca actgtggagg ccacggagac    8880
tgcctaaagg aacagtgtat ctgtgaccca ggctactcag ggccaaactg ctacttaact    8940
cacagcctga agactttcct gaaggagcgc tttgacagtg aggagatcaa gcctgactta    9000
tggatgtcct tggaaggcgg aagcacttgt acagagtgcg gggtcctcgc cgagaacact    9060
gcactctatt ttgggggatc cactgtgaga caagctatta ctcaagactt agatctcaga    9120
ggtgcaaaat tcctgcagta ctggggacgt atcggcagtg agaacaacat gacatcttgc    9180
catcggcctg tctgccggaa ggaaggcgtg ctgctggact tctctacgga tggaggaatc    9240
acttggacct tgcttcacga gatggatttc cagaaataca tttctgtgag gcacgactac    9300
atcctcctgc ctgaggggc cctcaccaac acaactcgac ttcgctggtg gcagcctttt    9360
gtcatcagca atgggctcgt ggtttccggg gtggagcgtg cgcagtgggc actggacaac    9420
attctgattg gtggagcaga aatcaatcca agccaactgg tggacacttt cgatgacgaa    9480
ggctcctccc atgaagaaaa ctggagtttt taccctaatg cagtaaggac agcaggattc    9540
tgtggcaacc catccttcca cctctactgg ccaaataaaa agaaggacaa gacccacaat    9600
gcactctcct cccgagagct cattatacag ccaggataca tgatgcaatt taaaattgtg    9660
gtgggttgtg aagccacttc atgtggtgac cttcattccg tgatgctgga gtacaccaag    9720
gatgcaaggt ccgattcctg gcagctcgtg cagacccagt gcctaccttc ctcttccaat    9780
agcattggct gctccccgtt ccagttccat gaagccacca tttataatgc tgtcaacagc    9840
tcaagctgga agaggatcac catccagctc ccagaccacg tctcgtcaag tgccacacag    9900
ttccgctgga tccagaaggg agaagaaacc gagaagcaaa gctgggccat cgaccacgtg    9960
tacatcggag aggcttgtcc caagctctgc agcgggcatg gctactgcac cacaggggcc   10020
gtctgcatct gcgatgaaag cttccaaggt gacgactgct ctgtcttcag tcacgagctt   10080
cctagttaca ttaaagataa tttttgaatca gcaagagtca ctgaagccaa ctgggaaacc   10140
atccagggtg gagtgatcgg aagtggctgt gggcagctgg cgccctatgc ccatggagat   10200
tcgctctact ttaatggttg tcagataagg caagctgcca ccaagccact ggacctcact   10260
cgagcaagca aaattatgtt tgtcttgcaa attgggagcc cagcccagac agacagttgc   10320
aacagcgacc tcagcggccc ccacaccgtg gacaaagcag tactgctgca gtacagtgtc   10380
aacaatggca tcacctggca cgtcatcgct cagcaccagc cgaaggactt cacacaagct   10440
cagcgggtgt cttacaacgt ccccctggaa gctcggatga aaggagttct actgcgctgg   10500
tggcagccac gccacaatgg aacaggtcat gatcaatggg ctttggacca tgtggaggtc   10560
gtcctagtaa gcactcgcaa acaaaattac atgatgaatt tttcacggca acatgggctc   10620
aggcacttct acaacagaag acgaaggtcg cttaggcgat acccatgaag aatccaagtt   10680
tatttccctt tccagcgtac aatgtgtccc ttcctggttt tttgaaacac ctctcactgc   10740
atctgatatc aggaaacaaa gatgaaggac ttggcgaaca gaaagccctt cgagatcttg   10800
tgtaccccac cttcccacac tgtgagctaa tgatgtgtgg tttctctgca cataagtaaa   10860
tgtcttcacg tcagtgcgtc cgtggaaatt gtgatctgtt gtaatatcag ttacagtggc   10920
agtattgaga ataagaaata gtttaacagg aaaaaacgtt taagcacaaa cattttttaag   10980 atcttatgtt ttaagtggca tttttagcaca gtatttaaca ttgttggtca ccgagctatt   11040
taagtagact gtatttcagc tctgtctctt gtttaatatg aataagttct cgtcgtttgt   11100
```

```
cctttatgta ttcttctcta ccgtataaca cactgaaact gtatctactt gctgtgttgc   11160
aatattttgc tgctggactt tgacctactt gtattatgca gaaagttaat gcagatacct   11220
attcaagatg ataactgtaa agacactgct gtctccttaa tatgctcctt aacacgtatg   11280
ttgatgtagc atcattttgt ggataggaaa aaaaatgttt gaccttcaga tattttctac   11340
ttaaaaaatt gtggatgaac gccctatctc cctcccacag tgagtcccca ttaccttgtc   11400
taaaacaatt ttttaatgtg ttctgtggcc gttttactga cagtaactgc catttcgtgt   11460
ctgtggtaac aaagtgactt gtaaaatggt ggatgtttcc ctcactgtgt tctcttcgtg   11520
ggttgtttcc ttgtgggtca tagtcatacc ttctgatgag gtggagccaa caccagcaaa   11580
gtatgatggc cctgtagcct ctgactagtc ctgaaacaga aggctgcact ctaggctgaa   11640
ccatgctaaa agcccatgct taaataaaaa atg                                 11673
```

<210> SEQ ID NO 24
<211> LENGTH: 3461
<212> TYPE: PRT
<213> ORGANISM: Mus musculus

<400> SEQUENCE: 24

```
Met Glu Arg Gly Cys Trp Ala Pro Arg Ala Leu Val Leu Ala Val Leu
1               5                   10                  15

Leu Leu Leu Ala Thr Leu Arg Ala Arg Ala Ala Thr Gly Tyr Tyr Pro
            20                  25                  30

Arg Phe Ser Pro Phe Phe Phe Leu Cys Thr His His Gly Glu Leu Glu
        35                  40                  45

Gly Asp Gly Glu Gln Gly Glu Val Leu Ile Ser Leu His Ile Ala Gly
    50                  55                  60

Asn Pro Thr Tyr Tyr Val Pro Gly Gln Glu Tyr His Val Thr Ile Ser
65                  70                  75                  80

Thr Ser Thr Phe Phe Asp Gly Leu Leu Val Thr Gly Leu Tyr Thr Ser
                85                  90                  95

Thr Ser Ile Gln Ser Ser Gln Ser Ile Gly Gly Ser Ser Ala Phe Gly
            100                 105                 110

Phe Gly Ile Met Ser Asp His Gln Phe Gly Asn Gln Phe Met Cys Ser
        115                 120                 125

Val Val Ala Ser His Val Ser His Leu Pro Thr Thr Asn Leu Ser Phe
    130                 135                 140

Val Trp Ile Ala Pro Pro Ala Gly Thr Gly Cys Val Asn Phe Met Ala
145                 150                 155                 160

Thr Ala Thr His Arg Gly Gln Val Ile Phe Lys Asp Ala Leu Ala Gln
                165                 170                 175

Gln Leu Cys Glu Gln Gly Ala Pro Thr Glu Ala Thr Ala Tyr Ser His
            180                 185                 190

Leu Ala Glu Ile His Ser Asp Ser Val Ile Leu Arg Asp Asp Phe Asp
        195                 200                 205

Ser Tyr Gln Gln Leu Glu Leu Asn Pro Asn Ile Trp Val Glu Cys Ser
    210                 215                 220

Asn Cys Glu Met Gly Glu Gln Cys Gly Thr Ile Met His Gly Asn Ala
225                 230                 235                 240

Val Thr Phe Cys Glu Pro Tyr Gly Pro Arg Glu Leu Thr Thr Thr Cys
                245                 250                 255

Leu Asn Thr Thr Thr Ala Ser Val Leu Gln Phe Ser Ile Gly Ser Gly
            260                 265                 270
```

```
Ser Cys Arg Phe Ser Tyr Ser Asp Pro Ser Ile Thr Val Ser Tyr Ala
    275                 280                 285

Lys Asn Asn Thr Ala Asp Trp Ile Gln Leu Glu Lys Ile Arg Ala Pro
    290                 295                 300

Ser Asn Val Ser Thr Val Ile His Ile Leu Tyr Leu Pro Glu Glu Ala
305                 310                 315                 320

Lys Gly Glu Ser Val Gln Phe Gln Trp Lys Gln Asp Ser Leu Arg Val
                325                 330                 335

Gly Glu Val Tyr Glu Ala Cys Trp Ala Leu Asp Asn Ile Leu Val Ile
                340                 345                 350

Asn Ser Ala His Arg Glu Val Val Leu Glu Asp Asn Leu Asp Pro Val
                355                 360                 365

Asp Thr Gly Asn Trp Leu Phe Phe Pro Gly Ala Thr Val Lys His Ser
    370                 375                 380

Cys Gln Ser Asp Gly Asn Ser Ile Tyr Phe His Gly Asn Glu Gly Ser
385                 390                 395                 400

Glu Phe Asn Phe Ala Thr Thr Arg Asp Val Asp Leu Ser Thr Glu Asp
                405                 410                 415

Ile Gln Glu Gln Trp Ser Glu Glu Phe Glu Ser Gln Pro Thr Gly Trp
                420                 425                 430

Asp Ile Leu Gly Ala Val Val Gly Ala Asp Cys Gly Thr Val Glu Ser
                435                 440                 445

Gly Leu Ser Leu Val Phe Leu Lys Asp Gly Glu Arg Lys Leu Cys Thr
    450                 455                 460

Pro Tyr Met Asp Thr Thr Gly Tyr Gly Asn Leu Arg Phe Tyr Phe Val
465                 470                 475                 480

Met Gly Gly Ile Cys Asp Pro Gly Val Ser His Glu Asn Asp Ile Ile
                485                 490                 495

Leu Tyr Ala Lys Ile Glu Gly Arg Lys Glu His Ile Ala Leu Asp Thr
                500                 505                 510

Leu Thr Tyr Ser Ser Tyr Lys Val Pro Ser Leu Val Ser Val Val Ile
                515                 520                 525

Asn Pro Glu Leu Gln Thr Pro Ala Thr Lys Phe Cys Leu Arg Gln Lys
    530                 535                 540

Ser His Gln Gly Tyr Asn Arg Asn Val Trp Ala Val Asp Phe Phe His
545                 550                 555                 560

Val Leu Pro Val Leu Pro Ser Thr Met Ser His Met Ile Gln Phe Ser
                565                 570                 575

Ile Asn Leu Gly Cys Gly Thr His Gln Pro Gly Asn Ser Val Ser Leu
                580                 585                 590

Glu Phe Ser Thr Asn His Gly Arg Ser Trp Ser Leu Leu His Thr Glu
                595                 600                 605

Cys Leu Pro Glu Ile Cys Ala Gly Pro His Leu Pro His Ser Thr Val
    610                 615                 620

Tyr Ser Ser Glu Asn Tyr Ser Gly Trp Asn Arg Ile Thr Ile Pro Leu
625                 630                 635                 640

Pro Asn Ala Ala Leu Thr Arg Asp Thr Arg Ile Arg Trp Arg Gln Thr
                645                 650                 655

Gly Pro Ile Leu Gly Asn Met Trp Ala Ile Asp Asn Val Tyr Ile Gly
                660                 665                 670

Pro Ser Cys Leu Lys Phe Cys Ser Gly Arg Gly Gln Cys Thr Arg His
                675                 680                 685

Gly Cys Lys Cys Asp Pro Gly Phe Ser Gly Pro Ala Cys Glu Met Ala
```

-continued

```
      690                   695                   700

Ser Gln Thr Phe Pro Met Phe Ile Ser Glu Ser Phe Gly Ser Ala Arg
705                   710                   715                   720

Leu Ser Ser Tyr His Asn Phe Tyr Ser Ile Arg Gly Ala Glu Val Ser
                  725                   730                   735

Phe Gly Cys Gly Val Leu Ala Ser Gly Lys Ala Leu Val Phe Asn Lys
                  740                   745                   750

Asp Gly Arg Arg Gln Leu Ile Thr Ser Phe Leu Asp Ser Ser Gln Ser
                  755                   760                   765

Arg Phe Leu Gln Phe Thr Leu Arg Leu Gly Ser Lys Ser Val Leu Ser
              770                   775                   780

Thr Cys Arg Ala Pro Asp Gln Pro Gly Glu Gly Val Leu Leu His Tyr
785                   790                   795                   800

Ser Tyr Asp Asn Gly Ile Thr Trp Lys Leu Leu Glu His Tyr Ser Tyr
                  805                   810                   815

Val Asn Tyr His Glu Pro Arg Ile Ile Ser Val Glu Leu Pro Asp Asp
                  820                   825                   830

Ala Arg Gln Phe Gly Ile Gln Phe Arg Trp Trp Gln Pro Tyr His Ser
                  835                   840                   845

Ser Gln Gly Glu Asp Val Trp Ala Ile Asp Glu Ile Val Met Thr Ser
              850                   855                   860

Val Leu Phe Asn Ser Ile Ser Leu Asp Phe Thr Asn Leu Val Glu Val
865                   870                   875                   880

Thr Gln Ser Leu Gly Phe Tyr Leu Gly Asn Val Gln Pro Tyr Cys Gly
                  885                   890                   895

His Asp Trp Thr Leu Cys Phe Thr Gly Asp Ser Lys Leu Ala Ser Ser
                  900                   905                   910

Met Arg Tyr Val Glu Thr Gln Ser Met Gln Ile Gly Ala Ser Tyr Met
                  915                   920                   925

Ile Gln Phe Ser Leu Val Met Gly Cys Gly Gln Lys Tyr Thr Pro His
              930                   935                   940

Met Asp Asn Gln Val Lys Leu Glu Tyr Ser Ala Asn His Gly Leu Thr
945                   950                   955                   960

Trp His Leu Val Gln Glu Glu Cys Leu Pro Ser Met Pro Ser Cys Gln
                  965                   970                   975

Glu Phe Thr Ser Ala Ser Ile Tyr His Ala Ser Glu Phe Thr Gln Trp
                  980                   985                   990

Arg Arg Val Thr Val Val Leu Pro  Gln Lys Thr Trp Ser  Gly Ala Thr
              995                   1000                  1005

Arg Phe  Arg Trp Ser Gln Ser  Tyr Tyr Thr Ala Gln  Asp Glu Trp
     1010                  1015                  1020

Ala Leu  Asp Asn Ile Tyr Ile  Gly Gln Gln Cys Pro  Asn Met Cys
     1025                  1030                  1035

Ser Gly  His Gly Ser Cys Asp  His Gly Val Cys Arg  Cys Asp Gln
     1040                  1045                  1050

Gly Tyr  Gln Gly Thr Glu Cys  His Pro Glu Ala Ala  Leu Pro Ser
     1055                  1060                  1065

Thr Ile  Met Ser Asp Phe Glu  Asn Pro Ser Ser Trp  Glu Ser Asp
     1070                  1075                  1080

Trp Gln  Glu Val Ile Gly Gly  Glu Val Val Lys Pro  Glu Gln Gly
     1085                  1090                  1095

Cys Gly  Val Val Ser Ser Gly  Ser Ser Leu Tyr Phe  Ser Lys Ala
     1100                  1105                  1110
```

Gly Lys Arg Gln Leu Val Ser  Trp Asp Leu Asp Thr  Ser Trp Val
    1115                1120                1125

Asp Phe Val Gln Phe Tyr Ile  Gln Ile Gly Gly Glu  Ser Ala Ala
    1130                1135                1140

Cys Asn Lys Pro Asp Ser Arg  Glu Glu Gly Ile Leu  Leu Gln Tyr
    1145                1150                1155

Ser Asn Asn Gly Gly Ile Gln  Trp His Leu Leu Ala  Glu Met Tyr
    1160                1165                1170

Phe Ser Asp Phe Ser Lys Pro  Arg Phe Val Tyr Leu  Glu Leu Pro
    1175                1180                1185

Ala Ala Gly Lys Thr Pro Cys  Thr Arg Phe Arg Trp  Trp Lys Pro
    1190                1195                1200

Val Phe Ser Gly Glu Asp Tyr  Asp Gln Trp Ala Val  Asp Asp Ile
    1205                1210                1215

Ile Ile Leu Ser Glu Lys Gln  Lys Gln Val Ile Pro  Val Val Asn
    1220                1225                1230

Pro Thr Leu Pro Gln Asn Phe  Tyr Glu Lys Pro Ala  Phe Asp Tyr
    1235                1240                1245

Pro Met Asn Gln Met Ser Val  Trp Leu Met Leu Ala  Asn Glu Gly
    1250                1255                1260

Met Ala Lys Asn Asp Ser Phe  Cys Ala Thr Thr Pro  Ser Ala Met
    1265                1270                1275

Val Phe Gly Lys Ser Asp Gly  Asp Arg Phe Ala Val  Thr Arg Asp
    1280                1285                1290

Leu Thr Leu Lys Pro Gly Tyr  Val Leu Gln Phe Lys  Leu Asn Ile
    1295                1300                1305

Gly Cys Thr Ser Gln Phe Ser  Ser Thr Ala Pro Val  Leu Leu Gln
    1310                1315                1320

Tyr Ser His Asp Ala Gly Met  Ser Trp Phe Leu Leu  Lys Glu Gly
    1325                1330                1335

Cys Phe Pro Ala Ser Ala Ala  Lys Gly Cys Glu Gly  Asn Ser Arg
    1340                1345                1350

Glu Leu Ser Glu Pro Thr Val  Tyr Tyr Thr Gly Asp  Phe Glu Glu
    1355                1360                1365

Trp Thr Arg Ile Thr Ile Ala  Ile Pro Arg Ser Leu  Ala Ser Ser
    1370                1375                1380

Lys Thr Arg Phe Arg Trp Ile  Gln Glu Ser Ser Ser  Gln Lys Asn
    1385                1390                1395

Val Pro Pro Phe Gly Leu Asp  Gly Val Tyr Ile Ser  Glu Pro Cys
    1400                1405                1410

Pro Ser Tyr Cys Ser Gly His  Gly Asp Cys Ile Ser  Gly Val Cys
    1415                1420                1425

Phe Cys Asp Leu Gly Tyr Thr  Ala Ala Gln Gly Thr  Cys Val Ser
    1430                1435                1440

Asn Thr Pro Asn His Ser Glu  Met Phe Asp Arg Phe  Glu Gly Lys
    1445                1450                1455

Leu Ser Pro Leu Trp Tyr Lys  Ile Thr Gly Gly Gln  Val Gly Thr
    1460                1465                1470

Gly Cys Gly Thr Leu Asn Asp  Gly Arg Ser Leu Tyr  Phe Asn Gly
    1475                1480                1485

Leu Gly Lys Arg Glu Ala Arg  Thr Val Pro Leu Asp  Thr Arg Asn
    1490                1495                1500

-continued

```
Ile Ser  Leu Val Gln Phe Tyr  Ile Gln Ile Gly Ser  Lys Thr Ser
    1505             1510             1515

Gly Ile  Thr Tyr Ile Thr Pro  Arg Ala Arg Tyr Glu  Gly Leu Val
    1520             1525             1530

Val Gln  Tyr Ser Asn Asp Asn  Gly Ile Leu Trp His  Leu Leu Arg
    1535             1540             1545

Glu Leu  Asp Phe Met Ser Phe  Leu Glu Pro Gln Ile  Ile Ser Ile
    1550             1555             1560

Asp Leu  Pro Arg Glu Ala Lys  Thr Pro Ala Thr Ala  Phe Arg Trp
    1565             1570             1575

Trp Gln  Pro Gln His Gly Lys  His Ser Ala Gln Trp  Ala Leu Gly
    1580             1585             1590

Asp Val  Leu Ile Gly Val Asn  Asp Ser Ser Gln Thr  Gly Phe Gln
    1595             1600             1605

Asp Lys  Leu Asp Gly Ser Ile  Asp Leu Gln Ala Asn  Trp Tyr Arg
    1610             1615             1620

Ile Gln  Gly Gly Gln Val Asp  Ile Asp Cys Leu Ser  Met Asp Thr
    1625             1630             1635

Ala Leu  Ile Phe Thr Glu Asn  Ile Gly Asn Pro Arg  Tyr Ala Glu
    1640             1645             1650

Thr Trp  Asp Phe His Val Ser  Glu Ser Ser Phe Leu  Gln Trp Glu
    1655             1660             1665

Met Asn  Met Gly Cys Ser Lys  Pro Phe Ser Gly Ala  His Gly Ile
    1670             1675             1680

Gln Leu  Gln Tyr Ser Leu Asn  Asn Gly Lys Asp Trp  Gln Leu Val
    1685             1690             1695

Thr Glu  Glu Cys Val Pro Pro  Thr Ile Gly Cys Val  His Tyr Thr
    1700             1705             1710

Glu Ser  Ser Thr Tyr Thr Ser  Glu Arg Phe Gln Asn  Trp Arg Arg
    1715             1720             1725

Val Thr  Val Tyr Leu Pro Leu  Ala Thr Asn Ser Pro  Arg Thr Arg
    1730             1735             1740

Phe Arg  Trp Ile Gln Thr Asn  Tyr Thr Val Gly Ala  Asp Ser Trp
    1745             1750             1755

Ala Ile  Asp Asn Val Ile Leu  Ala Ser Gly Cys Pro  Trp Met Cys
    1760             1765             1770

Ser Gly  Arg Gly Ile Cys Asp  Ser Gly Arg Cys Val  Cys Asp Arg
    1775             1780             1785

Gly Phe  Gly Gly Pro Phe Cys  Val Pro Val Val Pro  Leu Pro Ser
    1790             1795             1800

Ile Leu  Lys Asp Asp Phe Asn  Gly Asn Leu His Pro  Asp Leu Trp
    1805             1810             1815

Pro Glu  Val Tyr Gly Ala Glu  Arg Gly Asn Leu Asn  Gly Glu Thr
    1820             1825             1830

Ile Lys  Ser Gly Thr Cys Leu  Ile Phe Lys Gly Glu  Gly Leu Arg
    1835             1840             1845

Met Leu  Ile Ser Arg Asp Leu  Asp Cys Thr Asn Thr  Met Tyr Val
    1850             1855             1860

Gln Phe  Ser Leu Arg Phe Ile  Ala Lys Gly Thr Pro  Glu Arg Ser
    1865             1870             1875

His Ser  Ile Leu Leu Gln Phe  Ser Val Ser Gly Gly  Val Thr Trp
    1880             1885             1890

His Leu  Met Asp Glu Phe Tyr  Phe Pro Gln Thr Thr  Ser Ile Leu
```

-continued

```
        1895                    1900                    1905

Phe Ile Asn Val Pro Leu Pro  Tyr Gly Ala Gln Thr  Asn Ala Thr
    1910            1915            1920

Arg Phe Arg Leu Trp Gln Pro  Tyr Asn Asn Gly Lys  Lys Glu Glu
    1925            1930            1935

Ile Trp Ile Ile Asp Asp Phe  Ile Ile Asp Gly Asn  Asn Leu Asn
    1940            1945            1950

Asn Pro Val Leu Leu Leu Asp  Thr Phe Asp Phe Gly  Pro Arg Glu
    1955            1960            1965

Asp Asn Trp Phe Phe Tyr Pro  Gly Gly Asn Ile Gly  Leu Tyr Cys
    1970            1975            1980

Pro Tyr Ser Ser Lys Gly Ala  Pro Glu Glu Asp Ser  Ala Met Val
    1985            1990            1995

Phe Val Ser Asn Glu Val Gly  Glu His Ser Ile Thr  Thr Arg Asp
    2000            2005            2010

Leu Ser Val Asn Glu Asn Thr  Ile Ile Gln Phe Glu  Ile Asn Val
    2015            2020            2025

Gly Cys Ser Thr Asp Ser Ser  Ser Ala Asp Pro Val  Arg Leu Glu
    2030            2035            2040

Phe Ser Arg Asp Phe Gly Ala  Thr Trp His Leu Leu  Leu Pro Leu
    2045            2050            2055

Cys Tyr His Ser Ser Ser Leu  Val Ser Ser Leu Cys  Ser Thr Glu
    2060            2065            2070

His His Pro Ser Ser Thr Tyr  Tyr Ala Gly Thr Thr  Gln Gly Trp
    2075            2080            2085

Arg Arg Glu Val Val His Phe  Gly Lys Leu His Leu  Cys Gly Ser
    2090            2095            2100

Val Arg Phe Arg Trp Tyr Gln  Gly Phe Tyr Pro Ala  Gly Ser Gln
    2105            2110            2115

Pro Val Thr Trp Ala Ile Asp  Asn Val Tyr Ile Gly  Pro Gln Cys
    2120            2125            2130

Glu Glu Met Cys Tyr Gly His  Gly Ser Cys Ile Asn  Gly Thr Lys
    2135            2140            2145

Cys Ile Cys Asp Pro Gly Tyr  Ser Gly Pro Thr Cys  Lys Ile Ser
    2150            2155            2160

Thr Lys Asn Pro Asp Phe Leu  Lys Asp Asp Phe Glu  Gly Gln Leu
    2165            2170            2175

Glu Ser Asp Arg Phe Leu Leu  Met Ser Gly Gly Lys  Pro Ser Arg
    2180            2185            2190

Lys Cys Gly Ile Leu Ser Ser  Gly Asn Asn Leu Phe  Phe Asn Glu
    2195            2200            2205

Asp Gly Leu Arg Met Leu Val  Thr Arg Asp Leu Asp  Leu Ser His
    2210            2215            2220

Ala Arg Phe Val Gln Phe Phe  Met Arg Leu Gly Cys  Gly Lys Gly
    2225            2230            2235

Val Pro Asp Pro Arg Ser Gln  Pro Val Leu Leu Gln  Tyr Ser Leu
    2240            2245            2250

Asn Gly Gly Leu Ser Trp Ser  Leu Leu Gln Glu Phe  Leu Phe Ser
    2255            2260            2265

Asn Ser Ser Asn Val Gly Arg  Tyr Ile Ala Leu Glu  Met Pro Leu
    2270            2275            2280

Lys Ala Arg Ser Gly Ser Thr  Arg Leu Arg Trp Trp  Gln Pro Ser
    2285            2290            2295
```

-continued

```
Glu Asn Gly His Phe Tyr Ser Pro Trp Val Ile Asp Gln Ile Leu
    2300                 2305             2310

Ile Gly Gly Asn Ile Ser Gly Asn Thr Val Leu Glu Asp Asp Phe
    2315                 2320             2325

Ser Thr Leu Asp Ser Arg Lys Trp Leu Leu His Pro Gly Gly Thr
    2330                 2335             2340

Lys Met Pro Val Cys Gly Ser Thr Gly Asp Ala Leu Val Phe Ile
    2345                 2350             2355

Glu Lys Ala Ser Thr Arg Tyr Val Val Thr Thr Asp Ile Ala Val
    2360                 2365             2370

Asn Glu Asp Ser Phe Leu Gln Ile Asp Phe Ala Ala Ser Cys Ser
    2375                 2380             2385

Val Thr Asp Ser Cys Tyr Ala Ile Glu Leu Glu Tyr Ser Val Asp
    2390                 2395             2400

Leu Gly Leu Ser Trp His Pro Leu Val Arg Asp Cys Leu Pro Thr
    2405                 2410             2415

Asn Val Glu Cys Ser Arg Tyr His Leu Gln Arg Ile Leu Val Ser
    2420                 2425             2430

Asp Thr Phe Asn Lys Trp Thr Arg Ile Thr Leu Pro Leu Pro Ser
    2435                 2440             2445

Tyr Thr Arg Ser Gln Ala Thr Arg Phe Arg Trp His Gln Pro Ala
    2450                 2455             2460

Pro Phe Asp Lys Gln Gln Thr Trp Ala Ile Asp Asn Val Tyr Ile
    2465                 2470             2475

Gly Asp Gly Cys Leu Asp Met Cys Ser Gly His Gly Arg Cys Val
    2480                 2485             2490

Gln Gly Ser Cys Val Cys Asp Glu Gln Trp Gly Gly Leu Tyr Cys
    2495                 2500             2505

Asp Glu Pro Glu Thr Ser Leu Pro Thr Gln Leu Lys Asp Asn Phe
    2510                 2515             2520

Asn Arg Ala Pro Ser Asn Gln Asn Trp Leu Thr Val Ser Gly Gly
    2525                 2530             2535

Lys Leu Ser Thr Val Cys Gly Ala Val Ala Ser Gly Leu Ala Leu
    2540                 2545             2550

His Phe Ser Gly Gly Cys Ser Arg Leu Leu Val Thr Val Asp Leu
    2555                 2560             2565

Asn Leu Thr Asn Ala Glu Phe Ile Gln Phe Tyr Phe Met Tyr Gly
    2570                 2575             2580

Cys Leu Ile Thr Pro Ser Asn Arg Asn Gln Gly Val Leu Leu Glu
    2585                 2590             2595

Tyr Ser Val Asn Gly Gly Ile Thr Trp Asn Leu Leu Met Glu Ile
    2600                 2605             2610

Phe Tyr Asp Gln Tyr Ser Lys Pro Gly Phe Val Asn Ile Leu Leu
    2615                 2620             2625

Pro Pro Asp Ala Lys Glu Ile Ala Thr Arg Phe Arg Trp Trp Gln
    2630                 2635             2640

Pro Arg His Asp Gly Leu Asp Gln Asn Asp Trp Ala Ile Asp Asn
    2645                 2650             2655

Val Leu Ile Ser Gly Ser Ala Asp Gln Arg Thr Val Met Leu Asp
    2660                 2665             2670

Thr Phe Ser Ser Ala Pro Val Pro Gln His Glu Arg Ser Pro Ala
    2675                 2680             2685
```

-continued

```
Asp Ala  Gly Pro Val Gly Arg  Ile Ala Phe Glu Met  Phe Leu Glu
    2690             2695             2700

Asp Lys  Thr Ser Val Asn Glu  Asn Trp Leu Phe His  Asp Asp Cys
    2705             2710             2715

Thr Val  Glu Arg Phe Cys Asp  Ser Pro Asp Gly Val  Met Leu Cys
    2720             2725             2730

Gly Ser  His Asp Gly Arg Glu  Val Tyr Ala Val Thr  His Asp Leu
    2735             2740             2745

Thr Pro  Thr Glu Asn Trp Ile  Met Gln Phe Lys Ile  Ser Val Gly
    2750             2755             2760

Cys Lys  Val Pro Glu Lys Ile  Ala Gln Asn Gln Ile  His Val Gln
    2765             2770             2775

Phe Ser  Thr Asp Phe Gly Val  Ser Trp Ser Tyr Leu  Val Pro Gln
    2780             2785             2790

Cys Leu  Pro Ala Asp Pro Lys  Cys Ser Gly Ser Val  Ser Gln Pro
    2795             2800             2805

Ser Val  Phe Phe Pro Thr Glu  Gly Trp Lys Arg Ile  Thr Tyr Pro
    2810             2815             2820

Leu Pro  Glu Ser Leu Thr Gly  Asn Pro Val Arg Phe  Arg Phe Tyr
    2825             2830             2835

Gln Lys  Tyr Ser Asp Val Gln  Trp Ala Ile Asp Asn  Phe Tyr Leu
    2840             2845             2850

Gly Pro  Gly Cys Leu Asp Asn  Cys Gly Gly His Gly  Asp Cys Leu
    2855             2860             2865

Lys Glu  Gln Cys Ile Cys Asp  Pro Gly Tyr Ser Gly  Pro Asn Cys
    2870             2875             2880

Tyr Leu  Thr His Ser Leu Lys  Thr Phe Leu Lys Glu  Arg Phe Asp
    2885             2890             2895

Ser Glu  Glu Ile Lys Pro Asp  Leu Trp Met Ser Leu  Glu Gly Gly
    2900             2905             2910

Ser Thr  Cys Thr Glu Cys Gly  Val Leu Ala Glu Asn  Thr Ala Leu
    2915             2920             2925

Tyr Phe  Gly Gly Ser Thr Val  Arg Gln Ala Ile Thr  Gln Asp Leu
    2930             2935             2940

Asp Leu  Arg Gly Ala Lys Phe  Leu Gln Tyr Trp Gly  Arg Ile Gly
    2945             2950             2955

Ser Glu  Asn Asn Met Thr Ser  Cys His Arg Pro Val  Cys Arg Lys
    2960             2965             2970

Glu Gly  Val Leu Leu Asp Phe  Ser Thr Asp Gly Gly  Ile Thr Trp
    2975             2980             2985

Thr Leu  Leu His Glu Met Asp  Phe Gln Lys Tyr Ile  Ser Val Arg
    2990             2995             3000

His Asp  Tyr Ile Leu Leu Pro  Glu Gly Ala Leu Thr  Asn Thr Thr
    3005             3010             3015

Arg Leu  Arg Trp Trp Gln Pro  Phe Val Ile Ser Asn  Gly Leu Val
    3020             3025             3030

Val Ser  Gly Val Glu Arg Ala  Gln Trp Ala Leu Asp  Asn Ile Leu
    3035             3040             3045

Ile Gly  Gly Ala Glu Ile Asn  Pro Ser Gln Leu Val  Asp Thr Phe
    3050             3055             3060

Asp Asp  Glu Gly Ser Ser His  Glu Glu Asn Trp Ser  Phe Tyr Pro
    3065             3070             3075

Asn Ala  Val Arg Thr Ala Gly  Phe Cys Gly Asn Pro  Ser Phe His
```

-continued

```
        3080              3085              3090

Leu Tyr  Trp Pro Asn Lys Lys  Lys Asp Lys Thr His  Asn Ala Leu
    3095              3100              3105

Ser Ser  Arg Glu Leu Ile Ile  Gln Pro Gly Tyr Met  Met Gln Phe
    3110              3115              3120

Lys Ile  Val Val Gly Cys Glu  Ala Thr Ser Cys Gly  Asp Leu His
    3125              3130              3135

Ser Val  Met Leu Glu Tyr Thr  Lys Asp Ala Arg Ser  Asp Ser Trp
    3140              3145              3150

Gln Leu  Val Gln Thr Gln Cys  Leu Pro Ser Ser Ser  Asn Ser Ile
    3155              3160              3165

Gly Cys  Ser Pro Phe Gln Phe  His Glu Ala Thr Ile  Tyr Asn Ala
    3170              3175              3180

Val Asn  Ser Ser Ser Trp Lys  Arg Ile Thr Ile Gln  Leu Pro Asp
    3185              3190              3195

His Val  Ser Ser Ser Ala Thr  Gln Phe Arg Trp Ile  Gln Lys Gly
    3200              3205              3210

Glu Glu  Thr Glu Lys Gln Ser  Trp Ala Ile Asp His  Val Tyr Ile
    3215              3220              3225

Gly Glu  Ala Cys Pro Lys Leu  Cys Ser Gly His Gly  Tyr Cys Thr
    3230              3235              3240

Thr Gly  Ala Val Cys Ile Cys  Asp Glu Ser Phe Gln  Gly Asp Asp
    3245              3250              3255

Cys Ser  Val Phe Ser His Glu  Leu Pro Ser Tyr Ile  Lys Asp Asn
    3260              3265              3270

Phe Glu  Ser Ala Arg Val Thr  Glu Ala Asn Trp Glu  Thr Ile Gln
    3275              3280              3285

Gly Gly  Val Ile Gly Ser Gly  Cys Gly Gln Leu Ala  Pro Tyr Ala
    3290              3295              3300

His Gly  Asp Ser Leu Tyr Phe  Asn Gly Cys Gln Ile  Arg Gln Ala
    3305              3310              3315

Ala Thr  Lys Pro Leu Asp Leu  Thr Arg Ala Ser Lys  Ile Met Phe
    3320              3325              3330

Val Leu  Gln Ile Gly Ser Pro  Ala Gln Thr Asp Ser  Cys Asn Ser
    3335              3340              3345

Asp Leu  Ser Gly Pro His Thr  Val Asp Lys Ala Val  Leu Leu Gln
    3350              3355              3360

Tyr Ser  Val Asn Asn Gly Ile  Thr Trp His Val Ile  Ala Gln His
    3365              3370              3375

Gln Pro  Lys Asp Phe Thr Gln  Ala Gln Arg Val Ser  Tyr Asn Val
    3380              3385              3390

Pro Leu  Glu Ala Arg Met Lys  Gly Val Leu Leu Arg  Trp Trp Gln
    3395              3400              3405

Pro Arg  His Asn Gly Thr Gly  His Asp Gln Trp Ala  Leu Asp His
    3410              3415              3420

Val Glu  Val Val Leu Val Ser  Thr Arg Lys Gln Asn  Tyr Met Met
    3425              3430              3435

Asn Phe  Ser Arg Gln His Gly  Leu Arg His Phe Tyr  Asn Arg Arg
    3440              3445              3450

Arg Arg  Ser Leu Arg Arg Tyr  Pro
    3455              3460
```